US012605461B2

(12) United States Patent
Shoichet et al.

(10) Patent No.: US 12,605,461 B2
(45) Date of Patent: Apr. 21, 2026

(54) HYDROGEL COMPOSITIONS AND USES THEREOF

(71) Applicant: Molly Sandra Shoichet, York (CA)

(72) Inventors: Molly Sandra Shoichet, York (CA); Alexander Edgar Gilbert Baker, Toronto (CA); Roger Yue Tam, Ottawa (CA)

(73) Assignee: Molly Sandra Shoichet, York (CA)

( * ) Notice: Subject to any disclaimer, the term of this patent is extended or adjusted under 35 U.S.C. 154(b) by 745 days.

(21) Appl. No.: 17/623,716

(22) PCT Filed: Jul. 3, 2020

(86) PCT No.: PCT/CA2020/050927
§ 371 (c)(1),
(2) Date: Dec. 29, 2021

(87) PCT Pub. No.: WO2021/000050
PCT Pub. Date: Jan. 7, 2021

(65) Prior Publication Data

US 2023/0133656 A1 May 4, 2023

Related U.S. Application Data

(60) Provisional application No. 62/870,497, filed on Jul. 3, 2019.

(51) Int. Cl.

| | |
|---|---|
| ***A61K 47/69*** | (2017.01) |
| ***A61K 47/54*** | (2017.01) |
| ***C08B 37/08*** | (2006.01) |
| ***C12N 5/079*** | (2010.01) |
| ***C12N 5/0793*** | (2010.01) |

(52) U.S. Cl.
CPC .......... *A61K 47/6903* (2017.08); *A61K 47/54* (2017.08); *C08B 37/0072* (2013.01); *C12N 5/062* (2013.01); *C12N 5/0621* (2013.01); *C12N 2501/905* (2013.01); *C12N 2513/00* (2013.01)

(58) Field of Classification Search
None
See application file for complete search history.

(56) References Cited

U.S. PATENT DOCUMENTS

| | | | |
|---|---|---|---|
| 4,569,941 | A | 2/1986 | Suh et al. |
| 2004/0072793 | A1 | 4/2004 | Aeschlimann et al. |
| 2016/0361430 | A1 | 12/2016 | Siekmann et al. |

FOREIGN PATENT DOCUMENTS

| | | | |
|---|---|---|---|
| CA | 1341276 | C | 7/2001 |
| CA | 2633954 | A1 | 6/2007 |
| CA | 2858366 | C | 1/2020 |
| CN | 102573913 | B | 7/2012 |
| CN | 106852914 | A | 6/2017 |
| EP | 2820051 | A1 | 1/2015 |
| WO | WO-00/01733 | A1 | 1/2000 |
| WO | WO-2010/138074 | A1 | 12/2010 |
| WO | WO-2013/127374 | A1 | 9/2013 |
| WO | WO-2017/197056 | A1 | 11/2017 |

OTHER PUBLICATIONS

International Search Report and Written Opinion for International Application No. PCT/CA2020/050927, mailed Aug. 25, 2020 (12 pages).

International Preliminary Report on Patentability for International Application No. PCT/CA2020/050927, dated Dec. 28, 2021 (6 pages).

Babasola et al., "Chemically modified N-acylated hyaluronan fragments modulate proinflammatory cytokine production by stimulated human macrophages," J Biol Chem. 289(36):24779-91 (Sep. 5, 2014).

Baker et al., "Independently Tuning the Biochemical and Mechanical Properties of 3D Hyaluronan-Based Hydrogels with Oxime and Diels-Alder Chemistry to Culture Breast Cancer Spheroids," Biomacromolecules. 18(12):4373-4384 (Dec. 2017).

Benedetti et al., "Microspheres of hyaluronic acid esters—fabrication methods and in vitro hydrocortisone release," Journal of Controlled Release 13:33-41 (1990).

Bermejo-Velasco et al., "Injectable hyaluronic acid hydrogels with the capacity for magnetic resonance imaging," Carbohydr Polym. 197:641-8 (Oct. 1, 2018).

Bermejo-Velasco et al., "Modulating Thiol p Ka Promotes Disulfide Formation at Physiological pH: An Elegant Strategy To Design Disulfide Cross-Linked Hyaluronic Acid Hydrogels," Biomacromolecules 20(3):1412-20 (Feb. 6, 2019).

Bulpitt et al., "New strategy for chemical modification of hyaluronic acid: preparation of functionalized derivatives and their use in the formation of novel biocompatible hydrogels," J Biomed Mater Res. 47(2):152-69. (Nov. 1999).

Collins et al., "Comparison of the effectiveness of four different crosslinking agents with hyaluronic acid hydrogel films for tissue-culture applications," J Appl Polym Sci 104:3183-91 (2007).

Collins et al., "The emergence of oxime click chemistry and its utility in polymer science," Polymer Chemistry. 7:3812-3826. (May 2016).

(Continued)

*Primary Examiner* — Dale R Miller
(74) *Attorney, Agent, or Firm* — Clark & Elbing LLP

(57) ABSTRACT

The present invention relates to cross-linked polymers (e.g., hydrogels) including hyaluronan polymer and multimeric cross-linker for treating disorders (e.g., retinal detachment or osteoarthritis), for use in screening models (e.g., in vitro cell culture system), or for cell transplantation (e.g., in vivo cell delivery).

14 Claims, 64 Drawing Sheets

Specification includes a Sequence Listing.

(56) References Cited

OTHER PUBLICATIONS

De Boulle et al., "A review of the metabolism of 1,4-butanediol diglycidyl ether-crosslinked hyaluronic acid dermal fillers," Dermatol Surg. 39(12):1758-66 (Dec. 2013).
Eenschooten et al., "Preparation and structural characterisation of novel and versatile amphiphilic octenyl succinic anhydride-modified hyaluronic acid derivatives," 79:597-605 (2010).
Gu Qisheng et al., Practical Biomedical Materials, 1st ed., Shanghai Scientific & Technical Publishers, p. 124-5 (Sep. 30, 2005).
Huerta-Angeles et al., "Novel synthetic method for the preparation of amphiphilic hyaluronan by means of aliphatic aromatic anhydrides," Carbohydr Polym. 111:883-91 (Oct. 13, 2014).
Huerta-Angeles et al., "Synthesis of graft copolymers based on hyaluronan and poly(3-hydroxyalkanoates)," Carbohydr Polym. 171:220-8 (Sep. 1, 2017).
Jia et al., "Synthesis and characterization of in situ cross-linkable hyaluronic acid-based hydrogels with potential application for vocal fold regeneration," Macromolecules 37:3239-48 (2004).
Kenne et al., "Modification and cross-linking parameters in hyaluronic acid hydrogels—definitions and analytical methods," Carbohydr Polym. 91(1):410-8 (Jan. 2, 2013).
Kurisawa et al., "Injectable biodegradable hydrogels composed of hyaluronic acid-tyramine conjugates for drug delivery and tissue engineering," Chem Commun (Camb). (34):4312-4 (Sep. 14, 2005).
Lapcik Jr et al., "Chemical modification of hyaluronic acid: alkylation," International Journal of Polymer Anal. Charact. 15:486-96 (2010).
Leach et al., "Photocrosslinked Hyaluronic Acid Hydrogels: Natural, Biodegradable Tissue Engineering Scaffolds," Biotechnol Bioeng. 82:578-89 (2003).
Mergy et al., "Modification of polysaccharides via thiol-ene chemistry: a versatile route to functional biomaterials," Journal of Polymer Science Part A: Polymer Chemistry 50:4019-28 (2012).
Micochová et al., "Preparation and characterization of biodegradable alkylether derivatives of hyaluronan," Carbohydrate Polymers 69:344-52 (2007).
Micochova et al., "Synthesis and characterization of new biodegradable hyaluronan alkyl derivatives," Biopolymers 82(1):74-9 (May 2006).
Möller et al., "Synthesis and antiherpetic activity of carboxymethylated and sulfated hyaluronan derivatives," Carbohydr Polym. 90(1):608-15 (Sep. 1, 2012).
Oelschlaeger et al., "Synthesis, Structural and Micromechanical Properties of 3D Hyaluronic Acid-Based Cryogel Scaffolds," Biomacromolecules 17(2):580-9 (Feb. 8, 2016).
Ossipov et al., "Functionalization of hyaluronic acid with chemoselective groups via a disulfide-based protection strategy for in situ formation of mechanically stable hydrogels," Biomacromolecules 11(9):2247-54 (Sep. 13, 2010).
Ossipov et al., "Modular approach to functional hyaluronic acid hydrogels using orthogonal chemical reactions," Chem Commun (Camb). 46(44):8368-70 (Nov. 28, 2010).
Picotti et al., "Hyaluronic acid lipoate: synthesis and physicochemical properties," Carbohydr Polym. 93(1):273-8 (Mar. 1, 2013).
Pravata et al., "New amphiphilic lactic acid oligomer-hyaluronan conjugates: synthesis and physicochemical characterization," Biomacromolecules 9(1):340-8 (Jan. 2008).
Sahiner et al., "One-step synthesis of hyaluronic acid-based (sub)micron hydrogel particles: process optimization and preliminary characterization," Turk J Chem. 32(4):397-409 (2008).
Schante et al., "Chemical modifications of hyaluronic acid for the synthesis of derivatives for a broad range of biomedical applications," Carbohydrate Polymers. 85(3):469-489 (Jun. 2011).
Seidlits et al., "The effects of hyaluronic acid hydrogels with tunable mechanical properties on neural progenitor cell differentiation," Biomaterials 31(14):3930-40 (May 2010).
Serban et al., "Synthesis of hyaluronan haloacetates and biology of novel cross-linker-free synthetic extracellular matrix hydrogels," Biomacromolecules 8(9):2821-8 (Sep. 2007).
Serban et al., "Synthesis, characterization and chondroprotective properties of a hyaluronan thioethyl ether derivative," Biomaterials 29(10):1388-99 (Apr. 2008).
Shen et al., "Preparation of human umbilical cord hyaluronic acid and its animal experiments," Chinese Journal of Biochemical Pharmaceutics 3 (Dec. 31, 1996) (6 pages).
Smeds et al., "Photocrosslinkable polysaccharides for in situ hydrogel formation," J Biomed Mater Res. 54(1):115-21 (Jan. 2001).
Smejkalová et al., "Structural and conformational differences of acylated hyaluronan modified in protic and aprotic solvent system," Carbohydrate Polymers 87:1460-6 (2012).
Takahashi et al., "In situ cross-linkable hydrogel of hyaluronan produced via copper-free click chemistry," Biomacromolecules 14(10):3581-8 (Oct. 14, 2013).
Varghese et al., "In situ cross-linkable high molecular weight hyaluronan-bisphosphonate conjugate for localized delivery and cell-specific targeting: a hydrogel linked prodrug approach," J Am Chem Soc. 131(25):8781-3 (Jul. 1, 2009).
Varghese et al., "Synthesis of guanidinium-modified hyaluronic Acid hydrogel," Macromol Rapid Commun. 31(13):1175-80 (Jul. 1, 2010).
Vasi et al., "Chemical functionalization of hyaluronic acid for drug delivery applications," Mater Sci Eng C Mater Biol Appl. 38:177-85 (May 1, 2014).
Wirostko et al., "Ophthalmic Uses of a Thiol-Modified Hyaluronan-Based Hydrogel," Adv Wound Care (New Rochelle) 3(11):708-16 (Nov. 1, 2014).
Zhao, "Synthesis and characterization of a novel hyaluronic acid hydrogel," J Biomater Sci Polym Ed. 17(4):419-33 (2006).

1.05 wt% HAK + 0.15 wt% HAA, 60 mol% $PEGOA_4$ 0.90 wt% HAK + 0.30 wt% HAA, 60 mol% $PEGOA_4$ 0.60 wt% HAK + 0.60 wt% HAA, 60 mol% $PEGOA_4$ a. HA-oxime
b. HA-oxime-Ln
c. Matrigel
d. 2D TCPS a. HA-oxime
b. HA-oxime-Ln
c. Matrigel
d. 2D TCPS

SEQUENCE LISTING

```
<160> NUMBER OF SEQ ID NOS: 30

<210> SEQ ID NO 1
<211> LENGTH: 12
<212> TYPE: PRT
<213> ORGANISM: Artificial Sequence
<220> FEATURE:
<223> OTHER INFORMATION: Synthetic Construct

<400> SEQUENCE: 1

Gly Arg Gly Asp Ser Pro Ala Ser Ser Lys Lys Gly
1               5                   10


<210> SEQ ID NO 2
<211> LENGTH: 21
<212> TYPE: PRT
<213> ORGANISM: Artificial Sequence
<220> FEATURE:
<223> OTHER INFORMATION: Synthetic Construct

<400> SEQUENCE: 2

Ser Lys Ala Gly Ala Gly Pro Gln Gly Ile Trp Gly Gln Gly Ala Gly
1               5                   10                  15

Ala Lys Ser Lys Ser
            20


<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3

aaatcattgc caggttttcg                                                20


<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4

tgccacatgg taaggcataa                                                20


<210> SEQ ID NO 5
<211> LENGTH: 17
<212> TYPE: DNA
<213> ORGANISM: Artificial Sequence
<220> FEATURE:
<223> OTHER INFORMATION: Synthetic Construct

<400> SEQUENCE: 5

gccaacgcgc aggtcta                                                   17


<210> SEQ ID NO 6
```

<211> LENGTH: 14
<212> TYPE: DNA
<213> ORGANISM: Artificial Sequence
<220> FEATURE:
<223> OTHER INFORMATION: Synthetic Construct

<400> SEQUENCE: 6
gccgcagcct caga 14

<210> SEQ ID NO 7
<211> LENGTH: 23
<212> TYPE: DNA
<213> ORGANISM: Artificial Sequence
<220> FEATURE:
<223> OTHER INFORMATION: Synthetic Construct

<400> SEQUENCE: 7
gtcaggcaca tcagtaacaa ggg 23

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct

<400> SEQUENCE: 8
attcagcatc tccagcagca ggtc 24

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
cctctgacgt ccatcgtctc 20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
cggatcttct gctgccgtcg 20

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11
cgcaagtgta agaagtgcga a 21

<210> SEQ ID NO 12
<211> LENGTH: 25
<212> TYPE: DNA
<213> ORGANISM: Artificial Sequence
<220> FEATURE:
<223> OTHER INFORMATION: Synthetic Construct

<400> SEQUENCE: 12
cgtagcattt atggagagtg agtct 25

<210> SEQ ID NO 13
<211> LENGTH: 22
<212> TYPE: DNA
<213> ORGANISM: Artificial Sequence
<220> FEATURE:
<223> OTHER INFORMATION: Synthetic Construct

<400> SEQUENCE: 13
atctctcggt accttcggga gc 22

<210> SEQ ID NO 14
<211> LENGTH: 22
<212> TYPE: DNA
<213> ORGANISM: Artificial Sequence
<220> FEATURE:
<223> OTHER INFORMATION: Synthetic Construct

<400> SEQUENCE: 14
cctgatgcca ccttctaggt cc 22

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
ctgcagatgg agcatgttgt 20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
tcttcacgag gaggcttgat 20

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
atgatgcttg gctctggaat 20

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
ggtctttgcc tgctgagagt 20

<210> SEQ ID NO 19
<211> LENGTH: 18
<212> TYPE: DNA

<213> ORGANISM: Artificial Sequence
<220> FEATURE:
<223> OTHER INFORMATION: Synthetic Construct

<400> SEQUENCE: 19
gcggcgagtt tccgattt 18

<210> SEQ ID NO 20
<211> LENGTH: 19
<212> TYPE: DNA
<213> ORGANISM: Artificial Sequence
<220> FEATURE:
<223> OTHER INFORMATION: Synthetic Construct

<400> SEQUENCE: 20
gctcccgtct ccgtttttc 19

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
tactcccctg ccctcaacaa 20

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
catcgctatc tgagcagcgc 20

<210> SEQ ID NO 23
<211> LENGTH: 22
<212> TYPE: DNA
<213> ORGANISM: Artificial Sequence
<220> FEATURE:
<223> OTHER INFORMATION: Synthetic Construct

<400> SEQUENCE: 23
gaagaacggg gctaacaaag at 22

<210> SEQ ID NO 24
<211> LENGTH: 22
<212> TYPE: DNA
<213> ORGANISM: Artificial Sequence
<220> FEATURE:
<223> OTHER INFORMATION: Synthetic Construct

<400> SEQUENCE: 24
gtccatatga tccgtgatgt cc 22

<210> SEQ ID NO 25
<211> LENGTH: 21
<212> TYPE: DNA
<213> ORGANISM: Artificial Sequence
<220> FEATURE:
<223> OTHER INFORMATION: Synthetic Construct

<400> SEQUENCE: 25
tgcaaggcta ccagttacat t 21

-continued

<210> SEQ ID NO 26
<211> LENGTH: 21
<212> TYPE: DNA
<213> ORGANISM: Artificial Sequence
<220> FEATURE:
<223> OTHER INFORMATION: Synthetic Construct

<400> SEQUENCE: 26
ttagtgttct caggattggc t 21

<210> SEQ ID NO 27
<211> LENGTH: 19
<212> TYPE: DNA
<213> ORGANISM: Artificial Sequence
<220> FEATURE:
<223> OTHER INFORMATION: Synthetic Construct

<400> SEQUENCE: 27
tcgtgggcta cagcatggt 19

<210> SEQ ID NO 28
<211> LENGTH: 22
<212> TYPE: DNA
<213> ORGANISM: Artificial Sequence
<220> FEATURE:
<223> OTHER INFORMATION: Synthetic Construct

<400> SEQUENCE: 28
gccctctgaa gtcgaagaag aa 22

<210> SEQ ID NO 29
<211> LENGTH: 21
<212> TYPE: DNA
<213> ORGANISM: Artificial Sequence
<220> FEATURE:
<223> OTHER INFORMATION: Synthetic Construct

<400> SEQUENCE: 29
catgtacgtt gctatccagg c 21

<210> SEQ ID NO 30
<211> LENGTH: 21
<212> TYPE: DNA
<213> ORGANISM: Artificial Sequence
<220> FEATURE:
<223> OTHER INFORMATION: Synthetic Construct

<400> SEQUENCE: 30
ctccttaatg tcacgcacga t 21

HYDROGEL COMPOSITIONS AND USES THEREOF

SEQUENCE LISTING

The instant application contains a Sequence Listing which has been submitted electronically in ASCII format and is hereby incorporated by reference in its entirety. Said ASCII copy, created on Jul. 2, 2020, is named 51408-002WO2_Sequence_Listing_07.02.20_ST25 and is 6,115 bytes in size.

BACKGROUND OF THE INVENTION

Hyaluronan or hyaluronic acid (HA) is a nonsulfated glycosaminoglycan composed of repeating monomer units of D-glucuronic acid and D-N-acetylglucosamine. Hyaluronan is abundant in many tissues and is biodegradable. Consequently, hyaluronan has been used in both in vivo medical and in vitro cell culture applications. However, when hyaluronan is injected in vivo or used in vitro, it is cleared. Thus, there is a need for hyaluronan composition with enhanced longevity in vivo and in vitro.

SUMMARY OF THE INVENTION

The present disclosure features chemically modified and cross-linked hyaluronan derivatives that have enhanced longevity in vivo and in vitro. Such hyaluronan derivatives are useful for treating disorders (e.g., retinal detachment or osteoarthritis), for use in screening models (e.g., drug screening, e.g., in vitro cell culture system), or for cell transplantation (e.g., in vivo cell delivery).

Hyaluronan includes repeating units of D-glucuronic acid and D-N-acetylglucosamine. As used herein, the carbon-atom numbering for the sugar backbones of D-glucuronic acid and D-N-acetylglucosamine of hyaluronan is shown in Chart 1.

Chart 1

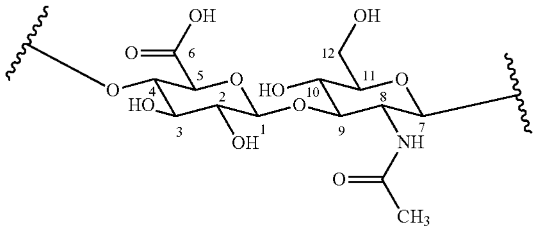

The present disclosure features derivatives of hyaluronan (e.g., hyaluronan bearing a keto group or an oxyamine group), and their use in synthesizing a cross-linked polymer (e.g., hydrogel) useful for treating disease (e.g., retinal detachment) or for use in screening models (e.g., 3D cell culture system).

In a first aspect, the invention features a compound of formula (I):

HAP-K (I), where HAP is a hyaluronan polymer; and K is a moiety covalently linked to the hyaluronan polymer having the structure of formula (Ia) or formula (Ib):

(Ia)

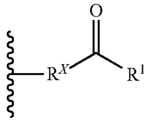

or (Ib)

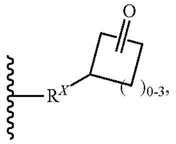

where $R^X$ is $C_{1-20}$ alkylene, $C_{2-20}$ alkenylene, $C_{2-20}$ alkynylene, $C_{1-20}$ heteroalkylene, $C_{2-20}$ heteroalkenylene, or $C_{2-20}$ heteroalkynylene, any of which is optionally substituted with one or more of oxo, halogen, hydroxyl, alkoxy, azido, cyano, nitro, amino, and thiol; and $R^1$ is $C_{1-6}$ alkyl, $C_{2-6}$ alkenyl, $C_{2-6}$ alkynyl, $C_{1-6}$ heteroalkyl, $C_{2-6}$ heteroalkenyl, $C_{2-6}$ heteroalkynyl, $C_{3-10}$ carbocyclyl, $C_{6-10}$ aryl, $C_{2-9}$ heterocyclyl, or $C_{2-9}$ heteroaryl, any of which is optionally substituted with one or more of oxo, halogen, hydroxyl, alkoxy, azido, cyano, nitro, amino, and thiol, or a salt thereof.

In some embodiments, K has the structure of formula (Ia):

(Ia)

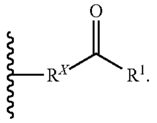

In some embodiments, K has the structure of formula (Ib):

(Ib)

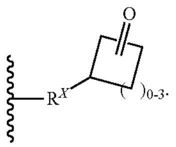

In some embodiments, K is covalently linked to the hyaluronan polymer through a substituent on C1 of D-glucuronic acid or derivative thereof. In some embodiments, K is covalently linked to the hyaluronan polymer through a substituent on C2 of D-glucuronic acid or derivative thereof. In some embodiments, K is covalently linked to the hyaluronan polymer through a substituent on C3 of D-glucuronic acid or derivative thereof. In some embodiments, K is covalently linked to the hyaluronan polymer through a substituent on C4 of D-glucuronic acid or derivative thereof. In some embodiments, K is covalently linked to the hyaluronan polymer through a substituent on C6 of D-glucuronic acid or derivative thereof. In some embodiments, K is covalently linked to the hyaluronan polymer through a substituent on C7 of D-N-acetylglucosamine or derivative thereof. In some embodiments, K is covalently linked to the hyaluronan polymer through a substituent on C8 of D-N-acetylglucosamine or derivative thereof. In some embodiments, K is covalently linked to the hyaluronan polymer through a substituent on C9 of D-N-acetylglucosamine or derivative thereof. In some embodiments, K is covalently linked to the hyaluronan polymer through a substituent on C10 of D-N-acetylglucosamine or derivative thereof. In some embodiments, K is covalently linked to the hyaluronan polymer through a substituent on C12 of D-N-acetylglucosamine or derivative thereof.

In some embodiments, the hyaluronan polymer comprises the structure of formula (II):

(II)

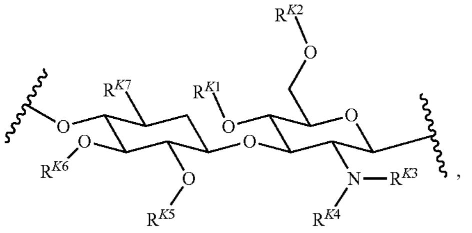

where each of $R^{K1}$, $R^{K2}$, $R^{K3}$, $R^{K4}$, $R^{K5}$, and $R^{K6}$ is, independently, H, $C_{1-12}$ alkyl optionally substituted with one or more of oxo, halogen, hydroxyl, alkoxy, azido, cyano, nitro, amino, and thiol, $C_{1-12}$ heteroalkyl optionally substituted with one or more of oxo, halogen, hydroxyl, alkoxy, azido, cyano, nitro, amino, and thiol, or a bond to K; $R^{K7}$ is

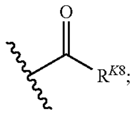

$R^{K8}$ is

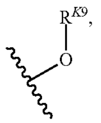

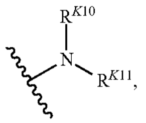

or a bond to K; and each of $R^{K9}$, $R^{K10}$ and $R^{K11}$ is, independently, H, $C_{1-12}$ alkyl optionally substituted with one or more of oxo, halogen, hydroxyl, alkoxy, azido, cyano, nitro, amino, and thiol, or $C_{1-12}$ heteroalkyl optionally substituted with one or more of oxo, halogen, hydroxyl, alkoxy, azido, cyano, nitro, amino, and thiol, where at least one of $R^{K1}$, $R^{K2}$, $R^{K3}$, $R^{K4}$, $R^{K5}$, $R^{K6}$, and $R^{K8}$ is a bond to K.

In some embodiments, $R^{K1}$ is H. In other embodiments, $R^{K2}$ is H. In still other embodiments, $R^{K3}$ is H. In some embodiments, $R^{K4}$ is

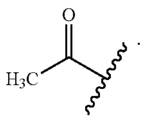

In some embodiments, $R^{K5}$ is H. In some embodiments, $R^{K6}$ is H. In particular embodiments, $R^{K8}$ is a bond to K. In some embodiments, $R^{K8}$ is

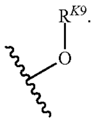

In some embodiments, $R^{K8}$ is

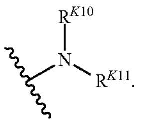

In some embodiments, $R^{K9}$ is H. In some embodiments, $R^{K10}$ is H. In some embodiments, $R^{K11}$ is H.

In some embodiments, the compound is further described by formula (III):

$$[A]_m[B]_n[C]_{1-(m+n)} \qquad \text{(III)},$$

where

[A] has the structure of formula (IIIa):

(IIIa)

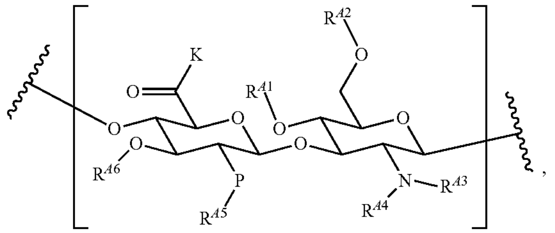

where each of $R^{A1}$, $R^{A2}$, $R^{A3}$, $R^{A4}$, $R^{A5}$, and RAS is, independently, H, $C_{1-12}$ alkyl optionally substituted with one or more of oxo, halogen, hydroxyl, alkoxy, azido, cyano, nitro, amino, and thiol, or $C_{1-12}$ heteroalkyl optionally substituted with one or more of oxo, halogen, hydroxyl, alkoxy, azido, cyano, nitro, amino, and thiol; and K is a moiety covalently linked to the hyaluronan polymer having the structure of formula (Ia) or formula (Ib):

(Ia)

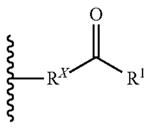

or (Ib)

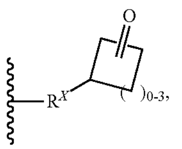

where $R^X$ is $C_{1-20}$ alkylene, $C_{2-20}$ alkenylene, $C_{2-20}$ alkynylene, $C_{1-20}$ heteroalkylene, $C_{2-20}$ heteroalkenylene, or $C_{2-20}$ heteroalkynylene, any of which is optionally substituted with one or more of oxo, halogen, hydroxyl, alkoxy, azido, cyano, nitro, amino, and thiol; and $R^1$ is $C_{1-6}$ alkyl, $C_{2-6}$ alkenyl, $C_{2-6}$ alkynyl, $C_{1-6}$ heteroalkyl, $C_{2-6}$ heteroalkenyl, $C_{2-6}$ heteroalkynyl, $C_{3-10}$ carbocyclyl, $C_{6-10}$ aryl, $C_{2-9}$ heterocyclyl, or $C_{2-9}$ heteroaryl, any of which is optionally substituted with one or more of oxo, halogen, hydroxyl, alkoxy, azido, cyano, nitro, amino, and thiol;

[B] has the structure of formula (IIIb):

(IIIb)

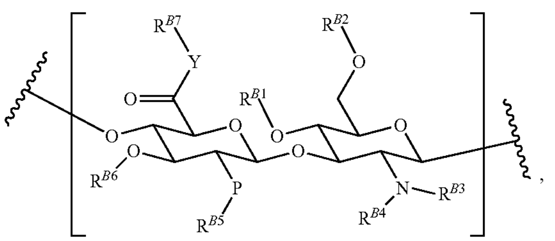

where each of $R^{B1}$, $R^{B3}$, $R^{B4}$, $R^{B5}$, and $R^{B6}$ is, independently, H, $C_{1-12}$ alkyl optionally substituted with one or more of oxo, halogen, hydroxyl, alkoxy, azido, cyano, nitro, amino, and thiol, or $C_{1-12}$ heteroalkyl optionally substituted with one or more of oxo, halogen, hydroxyl, alkoxy, azido, cyano, nitro, amino, and thiol; $R^{B2}$ is H, $C_{1-12}$ acyl, $C_{1-12}$ alkyl, or $C_{1-12}$ heteroalkyl, each of which is optionally substituted with one or more of oxo, halogen, hydroxyl, alkoxy, azido, cyano, nitro, amino, and thiol; $R^{B7}$ is H or $C_{1-6}$ alkyl; $Y^1$ is $NR^{B8}$, O, or S; $Z^1$ is $NR^{B9}$, O, or S; and each of $R^{B8}$ and $R^{B}$ is, independently, H or $C_{1-6}$ alkyl;

[C] has the structure of formula (IIc):

(IIIc)

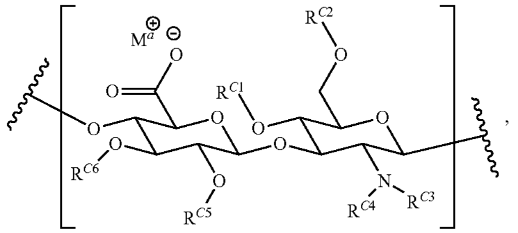

where each of $R^{C1}$, $R^{C2}$, $R^{C3}$, $R^{C4}$, $R^{C5}$, and $R^{C6}$ is, independently, H, $C_{1-12}$ alkyl optionally substituted with one or more of oxo, halogen, hydroxyl, alkoxy, azido, cyano, nitro, amino, and thiol, or $C_{1-12}$ heteroalkyl optionally substituted with one or more of oxo, halogen, hydroxyl, alkoxy, azido, cyano, nitro, amino, and thiol; and $M^a$ is a cation (e.g., an alkali metal cation, such as sodium, or alkaline earth cation);

and each of m and n is, independently, a fraction greater than zero and less than 1, where (m+n)<1.

In particular embodiments, $R^1$ is $C_{1-6}$ alkyl, $C_{2-6}$ alkene, $C_{2-6}$ alkyne, or $C_{1-6}$ heteroalkyl. For example, $R^1$ can be $C_{1-6}$ alkyl (e.g., $-CH_3$ or $-CH_2CH_3$).

In some embodiments, $R^{A1}$ is H. In other embodiments, $R^{A2}$ is H. In still other embodiments, $R^{A3}$ is H. In some embodiments, $R^{A4}$ is

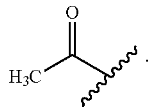 [SMILES: *C(C)=O]

In some embodiments, $R^{A5}$ is H. In some embodiments, $R^{A6}$ is H.

In some embodiments, K has the structure of formula (Ia):

(Ia)

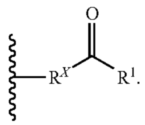

In some embodiments, K has the structure of formula (Ib):

(Ib)

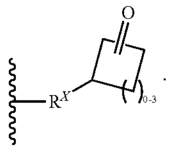

In particular embodiments, K has the structure of

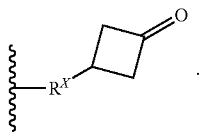

In particular embodiments, $R^{B1}$ is H. In some embodiments, $R^{B2}$ is H or $C_{1-6}$ acyl. In particular embodiments, $R^{B2}$ is H. In still other embodiments, $R^{B3}$ is H. In some embodiments, $R^{B4}$ is

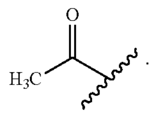 [SMILES: *C(C)=O]

In some embodiments, $R^{B5}$ is H. In some embodiments, $R^{B6}$ is H. In some embodiments, $R^{B7}$ is H. In still other embodiments, $Y^1$ is O. In some embodiments, $Y^1$ is $NR^{B8}$. In certain embodiments, $Z^1$ is O. In some embodiments, $R^{B8}$ is H.

In particular embodiments, $R^{C1}$ is H. In some embodiments, $R^{C2}$ is H. In still other embodiments, $R^{C3}$ is H. In some embodiments, $R^{C4}$ is

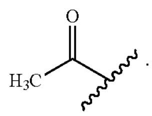 [SMILES: *C(C)=O]

In some embodiments, $R^{C5}$ is H. In some embodiments, $R^{C6}$ is H.

In particular embodiments, m and n are between 0.35 and 0.65. In other embodiments, m and n are between 0.45 and 0.55.

In some embodiments, $R^X$ is $C_{1-20}$alkylene or $C_{2-20}$ heteroalkenylene, any of which is optionally substituted with one or more of oxo, halogen, hydroxyl, alkoxy, azido, cyano, nitro, amino, and thiol. In particular embodiments, $R^X$ is $C_{2-20}$ heteroalkenylene, which is optionally substituted with one or more of oxo, halogen, hydroxyl, alkoxy, azido, cyano, nitro, amino, and thiol.

In some embodiments, [A] has the structure of formula (A1):

(A1)

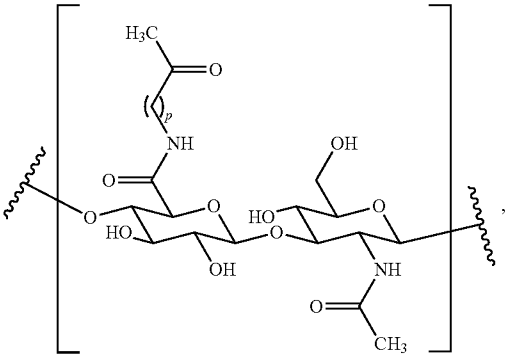

where p is 1, 2, 3, 4, 5, or 6. In particular embodiments, p is 3.

In some embodiments, [A] has the structure of formula (A2):

(A2)

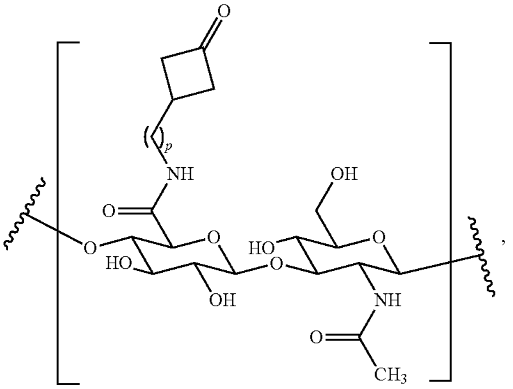

where p is 1, 2, 3, 4, 5, or 6. In particular embodiments, p is 1.

In some embodiments, [B] has the structure of formula (B1):

(B1)

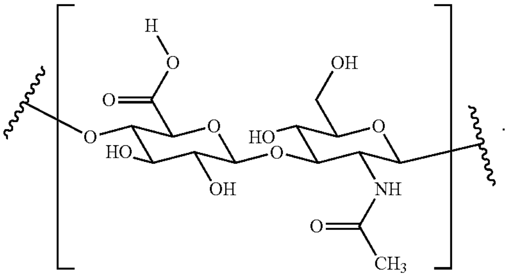

In some embodiments, [B] has the structure of formula (B2):

(B2)

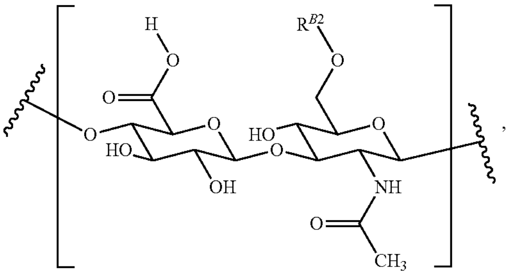

where $R^{B2}$ is $C_{1-12}$ acyl, $C_{1-12}$ alkyl, or $C_{1-12}$ heteroalkyl, each of which is optionally substituted with one or more of oxo, halogen, hydroxyl, alkoxy, azido, cyano, nitro, amino, and thiol.

In some embodiments, [C] has the structure of formula (C1):

(C1)

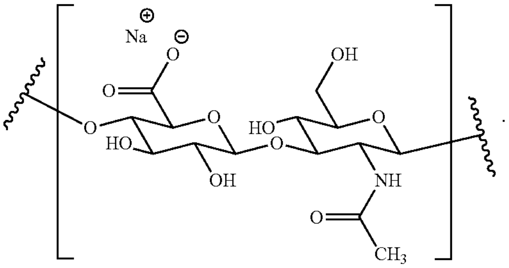

In some embodiments, [C] has the structure of formula (C2):

(C2)

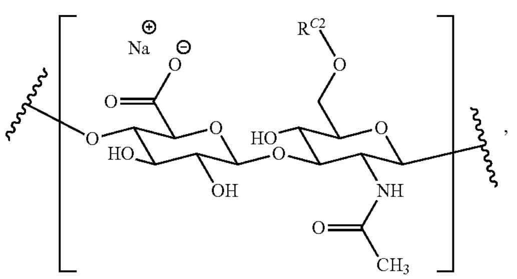

where $R^{C2}$ is $C_{1-12}$ alkyl optionally substituted with one or more of oxo, halogen, hydroxyl, alkoxy, azido, cyano, nitro, amino, and thiol.

In a related aspect, the invention features a cross-linked polymer of (i) a hyaluronan polymer (e.g., a compound of formula (I) (e.g., a compound of formula (III)) or a hyaluronan polymer including the structure of formula (II)); and (ii) a multimeric polymeric cross-linker conjugated through at least one linkage group of formula (IV-i) or formula (IV-ii):

(IV-i)

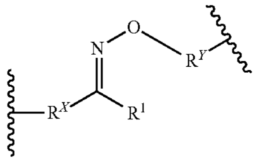

(IV-ii)

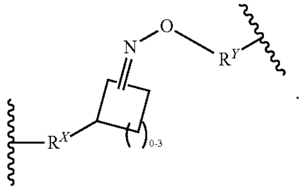

where $R^1$ is $C_{1-6}$ alkyl, $C_{2-6}$ alkenyl, $C_{2-6}$ alkynyl, $C_{1-6}$ heteroalkyl, $C_{2-6}$ heteroalkenyl, $C_{2-6}$ heteroalkynyl, $C_{3-10}$ carbocyclyl, $C_{6-10}$ aryl, $C_{2-9}$ heterocyclyl, or $C_{2-9}$ heteroaryl, any of which is optionally substituted with one or more of oxo, halogen, hydroxyl, alkoxy, azido, cyano, nitro, amino, and thiol; $R^X$ is a moiety covalently linked to the hyaluronan polymer; $R^X$ is $C_{1-20}$ alkylene, $C_{2-20}$ alkenylene, $C_{2-20}$ alkynylene, $C_{1-20}$ heteroalkylene, $C_{2-20}$ heteroalkenylene, or $C_{2-20}$ heteroalkynylene, any of which is optionally substituted with one or more of oxo, halogen, hydroxyl, alkoxy, azido, cyano, nitro, amino, and thiol; and RY is a fragment formed from the multimeric polymeric cross-linker, or a salt thereof.

In particular embodiments, the multimeric polymeric cross-linker is a dimer capable of covalently linking to two linkage groups of formula (IV-i), a trimer capable of covalently linking to three linkage groups of formula (IV-i), a tetramer capable of covalently linking to four linkage groups of formula (IV-i), a pentamer capable of covalently linking to five linkage groups of formula (IV-i), a hexamer capable of covalently linking to six linkage groups of formula (IV-i), a heptamer capable of covalently linking to seven linkage groups of formula (IV-i), or an octamer capable of covalently linking to eight linkage groups of formula (IV-i).

In particular embodiments, the multimeric polymeric cross-linker is a dimer capable of covalently linking to two linkage groups of formula (IV-ii), a trimer capable of covalently linking to three linkage groups of formula (IV-ii), a tetramer capable of covalently linking to four linkage groups of formula (IV-ii), a pentamer capable of covalently linking to five linkage groups of formula (IV-ii), a hexamer capable of covalently linking to six linkage groups of formula (IV-ii), a heptamer capable of covalently linking to seven linkage groups of formula (IV-ii), or an octamer capable of covalently linking to eight linkage groups of formula (IV-ii).

In some embodiments, the multimeric polymeric cross-linker has an average molecular weight of less than 100 MDa, 75 MDa, 50 MDa, 30 MDa, 20 MDa, 15 MDa, 10 MDa, 6 MDa, 5 MDa, 1 MDa, 500 kDa, 250 kDa, 100 kDa, 50 kDa, 30 kDa, 20 kDa, 15 kDa, 10 kDa, 6 kDa, 5 kDa, or 1 kDa. In some embodiments, the multimeric polymeric cross-linker has an average molecular weight of less than 100 MDa, 75 MDa, 50 MDa, 30 MDa, 20 MDa, 15 MDa, 10 MDa, 6 MDa, 5 MDa, or 1 MDa. In some embodiments, the multimeric polymeric cross-linker has an average molecular weight of less than 500 kDa, 250 kDa, 100 kDa, 50 kDa, 30 kDa, 20 kDa, 15 kDa, 10 kDa, 6 kDa, 5 kDa, or 1 kDa.

In some embodiments, the multimeric polymeric cross-linker has an average molecular weight of 100 Da to 1 kDa, 1 kDa to 30 kDa, 30 kDa to 50 kDa, 50 kDa to 100 kDa, 100 kDa to 250 kDa, 250 kDa to 500 kDa, 500 kDa to 1 MDa, 1 MDa to 5 MDa, 5 MDa, to 15 MDa, 15 MDa to 30 MDa, 30 MDa to 50 MDa, or 50 MDa to 100 MDa. In some embodiments, the multimeric polymeric cross-linker has an average molecular weight of 100 Da to 1 kDa, 1 kDa to 30 kDa, 30 kDa to 50 kDa, 50 kDa to 100 kDa, 100 kDa to 250 kDa, or 250 kDa to 500 kDa. In some embodiments, the multimeric polymeric cross-linker has an average molecular weight of 500 kDa to 1 MDa, 1 MDa to 5 MDa, 5 MDa, to 15 MDa, 15 MDa to 30 MDa, 30 MDa to 50 MDa, or 50 MDa to 100 MDa.

In some embodiments, RY includes $C_{1-200}$ alkylene, $C_{2-200}$ alkenylene, $C_{2-200}$ alkynylene, $C_{1-200}$ heteroalkylene, $C_{2-200}$ heteroalkenylene, or $C_{2-200}$ heteroalkynylene, any of which is optionally substituted with one or more of oxo, halogen, hydroxyl, alkoxy, azido, cyano, nitro, amino, and thiol. In some embodiments, RY includes $C_{1-200}$ heteroalkylene optionally substituted with one or more of oxo, halogen, hydroxyl, alkoxy, azido, cyano, nitro, amino, and thiol. In some embodiments, RY includes $C_{1-100}$ heteroalkylene optionally substituted with one or more of oxo, halogen, hydroxyl, alkoxy, azido, cyano, nitro, amino, and thiol. In particular embodiments, RY is $C_{1-200}$ heteroalkylene optionally substituted with one or more of oxo, halogen, hydroxyl, alkoxy, azido, cyano, nitro, amino, and thiol.

In particular embodiments, the multimeric polymeric cross-linker used to form the cross-linked polymer of formula IV-i) or formula (IV-ii) has the structure of formula (IVa):

(IVa)

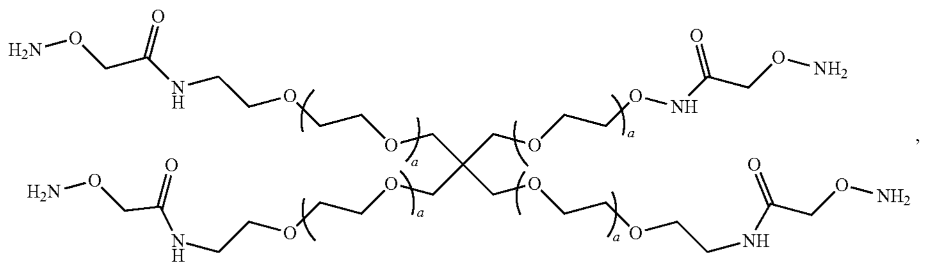

wherein a is an integer between 1 and 90 (e.g., between 6 and 40, between 10 and 40, between 15 and 40, between 6 and 60, or between 20 and 60), or a salt thereof. In some embodiments, a is about 29. In other embodiments, a is about 54.

In particular embodiments, the multimeric polymeric cross-linker used to form the cross-linked polymer of formula (IV-i) or formula (IV-ii) has the structure of formula (IVb):

(IVb)

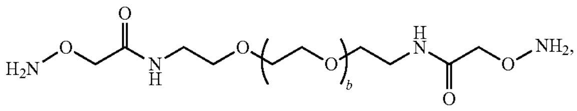

wherein b is an integer between 1 and 90 (e.g., between 6 and 40, between 10 and 40, between 15 and 40, between 6 and 60, between), or a salt thereof. In some embodiments, b is about 75.

In some embodiments, RY includes polyurethane, polyurea, polyamide, polyalkylene oxide, polycarbonate, polyester, polylactone, polysilicone, polyethersulfone, polyolefin, polypeptide, polysaccharide, polysiloxane, polydimethylsiloxane, polyethylene-butylene, polyisobutylene, polybutadiene, or polyethylenebutylene segments. For example, the multimeric polymeric cross-linker can include a polyalkylene oxide segment selected from polypropylene oxide, polyethylene oxide, and polytetramethylene oxide.

In some embodiments, RY further includes a polypeptide. In some embodiments, the polypeptide includes a cell adhesive peptide (e.g., RGD peptide (e.g. a peptide including the sequence of SEQ ID NO: 1 GRGDSPASSKKG)). In some embodiments, the polypeptide includes a degradable peptide (e.g., MMP peptide (e.g., a peptide including the sequence of SEQ ID NO: 2 SKAGAGPQGIWGQGAGAKSKS).

The invention features a hydrogel including any of the foregoing cross-linked polymers (e.g. a cross-linked polymer of (i) a hyaluronan polymer (e.g., a compound of formula (I) (e.g., a compound of formula (III)) or a hyaluronan polymer including the structure of formula (II)); and (ii) a multimeric polymeric cross-linker conjugated through at least one linkage group of formula (IV-i) or formula (IV-ii)). In particular embodiments, the hydrogel is a vitreous substitute.

The invention further features a method of treating a disorder (e.g., an ocular disorder such as retinal detachment), the method including injecting the vitreous substitute intravitreally, e.g., into the eye, of a subject (e.g., a human subject) in need thereof.

The invention also features a method of treating a disorder (e.g., an ocular disorder such as retinal detachment), the method including injecting the vitreous substitute intraarticularly to a subject (e.g., a human subject) in need thereof.

The invention further features a method of treating a disorder (e.g., an ocular disorder such as retinal detachment), the method including injecting the vitreous substitute into the synovial cavity of a subject (e.g., a human subject) in need thereof.

The invention features a hydrogel cell culture including any of the foregoing cross-linked polymers (e.g., a cross-linked polymer of formula (IV-i) or formula (IV-ii)) and at least one cell. In particular embodiments, the hydrogel cell culture further includes at least one agent that promotes growth of a physiologically relevant tissue and/or an extracellular matrix protein (e.g., collagen, fibronectin, vitronectin, and laminin). The hydrogel cell culture can be a screening model for cancer (e.g., breast cancer, colon cancer, pancreatic cancer, lymphoma cancer, lung cancer, brain cancer, ovarian cancer, or prostate cancer).

In another aspect, the invention features a method of making any of the foregoing cross-linked polymers (e.g. a cross-linked polymer of (i) a hyaluronan polymer (e.g., a compound of formula (I) (e.g., a compound of formula (III)) or a hyaluronan polymer including the structure of formula (II)); and (ii) a multimeric polymeric cross-linker conjugated through at least one linkage group of formula (IV-i) or formula (IV-ii)), said method comprising: (i) providing a first composition comprising any of the foregoing compounds (e.g., a compound of formula (I) (e.g., a compound of formula (III))); (ii) providing a second composition comprising a multimeric polymeric cross-linker bearing one or more terminal oxyamine groups; and (iii) combining the first composition and the second composition to form a mixture.

In another aspect, the invention features a method of making a hydrogel including any of the foregoing cross-linked polymers (e.g., a cross-linked polymer of (i) a hyaluronan polymer (e.g., a compound of formula (I) (e.g., a compound of formula (III)) or a hyaluronan polymer including the structure of formula (II)); and (ii) a multimeric polymeric cross-linker conjugated through at least one linkage group of formula (IV-i) or formula (IV-ii)), said method comprising: (i) providing a first composition comprising any of the foregoing compounds (e.g. a compound of formula (I) (e.g., a compound of formula (III))); (ii) providing a second composition comprising a multimeric polymeric cross-linker bearing one or more terminal oxyamine groups; and (iii) combining the first composition and the second composition to form a mixture.

The invention also features a method of forming a vitreous substitute including any of the foregoing cross-linked polymers (e.g. a cross-linked polymer of (i) a hyaluronan polymer (e.g., a compound of formula (I) (e.g., a compound of formula (III)) or a hyaluronan polymer including the structure of formula (II)); and (ii) a multimeric polymeric cross-linker conjugated through at least one linkage group of formula (IV-i) or formula (IV-ii)), the method including: (i) providing a first composition comprising any of the foregoing compounds (e.g. a compound of formula (I) (e.g., a compound of formula (III))); (ii) providing a second composition comprising a multimeric polymeric cross-linker bearing one or more terminal oxyamine groups; and (iii) combining the first composition and the second composition to form a mixture, where the mixture is injected into the eye of a subject (e.g., a subject suffering from or at risk of retinal detachment, such as a human subject). In some embodiments, step (iii) results in the mixture replacing the vitreous humor of the eye of the subject The invention features a method of forming a three-dimensional hydrogel including any of the foregoing cross-linked polymers (e.g. a cross-linked polymer of (i) a hyaluronan polymer (e.g., a compound of formula (I) (e.g., a compound of formula (III)) or a hyaluronan polymer including the structure of formula (II)); and (ii) a multimeric polymeric cross-linker conjugated through at least one linkage group of formula (IV-i) or formula (IV-ii)), the method including: (i) providing a first composition comprising any of the foregoing compounds (e.g. a compound of formula (I) (e.g., a compound of formula (III))); (ii) providing a second composition comprising a multimeric polymeric cross-linker bearing one or more terminal oxyamine groups; and (iii) combining the first composition and the second composition to form a mixture in the presence of at least one cell, where the three-dimensional hydrogel supports growth of a physiologically relevant tissue when at least one cell is cultured in the three-dimensional hydrogel. The mixing can be performed in the presence of at least one agent that promotes growth of a physiologically relevant tissue. In particular embodiments, the mixing is performed in the presence of an extracellular matrix protein. The extracellular matrix protein is, e.g., collagen, fibronectin, vitronectin, or laminin. In particular embodiments, the cell is a cancer cell (e.g., breast cancer cell, colon cancer cell, pancreatic cancer cell, or lymphoma cancer cell).

In some embodiments, the concentration of the mixture is at least 0.1 wt % (e.g., at least 0.5 wt %, at least 1 wt %, at least 10 wt %, or at least 20 wt %) cross-linked polymer. In some embodiments, step (iii) is performed at a temperature of about 37° C. In some embodiments, the pH level of the mixture is less than 9.0. In particular embodiments, the pH level of the mixture is about 6.0 to about 8.5. In still other embodiments, the pH level of the mixture is about 7.0 to about 8.0. In some embodiments, the pH level of the mixture is about 7.4. In some embodiments, step (iii) comprises forming a mixture comprising a molar ratio of about 5:1 to about 1:1 (e.g., about 4:1, about 3:1, or about 2:1) of the first composition and the second composition.

In particular embodiments, the multimeric polymeric cross-linker bears two, three, four, five, six, seven, eight, or more terminal oxyamine groups. In some embodiments, the degree of crosslink of any of the foregoing compounds (e.g., a compound of formula (I) (e.g., a compound of formula (III))) with the multimeric polymeric cross-linker bearing two or more terminal oxyamine groups is between 0.01-1%, 0.01-5%, 0.1-1%, 0.01-5%, 0.1-10%, 0.01-80%, 1-5%, 10-50%, 20-40%, 20-99%, 50-99%, 70-90%, 80-95%, 90-99%, 95-99%, 98-99.5%, or 99-99.9%.

In some embodiments, the method further comprises: (iv) providing a third composition comprising an aldehyde-modified hyaluronan; and (v) combining the mixture and the third composition.

In particular embodiments, step (iii) and/or step (v), when present, has a gelation time between 1 second and 48 hours, 1 second and 24 hours, 1 second and 30 seconds, 10 seconds and 1 minute, 30 seconds and 5 minutes, 1 minute and 30 minutes, 1 minute and 1 hour, 30 minutes and 1 hour, 1 hour and 24 hours, 1 hour and 2 hours, 2 hours and 3 hours, 3 hours and 5 hours, 5 hours and 10 hours, 10 hours and 15 hours, 10 hours and 24 hours, 15 hours and 24 hours, or 24 hours and 48 hours in HBS at about 37° C. In other embodiments, the cross-linked polymer loses at most 10% (e.g., at most 9%, at most 8%, at most 7%, at most 6%, at most 5%, at most 4%, at most 3%, at most 2%, at most 1%, or at most 0.1%) of mass over about 28 days in Hanks' Balanced Salt solution (HBS) at about 37° C. In other embodiments, the cross-linked polymer loses at most 25% (e.g., at most 20%, at most 15%, at most 10%, at most 5%, or at most 1%) of mass over about 28 days in HBS at about 37° C.

In a related aspect, the invention features a compound of formula (V):

HAP-OA (V), where HAP is a hyaluronan polymer; and OA is a moiety covalently linked to the hyaluronan polymer having the structure of formula (Va):

(Va)

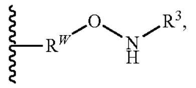

where $R^W$ is $C_{1-20}$ alkylene, $C_{2-20}$ alkenylene, $C_{2-20}$ alkynylene, $C_{1-20}$ heteroalkylene, $C_{2-20}$ heteroalkenylene, or $C_{2-20}$ heteroalkynylene, any of which is optionally substituted with one or more of oxo, halogen, hydroxyl, alkoxy, azido, cyano, nitro, amino, and thiol; and $R^3$ is H, $C_{1-6}$ alkyl, or $C_{1-6}$ heteroalkyl, any of which is optionally substituted with one or more of oxo, halogen, hydroxyl, alkoxy, azido, cyano, nitro, amino, and thiol, or a salt thereof.

In some embodiments, OA is covalently linked to the hyaluronan polymer through a substituent on C1 of D-glucuronic acid or derivative thereof. In some embodiments, OA is covalently linked to the hyaluronan polymer through a substituent on C2 of D-glucuronic acid or derivative thereof. In some embodiments, OA is covalently linked to the hyaluronan polymer through a substituent on C3 of D-glucuronic acid or derivative thereof. In some embodiments, OA is covalently linked to the hyaluronan polymer through a substituent on C4 of D-glucuronic acid or derivative thereof. In some embodiments, OA is covalently linked to the hyaluronan polymer through a substituent on C6 of D-glucuronic acid or derivative thereof. In some embodiments, OA is covalently linked to the hyaluronan polymer through a substituent on C7 of D-N-acetylglucosamine or derivative thereof. In some embodiments, OA is covalently linked to the hyaluronan polymer through a substituent on C8 of D-N-acetylglucosamine or derivative thereof. In some embodiments, OA is covalently linked to the hyaluronan polymer through a substituent on C9 of D-N-acetylglucosamine or derivative thereof. In some embodiments, OA is covalently linked to the hyaluronan polymer through a substituent on C10 of D-N-acetylglucosamine or derivative thereof. In some embodiments, OA is covalently linked to the hyaluronan polymer through a substituent on C12 of D-N-acetylglucosamine or derivative thereof.

In some embodiments, the hyaluronan polymer comprises the structure of formula (VI):

(VI)

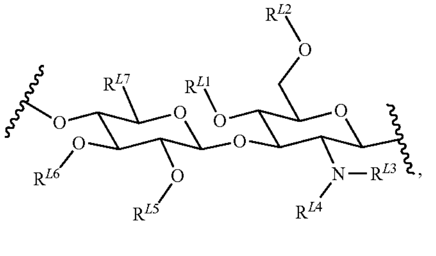

where each of $R^{L1}$, $R^{L2}$, $R^{L3}$, $R^{L4}$, $R^{L5}$, and $R^{L6}$ is, independently, H, $C_{1-12}$ alkyl optionally substituted with one or more of oxo, halogen, hydroxyl, alkoxy, azido, cyano, nitro, amino, and thiol, $C_{1-12}$ heteroalkyl optionally substituted with one or more of oxo, halogen, hydroxyl, alkoxy, azido, cyano, nitro, amino, and thiol, or a bond to OA; $R^{L7}$ is

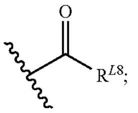

$R^{LB}$ is

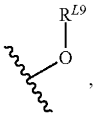

,

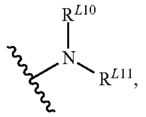

or a bond to OA; and each of $R^{L9}$, $R^{L10}$, and $R^{L11}$ is, independently, H, $C_{1-12}$ alkyl optionally substituted with one or more of oxo, halogen, hydroxyl, alkoxy, azido, cyano, nitro, amino, and thiol, or $C_{1-12}$ heteroalkyl optionally substituted with one or more of oxo, halogen, hydroxyl, alkoxy, azido, cyano, nitro, amino, and thiol, where at least one of $R^{L1}$, $R^{L2}$, $R^{L3}$, $R^{L4}$, $R^{L5}$, $R^{L6}$, and $R^{L8}$ is a bond to OA.

In some embodiments, $R^{L1}$ is H. In other embodiments, $R^{L2}$ is H. In still other embodiments, $R^{L3}$ is H. In some embodiments, $R^{L4}$ is

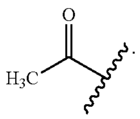

In some embodiments, $R^{L5}$ is H. In some embodiments, $R^{L6}$ is H. In particular embodiments, $R^{L8}$ is a bond to K. In some embodiments, $R^{L8}$ is

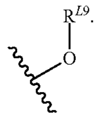

In some embodiments, $R^{L8}$ is

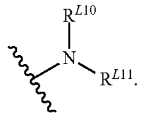

In some embodiments, $R^{L9}$ is H. In some embodiments, $R^{L10}$ is H. In some embodiments, $R^{L11}$ is H.

In some embodiments, the compound is further described by formula (VII):

$$[D]_q[E]_r[F]_{1-(q+r)} \quad \text{(VII)},$$

where

[D] has the structure of formula (VIIa):

(VIIa)

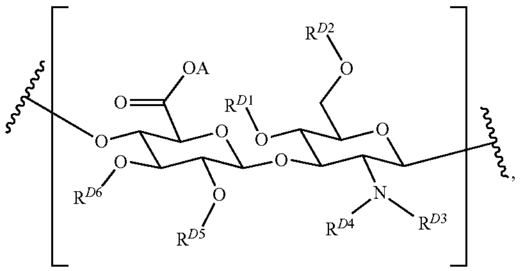

where each of $R^{D1}$, $R^{D2}$, $R^{D3}$, $R^{D4}$, $R^{D5}$, and $R^{D6}$ is, independently, H, $C_{1-12}$ alkyl optionally substituted with one or more of oxo, halogen, hydroxyl, alkoxy, azido, cyano, nitro, amino, and thiol, or $C_{1-12}$ heteroalkyl optionally substituted with one or more of oxo, halogen, hydroxyl, alkoxy, azido, cyano, nitro, amino, and thiol; and OA is a moiety covalently linked to the hyaluronan polymer having the structure of formula (Va):

(Va)

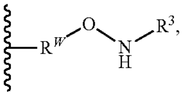

where $R^W$ is polypeptide, $C_{1-20}$ alkylene, $C_{2-20}$ alkenylene, $C_{2-20}$ alkynylene, $C_{1-20}$ heteroalkylene, $C_{2-20}$ heteroalkenylene, or $C_{2-20}$ heteroalkynylene, any of which is optionally substituted with one or more of oxo, halogen, hydroxyl, alkoxy, azido, cyano, nitro, amino, and thiol; and $R^3$ is H, $C_{1-6}$ alkyl, or $C_{1-6}$ heteroalkyl, any of which is optionally substituted with one or more of oxo, halogen, hydroxyl, alkoxy, azido, cyano, nitro, amino, and thiol, or a salt thereof;

[E] has the structure of formula (VIIb):

(VIIb)

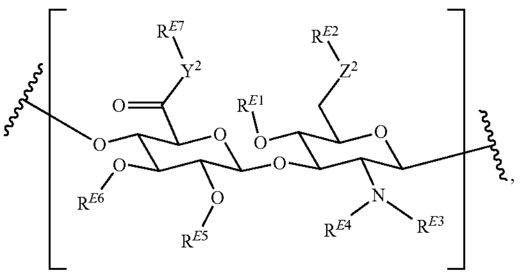

where each of $R^{E1}$, $R^{E3}$, $R^{E4}$, $R^{E5}$, and $R^{E6}$ is, independently, H, $C_{1-12}$ alkyl optionally substituted with one or more of oxo, halogen, hydroxyl, alkoxy, azido, cyano, nitro, amino, and thiol, or $C_{1-12}$ heteroalkyl optionally substituted with one or more of oxo, halogen, hydroxyl, alkoxy, azido, cyano, nitro, amino, and thiol; $R^{E2}$ is H, $C_{1-12}$ acyl, $C_{1-12}$ alkyl, or $C_{1-12}$ heteroalkyl, each of which is optionally substituted with one or more of oxo, halogen, hydroxyl, alkoxy, azido, cyano, nitro, amino, and thiol; $R^{E7}$ is H or $C_{1-6}$ alkyl; $Y^2$ is $NR^{E8}$, O, or S; $Z^3$ is $NR^{E9}$, O, or S; and each of $R^{E8}$ and $R^{E9}$ is, independently, H or $C_{1-6}$ alkyl;

[F] has the structure of formula (VIIc):

(VIIc)

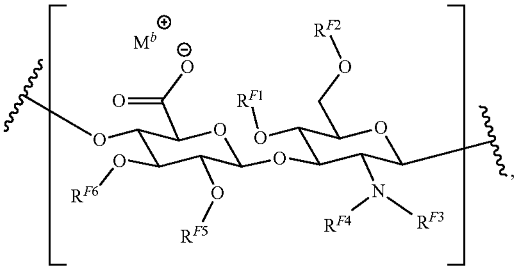

where each of $R^{F1}$, $R^{F2}$, $R^{F3}$, $R^{F4}$, $R^{F5}$, and $R^{F6}$ is, independently, H or $C_{1-12}$ alkyl optionally substituted with one or more of oxo, halogen, hydroxyl, alkoxy, azido, cyano, nitro, amino, and thiol; and $M^b$ is a cation (e.g., an alkali metal cation, such as sodium, or alkaline earth cation); and each of q and r is, independently, a fraction greater than zero and less than 1, wherein (q+r)<1.

In some embodiments, $R^{D1}$ is H. In other embodiments, $R^{D2}$ is H. In still other embodiments, $R^{D3}$ is H. In some embodiments, $R^{D4}$ is

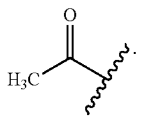

In some embodiments, $R^{D5}$ is H. In some embodiments, $R^{D6}$ is H.

In particular embodiments, $R^3$ is H. In some embodiments, $R^3$ is $C_{1-6}$ alkyl (e.g., $—CH_3$ or $—CH_2CH_3$).

In particular embodiments, $R^{E1}$ is H. In some embodiments, $R^{E2}$ is H or $C_{1-6}$ acyl. In particular embodiments, $R^{E2}$ is H. In still other embodiments, $R^{E3}$ is H. In some embodiments, $R^{E4}$ is

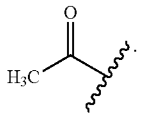 [SMILES: *C(C)=O]

In some embodiments, $R^{E5}$ is H. In some embodiments, $R^{E6}$ is H. In some embodiments, $R^{E7}$ is H. In still other embodiments, $Y^2$ is O. In some embodiments, $Y^1$ is $NR^{E8}$. In certain embodiments, $Z^2$ is O. In some embodiments, $R^{E8}$ is H.

In particular embodiments, $R^{F1}$ is H. In some embodiments, $R^{F2}$ is H. In still other embodiments, $R^{F3}$ is H. In some embodiments, $R^{F4}$ is

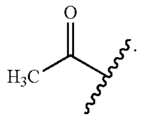 [SMILES: *C(C)=O]

In some embodiments, $R^{F5}$ is H. In some embodiments, $R^{F6}$ is H.

In particular embodiments, q and r are between 0.35 and 0.65. In other embodiments, q and r are between 0.45 and 0.55.

In some embodiments, [D] has the structure of formula (D1):

(D1)

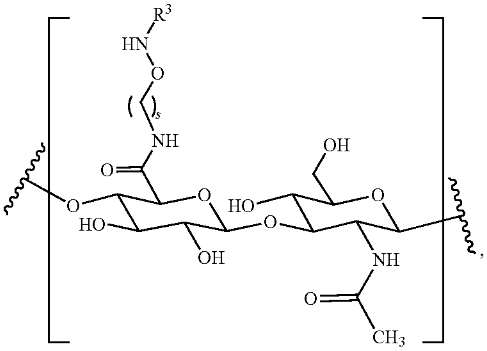

where s is 1, 2, 3, 4, 5, or 6. In some embodiments, s is 2. In some embodiments, $R^3$ is

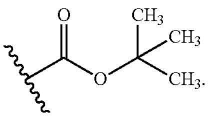 [SMILES: *C(=O)OC(C)(C)C]

In some embodiments, [E] has the structure of formula (E1):

(E1)

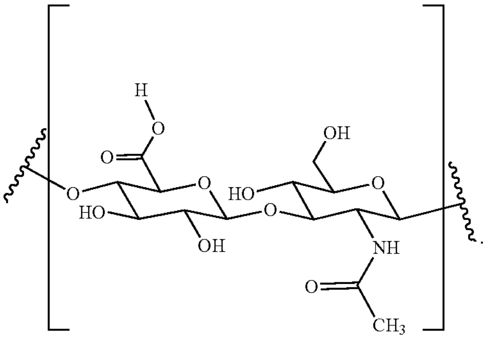

In some embodiments, [E] has the structure of formula (E2):

(E2)

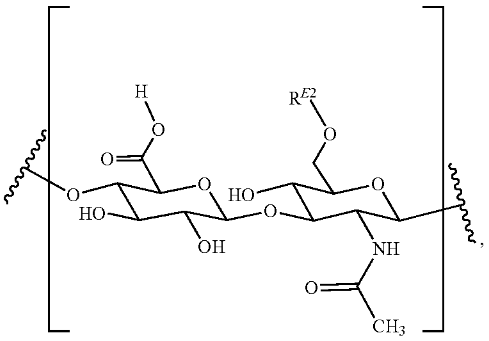

where $R^{E2}$ is $C_{1-12}$ acyl, $C_{1-12}$ alkyl, or $C_{1-12}$ heteroalkyl, each of which is optionally substituted with one or more of oxo, halogen, hydroxyl, alkoxy, azido, cyano, nitro, amino, and thiol.

In some embodiments, [F] has the structure of formula (F1):

(F1)

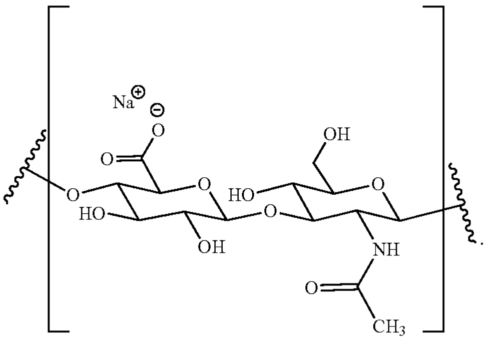

In some embodiments, [F] has the structure of formula (F2):

(F2)

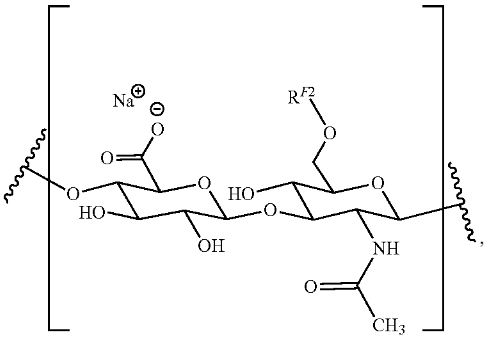

where $R^{F2}$ is $C_{1-12}$ alkyl optionally substituted with one or more of oxo, halogen, hydroxyl, alkoxy, azido, cyano, nitro, amino, and thiol.

In a related aspect, the invention features a cross-linked polymer of (i) a hyaluronan polymer and (ii) a multimeric polymeric cross-linker conjugated through at least one linkage group of formula (VIII-i) or formula (VIII-ii):

(VIII-i)

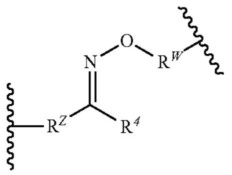

(VIII-ii)

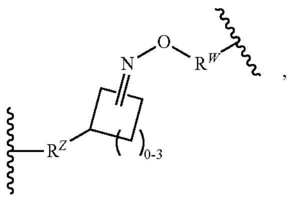

where $R^4$ is $C_{1-6}$ alkyl, $C_{2-6}$ alkenyl, $C_{2-6}$ alkynyl, $C_{1-6}$ heteroalkyl, $C_{2-6}$ heteroalkenyl, $C_{2-6}$ heteroalkynyl, $C_{3-10}$ carbocyclyl, $C_{6-10}$ aryl, $C_{2-9}$ heterocyclyl, or $C_{2-9}$ heteroaryl, any of which is optionally substituted with one or more of oxo, halogen, hydroxyl, alkoxy, azido, cyano, nitro, amino, and thiol; $R^W$ is a moiety covalently linked to the hyaluronan polymer; $R^W$ is polypeptide, $C_{1-20}$ alkylene, $C_{2-20}$ alkenylene, $C_{2-20}$ alkynylene, $C_{1-20}$ heteroalkylene, $C_{2-20}$ heteroalkenylene, or $C_{2-20}$ heteroalkynylene, any of which is optionally substituted with one or more of oxo, halogen, hydroxyl, alkoxy, azido, cyano, nitro, amino, and thiol; and $R^Z$ is a fragment formed from the multimeric polymeric cross-linker, or a salt thereof.

In particular embodiments, $R^4$ is $C_{1-6}$ alkyl, $C_{2-6}$ alkene, $C_{2-6}$ alkyne, or $C_{1-6}$ heteroalkyl. For example, $R^4$ can be $C_{1-6}$ alkyl (e.g., $—CH_3$ or $—CH_2CH_3$).

In particular embodiments, the multimeric polymeric cross-linker is a dimer capable of covalently linking to two linkage groups of formula (VIII-i), a trimer capable of covalently linking to three linkage groups of formula (VIII-i), a tetramer capable of covalently linking to four linkage groups of formula (VIII-i), a pentamer capable of covalently linking to five linkage groups of formula (VIII-i), a hexamer capable of covalently linking to six linkage groups of formula (VIII-i), a heptamer capable of covalently linking to seven linkage groups of formula (VIII-i), or an octamer capable of covalently linking to eight linkage groups of formula (VIII-i).

In particular embodiments, the multimeric polymeric cross-linker is a dimer capable of covalently linking to two linkage groups of formula (VIII-ii), a trimer capable of covalently linking to three linkage groups of formula (VIII-ii), a tetramer capable of covalently linking to four linkage groups of formula (VIII-ii), a pentamer capable of covalently linking to five linkage groups of formula (VIII-ii), a hexamer capable of covalently linking to six linkage groups of formula (VIII-ii), a heptamer capable of covalently linking to seven linkage groups of formula (VIII-ii), or an octamer capable of covalently linking to eight linkage groups of formula (VIII-ii).

In some embodiments, the multimeric polymeric cross-linker has an average molecular weight of less than 100 MDa, 75 MDa, 50 MDa, 30 MDa, 20 MDa, 15 MDa, 10 MDa, 6 MDa, 5 MDa, 1 MDa, 500 kDa, 250 kDa, 100 kDa, 50 kDa, 30 kDa, 20 kDa, 15 kDa, 10 kDa, 6 kDa, 5 kDa, or 1 kDa. In some embodiments, the multimeric polymeric cross-linker has an average molecular weight of less than 100 MDa, 75 MDa, 50 MDa, 30 MDa, 20 MDa, 15 MDa, 10 MDa, 6 MDa, 5 MDa, or 1 MDa. In some embodiments, the multimeric polymeric cross-linker has an average molecular weight of less than 500 kDa, 250 kDa, 100 kDa, 50 kDa, 30 kDa, 20 kDa, 15 kDa, 10 kDa, 6 kDa, 5 kDa, or 1 kDa.

In some embodiments, the multimeric polymeric cross-linker has an average molecular weight of 100 Da to 1 kDa, 1 kDa to 30 kDa, 30 kDa to 50 kDa, 50 kDa to 100 kDa, 100 kDa to 250 kDa, 250 kDa to 500 kDa, 500 kDa to 1 MDa, 1 MDa to 5 MDa, 5 MDa, to 15 MDa, 15 MDa to 30 MDa, 30 MDa to 50 MDa, or 50 MDa to 100 MDa. In some embodiments, the multimeric polymeric cross-linker has an average molecular weight of 100 Da to 1 kDa, 1 kDa to 30 kDa, 30 kDa to 50 kDa, 50 kDa to 100 kDa, 100 kDa to 250 kDa, or 250 kDa to 500 kDa. In some embodiments, the multimeric polymeric cross-linker has an average molecular weight of 500 kDa to 1 MDa, 1 MDa to 5 MDa, 5 MDa, to 15 MDa, 15 MDa to 30 MDa, 30 MDa to 50 MDa, or 50 MDa to 100 MDa.

In some embodiments, $R^Z$ includes $C_{1-200}$ alkylene, $C_{2-200}$ alkenylene, $C_{2-200}$ alkynylene, $C_{1-200}$ heteroalkylene, $C_{2-200}$ heteroalkenylene, or $C_{2-200}$ heteroalkynylene, any of which is optionally substituted with one or more of oxo, halogen, hydroxyl, alkoxy, azido, cyano, nitro, amino, and thiol. In some embodiments, $R^Z$ includes $C_{1-200}$ heteroalkylene optionally substituted with one or more of oxo, halogen, hydroxyl, alkoxy, azido, cyano, nitro, amino, and thiol. In some embodiments, $R^Z$ includes $C_{1-100}$ heteroalkylene optionally substituted with one or more of oxo, halogen, hydroxyl, alkoxy, azido, cyano, nitro, amino, and thiol. In particular embodiments, $R^Z$ is $C_{1-200}$ heteroalkylene optionally substituted with one or more of oxo, halogen, hydroxyl, alkoxy, azido, cyano, nitro, amino, and thiol.

In some embodiments, $R^Z$ includes polyurethane, polyurea, polyamide, polyalkylene oxide, polycarbonate, polyester, polylactone, polysilicone, polyethersulfone, polyolefin, polypeptide, polysaccharide, polysiloxane, polydimethylsiloxane, polyethylene-butylene, polyisobutylene, polybutadiene, or polyethylenebutylene segments. For example, the multimeric polymeric cross-linker can include a polyalkylene oxide segment selected from polypropylene oxide, polyethylene oxide, and polytetramethylene oxide.

In some embodiments, $R^Z$ further includes a polypeptide. In some embodiments, the polypeptide includes a cell adhesive peptide (e.g., RGD peptide (e.g. a peptide including the sequence of SEQ ID NO: 1 GRGDSPASSKKG)). In some embodiments, the polypeptide includes a degradable peptide (e.g., MMP peptide (e.g., a peptide including the sequence of SEQ ID NO: 2 SKAGAGPQGIWGQGAGAKSKS).

The invention features a hydrogel including any of the foregoing cross-linked polymers (e.g., a cross-linked polymer of (i) a hyaluronan polymer; and (ii) a multimeric polymeric cross-linker conjugated through at least one linkage group of formula (VIII-i) or formula (VIII-ii)). In particular embodiments, the hydrogel is a vitreous substitute.

The invention further features a method of treating a disorder (e.g., an ocular disorder such as retinal detachment), the method including injecting the vitreous substitute intravitreally, e.g., into the eye of a subject (e.g., a human subject) in need thereof.

The invention also features a method of treating a disorder (e.g., an ocular disorder such as retinal detachment), the method including injecting the vitreous substitute intraarticularly to a subject (e.g., a human subject) in need thereof.

The invention further features a method of treating a disorder (e.g., an ocular disorder such as retinal detachment), the method including injecting the vitreous substitute into the synovial cavity of a subject (e.g., a human subject) in need thereof.

The invention features a hydrogel cell culture including any of the foregoing cross-linked polymers (e.g., a cross-linked polymer of (i) a hyaluronan polymer; and (ii) a multimeric polymeric cross-linker conjugated through at least one linkage group of formula (VIII-i) or formula (VIII-ii)) and at least one cell. In particular embodiments, the hydrogel cell culture further includes at least one agent that promotes growth of a physiologically relevant tissue and/or an extracellular matrix protein (e.g., collagen, fibronectin, vitronectin, and laminin). The hydrogel cell culture can be a screening model for cancer (e.g., breast cancer, colon cancer, pancreatic cancer, lymphoma cancer, lung cancer, brain cancer, ovarian cancer, or prostate cancer).

In another aspect, the invention features a method of making any of the foregoing cross-linked polymers (e.g. a cross-linked polymer of (i) a hyaluronan polymer; and (ii) a multimeric polymeric cross-linker conjugated through at least one linkage group of formula (VIII-i) or formula (VIII-ii)), said method comprising: (i) providing a first composition comprising any of the foregoing compounds (e.g., a compound of formula (V) (e.g., a compound of formula (VII))); (ii) providing a second composition comprising a multimeric polymeric cross-linker bearing one or more terminal oxyamine groups; and (iii) combining the first composition and the second composition to form a mixture.

In another aspect, the invention features a method of making a hydrogel including any of the foregoing cross-linked polymers (e.g., a cross-linked polymer of (i) a hyaluronan polymer; and (ii) a multimeric polymeric cross-linker conjugated through at least one linkage group of formula (VIII-i) or formula (VIII-ii)), said method comprising: (i) providing a first composition comprising any of the foregoing compounds (e.g. a compound of formula (V) (e.g., a compound of formula (VII))); (ii) providing a second composition comprising a multimeric polymeric cross-linker bearing one or more terminal oxyamine groups; and (iii) combining the first composition and the second composition to form a mixture.

The invention also features a method of forming a vitreous substitute including any of the foregoing cross-linked polymers (e.g. a cross-linked polymer of (i) a hyaluronan polymer; and (ii) a multimeric polymeric cross-linker conjugated through at least one linkage group of formula (VIII-i) or formula (VIII-ii)), the method including: (i) providing a first composition comprising any of the foregoing compounds (e.g. a compound of formula (V) (e.g., a compound of formula (VII))); (ii) providing a second composition comprising a multimeric polymeric cross-linker bearing one or more terminal oxyamine groups; and (iii) combining the first composition and the second composition to form a mixture, where the mixture is injected into the eye of a subject (e.g., a subject suffering from or at risk of retinal detachment, such as a human subject).

The invention features a method of forming a three-dimensional hydrogel including any of the foregoing cross-linked polymers (e.g. a cross-linked polymer of (i) a hyaluronan polymer; and (ii) a multimeric polymeric cross-linker conjugated through at least one linkage group of formula (VIII-i) or formula (VIII-ii)), the method including: (i) providing a first composition comprising any of the foregoing compounds (e.g. a compound of formula (V) (e.g., a compound of formula (VII))); (ii) providing a second composition comprising a multimeric polymeric cross-linker bearing one or more terminal oxyamine groups; and (iii) combining the first composition and the second composition to form a mixture in the presence of at least one cell, where the three-dimensional hydrogel supports growth of a physiologically relevant tissue when at least one cell is cultured in the three-dimensional hydrogel. The mixing can be performed in the presence of at least one agent that promotes growth of a physiologically relevant tissue. In particular embodiments, the mixing is performed in the presence of an extracellular matrix protein. The extracellular matrix protein is, e.g., collagen, fibronectin, vitronectin, or laminin. In particular embodiments, the cell is a cancer cell (e.g., breast cancer cell, colon cancer cell, pancreatic cancer cell, or lymphoma cancer cell).

In some embodiments, the concentration of the mixture is at least 0.1 wt % (e.g., at least 0.5 wt %, at least 1 wt %, at least 10 wt %, or at least 20 wt %) cross-linked polymer. In some embodiments, step (iii) is performed at a temperature of about 37° C. In some embodiments, the pH level of the mixture is less than 9.0. In particular embodiments, the pH level of the mixture is about 6.0 to about 8.5. In still other embodiments, the pH level of the mixture is about 7.0 to about 8.0. In some embodiments, the pH level of the mixture is about 7.4. In some embodiments, step (iii) comprises forming a mixture comprising a molar ratio of about 5:1 to about 1:1 (e.g., about 4:1, about 3:1, or about 2:1) of the first composition and the second composition In particular embodiments, the multimeric polymeric cross-linker bears two, three, four, five, six, seven, eight, or more terminal oxyamine groups. In some embodiments, the degree of crosslink of any of the foregoing compounds (e.g., a compound of formula (V) (e.g., a compound of formula (VII))) with the multimeric polymeric cross-linker bearing two or more terminal oxyamine groups is between 0.01-1%, 0.01-5%, 0.1-1%, 0.01-5%, 0.1-10%, 0.01-80%, 1-5%, 10-50%, 20-40%, 20-99%, 50-99%, 70-90%, 80-95%, 90-99%, 95-99%, 98-99.5%, or 99-99.9%.

In some embodiments, the method further comprises: (iv) providing a third composition comprising an aldehyde-modified hyaluronan; and (v) combining the mixture and the third composition.

In particular embodiments, step (iii) and/or step (v), when present, has a gelation time between 1 second and 48 hours, 1 second and 24 hours, 1 second and 30 seconds, 10 seconds and 1 minute, 30 seconds and 5 minutes, 1 minute and 30 minutes, 1 minute and 1 hour, 30 minutes and 1 hour, 1 hour and 24 hours, 1 hour and 2 hours, 2 hours and 3 hours, 3 hours and 5 hours, 5 hours and 10 hours, 10 hours and 15 hours, 10 hours and 24 hours, 15 hours and 24 hours, or 24 hours and 48 hours in HBS at about 37° C. In other embodiments, the cross-linked polymer loses at most 10% (e.g., at most 9%, at most 8%, at most 7%, at most 6%, at most 5%, at most 4%, at most 3%, at most 2%, at most 1%, or at most 0.1%) of mass over about 28 days in Hanks' Balanced Salt solution (HBS) at about 37° C. In other embodiments, the cross-linked polymer loses at most 25% (e.g., at most 20%, at most 15%, at most 10%, at most 5%, or at most 1%) of mass over about 28 days in HBS at about 37° C.

Chemical Terms

It is to be understood that the terminology employed herein is for the purpose of describing particular embodiments and is not intended to be limiting.

For any of the following chemical definitions, a number following an atomic symbol indicates that total number of atoms of that element that are present in a particular chemical moiety. As will be understood, other atoms, such as hydrogen atoms, or substituent groups, as described herein, may be present, as necessary, to satisfy the valences of the atoms. For example, an unsubstituted $C_2$ alkyl group has the formula —$CH_2CH_3$. When used with the groups defined herein, a reference to the number of carbon atoms includes the divalent carbon in acetal and ketal groups but does not include the carbonyl carbon in acyl, ester, carbonate, or carbamate groups. A reference to the number of atoms, e.g., carbon, oxygen, nitrogen, or sulfur, in a cyclic group (e.g., carbocyclyl, aryl, heterocyclyl, or heteroaryl) only includes those atoms that form a part of the ring structure.

The term "acyl," as used herein, represents a hydrogen or an alkyl group that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, or 1 to 6 carbon atoms). An alkylene is a divalent alkyl group.

The term "alkenyl," as used herein, alone or in combination with other groups, refers to a straight-chain or branched hydrocarbon residue having a carbon-carbon double bond and having 2 to 20 carbon atoms (e.g., 2 to 16 carbon atoms, 2 to 10 carbon atoms, 2 to 6, or 2 carbon atoms). An alkenylene is a divalent alkenyl group.

The term "alkynyl," as used herein, alone or in combination with other groups, refers to a straight-chain or branched hydrocarbon residue having a carbon-carbon triple bond and having 2 to 20 carbon atoms (e.g., 2 to 16 carbon atoms, 2 to 10 carbon atoms, 2 to 6, or 2 carbon atoms). An alkynylene is a divalent alkynyl group.

The term "amino," as used herein, represents —$N(R^{N1})_2$, wherein each $R^{N1}$ is, independently, H, alkyl, alkenyl, alkynyl, aryl, carbocyclyl, heteroalkyl, heteroalkenyl, heteroalkynyl, heteroaryl, heterocyclyl, —OH, —$NO_2$, —$N(R^{N2})_2$, —$SO_2OR^{N2}$, —$SO_2R^{N2}$, —$SOR^{N2}$, or acyl (e.g., acetyl, trifluoroacetyl, or others described herein); or two $R^{N1}$ combine to form a heterocyclylene, and wherein each $R^{N2}$ is, independently, H, alkyl, alkenyl, alkynyl, aryl, carbocyclyl, heteroalkyl, heteroalkenyl, heteroalkynyl, heteroaryl, heterocyclyl.

As used herein, the term "oxyamine" represents $R^{O1}O—NH_2$, wherein $R^{O1}$ is acyl, alkyl, alkenyl, alkynyl, aryl, carbocyclyl, heteroalkyl, heteroalkenyl, heteroalkynyl, heteroaryl, or heterocyclyl. In an embodiment, $R^{O1}$ is alkyl or heteroalkyl, each of which is optionally substituted with one or more substituents including oxo, halogen (e.g., fluoro), hydroxyl, alkyl, heteroalkyl (e.g., substituted and unsubstituted alkoxy (e.g., methoxy or ethoxy) or thioalkoxy), azido, cyano, nitro, amino, or thiol.

The term "aryl," as used herein, refers to an aromatic monocyclic or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "azido," as used herein, represents a $—N_3$ group.

The term "cyano," as used herein, represents a CN group.

The terms "carbocyclyl," as used herein, refer to a non-aromatic $C_3$-$C_{12}$ monocyclic, bicyclic, or tricyclic radical of 3 to 12 carbon atoms. Carbocyclyl structures include cycloalkyl groups and unsaturated carbocyclyl radicals.

The term "cycloalkyl," as used herein, refers to a saturated, non-aromatic, monovalent, and monocyclic or polycarbocyclic radical of 3 to 12 carbon atoms, preferably 3 to 6 carbon atoms. This term is further exemplified by radicals such as cyclopropyl, cyclobutyl, cyclopentyl, cyclohexyl, cycloheptyl, norbornyl, and adamantyl.

The term "halo," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. Examples of heteroalkyl groups are an "alkoxy" which, as used herein, refers to alkyl-O— (e.g., methoxy and ethoxy); a "carbamate" which, as used herein refers to

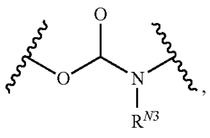

wherein $R^{N3}$ is, e.g., H or alkyl; and a "hydrazide" which, as used herein refers to

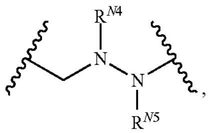

wherein each of $R^{N4}$ and $R^{N5}$ is, independently, e.g., H or alkyl. Examples of a heteroalkyl group substituted with one or more oxo groups include

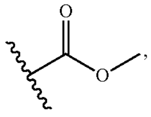

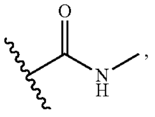

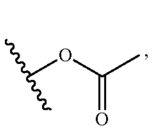

and

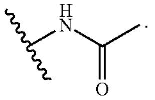

A heteroalkylene is a divalent heteroalkyl group.

The term "heteroalkenyl," as used herein, refers to an alkenyl group, as defined herein, in which one or more of the constituent carbon atoms have been replaced by nitrogen, oxygen, or sulfur. Examples of heteroalkenyl groups are an "alkenoxy" which, as used herein, refers alkenyl-O—. A heteroalkenylene is a divalent heteroalkenyl group.

The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers alkynyl-O—. A heteroalkynylene is a divalent heteroalkynyl group.

The term "heteroaryl," as used herein, refers to an aromatic monocyclic or polycyclic radical of 5 to 12 atoms having at least one aromatic ring containing one, two, three, or four ring heteroatoms selected from N, O, and S, with the remaining ring atoms being C. One or two ring carbon atoms of the heteroaryl group may be replaced with a carbonyl group. Examples of heteroaryl groups include pyridyl, pyrazoyl, benzooxazolyl, benzoimidazolyl, benzothiazolyl, imidazolyl, oxaxolyl, and thiazolyl.

The term "heterocyclyl," as used herein, denotes a monocyclic or polycyclic radical having 3 to 12 atoms having at least one ring containing one, two, three, or four ring heteroatoms selected from N, O or S, wherein no ring is aromatic. Examples of heterocyclyl groups include morpholinyl, thiomorpholinyl, furyl, piperazinyl, piperidinyl, pyranyl, pyrrolidinyl, tetrahydropyranyl, tetrahydrofuranyl, and 1,3-dioxanyl. A heterocyclylene is a divalent heterocyclyl group.

The term "hydroxyl," as used herein, represents an —OH group.

The term "nitro," as used herein, represents an $NO_2$ group.

The term "thiol," as used herein, represents an —SH group.

The alkyl, alkenyl, alkynyl, heteroalkyl, heteroalkenyl, and heteroalkynyl may be substituted or unsubstituted. When substituted, there will generally be 1 to 10 (e.g., 1 to 4, 1 to 3, or 1 to 2) substituents present, unless otherwise specified. Substituents include, for example: oxo, halogen (e.g., fluoro), hydroxyl, alkyl, heteroalkyl (e.g., substituted and unsubstituted alkoxy (e.g., methoxy or ethoxy) or thioalkoxy), azido, cyano, nitro, amino, orthiol.

Definitions

In this application, unless otherwise clear from context, (i) the term "a" may be understood to mean "at least one"; (ii) the term "or" may be understood to mean "and/or"; and (iii) the terms "comprising" and "including" may be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal (e.g., as a vitreous substitute).

The term "degree of crosslink or substitution," as used herein, means the quantity of pairs of functional groups converted into crosslinking or grafting bonds relative to the total quantity of pairs of functional groups initially present on the hyaluronan polymer and the multimeric polymeric cross-linker, expressed as a percentage. For example 20%, 40%, 60%, or 80% indicates the quantity of crosslinking groups relative to total functional groups present on the hyaluronan polymer.

As used herein, the term "hyaluronan polymer" refers to linear heteropolysaccharides composed of D-glucuronic acid or derivative thereof, and D-glucosamine (e.g., D-N-acetylglucosamine) or derivative thereof, which are linked together via alternating β-1,4 and β-1,3 glycosidic bonds, and which permit covalent attachment to a multimeric polymeric cross-linker at one or more points, and salts (e.g., physiologically acceptable salts) thereof. Suitable HA polymers according to the invention encompass polysaccharides composed of up to 12,500 disaccharide repeats, and range in size from about 500 to 5,000,000 Da depending on the origin, in particular from about 500 to 3,000,000 Da. Each repeat unit bears a chemical group (e.g., a carboxylic acid or carboxylate) on the D-glucuronic acid motif which can be potentially tethered to form a cross-linked polymer according to the invention. According to a particular aspect, the degree of substitution of those chemical groups (e.g., a carboxylic acid or carboxylate) with a multimeric polymeric cross-linker of the invention is between about 0.01-1%, 0.01-5%, 0.1-1%, 0.01-5%, 0.1-10%, 1-5%, 10-50%, 20-40%, 20-99%, 50-99%, 70-90%, 80-95%, 90-99%, 95-99%, 98-99.5%, or 99-99.9%. Hyaluronan polymer derivatives include, but are not limited to: (i) salts with organic and/or inorganic bases; (ii) esters of hyaluronic acid with alcohols of the aliphatic, aromatic, cyclic, or heterocyclic series, with an esterification percentage which can vary according to the type of alcohol and length of the alcohol used (e.g., HYAFF® and/or as described in EP 0216453 B1); (iii) amides of hyaluronic acid with amines of the aliphatic, aromatic, cyclic, or heterocyclic series (e.g., HYADD® and/or as described in EP 1095064 B1); (iv) O-sulfated derivatives (e.g., as described in EP 0702699 B1) or N-sulfated derivatives of hyaluronic acid (e.g., as described in EP 0971961 A1); (v) internal esters of hyaluronic acid (e.g., ACP® and/or as described in EP 0341745 B1); (vi) deacylated products of HA: the N-acetylglucosamine fraction is deacetylated (e.g., as described in EP 1313772 B1); (vii) percarboxylated products of HA obtained from the oxidation of the primary hydroxyl of the N-acetylglucosamine fraction with a percarboxylation degree ranging from 0.1 to 100% (e.g., HYOXX® and/or as described in EP 1339753 A1).

As used herein, the terms "peptide," "polypeptide," and "protein" refer to any chain of two or more natural or unnatural amino acid residues, regardless of post-translational modifications (e.g., glycosylation or phosphorylation). The polypeptides incorporated into the materials of the invention can include from 3 to 50 natural or unnatural amino acid residues (e.g., from 3 to 15, from 5 to 20, or from 15 to 50 natural or unnatural amino acid residues). The polypeptide can be a cell adhesive peptide, such as an RGD peptide.

The term "X-modified hyaluronan," as used herein, refers to hyaluronan derivative comprising the functional group X. For example "ketone-modified hyaluronan" refers to hyaluronan derivative including a ketone substituent (e.g., a compound of formula (I)); "oxyamine-modified hyaluronan" refers to hyaluronan derivative including an oxyamine substituent (e.g., a compound of formula (V)); and "aldehyde-modified hyaluronan" refers to hyaluronan derivative including an aldehyde substituent (e.g., the compound synthesized in Example 3).

The compositions described herein may have ionizable groups so as to be capable of preparation as physiologically acceptable salts. These salts may be acid addition salts involving inorganic or organic acids or the salts may, in the case of acidic forms of the compounds described herein, be prepared from inorganic or organic bases. Frequently, the compounds are prepared or used as physiologically acceptable salts prepared as addition products of physiologically acceptable acids or bases. Suitable physiologically acceptable acids and bases and methods for preparation of the appropriate salts are well-known in the art. Salts may be prepared from physiologically acceptable non-toxic acids and bases including inorganic and organic acids and bases. Representative acid addition salts include acetate, adipate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean both therapeutic treatment and prophylactic or preventative measures wherein the object is to prevent or slow down (lessen) an undesired physiological condition, disorder, or disease (e.g., ocular disorder such as retinal detachment), or obtain beneficial or desired clinical results. Beneficial or desired clinical results include, but are not limited to, alleviation of symptoms (e.g., reduced vision, blurred vision, or photopsia); diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects.

As used herein, the term "vitreous humor" refers to the material (e.g., gel) located in the eyeball behind the lens.

The details of one or more embodiments of the invention are set forth in the description below. Other features, objects, and advantages of the invention will be apparent from the description and from the claims.

BRIEF DESCRIPTION OF THE DRAWINGS

As shown in FIG. 5A, representative images of surface tension and contact angle measurements performed on HA-oxime and Silicone oil at room temperature with air. FIG. 5B is a graph illustrating the surface tension of HA-oxime hydrogel (1.05:0.20 HAK: HAA) is significantly higher than silicone oil (n=4, mean±standard deviation ***$p<0.001$ student's t-test).

FIG. 6A is a graph which illustrates enzymatic degradation of HA-oxime-AF647 labelled hydrogel treated with hyaluronidase over 10 days measured by fluorescence at $\lambda_{ex}$=640 nm and $\lambda_{em}$=675 nm (n=5, mean±standard deviation). FIG. 6B is a graph illustrating the transparency of HA-oxime over 10 days with hyaluronidase treatment measured between λ=380-740 nm with subtraction of phosphate buffered saline (n=3, mean±standard deviation shown for day 0).

As shown in FIG. 7A, the viability of human-derived RPE-CA1 cells cultured with or without HA-oxime is maintained over 24 h quantified by live/dead staining using Imaris (n=3 biological replicates, mean±standard deviation, p=0.23 student's t-test). As shown in FIG. 7B, Live/dead images of RPE-CA1 cells stained with calcein AM (live) and ethidium homodimer (dead) after 24 h culture. Scale bars represent 50 µm. As shown in FIG. 7C, the viability of mouse cod cells cultured with or without HA-oxime over 96 h quantified by live/dead staining using Imaris (n=3 biological replicates, mean±standard deviation, p=0.84 student's t-test). As shown in FIG. 7D, live/dead images of cod cells stained with calcein AM (live), ethidium homodimer (dead) and Hoechst 33342 (nuclei) after culture for 4 days. Scale bars represent 200 µm.

FIG. 10A illustrates the fluorescence stability of Alexa Fluor 647 labelled HAK under ambient light over 28 days measured by fluorescence at $\lambda_{ex}$=640 nm and $\lambda_{em}$=675 nm (n=3, mean t standard deviation). Image of HA-oxime-AF647 and HA-oxime samples prepared with and without 0.25 wt % Alexa Fluor 647 labelled HA under UV light. FIG. 10B illustrates a cryosectioned rabbit eyes following vitrectomy and injection of fluorescently tagged HA-oxime-AF647 present or silicone oil which fills the cavity as a liquid.

FIG. 11A is a graph illustrating modeled stability of HA-oxime hydrogel in vivo with a half-life of 43 days calculated from the fluorescence data using a non-linear fit one phase decay with least squares fit. FIG. 11B illustrates the fluorescence of hydrogels dissected from rabbit eyes digested with hyaluronidase measured at $\lambda_{ex}$=640 nm and $\lambda_{em}$=675 nm and normalized relative to day 1 (n=3 for day 1; n=5 for day 14 and 28; n=7 for day 56, mean±standard deviation, *$p<0.05$, $p<0.01$ and *$p<0.001$ one-way ANOVA Tukey's post hoc test). Hydrogels were collected from the eyes to determine sample mass which was normalized relative to day 1 (n=4 for day 1; n=5 for day 14 and 28; n=6 for day 56, mean±standard deviation, *$p<0.05$, $p<0.01$ and *$p<0.001$ one-way ANOVA Tukey's post hoc test) (FIG. 11C).

FIG. 12A illustrates representative sections of retina stained with hematoxylin and eosin (H&E) following injection of HA-oxime hydrogel after 7, 28 and 56 days, or silicone oil after 7 and 28 days, and sham with infusion of balanced saline after 7 days (scale bars represent 100 μm). FIG. 12B and FIG. 12C show a graph illustrating the quantification of the rabbit inner nuclear layer (FIG. 12B) and outer nuclear layer (FIG. 12C) retina thickness by number of nuclei at 7, 28 and 56 days following injection of HA-oxime, silicone oil or sham surgery (n=7 for HA-oxime and sham day 7; n=4 for silicone oil day 7; n=4 for HA-oxime day 28; n=6 for silicone oil day 28; n=6 for HA-oxime day 56, mean±standard deviation p=0.855 (INL) and p=0.034 (ONL) one-way ANOVA Tukey's post hoc test.

As shown in FIG. 14A, reconstruction of a histological section from the rabbit eye stained with H&E 7 days after induction of a retinal detachment and hydrogel injection. Magnified histological cross section of the rabbit retina following retinal detachment, scale bar represents 200 μm. As shown in FIG. 14B, quantification of the inner and outer nuclear layer (INL and ONL) thickness 7 days after the injection of the HA-oxime hydrogel.

FIG. 15A illustrates representative sections of retina stained with hematoxylin and eosin (H&E) following injection of HA-oxime hydrogel containing 0.4M sucrose after 7 and 28 days, As shown in FIG. 15B and FIG. 15C, the quantification of the rabbit inner nuclear layer (FIG. 15B) and outer nuclear layer (FIG. 15C) retina thickness by number of nuclei at 7 and 28 days following injection of HA-oxime containing 0.4M sucrose (n=3 for HA-oxime containing 0.4M sucrose day 7; n=2 for HA-oxime containing 0.4M sucrose following induced retinal detachment day 7; n=4 for HA-oxime containing 0.4M sucrose day 28; mean±standard deviation).

FIG. 17A shows the overall goal was to benchmark the gene expression profile of cells cultured in vitro in our novel HA-oxime hydrogels relative to conventional culture in either Matrigel or 2D tissue culture polystyrene (TCPS) to those cells grown in vivo. This methodology allows us to identify pathways that can then be targeted in drug screening assays. The illustration in FIG. 17B shows HA-oxime crosslinked hydrogels comprised of HA-ketone (HAK), HA-aldehyde (HAA), and poly(ethylene glycol)-tetraoxyamine ($PEGOA_4$) and formed in the presence of laminin and breast cancer cells, which resulted in uniformly distributed cells. FIG. 17C shows the distribution of encapsulated MDA-MB-468 cells after 24 hours in HA-oxime hydrogels: in HAK crosslinked gels, cells aggregate at the bottom of the well due to the slow gelation whereas in HAK:HAA (3:1 mass ratio), cells are evenly distributed. Cells were stained for viability with calcein AM (live) and ethidium homodimer-1 (dead); scale bar represents 200 μm (n=3 independent experiments; mean+s.d. plotted, *p<0.001, one-way ANOVA, Tukey's post-hoc test). FIG. 17D shows gelation time of HA-oxime hydrogels crosslinked with $PEGOA_4$ (n=3, mean+s.d., *p<0.001, one-way ANOVA, Tukey's post-hoc test). FIG. 17E shows compressive modulus of HA-oxime hydrogels compared to growth factor reduced Matrigel (n=4, mean+s.d. plotted, *p<0.05; **p<0.01, one-way ANOVA, Tukey's post-hoc test). The shaded area represents the range in stiffness of mouse tumours reported in the literature (Paszek et al., Cancer cell, 8:241 (2005). FIG. 17F shows HA-oxime hydrogel prepared from 3:1 HA-ketone (0.90 wt %) and HA-aldehyde (0.30 wt %) crosslinked with $PEGOA_4$ (1.04 wt %) was stable over 28 days at 37° C. in Hank's balanced salt solution (HBSS) and in the presence of collagenase, but degraded in the presence of hyaluronidase. The percent of remaining hydrogel was determined from the mass measurements (n=3, mean+s.d. plotted).

FIG. 20A shows the stability of HAK/HAA or HA/HAA hydrogels crosslinked with 80 mol % $PEGOA_2$ over 28 days (n=3 independent samples, data represents mean+standard deviation, linear regression analysis of swelling slope HAK/HAA does not deviate significantly from a zero slope p=0.089 whereas HA/HAA significantly deviates from zero slope p<0.0001). FIG. 20B and FIG. 20C show the swelling of HA-oxime hydrogels prepared from 1.20 wt % HAK, 0.15 wt % HAA and crosslinked 2-arm or 4-arm oxyamine-modified PEG. In particular, FIG. 20B uses 60 mol % crosslinker (i.e., 1.40 wt % $PEGOA_2$ or 1.09 wt % $PEGOA_4$) (n=4 independent samples, mean±standard deviation plotted, **p<0.01 at each day after day 0, one-way ANOVA, Tukey's post-hoc test). FIG. 20C uses 80 mol % crosslinker (i.e., 1.86 wt % $PEGOA_2$ or 1.45 wt % $PEGOA_4$) (n=4 independent samples, mean±standard deviation plotted, *p<0.05 at each day after day 0, one-way ANOVA, Tukey's post-hoc test).

FIG. 21A, FIG. 21B, and FIG. 21C illustrate the rheology of 1.20 wt % HA-oxime hydrogels at 37° C. FIG. 21A, FIG. 21B, and FIG. 21C are representative plots of 1.20 wt % HAK hydrogels crosslinked with $PEGOA_4$ at 0.60 moles oxyamine to ketone. FIG. 21A is a time sweep. FIG. 21B is a frequency sweep. FIG. 21C is a strain sweep. FIG. 21D, FIG. 21E, and FIG. 21F illustrate rheology of 1.20 wt % HAK:HAA hydrogels crosslinked with $PEGOA_4$ at 0.60 moles oxyamine to ketone+aldehyde. FIG. 21D, FIG. 21E, and FIG. 21F are representative plots of time sweep rheological plots for HA-oxime hydrogels with HAK:HAA ratios of 7:1 (FIG. 21D), 3:1 (FIG. 21E), and 1:1 (FIG. 21F). n=3 independent samples, data represents mean+standard deviation.

FIG. 22A shows the distribution along the z-axis of cells encapsulated in HA-oxime hydrogels. Distribution was quantified using Imaris from Bitplane (n=3 independent studies; mean+standard deviation plotted, * $p<0.05$, one-way ANOVA, Tukey's post-hoc test). FIG. 22B illustrates the viability of cells after 24 hours encapsulated in HA-oxime hydrogels quantified using calcein AM and ethidium homodimer-1 using Imaris from Bitplane (n=3 independent studies, mean+standard deviation plotted, *$p<0.05$, no significance (ns) by one-way ANOVA, Tukey's post-hoc test). FIG. 22C shows the distribution along the z-axis of MDA-MB-468 spheroids encapsulated as single cells in HA-oxime, Matrigel and HyStem-C hydrogels after 14 days shows a more even distribution in HA-oxime vs. Matrigel and HyStem-C. Distribution was quantified using Imaris from Bitplane (n=3 independent studies; mean+standard deviation plotted, * $p<0.05$, one-way ANOVA, Tukey's post-hoc test).

FIG. 25A shows the amount of Ln retained in HA-oxime hydrogels crosslinked with $PEGOA_4$ quantified by ELISA after 7 days, Ln was not detected (nd) from supernatant 24 h after adding PBS to HA-oxime-Ln hydrogels (n=3 independent samples; mean+standard deviation plotted, no significant differences (ns), **$p<0.01$, one-way ANOVA, Tukey's post-hoc test). FIG. 25B shows the fold change in the number of breast cancer cells on HA-oxime gels crosslinked with $PEGOA_4$ containing Ln versus those on Matrigel (n=3 independent studies; mean+standard deviation plotted, *$p<0.05$; one-way ANOVA, Tukey's post-hoc test).

FIG. 27A shows compressive modulus of HA-oxime hydrogels with and without 75 $\mu g \cdot mL^{-1}$ Ln (n=4 HA-oxime and n=3 HA-oxime-Ln independent studies; mean+standard deviation plotted, no significance (ns) by student's t-test). FIG. 27B and FIG. 27C are representative of MDA-MB-468 cells encapsulated and distributed in growth factor reduced Matrigel and HA-oxime-Ln after 24 hours. Cells stained with Calcein AM (live), Ethidium homodimer-1 (dead), 3D reconstruction of z-stack images using Imaris from Bitplane. Scale bar represents 200 μm. FIG. 27D shows the distribution along the z-axis of MDA-MB-468 cells encapsulated in Matrigel, or HA-oxime-Ln hydrogels. Distribution was quantified using Imaris from Bitplane (n=3 independent studies; mean+standard deviation plotted, *$p<0.05$, one-way ANOVA, Tukey's post-hoc test). FIG. 27E shows representative brightfield images of BT474 spheroids encapsulated in HA-oxime+/−Ln and Matrigel. Images were captured after 10 days of cell culture using a GelCount instrument in a 96-well plate format. FIG. 27F and FIG. 27G show the average diameter and number of BT474 spheroids per well after 10 days of culture encapsulated in HA-oxime+/−Ln and Matrigel. n=3 independent studies; mean+standard deviation plotted, no significance (ns) by one-way ANOVA, Tukey's post hoc test.

FIG. 28A shows cancer spheroids stained for CD44, nuclei, and F-actin. FIG. 28B shows cancer spheroids stained for E-cadherin, nuclei, and F-actin. FIG. 28C shows cancer spheroids stained with $\beta_1$ integrin, nuclei, and F-actin. FIG. 28D shows cancer spheroids stained with HIF-1α, nuclei, and F-actin. Scale bar represents 50 μm, images were acquired with a 40× objective lens.

FIG. 30B shows the cell growth of luminal cancer cells cultured on 2D TCPS, in Matrigel, HA-oxime and HA-oxime-Ln was measured with RealTime-Glo MT (n=3 technical replicates; mean+standard deviation plotted, *$p<0.05$, one-way ANOVA, Tukey's post-hoc test).

FIG. 31A shows MCF7; FIG. 31B shows T47D; FIG. 31C shows BT474; FIG. 31D shows MDA-MB-231 H2N; and FIG. 31E shows MDA-MB-468.

FIG. 32A illustrates qPCR for MCF7; FIG. 32B illustrates qPCR for T47D; FIG. 32C illustrates qPCR for BT474; FIG. 32D illustrates qPCR for MDA-MB-231-H2N. and FIG. 32**E illustrates qPCR for MDA-MB-468.

FIG. 34A shows cell growth at day 7 relative to day 1 (n=3; mean+s.d. plotted, *p<0.05, one-way ANOVA, Tukey's post-hoc test). FIG. 34B shows tumour spheroid diameter after 21 days of culture for cells embedded in HA-oxime, HA-oxime-Ln or Matrigel (n=3; mean+s.d. plotted, *p<0.05, one-way ANOVA, Tukey's post-hoc test). No spheroids were formed on 2D TCPS.

FIG. 36A is a dose response curve, and FIG. 36B shows $IC_{50}$ values for MDA-MB-468 cells treated with Erlotinib when cultured on 2D TCPS or in 3D with Matrigel, HA-oxime+/−Ln after 7 days of treatment quantified by PrestoBlue cell viability reagent. $IC_{50}$ values were calculated and shown to be significantly different between 2D cultures and 3D cultures (n=3 independent studies; mean±standard deviation plotted, **p<0.01, one-way ANOVA, Tukey's post-hoc test).

FIG. 37A shows fold change in the number of MDA-MB-468 cells adhered to HA-oxime gels crosslinked with $PEGOA_4$ containing RGDOA. N=3 independent studies; mean+standard deviation plotted, * p<0.05;  p<0.01, one-way ANOVA, Tukey's post hoc test. FIG. 37B shows the amount of RGDOA immobilized to HA-oxime hydrogels crosslinked with $PEGOA_4$ after 1 hour or 24 hours conjugation. RGDOA concentration was quantified by amino acid analysis using arginine and alanine peaks. N=3 independent samples, data represents mean+standard deviation,  p<0.01, one-way ANOVA, Tukey's post hoc test.

FIG. 41B shows the quantified fluorescence from an IVIS Spectrum in vivo imaging system (n=2 mean±standard deviation).

DETAILED DESCRIPTION OF THE INVENTION

Figure 1:
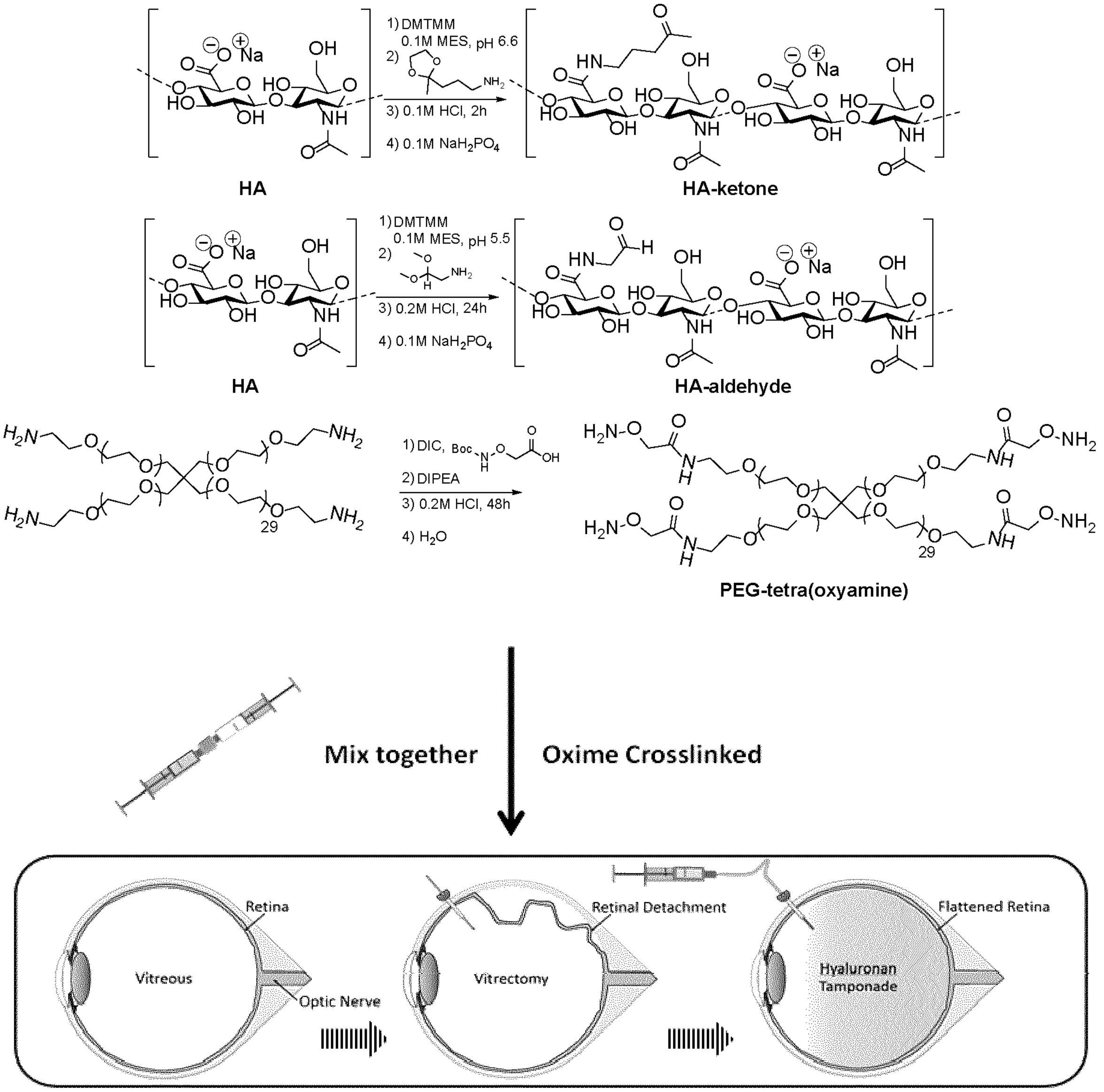
FIG. 1 illustrates the synthesis of polymers for the vitreous gel and the formation of oxime crosslinks. Schemes describing the synthesis of ketone-modified and aldehyde-modified hyaluronan (HAK and HAA respectively) and poly(ethylene glycol) tetra(oxyamine) ($PEGOA_4$) are described. The synthesis of HA-ketone was conducted using DMTMM to couple HA with 3-(2-methyl-1,3-dioxolan-2-yl)propan-1-amine followed by acid-catalyzed deprotection, and neutralization. The synthesis of HA-aldehyde was conducted using DMTMM to couple HA with aminoacetaldehyde dimethyl acetal followed by acid-catalyzed deprotection, and neutralization. When HAK, HAA, and $PEGOA_4$ are mixed together, they react to form oxime bonds and a hydrogel once injected into the eye to flatten the retina.

The present disclosure features hyaluronan polymer derivatives bearing a keto group and their use in synthesizing a cross-linked polymer (e.g., hydrogel) useful for treating disease (e.g., retinal detachment) or for use in screening models (e.g., 3D cell culture system). The invention features hydrogel precursor compositions (e.g., solutions of compounds of formulas (I) or (III) or solutions of compounds of formulas (V) or (VII)) and multimeric polymeric cross-linker compositions bearing one, two, three, four, or more terminal oxyamine groups, which are combined to form cross-linked polymers (e.g., cross-linked polymers of (i) a hyaluronan polymer; and (ii) a multimeric polymeric cross-linker conjugated through at least one linkage group of formula (IV-i) or formula (IV-ii); or cross-linked polymers of (i) a hyaluronan polymer; and (ii) a multimeric polymeric cross-linker conjugated through at least one linkage group of formula (VIII-i) or formula (VIII-ii)) useful as a vitreous substitute or for forming three-dimensional hydrogels that support growth of physiologically relevant tissue when at least one cell is cultured in or on the three-dimensional hydrogel.

Hyaluronan or Hyaluronic Acid (HA)

Hyaluronan or hyaluronic acid (HA) is a nonsulfated glycosaminoglycan composed of D-glucuronic acid and D-N-acetylglucosamine. As stated above, the carbon-atom numbering for the sugar backbones of D-glucuronic acid and D-N-acetylglucosamine of hyaluronan used herein is described in Chart 1.

Chart 1

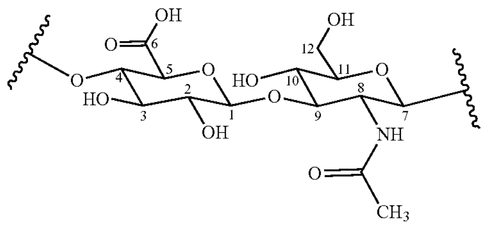

An example of a ketone-modified hyaluronan polymer where the ketone-containing moiety (e.g., K as described above) is covalently linked to the hyaluronan polymer through a substituent on C6 of D-glucuronic acid or derivative thereof is shown below:

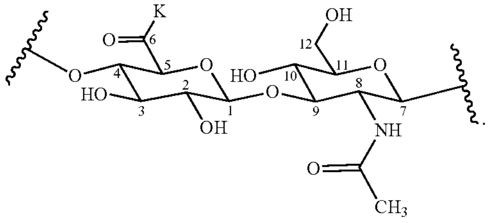

An example of a ketone-modified hyaluronan polymer where the ketone-containing moiety (e.g., K as described above) is covalently linked to the hyaluronan polymer through a substituted on C3 of D-glucuronic acid or derivative thereof is shown below:

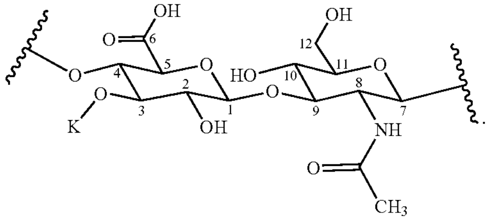

An example of a ketone-modified hyaluronan polymer where the ketone-containing moiety (e.g., K as described above) is covalently linked to the hyaluronan polymer through a substituted on C2 of D-glucuronic acid or derivative thereof is shown below:

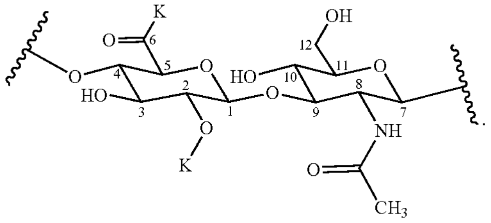

An example of a ketone-modified hyaluronan polymer where the ketone-containing moiety (e.g., K as described above) is covalently linked to the hyaluronan polymer through a substituted on C8 of D-glucuronic acid or derivative thereof is shown below:

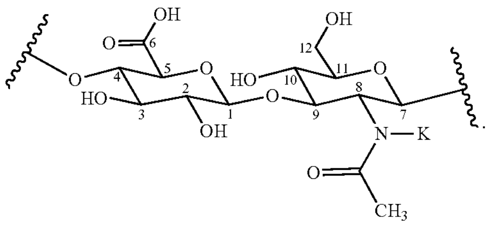

An example of a ketone-modified hyaluronan polymer where the ketone-containing moiety (e.g., K as described above) is covalently linked to the hyaluronan polymer through a substituent on C12 of D-N-acetylglucosamine or derivative thereof is shown below:

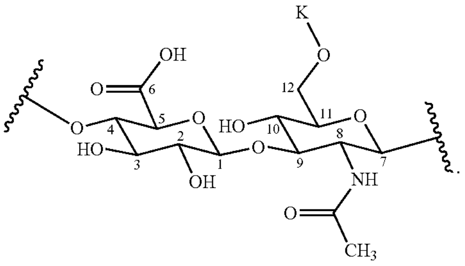

An example of a ketone-modified hyaluronan polymer where the ketone-containing moiety (e.g., K as described above) is covalently linked to the hyaluronan polymer through a substituent on C10 of D-N-acetylglucosamine or derivative thereof is shown below:

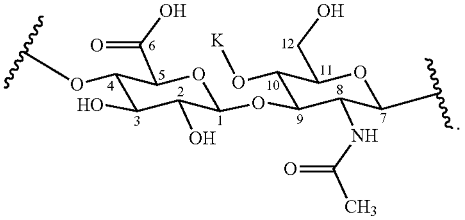

Similarly, an example of an oxyamine-modified hyaluronan polymer where the oxyamine-containing moiety (e.g., OA as described above) is covalently linked to the hyaluronan polymer through a substituent on C6 of D-glucuronic acid or derivative thereof is shown below:

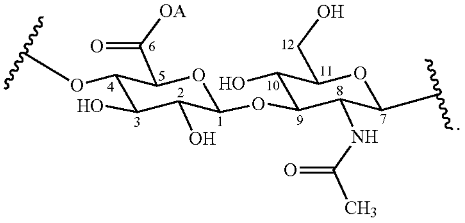

An example of an oxyamine-modified hyaluronan polymer where the oxyamine-containing moiety (e.g., OA as described above) is covalently linked to the hyaluronan polymer through a substituted on C3 of D-glucuronic acid or derivative thereof is shown below:

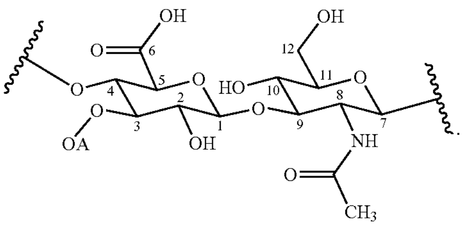

An example of an oxyamine-modified hyaluronan polymer where the oxyamine-containing moiety (e.g., OA as described above) is covalently linked to the hyaluronan polymer through a substituted on C2 of D-glucuronic acid or derivative thereof is shown below:

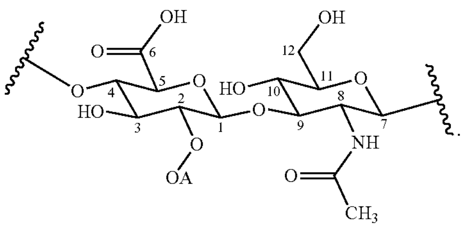

An example of an oxyamine-modified hyaluronan polymer where the oxyamine-containing moiety (e.g., OA as described above) is covalently linked to the hyaluronan polymer through a substituted on C8 of D-glucuronic acid or derivative thereof is shown below:

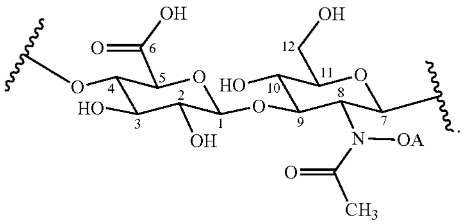

An example of an oxyamine-modified hyaluronan polymer where the oxyamine-containing moiety (e.g., OA as described above) is covalently linked to the hyaluronan polymer through a substituent on C12 of D-N-acetylglucosamine or derivative thereof is shown below:

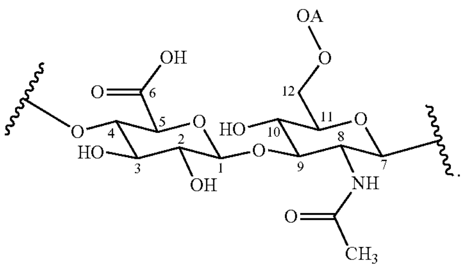

An example of an oxyamine-modified hyaluronan polymer where the oxyamine-containing moiety (e.g., OA as described above) is covalently linked to the hyaluronan polymer through a substituted on C10 of D-glucuronic acid or derivative thereof is shown below

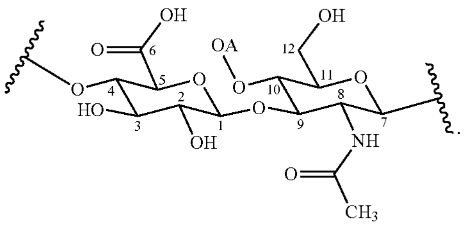

Hyaluronan derivatives include, but are not limited to, salts with organic and/or inorganic bases; external ester derivatives (e.g., formed with HA and alcohols); internal ester derivatives; amide derivatives (e.g., formed with HA and amines); O-sulfated derivatives; N-sulfated derivatives; deacetylated derivatives (e.g., HA including D-glucosamine), percarboxylated derivatives; reduced derivatives; and/or ether derivatives. For example, an ether derivative of hyaluronan can be synthesized via a Williamson ether synthesis.

Ketone-Modified Hyaluronan (HA-ketone or HAK)

The hydrogels of the invention are formed from a precursor solution containing a ketone-modified hyaluronan polymer of formula (I):

HAP-K (I), where HAP is a hyaluronan polymer; and K is a moiety covalently linked to the hyaluronan polymer having the structure of formula (Ia) or formula (Ib):

(Ia)

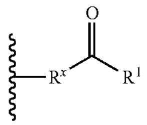

or (Ib)

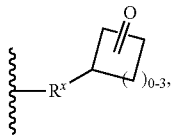

, where $R^X$ and $R^1$ are as defined above. Ketone-modified hyaluronan polymers can be prepared as described in Example 1.

Any suitable form or derivative of hyaluronan polymer can be used to form the ketone-modified hyaluronan polymer. In some embodiments, the ketone-modified hyaluronan polymer is formed from a soluble form of isolated hyaluronan. In some embodiments, the hyaluronan polymer has a molecular weight of from about 20 kDa to 400 kDa, 20 kDa to 100 kDa, 20 kDa to 200 kDa, 50 kDa to 200 kDa, 50 kDa to 400 kDa, 100 kDa to 150 kDa, 100 kDa to 400 kDa, 150 kDa to 300 kDa, 150 kDa to 400 kDa, 250 kDa to 1000 kDa, 500 kDa to 1500 kDa, 1000 kDa to 2000 kDa, 1000 kDa to 3000 kDa, or 2000 kDa to 3000 kDa. In a preferred embodiment, the hyaluronan polymer has a molecular weight of from about 100 to 150 kDa or 150 kDa to 300 kDa.

Examples of ketone-modified hyaluronan polymers include compounds of formula (III):

$[A]_m[B]_n[C]_{1-(m+n)}$ (III), where [A] has the structure of formula (IIIa):

(IIIa)

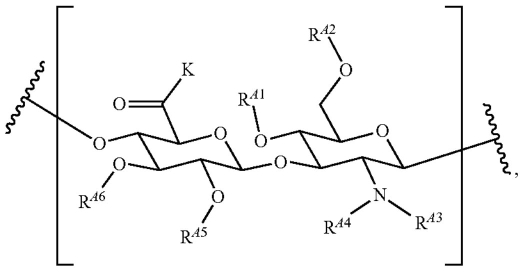

, where $R^{A1}$, $R^{A2}$, $R^{A3}$, $R^{A4}$, $R^{A5}$, and $R^{A6}$ are as defined above; and K is a moiety covalently linked to the hyaluronan polymer having the structure of formula (Ia) or formula (Ib):

(Ia)

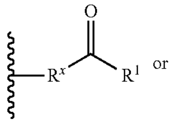

or (Ib)

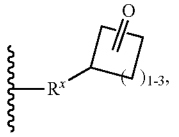

where $R^X$ and $R^1$ are as defined above;

[B] has the structure of formula (IIIb):

(IIIb)

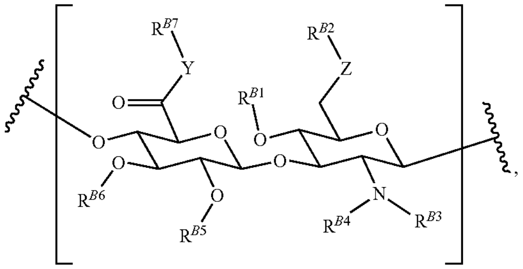

where $B^{B1}$, $R^{B3}$, $R^{B4}$, $R^{B5}$, $R^{B6}$, $R^{B2}$, $R^{B7}$, $Y^1$, and $Z^1$ are as described above;

[C] has the structure of formula (IIc):

(IIIc)

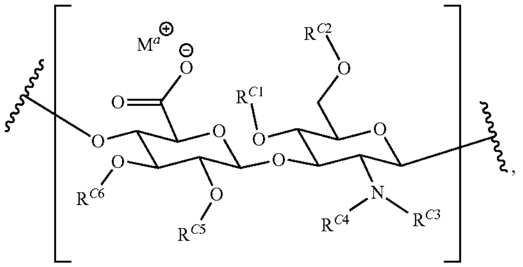

where $R^{C1}$, $R^{C2}$, $R^{C3}$, $R^{C4}$, $R^{C}$S, $R^{C6}$, and $M^a$ are as described above; and each of m and n is, independently, a fraction greater than zero and less than 1, where (m+n)<1.

Examples of [A] include the structure of formula (A1):

(A1)

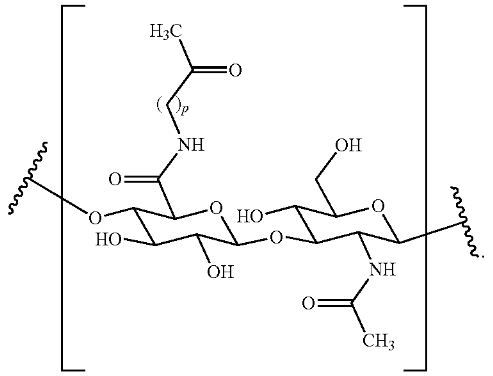

Examples of [B] include the structure of formula (B1) and the structure of formula (B2):

(B1)

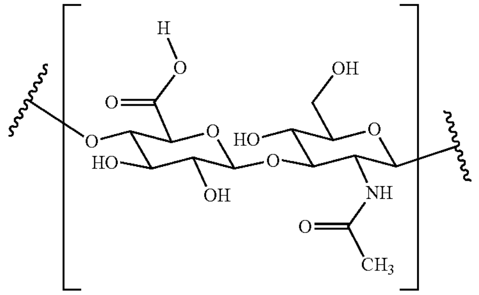

(B2)

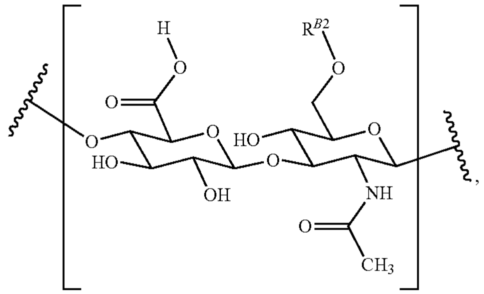

where $R^{B2}$ is as defined above.

Examples of [C] include the structure of formula (C1) and the structure of formula (C2):

(C1)

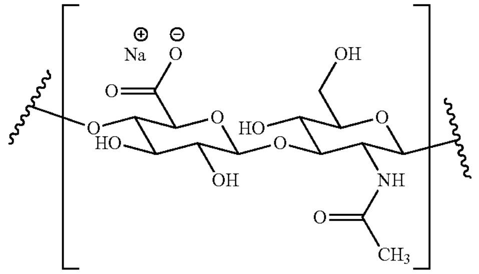

-continued (C2)

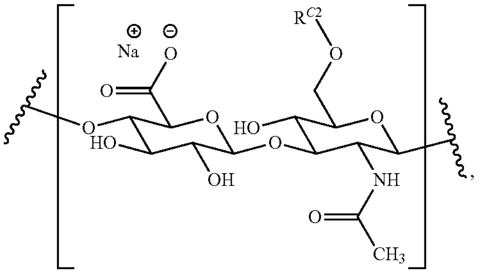

where $R^{C2}$ is as described above.

Oxyamine-Modified Hyaluronan (HA-Oxyamine or HA-OA)

The hydrogels of the invention can also be formed from a precursor solution containing an oxyamine-modified hyaluronan polymer of formula (V):

HAP-OA (V), where HAP is a hyaluronan polymer; and OA is a moiety covalently linked to the hyaluronan polymer having the structure of formula (Va):

(Va)

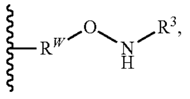

where $R^W$ and $R^3$ are as defined above. Oxyamine-modified hyaluronan polymers can be prepared as described in Example 10.

Any suitable form or derivative of hyaluronan polymer can be used to form the oxyamine-modified hyaluronan polymer. In some embodiments, the oxyamine-modified hyaluronan polymer is formed from a soluble form of isolated hyaluronan. In some embodiments, the hyaluronan polymer has a molecular weight of from about 20 kDa to 400 kDa, 20 kDa to 100 kDa, 20 kDa to 200 kDa, 50 kDa to 200 kDa, 50 kDa to 400 kDa, 100 kDa to 150 kDa, 100 kDa to 400 kDa, 150 kDa to 300 kDa, 150 kDa to 400 kDa, 250 kDa to 1000 kDa, 500 kDa to 1500 kDa, 1000 kDa to 2000 kDa, 1000 kDa to 3000 kDa, or 2000 kDa to 3000 kDa. In a preferred embodiment, the hyaluronan polymer has a molecular weight of from about 100 to 150 kDa or 150 kDa to 300 kDa.

Examples of oxyamine-modified hyaluronan polymers include compounds of formula (VII):

$[D]_q[E]_r[F]_{1-(q+r)}$ (VII), wherein [D] has the structure of formula (VIIa):

(VIIa)

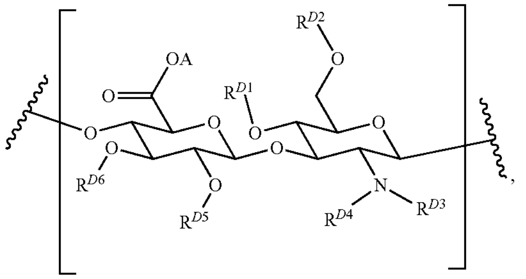

where $R^{D1}$, $R^{D2}$, $R^{D3}$, $R^{D4}$, $R^{D5}$, and $R^{D6}$ are as described above; and OA is a moiety covalently linked to the hyaluronan polymer having the structure of formula (Va):

(Va)

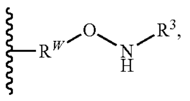

where $R^W$ and $R^3$ are as described above;

[E] has the structure of formula (VIIb):

(VIIb)

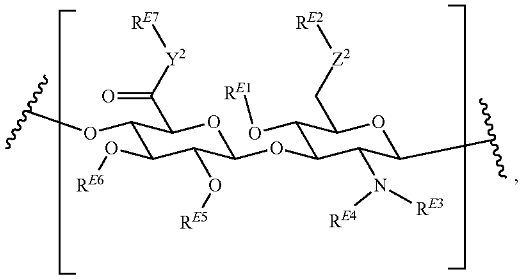

where $R^{E1}$, $R^{E2}$, $R^{E3}$, $R^{E4}$, $R^{E5}$, $R^{E2}$, $R^{E7}$, $Y^2$, and $Z^2$ are as described above;

[F] has the structure of formula (VIIc):

(VIIc)

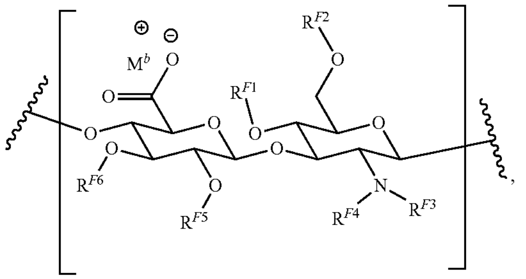

where $R^{F1}$, $R^{F2}$, $R^{F3}$, $R^{F4}$, $R^{F}S$, $R^{F6}$, and $M^b$ are as described above; and each of q and r is, independently, a fraction greater than zero and less than 1, wherein (q+r)<1.

Examples of [D] include the structure of formula (D1):

(D1)

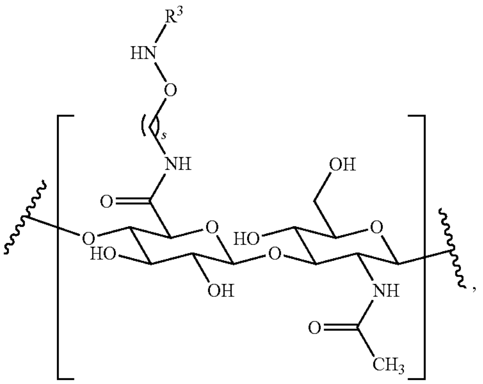

wherein s and $R^3$ are as defined above.

Examples of [E] include the structure of formula (E1) and the structure of formula (E2):

(E1)

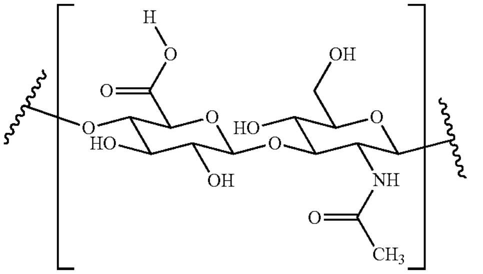

(E2)

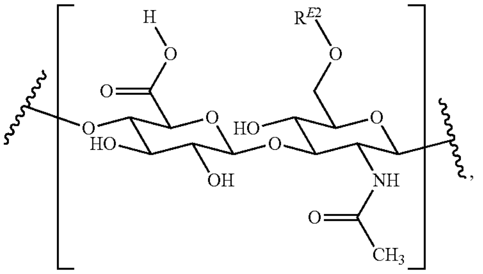

where $R^{E2}$ is as described above.

Examples of [F] include the structure of formula (F1) and the structure of formula (F2):

(F1)

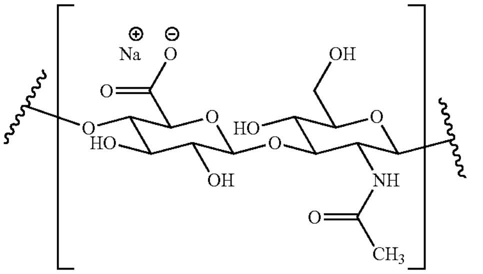

-continued (F2)

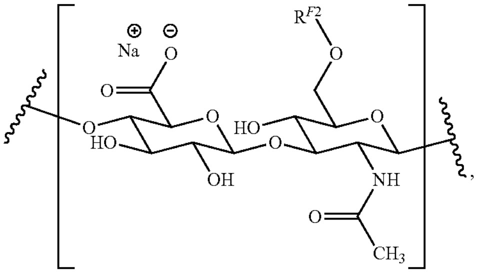

where $R^{F2}$ is as described above.

Multimeric Polymeric Cross-Linker

The hydrogels of the invention are also formed from a precursor solution containing multimeric polymeric cross-linker bearing two or more terminal oxyamine groups. Such multimeric cross-linkers can be prepared from a polyamine using the protocols described in Example 4. In some embodiments, the multimeric polymeric cross-linker has an average molecular weight of less than 30 kDa, 20 kDa, 15 kDa, or 10 kDa.

In some embodiment, the multimeric polymeric cross-linker is conjugated to the hyaluronan polymer through at least one linkage group of formula (IV-i) or formula (IV-ii):

(IV-i)

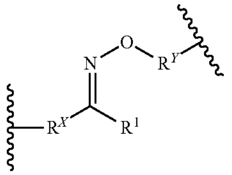

(IV-ii)

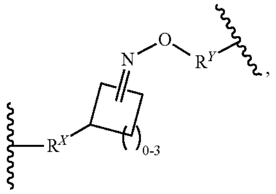

wherein $R^X$, $R^1$, and RY are as defined above.

The multimeric polymeric cross-linker used to form the cross-linked polymers of the invention can have the general formula:

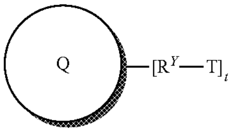

where

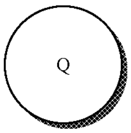

is a multimeric or polymeric core covalently linked moiety RY-T; RY is as described above; T is a terminal group —$ONH_2$; and t is an integer from 1 to 8. In particular embodiments,

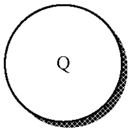

is $C_{1-6}$ alkyl, $C_{2-6}$ alkenyl, $C_{2-6}$ alkynyl, $C_{1-6}$ heteroalkyl, $C_{2-6}$ heteroalkenyl, $C_{2-6}$ heteroalkynyl, $C_{3-10}$ carbocyclyl, $C_{6-10}$ aryl, $C_{2-9}$ heterocyclyl, or $C_{2-9}$ heteroaryl, any of which is optionally substituted with one or more of oxo, halogen, hydroxyl, alkoxy, azido, cyano, nitro, amino, and thiol.

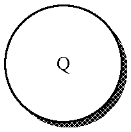

can be a multimeric or polymeric core having the structure of, e.g.

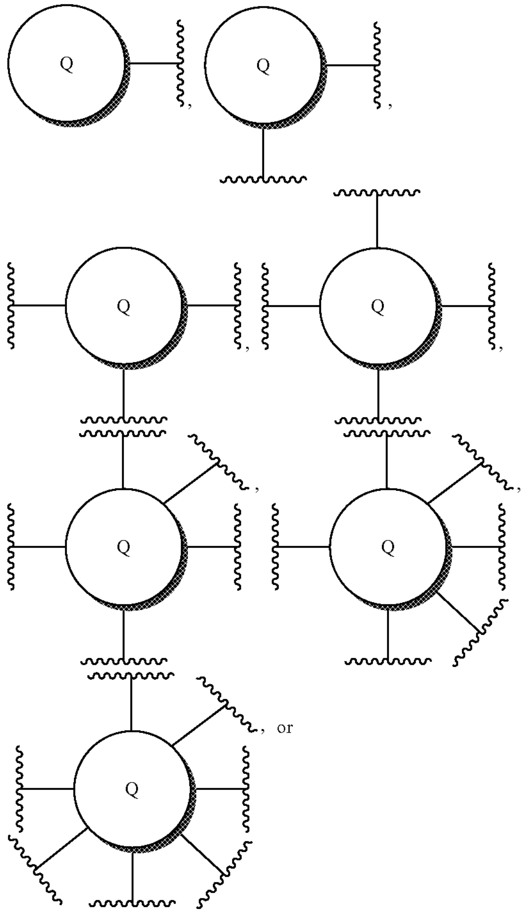

, or

-continued

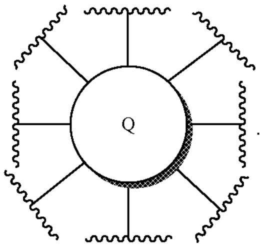

.

Examples of Q include, but are not limited to, $C_{1-6}$ alkyl,

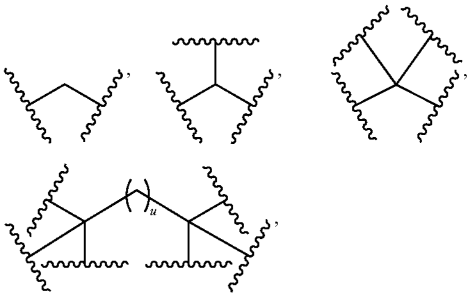

, or

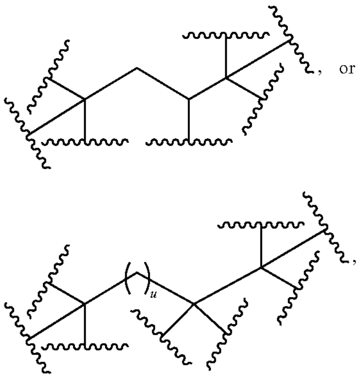

, where u is an integer from 1 to 12.

In particular embodiments, the multimeric polymeric cross-linker used to form the cross-linked polymer of formula (IV-i) or formula (IV-ii) has the structure of formula (IVa):

(IVa)

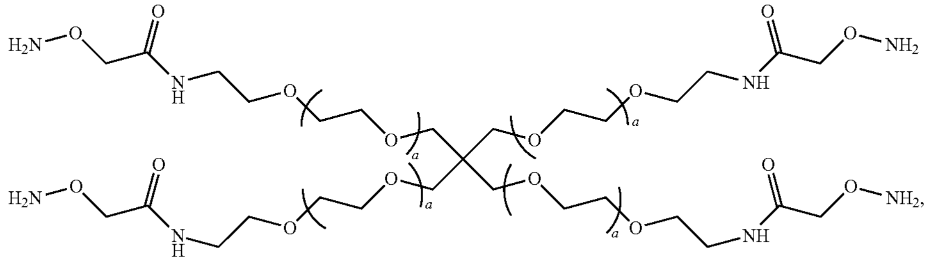

where a is an integer between 1 and 90 (e.g., between 6 and 40, between 10 and 40, between 15 and 40, between 6 and 60, or between 20 and 60). In some embodiments, a is about 29. In other embodiments, a is about 54.

In still other embodiments, the multimeric polymeric cross-linker used to form the cross-linked polymer of formula (IV-i) or formula (IV-ii) has the structure of formula (IVb):

(IVb)

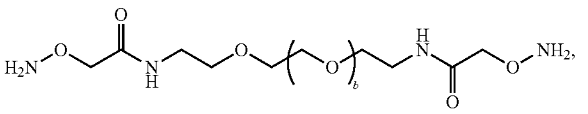

where b is an integer between 1 and 90 (e.g., between 6 and 40, between 10 and 40, between 15 and 40, between 6 and 60, between). In some embodiments, b is about 75.

In some embodiments, the multimeric polymeric cross-linker is conjugated to the hyaluronan polymer through at least one linkage group of formula (VIII-i) or formula (VIII-ii):

(VIII-i)

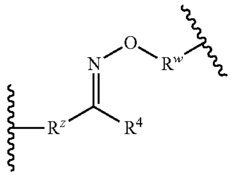

(VIII-ii)

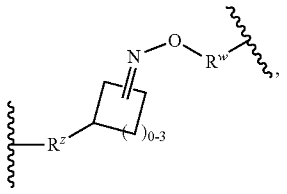

wherein $R^Z$, $R^4$, and $R^W$ are as defined above.

Hydrogel Formation

The cross-linked polymer of the invention can be prepared by mixing a compound of formulas (I) or (II) (e.g., the ketone-modified hyaluronan polymer) with a multimeric polymeric cross-linker bearing two or more terminal oxyamine groups. As described in Examples 6 and 7, the resulting hydrogels can have desirable biophysical properties (e.g., density) that allow for the precursor compositions to be mixed for use (i) as a vitreous substitute (e.g., vitreous hydrogel), or (ii) a three-dimensional hydrogel that supports growth of a physiologically relevant tissue when at least one cell is cultured in the three-dimensional hydrogel. The hydrogel precursor solution includes at least two hydrogel precursor components dissolved in the aqueous medium to form a hydrogel precursor solution for use as vitreous substitute or for forming a three-dimensional hydrogel that supports growth of physiologically relevant tissue, wherein the hydrogel includes at least: (i) a hydrogel precursor comprising ketone-modified hyaluronan (HAK); and (ii) oxime linkage with multimeric polymeric cross-linker. Optionally, additional agents, additives, buffers, or salts (e.g., to support cell growth or improve biocompatibility (e.g., nutrients for cell growth)) are included with one or both of the precursor solutions to produce a hydrogel having the desired properties and/or functionality. In some embodiments, the hydrogel further includes an extracellular matrix protein (e.g., collagen, fibronectin, vitronectin, and laminin). In particular embodiments, the extracellular matrix protein is reversibly or irreversibly chemically immobilized (e.g., via Schiff-base formation (e.g., between an amine on the protein and a ketone substituent on the HAK)).

Any suitable aqueous medium can be used as a solvent for the hydrogel precursor solution. In some embodiments, the aqueous medium comprises water. In some embodiments, the aqueous medium comprises saline (e.g., phosphate buffered saline (PBS) or Hank's balanced salt (HBS) solution). In some embodiments, the aqueous medium comprises a cell culture medium. It should be appreciated that any culture medium described herein could be used as the cell culture medium. Other suitable media would be apparent to the skilled artisan. In some embodiments, the aqueous medium comprises a sugar solution. In some embodiments, the aqueous medium comprises a solvent (e.g., DMSO).

The hydrogel precursor composition (e.g., solution) can be formulated with different concentrations of the components (e.g., ketone-modified hyaluronan, aldehyde-modified hyaluronan, or polymeric cross-linker (e.g., poly(ethylene glycol) tetra(oxyamine)). In preferred embodiments, the ratio of hyaluronan polymers (e.g., ketone-modified hyaluronan, aldehyde-modified hyaluronan, or a mixture thereof) to the cross-linker is 40-60%. The hydrogel precursor composition (e.g., solution) can further include addition a solution of extracellular matrix protein (e.g., collagen, fibronectin, vitronectin, laminin, or a mixture thereof).

Vitreous Substitutes

The vitreous humor is a clear gelatinous substance composed of collagen (types II, V/XI, and IX) and hyaluronic acid that occupies the space between the lens and the retina. As the eye ages the vitreous undergoes a transformation from a gel-like substance to a fluid-like substance. Accordingly, a need exists for better hydrogel compositions for use as vitreous substitute, e.g., for the treatment of retinal detachment in order to improve the quality of the lives of those afflicted by such conditions. The present disclosure relates to hydrogel compositions and their use, e.g., as vitreous substitute for the treatment of disorders, e.g., retinal detachment.

Retinal detachment is a disorder in which the retina in the eye peels away from its underlying layer of support tissue. Retinal detachment is a significant cause of vision loss, with an incidence of approximately 12 per 100,000 individuals in the US, approximately 38,000 surgeries per year. In severe cases of retinal detachment, patients must undergo a pars plana vitrectomy in order to remove the vitreous within the eye and replace it with an intraocular tamponade to re-attach the retina. The most common tamponades are gas and oils. Gas tamponades require face-down positioning in cases of inferior detachments and are resorbed. In contrast, oil replacements (e.g., silicone oil) do not degrade and must be removed with additional surgery. Natural biomaterials such as hyaluronan and collagen have been explored as vitreous substitutes, but to the best of our knowledge, all studies to date have shown limited applicability due to lack of stability of the biomaterial.

Initial detachment may be localized or broad, but without rapid treatment the entire retina may detach, leading to vision loss and blindness. In severe cases to re-attach the retina patients must undergo a pars plana vitrectomy followed by laser or cryopexy to re-attach the retina and finally the vitreous cavity is filled with a tamponade. The most common tamponades currently used are gas, perfluorocarbon liquids, and silicone oils.

The most common tamponades currently used are gas, perfluorocarbon liquids, and silicone oils that can only be used temporarily and they come with significant drawbacks. Gas tamponades may limit the patient from air travel, and require face-down positioning in cases of inferior detachments but have the advantage of being spontaneously resorbed. This has led to the development of heavier than liquid replacements that do not degrade, can result in ocular hypertension and often require removal with an additional surgery. The ideal vitreous substitute will be capable of being left in the eye for a long time, undergo degradation to avoid surgical resection and will demonstrate biocompatibility.

Synthetic polymers such as poly(methacrylamide), poly (methacrylate), poly(ethylene glycol) or poly(vinyl alcohol) have all been formulated as hydrogels to treat retinal detachment. (Hayashi et al., Fast-forming hydrogel with ultralow polymeric content as an artificial vitreous body. Nature Biomedical Engineering, 1:0044 (2017); Liang et al., Synthesis and characterization of in situ forming anionic hydrogel as vitreous substitutes. Journal of biomedical materials research Part B, Applied biomaterials, 105:977-88(2017)). Often these vitreous substitutes use small molecules to crosslink polymers, require potentially harmful UV light or use functional groups unstable in the presence of air. However, these can be too stable which has caused complications in 8.5% of patients treated with MIRAgel (co-poly(methylacrylate-2 hydroxyethyl acrylate)) after 7-11 years attributed to hydrolysis which caused the hydrogel buckle to swell and must be removed. In the case of poly(alkylimide) hydrogels it was found to induce severe retinal damage.

Natural biomaterials such as hyaluronan (HA) and collagen have the ability to be degraded and been explored as alternative retinal tamponades, but often require chemical crosslinking to avoid clearance. References to date have shown limited stability and often have lower densities than water as summarized in Table 1 (Su et al., Biomacromolecules, 16:3093-102 (2015); Schnichels et al., PloS one. 12:e0172895 (2017); Schramm et al., Invest. Ophthalmol. Vis. Sci. 53:613-21 (2012); Pruett et al., Archives of Ophthalmology, 88:540-3 (1972)).

TABLE 1

Compositions of hydrogels used as vitreous substitutes in rabbit models.

| Composition | Crosslinking | Content* | Model | Stability (days) |
|---|---|---|---|---|
| Hyaluronan and collagen | None | 2.0 wt % COL<br>1.0 wt % HA | Pigmented rabbits | 5.7 COL<br>2.1 HA[1]<br>8.4 COL + HA |
| Thiol-modified hyaluronan | Disulfide | 1.0 or 2.2 wt % HA | Chinchilla bastard rabbits | Unconfirmed[2] |
| Glycidyl methacrylate-modified hyaluronan and N-vinyl-pyrrolidinone (NVP) | UV irradiation | 1.0 wt % HA<br>5.0 wt % NVP | Rabbits | 42 |
| Healaflow Hyaluronan and 1,4-butanediol diglycidyl ether (BDDE) | Epoxide-ring opening | 2.25 wt % HA | Pigmented Rabbits | 14 |
| Aldehyde-modified hyaluronan and adipic acid dihydrazide | Hydrazone | 4.8 wt % | New Zealand white rabbits | Unconfirmed[3] |
| PanaceaGel SPG-178 | Self-assembling peptide | 0.1 wt % Peptide | New Zealand white rabbits | Unconfirmed[4] |
| Poly(ethylene glycol) (PEG) thiol and maleimide | Thiol-maleimide | 0.7 wt % PEG | Dutch pigmented rabbits | 410 |
| Poly(vinyl alcohol) (PVA) | γ irradiation | 3% PVA | Rabbits | 180 |

*Hyaluronan (HA), Collagen (COL).

TABLE 1-continued

Compositions of hydrogels used as vitreous substitutes in rabbit models.

| Composition | Crosslinking | Content* | Model | Stability (days) |
| --- | --- | --- | --- | --- |

[1]Reported stability is the half-life.
[2]Study duration was 28 days.
[3]Study duration was 21 days.
[4]Study duration was 84 days.

As described in Example 6, oxime click chemistry is used to generate our vitreous gel with a clinically relevant gelation time (less than 1 hour) with stable aldehyde and ketone-substituted HA to crosslink with the oxyamine functionality on poly(ethylene glycol) (PEG) at pH 7-7.4. An oxime hydrogel was engineered using a click-crosslinked system including HA-aldehyde, HA-ketone, and PEG-oxyamine. Gelation was controlled by the concentration of the functional groups, which were tuned from minutes to hours after mixing and before injection into the eye (FIG. 1). The physical properties of this hydrogel were characterized by evaluating in vitro with primary photoreceptors and in vivo with New Zealand White rabbits to characterize the stability and biocompatibility over the course of 56 days. Together, these studies establish oxime-crosslinked HA as a potential vitreous substitute for the treatment of retinal detachment (e.g., injecting vitreous substitute into eye in subject in need thereof, injecting vitreous substituted into synovial cavity in subject in need thereof, or injecting vitreous substituted intraarticularly).

3D Cell Culture

Three-dimensional (3D) cultures have proven invaluable for expanding human tissues for research or clinical applications. For both applications, 3D cultures are most useful when they (1) support the outgrowth of tissues from primary human cells that have not been immortalized through extensive culture or viral infection, and (2) include defined, physiologically-relevant components.

As described in Example 7, HA-oxime gels were synthesized in the presence of cells to produce 3D cell cultures.

Optionally, additional agents, additives, buffers, or salts (e.g., to support cell growth or improve biocompatibility) are included with one or both of the precursor solutions to produce a hydrogel having the desired properties and/or functionality. In particular embodiments, the mixing is performed in the presence of an extracellular matrix protein. Generally, extracellular matrix proteins are selected based on the composition of extracellular matrix proteins present in vivo in a tissue of interest. Exemplary extracellular matrix proteins include, without limitation, collagen, fibronectin, laminin, elastin, and fragments and subunits thereof. In some embodiments, the extracellular matrix protein is laminin. Any suitable form of laminin can be used as the first hydrogel precursor component. In some embodiments, the type of laminin used is based on the laminin present in vivo for the type of physiologically relevant tissue of interest. In some embodiments, the laminin comprises a soluble form of laminin. In some embodiments, the laminin comprises isolated laminin. In some embodiments, the laminin comprises recombinant laminin. In some embodiments, the laminin comprises human laminin. In some embodiments, the laminin comprises mouse laminin. In some embodiments, the laminin comprises a fragment or variant of any of the above forms of laminin. In some embodiments, the laminin is not functionalized. In some embodiments, the laminin is not chemically modified to be conjugated to the hydrogel via a linker. In further embodiments, the laminin can form reversible bonds (e.g., via Schiff-base formation (e.g., between an amine on the protein and a ketone substituent on the HAK)).

Articular Joint Repair

Hyaluronan has been used to treat osteoarthritis but is rapidly cleared without chemical modification or crosslinking. As described in Example 13, HA-oxime gels were prepared to be injected into the synovial cavity to preserve joints.

Cell Delivery In Vivo

Ensuring cell survival and localized delivery is challenging for in vivo applications without using a matrix to support the cells. As described in Example 14, HA-oxime gels were prepared to be injected with cells to promote survival and growth in vivo.

EXAMPLES

Example 1—Synthesis of Ketone-Modified Hyaluronan (HA-Ketone or HAK)

This example describes the synthesis of ketone-modified hyaluronan (HAK).

Background: The traditional route to synthesize hyaluronan with an aldehyde functional group is often done with strong oxidants. This strategy does not generate a ketone functional group, so a different approach is needed. Additionally, the synthesis of hyaluronan with aldehyde groups typically require hyaluronan to include a protecting group that is stable and requires sustained concentrated acid to remove at a later step, which causes the molecular weight of the hyaluronan to decrease.

Methods: Ketone-modified hyaluronan (HAK) was synthesized as described in the schemes below.

First, compound 1-c was synthesized according to the following scheme:

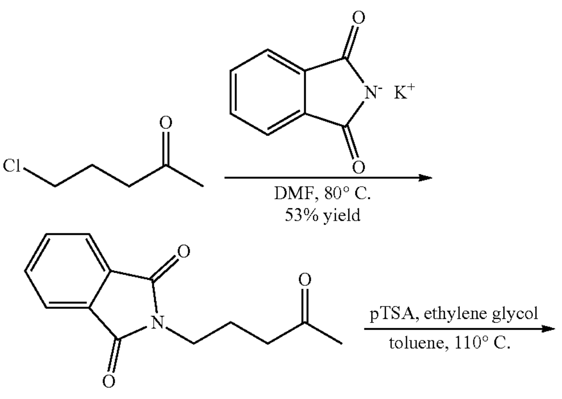

1-a

-continued

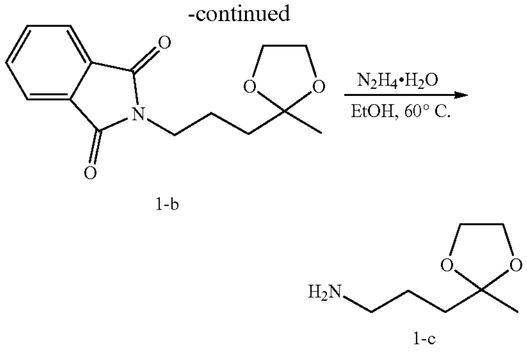

1-b 1-c

Then compound 1-c was then reacted with hyaluronan to prepare ketone-modified hyaluronan as shown in the scheme described below:

dried over magnesium sulfate resulting in phthalimide modified pentanone (compound 1-a) as a white solid (27.2 g, 53% yield).

$^1$H NMR ($CD_3OD$, 400 MHz) 1.89-1.96 (m, 2H), 2.14 (s, 3H), 2.59 (t, J=8 Hz, 2H), 3.69 (t, J=8 Hz, 2H), 7.83 (m, 4H).

$^{13}$C NMR ($CD_3OD$, 100 MHz) 23.5, 29.83, 38.1, 41.2, 124.1, 133.3, 135.3, 169.9, 210.6.

(HRMS ESI): $[M]^+$ calcd. For $C_{13}H_{13}NO_3$: 232.0968; found 232.0974.

Step 2: Phthalimide modified pentanone (compound 1-a) (27.2 g, 118 mmol) was suspended in toluene (600 mL) and mixed with ethylene glycol (37 g, 59 mmol) and p-toluenesulfonic acid monohydrate (1.12 g, 5.9 mmol) and heated to 110° C. for 6 hours. The aqueous fraction was collected with Dean-Stark apparatus and fresh ethylene glycol (37 g, 59 mmol) was added. The organic fraction was washed with saturated sodium bicarbonate (3×200 mL). The organic fraction was washed with brine and dried over magnesium

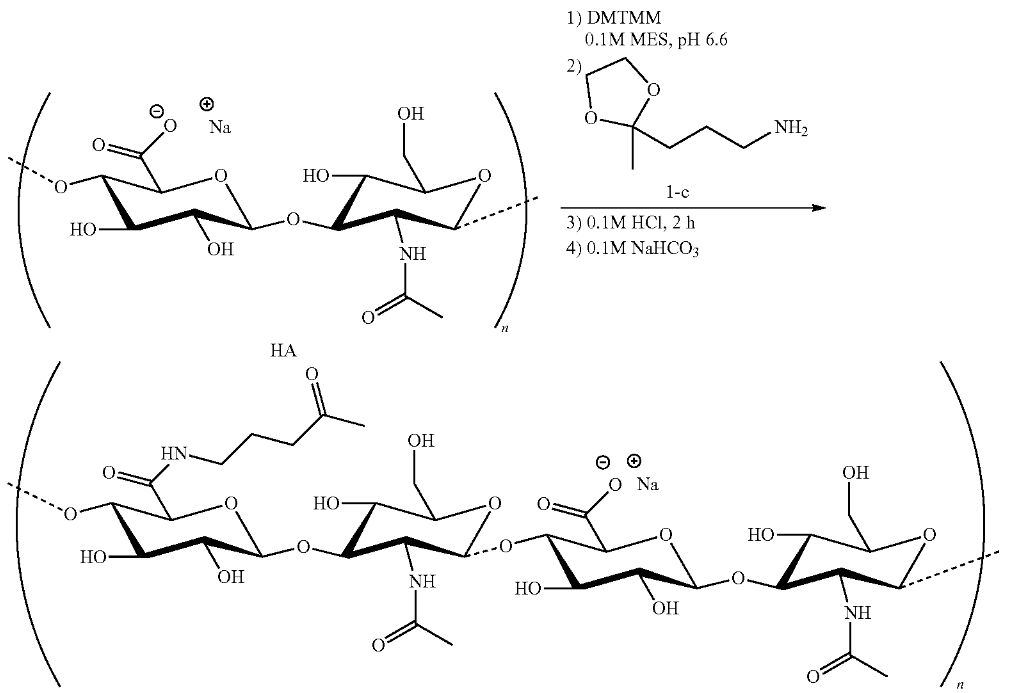

HA

HA-ketone

The procedures for the synthetic steps described in the schemes above are detailed below.

Synthesis of Compound 1-c

Step 1: 5-chloro-2-pentanone was distilled before use at 135° C. under reduced pressure resulting in a colorless oil.

To a solution of potassium phthalimide (41.3 g, 0.223 mol) dissolved in dimethylformamide (DMF) (130 mL), 5-chloro-2-pentanone (26.9 g, 0.223 mol) was added. The reaction was heated at 80° C. for 24 hours and then cooled to room temperature. The reaction mixture was added to ice water (750 mL) and stirred for 1 hour. The precipitate was collected by filtration and was washed with cold water (500 mL). The crude material was extracted with toluene (600 mL) heated until dissolved and washed with sodium hydroxide solution (1 M, 3×200 mL) and brine. The product was sulfate. The solution was concentrated, suspended in ethanol and evaporated to remove ethylene glycol phthalimide pentanone. A white solid was obtained (29.9 g, quantitative yield).

$^1$H NMR ($CD_2Cl_2$, 400 MHz) 1.26 (s, 3H), 1.65-1.67 (m, 2H), 1.71-1.77 (m, 2H), 3.67 (t, J=8 Hz, 2H), 3.89 (m, 4H), 7.73 (m, 2H), 7.83 (m, 2H).

$^{13}$C NMR ($CD_2Cl_2$, 100 MHz) 23.8, 24.3, 36.9, 38.5, 65.26, 123.5, 123.9, 134.4, 134.8, 168.0.

(HRMS ESI): $[M+H]^+$ calcd. For $C_{15}H_{18}NO_4$: 276.1237; found 276.1236.

Step 3: An aqueous solution of hydrazine hydrate (50% weight) (15.2 g, 152 mmol) and ethylene glycol phthalimide pentanone (compound 1-b) (29.9 g, 109 mmol) were dissolved in ethanol (300 mL) and heated to 65° C. for 2 hours. The solution was cooled and potassium hydroxide (7.38 g, 131 mmol) added in ethanol (40 mL) overnight resulting in a white precipitate, which was collected by suction filtration through a pad of Celite. The filtrate was concentrated in vacuo and the crude was again filtered and washed with chloroform. The filtrate was again concentrated and filtered through Celite® before being purified by vacuum distillation at 15 mbar at 87° C. resulting in amino ketal (compound 1-c) as a colorless oil (9.19 g, 61% yield).

$^1$H NMR ($CD_2Cl_2$, 400 MHz) 1.28 (s, 3H), 1.44-1.51 (m, 2H), 1.60-1.64 (m, 2H), 2.64 (t, J=8 Hz, 2H), 3.87-3.89 (m, 2H), 3.90-3.91 (m, 2H), 5.33 (s, 1H).

$^{13}$C NMR ($CD_2Cl_2$, 100 MHz) 24.1, 28.9, 37.0, 42.9, 61.2, 110.4.

(HRMS ESI): $[M+H]^+$ calcd. For $C7H16NO_2$: 146.1178; found 146.1176.

Synthesis of HA-Ketone

Steps 1 and 2: Sodium hyaluronate (1.00 g, 242 kDa) was dissolved in 2-(N-morpholino)ethanesulfonic acid (MES) buffer (100 mL, 0.1 M in water, pH 6.6) and stirred with DMTMM (4-(4,6-dimethoxy-1,3,5-triazin-2-yl)-4-methylmorpholinium chloride) (1.2 g, 4.36 mmol). After 30 minutes, 3-(2-methyl-1,3-dioxolan-2-yl)propan-1-amine (compound 1-c; 0.36 g, 2.5 mmol) was added dropwise and stirred for 48 hours. The solution was dialyzed in 0.1 M NaCl using methyl cellulose dialysis membrane (12-14 kDa molecular weight cut-off) for 48 hours followed by distilled water for 24 hours. The purified solution was lyophilized and was analyzed by $^1$H NMR in deuterium oxide to determine ketal substitution (42%).

Steps 3 and 4: Ketal-substituted hyaluronan (HA-ketal) was dissolved in distilled water (1.0% w/v, HA-ketal) and dialyzed against 0.2 M HCl for 2 hours. The solution was changed to pH 4.0 with a sodium bicarbonate solution (0.1 M) overnight and then dialyzed against distilled water for 48 hours. The dialysate was sterile filtered (0.22 μm, Millipore) and lyophilized resulting in 0.88 g of a white fluffy solid. The degree of substitution was analyzed by $^1$H NMR in deuterium oxide to be 42% ketone-modified.

Example 2—Synthesis of Alexa Fluor 647/Ketone-Modified Hyaluronan (HAK-647)

This example describes the synthesis of Alexa Fluor 647/ketone-modified hyaluronan. Alexa Fluor® 647 is a useful fluorescent dye that can be conjugated to molecules or antibodies.

Methods: Alexa Fluor® 647/ketone-modified hyaluronan was synthesized by dissolving sodium hyaluronate (1.00 g, 242 kDa) in 2-(N-morpholino)ethanesulfonic acid (MES) buffer (100 mL, 0.1 M in water, pH 6.6) and stirred with DMTMM (1.21 g, 4.36 mmol). After 30 minutes, 3-(2-methyl-1,3-dioxolan-2-yl)propan-1-amine (0.36 g, 2.5 mmol) was added dropwise and stirred for 48 hours. The solution was dialyzed in 0.1 M NaCl using methyl cellulose dialysis membrane (12-14 kDa molecular weight cut-off) for 48 hours followed by distilled water for 24 hours. The purified solution was lyophilized and was analyzed by $^1$H NMR in deuterium oxide to determine ketal substitution (40-45%). Ketal-substituted hyaluronan (HA-ketal) (500 mg) was dissolved in 0.1 M MES buffer, pH 6.6 (50 mL) and stirred with DMTMM (0.346 g, 1.25 mmol). After 30 minutes, Alexa Fluor 647 hydrazide (3 mg, dissolved in DMSO) was added Alexa Fluor 647/ketal-substituted hyaluronan (HA-ketal) was dissolved in distilled water (1.0% w/v, HA-ketal) and dialyzed against 0.2 M HCl for 2 hours. The solution was changed to pH 5.0 with a sodium bicarbonate solution (0.1 M) overnight and then dialyzed against sodium phosphate buffer pH 5.0 three times before lyophilisation. The degree of substitution was analyzed by $^1$H NMR in deuterium oxide to be 40-45% ketone-modified and the fluorophore concentration was determined by generating a standard curve of Alexa Fluor 647 hydrazide with 10 mg·mL$^{-1}$ HA and compared to HAK-647 by measuring the absorbance at 650 nm with a NanoDrop instrument.

Example 3—Synthesis of Aldehyde-Substituted Hyaluronan (HA-Aldehyde or HAA)

This example describes the synthesis of Aldehyde-substituted hyaluronan (HAA).

Methods: Aldehyde-modified hyaluronan (HAA) was synthesized as described in the scheme below.

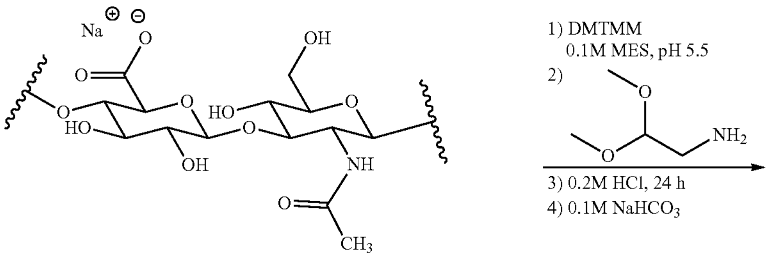

Sodium Hyaluronate (242 kDa)

-continued

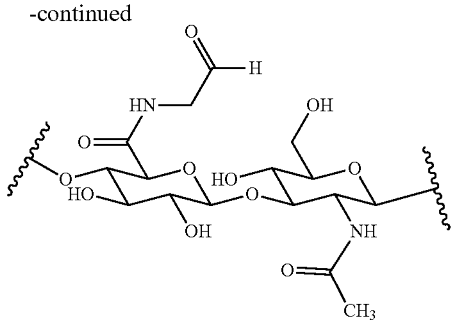

HA-aldehyde

The procedures for the synthetic steps described above are detailed below.

Steps 1 and 2: Sodium hyaluronate (1.00 g, 242 kDa) was dissolved in MES buffer (120 mL, 0.1 M in water, pH 5.5), and stirred with DMTMM (0.69 g, 2.5 mmol). After 15 minutes, aminoacetaldehyde dimethyl acetal (105 mg, 1.0 mmol) was added dropwise and stirred at 60° C. After 24 hours the solution was dialyzed in 0.1 M NaCl using methyl cellulose dialysis membrane (12-14 kDa molecular weight cut-off) for 48 hours followed by distilled water for 24 hours. The purified solution was lyophilized to determine acetal substitution (43% acetal-modified).

Steps 3 and 4: Acetal-substituted hyaluronan (HA-acetal) was dissolved in distilled water and dialyzed against 0.2 M HCl for 48 hours. The solution was changed to pH 4.0 with a sodium bicarbonate solution (0.1 M) overnight and then dialyzed against distilled water for 48 hours. The dialysate was sterile filtered (0.22 μm, Millipore) and lyophilized, resulting in a white fluffy solid.

Example 4—Synthesis of Star-PEG-Tetra(Oxyamine) ($PEGOA_4$) Cross-Linker

This example describes the synthesis of ketone-modified hyaluronan (HAK).

Methods: Star-PEG-tetra(oxyamine) ($PEGOA_4$) was synthesized as described in the scheme below.

The procedures for the synthetic steps described above are detailed below.

Steps 1 and 2: (Boc-aminooxy)acetic acid (0.43 g, 2.3 mmol) and N,N'-diisopropylcarbodiimide (DIC) (0.57 mL, 4.6 mmol) were dissolved in 25 mL of dichloromethane (DCM) at 0° C. under nitrogen. After 1 hour, PEG-tetramine (1.0 g, 5250 Da) was added followed by N,N-diisopropylethylamine (1.18 mL, 9.14 mmol), and the reaction was stirred for 48 hours at room temperature. DCM was removed in vacuo and the crude was stirred with distilled water and filtered through a 0.22 μm filter to remove the N,N-diisopropylurea byproduct. The filtrate was then dialyzed using methyl cellulose dialysis membrane (1,000 Da molecular weight cut-off) in sodium chloride (0.1 M) for 24 hours followed by distilled water for 48 hours before being lyophilized. Boc-protected Star-PEG-tetra(oxyamine) was obtained as a white solid and characterized for substitution by $^1H$ NMR.

Steps 3 and 4: Boc-protected Star-PEG-tetra(oxyamine) was deprotected by dialysis in hydrochloride acid (0.2 M) for 48 hours followed by distilled water for 48 hours. The dialysate was lyophilized to give star-PEG-tetra(oxyamine) ($PEGOA_4$), which was obtained as a white crystalline solid (0.95 g, 46.1% yield). $^1H$ NMR in $CDCl_3$ was performed to determine the completion of deprotection. The solution was changed to pH 4.0 with a sodium bicarbonate solution (0.1 M) overnight and then dialyzed against distilled water for 48

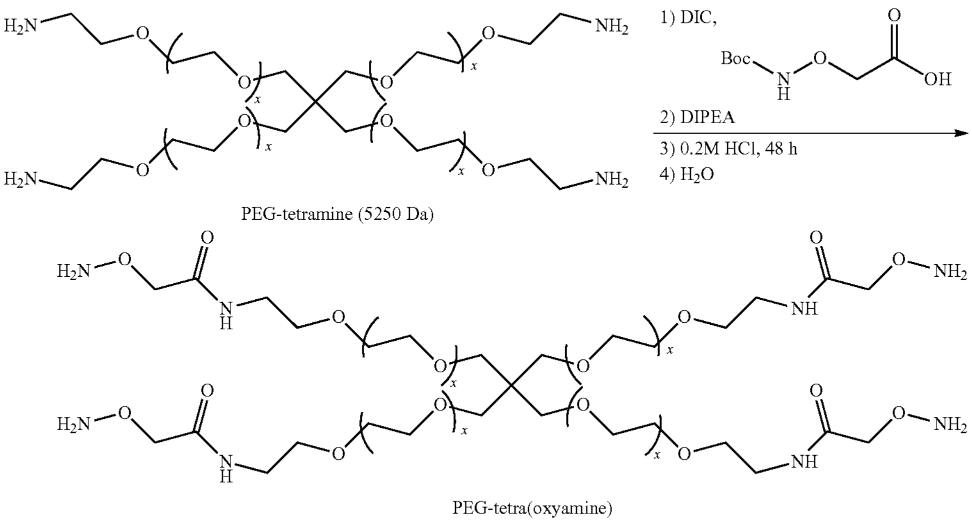

PEG-tetramine (5250 Da)

PEG-tetra(oxyamine)

hours. $PEGOA_4$ was dissolved in PBS and sterile filtered (0.22 μm, Millipore) for cell culture.

Example 5—Synthesis, Formulation, and Characterization of a Vitreous Substitute Hydrogel This example describes the synthesis of vitreous hydrogel including HAK, HAA, and $PEGOA_4$.

Methods: The methods for the synthesis, formulation, and characterization of vitreous hydrogel are described below.

Endotoxin Removal and Detection: The HA used is produced by bacteria and rabbit eyes and sensitive to endotoxins (Buchen et al., "Rabbit ocular reactivity to bacterial endotoxin contained in aqueous solution and ophthalmic viscosurgical devices," Ophthalmology, 119:e4 (2012)). Therefore, the individual components of the HA-oxime hydrogel were treated with γ phase alumina oxide and achieved an endotoxin concentration of 0.4±0.1 $EU \cdot mL^{-1}$, which is within an acceptable range of 0.08-0.60 $EU \cdot mL^{-1}$ for New Zealand White rabbit eyes (Buchen et al., "Rabbit ocular reactivity to bacterial endotoxin contained in aqueous solution and ophthalmic viscosurgical devices," Ophthalmology, 119:e4 (2012)). The alumina oxide was separated from the polymers by centrifugation followed by sterile-filtration of the supernatant to provide sterile polymer. To remove endotoxins, each of HAK and HAA were dissolved in $ddH_2O$ at 25 $mg \cdot mL^{-1}$ and $PEGOA_4$ at 109.5 $mg \cdot mL^{-1}$. Alumina oxide γ phase was added at 2 wt % and samples were shaken for 24 hours at room temperature. Samples were centrifuged at 2000 rpm to force the alumina to settle. The supernatant was sterile filtered after dilution in $ddH_2O$ through a 0.22 μM filter. Samples were then lyophilized. Endotoxin concentrations were determined using a Genscript chromogenic kit by dissolving untreated and alumina treated HAK and HAA at 25 $mg \cdot mL^{-1}$ and $PEGOA_4$ at 109.5 $mg \cdot mL^{-1}$ in PBS. Standard endotoxin solutions were prepared following the kit protocol and were quantified using a NanoDrop instrument by measuring absorbance at 545 nm. A linear regression was calculated to determine the concentration of endotoxins in HAK 0.022±0.009 $EU \cdot mg^{-1}$, HAA 0.01±0.01 $EU \cdot mg^{-1}$ and $PEGOA_4$ 0.003±0.002 $EU \cdot mg^{-1}$.

Oxime Gel Vitreous Substitute: Endotoxin reduced HAK and HAA polymers were dissolved at 25 $mg \cdot mL^{-1}$ in PBS and incubated at 37° C. for 2 hours to dissolve. Endotoxin reduced $PEGOA_4$ was dissolved at 109.5 $mg \cdot mL^{-1}$ in 0.1 M phosphate buffer pH 7.4 and sterile filtered. HAK was combined with HAA to give a final polymer concentration of 10.0 $mg \cdot mL^{-1}$ and 2.5 $mg \cdot mL^{-1}$, respectively when mixed with 9.48 $mg \cdot mL^{-1}$ of $PEGOA_4$. For in vivo studies the polymers were loaded in syringes and combined at a volume ratio of 4:1 (HAK+HAA):$PEGOA_4$, which were mixed through a syringe to syringe connector nine times before being injected.

Results: The results of the formulation of vitreous substitute hydrogel are described below.

Figure 2:
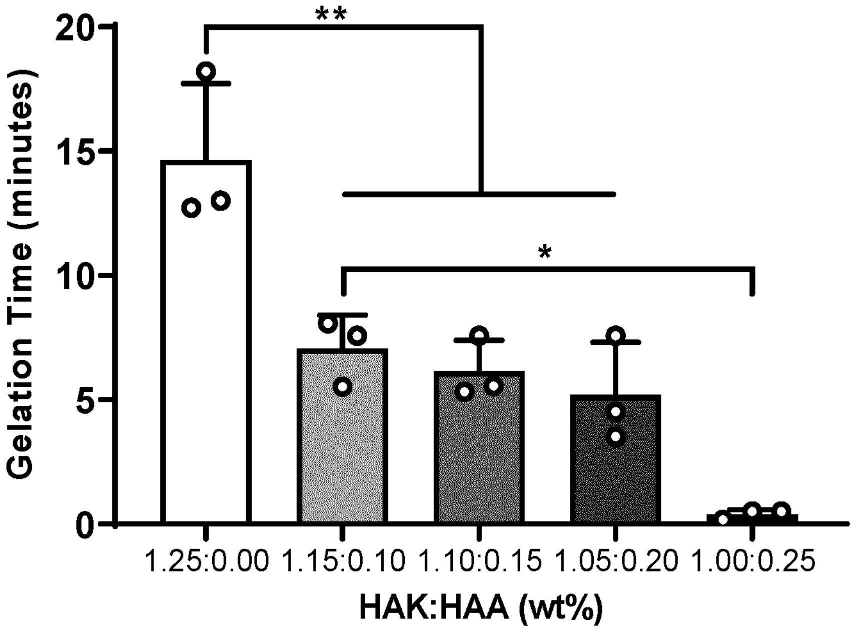
FIG. 2 is a graph illustrating the gelation time for formulations of HAK, HAA, and $PEGOA_4$ which decreases with an increased weight percent of HAA measured by rheology (n=3, mean+standard deviation, *$p<0.05$, **$p<0.01$ one-way ANOVA Tukey's post hoc test).
Figure 3:
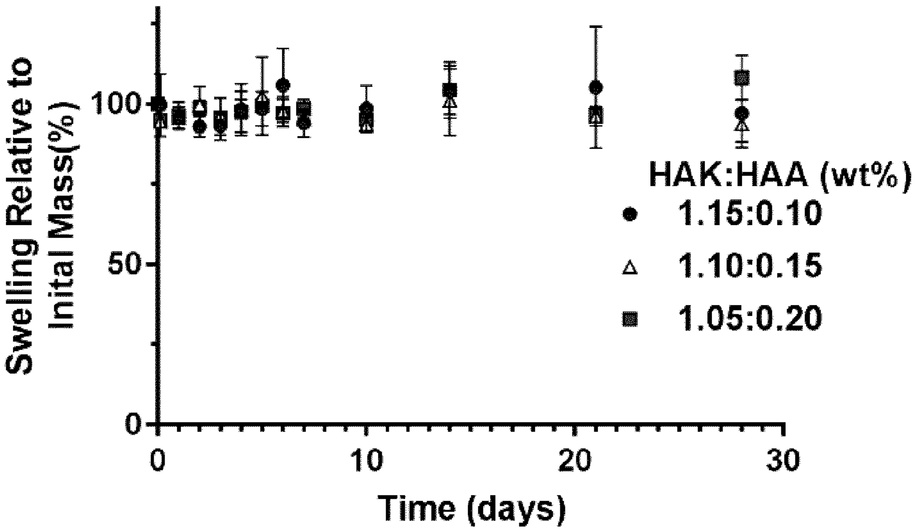
FIG. 3 is a graph illustrating the swelling stability of HA-oxime hydrogels over 28 days in balanced saline solution is minimal as measured by change in mass relative to initial hydrogel mass (n=3 for 1.15:0.10; n=5 for 1.10:0.15; n=4 for 1.05:0.20, mean±standard deviation).
Figure 4:
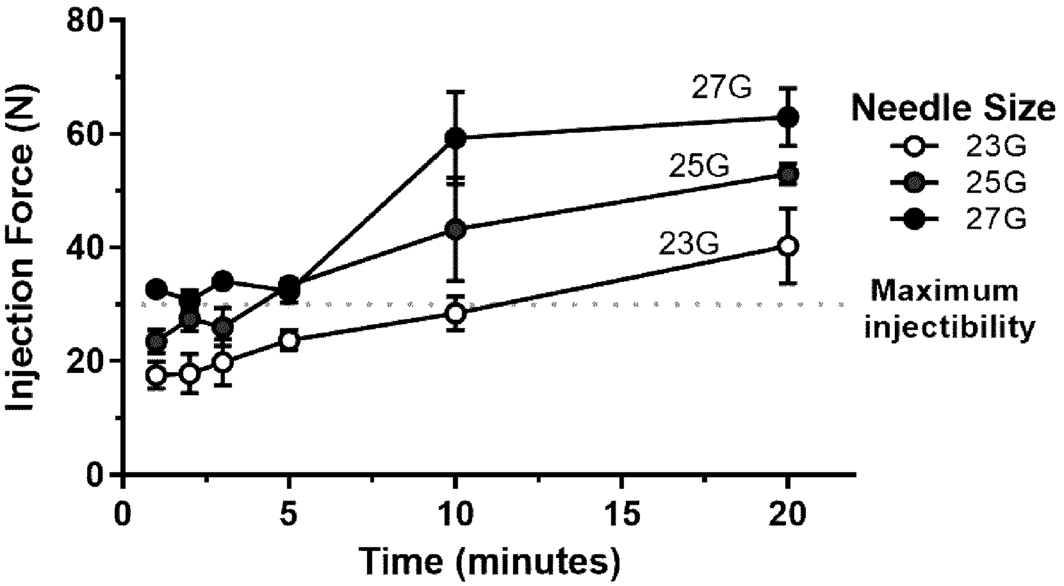
FIG. 4 is a graph illustrating the injectability of HA-oxime hydrogel (1.05:0.20 HAK:HAA) through a 23 Ga, 25 Ga and 27 Ga needle at room temperature. The gel is injectable by hand though a 23 Ga needle over 10 minutes and 25 Ga needle over 5 minutes (n=3, mean±standard deviation).

Formulation of HA-oxime vitreous substitute hydrogel: The gelation of the HA-oxime system (FIG. 1) was evaluated by varying the ratio of HAK to HAA at constant polymer content (1.25 wt %) with 0.85 wt % $PEGOA_4$ and a molar ratio of 0.5 oxyamine to (aldehyde+ketone). Gelation was faster with increased HAA, from 15±3 min to 0.4±0.2 min, as extrapolated from the intersection of storage and loss moduli (FIG. 2). The hydrogels with 0.10-0.20 wt % HAA were stable during in vitro swelling experiments with balanced saline solution (BSS) used for vitrectomy procedures and remained between 94 and 108% the initial mass over 28 days (FIG. 3). These 1.25 wt % HA and 0.95 wt % PEG HA-oxime hydrogels are more stable than higher polymer content 5 wt % PEG hydrazone hydrogels which degraded by 6 days in vitro (Boehnke et al., "Imine Hydrogels with Tunable Degradability for Tissue Engineering," Biomacromolecules, 16:2101 (2015)). Changes in hydrogel mass can be attributed to hydrolysis of either the HA backbone or the oxime linkage (Kalia et al., "Hydrolytic stability of hydrazones and oximes," Angew. Chem. Int. Ed. Engl., 47:7523 (2008)) and are minimal over the first month. To test injectability of HA-oxime gels, HAK and HAA were mixed with $PEGOA_4$ using a syringe coupler prior to injection. Solutions of 1.05:0.20 HAK:HAA, wt %/wt % were readily injectable by hand through 23 and 25 gauge needles typically used in surgery (FIG. 4). Importantly, the mixing and injection processes are both rapid in combination with the controlled gelation to enable injection into the vitreous cavity.

Figure 5A:
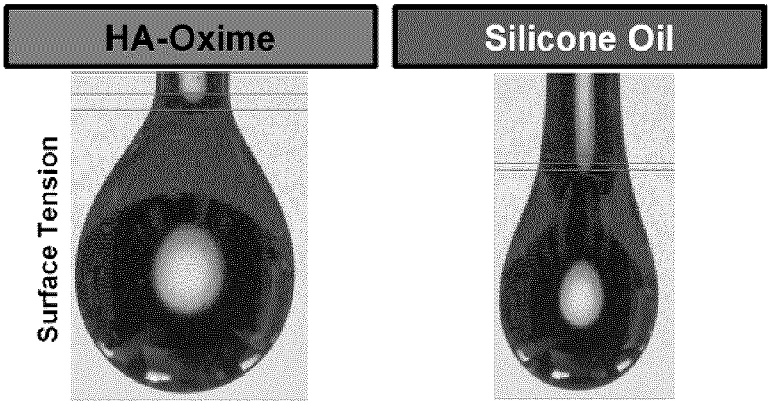
FIG. 5A and FIG. 5B illustrate the characterization of HA-oxime hydrogel surface tension.
Figure 5B:
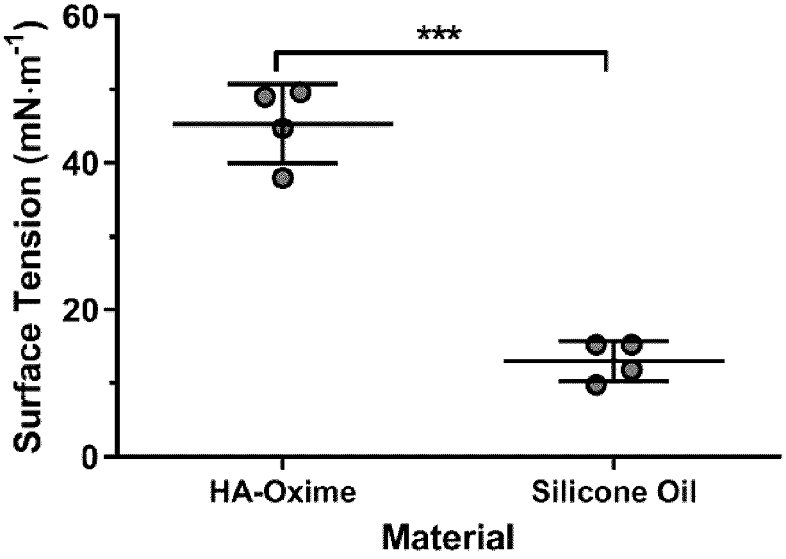
Figure 6A:
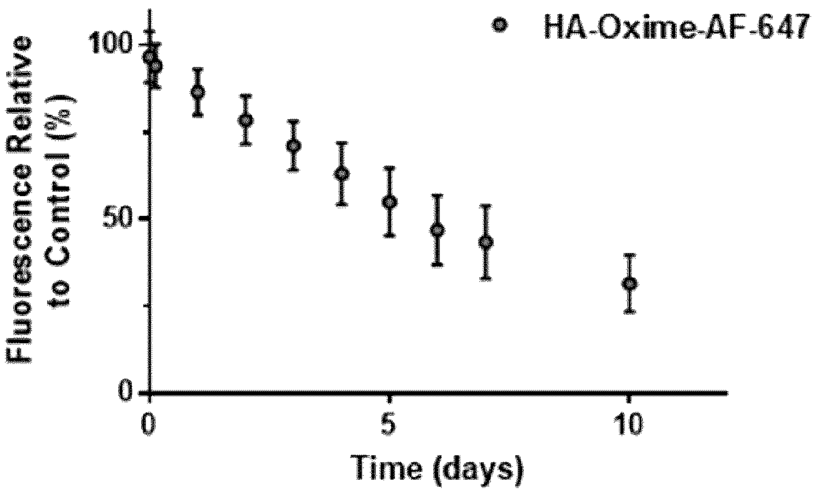
FIG. 6A and FIG. 6B illustrate the transparency of HA-oxime hydrogels with enzymatic degradation.
Figure 6B:
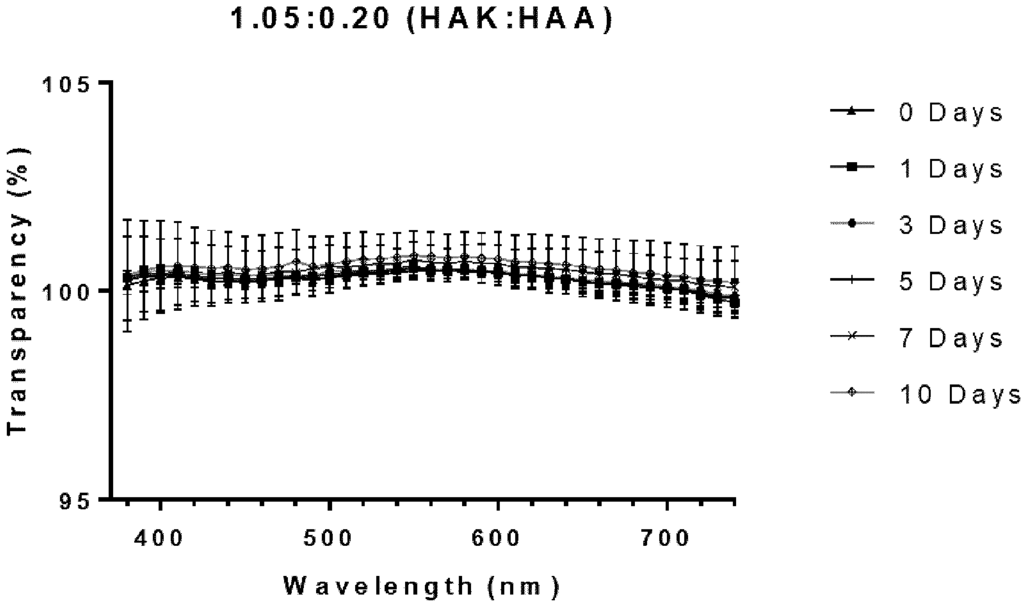

Physical properties of the HA-oxime vitreous substitute: The HA-oxime hydrogel was designed to match the properties of the native vitreous and compared these to silicone oil in terms of density, refractive index, transparency and surface tension. The density of the HA-oxime hydrogel is 1.01±0.05 $g \cdot mL^{-1}$, which is similar to the density of native vitreous (1.01 $g \cdot mL^{-1}$) and higher than the density of silicone oil (0.97 $g \cdot mL^{-1}$). Thus, our HA-oxime hydrogel should fill the vitreous whereas the silicone oil would float. While the latter can be overcome with the use of dense intraoperative perfluorocarbon liquids, these are limited by retinal toxicity if left more than 2 weeks (Li et al., "Effects of perfluorooctane on the retina as a short-term and small amounts remnant in rabbits," International Journal of Ophthalmology, 12:381 (2019); Stolba et al., "The effect of specific gravity of perfluorocarbon liquid on the retina after experimental vitreous substitution," Graefes Arch Clin Exp Ophthalmol, 242:931 (2004)). The refractive index of the HA-oxime hydrogel is 1.356±0.002, which is similar to the native vitreous (1.334) due to the high water content in both the HA-oxime hydrogel and the vitreous whereas silicone oil has a higher refractive index (1.404). Silicone oil is known to migrate beyond the vitreous chamber and emulsify over time, which reduces transparency, causing blurred vision. The surface tension of the HA-oxime gel was characterized and compared to the surface tension of silicone oil (FIG. 5A). The surface tension of HA-oxime is significantly higher (45±5 $mN \cdot m^{-1}$) than that of silicone oil (13±3 $mN \cdot m^{-1}$), which suggests that the HA-oxime hydrogel will neither migrate though retinal tears nor into the anterior chamber (FIG. 5B). An advantage of using an HA hydrogel is its natural biodegradation with hyaluronidase in the vitreous (Schwartz et al., "Human vitreous hyaluronidase: isolation and characterization," Curr. Eye Res. 15:1156 (1996). To mimic hydrogel biodegradation, samples were treated with hyaluronidase and measured the transparency over 10 days (FIG. 6A). The transparency of the hydrogel was maintained during degradation, suggesting that vision would not be impacted in vivo during degradation (FIG. 6B).

Example 6—Stability and Compatibility of Vitreous Substitute Hydrogels

This example describes in vitro cell culture experiments using retinal pigmented epithelial cells, photoreceptors, and retinal explant compatibility studies conducted in rabbits with vitreous substitute hydrogel formulations described in a previous example.

Methods: The methods for the in vitro experiments and in vivo rabbit surgeries are described below.

Retinal Pigmented Epithelial Cell Compatibility: RPE cells were differentiated from the CA1 human embryonic stem cell line following established procedure (Parker, J.; Mitrousis, N.; Shoichet, M. S., "Hydrogel for Simultaneous Tunable Growth Factor Delivery and Enhanced Viability of Encapsulated Cells in Vitro," Biomacromolecules, 17:476 (2016)). RPE cells were dissociated with trypsin and plated at 5,000 cells per well in MEM/F-12, DMEM/F-12 containing 10% fetal bovine serum on 0.4 μm transparent transwells (Corning Life Sciences; catalogue number: C353095) with 300 μL of media beneath the transwell in 24 well plate format. Media above the cells in the transwell was removed and 120 μL of the HA-oxime hydrogel was added directly onto the RPE cells. The plate was maintained at 37° C. for 1 hour before an additional 100 μL of media was added above the hydrogel. After 24 hours, the media above the hydrogel was removed and replaced with media containing 1/250 Hoechst 33342 (nuclei) from a 25 $mg \cdot mL^{-1}$ solution in $dH_2O$ (Cell Signaling Technology; catalogue number: 4082S), 1/500 calcein AM (live cells) from a 4 mM solution in DMSO (Biotium Inc., catalogue number: 80011-1), and 1/250 ethidium homodimer (dead cells) from a 2 mM solution in DMSO (Biotium Inc., catalogue number: 40014) and incubated for 45 minutes. The cells were visualized using an Olympus FV1000 confocal microscope and analyzed using Imaris 8 software by Bitplane. Average viability was obtained from three biological replicates.

$Nrl^{-/-}$ Photoreceptor Cell Compatibility: Photoreceptors were harvested from postnatal day 3-5 mice retina in C02 independent media (Fisher Scientific) and dissociated with papain (Worthington Biochemical, UK) following the manufacturer's protocol. Cells were washed in PBS ($Ca^{2+}/Mg^{2+}$-free) and live cells were counted using 0.4% Trypan blue (Sigma Aldrich; catalogue number: G5516-500ML) as a viability counter stain before being resuspended in media. Cells were maintained on ice for less than 1 hour before being plated at $10^4$ cells per well in MEM/F-12, DMEM/F-12 containing 10% fetal bovine serum on 0.4 μm transparent transwells (Corning Life Sciences; catalogue number: C353095) with 500 μL of media beneath each transwell in a 24 well plate format. 100 μL of HA-oxime hydrogel was added per well on the photoreceptor cells once media above the transwell was removed. The plate was maintained at 37° C. for 1 hour before an additional 100 μL of media was added above the hydrogel. After 24 hours the media above the hydrogel was removed and cells were analyzed by live/dead staining. The cells were visualized using an Olympus FV1000 confocal microscope and analyzed using Imaris 8 software by Bitplane. Average viability was obtained from three biological replicates.

Retinal Explant Compatibility: Retinas were dissected from P4 GFP albino mice, Actin.gfp (transgenic mouse line with photoreceptors expressing GFP). They were flat-mounted on transwells (6-well format) and cultured with 1.5 mL serum free media on the explant and 2 mL beneath each transwell. 500 μL of the HA-oxime hydrogel was added per explant after 1 day of culture by removing as much media as possible above the explant. After 1 hour, 1 mL of media was added on top of the explant which was maintained for 24 hours before wells containing hydrogel on the retina were carefully removed and tissue dissociated with papain. Viable photoreceptors were quantified by flow cytometry selecting for GFP labelled cells, annexin V and 7-aminoactinomycin D (ThermoFisher Scientific Pacific Blue™ Annexin V/SYTOX™ AADvanced™ Apoptosis kit for flow cytometry; catalogue number: A35136) according to manufacturer's instructions. Average viability was obtained from 3 retinal explants for HA-oxime and 8 retinal explants for media controls.

Rabbit Retinal Surgeries: Experimental procedures were performed in accordance with the Guide to the Care and Use of Experimental Animals and approved by the Animal Care Committee at the University of Toronto in adherence to the guidelines of the Canadian Council on Animal Care. New Zealand white rabbits (3-4 months) were purchased from Charles River. The surgeries were performed under general anesthesia with acepromazine 1 $mg \cdot kg^{-1}$ prior to induction with isoflurane and intramuscular injection of ketamine 35 $mg \cdot kg^{-1}$ and xylazine 5 $mg \cdot kg^{-1}$. Subcutaneous injection of meloxicam 0.2 $mg \cdot kg^{-1}$ was administered for pain control and cephalosporin 20 $mg \cdot kg^{-1}$ was provided to minimize intraoperative risk of infection and fur surrounding the eye was sterilized with alcohol wipes and iodine. The pupils were dilated using 0.5% tropicamide and 0.5% phenylephrine, and topical anesthesia with alcaine drops. A surgical microscope (Moller Hi-R 900C) was used to visualize the surgery performed using a Constellation instrument (Alcon) to remove the vitreous with a 23 GA TotalPlus® Vitrectomy Pak while eye pressure was maintained using a balanced saline solution, trochars were carefully placed to avoid touching the lens. The saline was exchanged with gas, and then approximately 1 mL of vitreous gel (HAK, HAA and $PEGOA_4$) or silicone oil (1000-centistoke) was injected into the vitreous cavity. After surgery, trochars were removed and the areas were sealed with 8-0 vicryl sutures. Animals were treated with Tobradex and received subcutaneous injection of meloxicam 0.2 $mg \cdot kg^{-1}$ once a day for at least 2-3 days following surgery for post-op analgesia. They also received daily application of ophthalmic maxidex to prevent conjunctivitis for at least 2 days, and then as needed. Sham surgeries were performed by placing trochars and infusing saline without a vitrectomy being performed. Intraocular pressure (IOP) was measured using a Tono-Pen tonometer at −1, 0 and every 3 days after surgery. The rabbits were sacrificed after 1, 14, 28 or 60 days and both the right and left eyes were harvested from these animals. The eyes were either fixed with Davidson's fix overnight then rinsed with 70% ethanol+0.9% NaCl or covered with 70% ethanol+0.9% NaCl to cover each eye. The eyes were then embedded in paraffin and stained with hematoxylin and eosin (H&E stain) for visualization by microscopy and analysis. Cryosectioned eyes were harvested and immediately flash frozen in 2-methylbutane with dry ice which were stored at −80° C. until sectioning.

Stability of Vitreous Gel: After injecting the vitreous gel with or without AlexaFluor-647 labelled HAK the remaining hydrogel was collected. The hydrogel was incubated at 37° C. with PBS (1.5 $mL \cdot mL^{-1}$ of gel) until the animals were sacrificed. Tissue was dissected to retrieve the hydrogel and weighed. Hydrogels were washed with PBS over 1 hour. Hydrogels were speed mixed for 1 min at 3,500 rpm to mechanically dissociate the hydrogel. Hyaluronidase was added to the hydrogel from a 10,000 $U \cdot mL^{-1}$ stock solution dissolved in PBS to give a final concentration of 1,500 $U \cdot g^{-1}$ vitreous gel. The suspension was incubated overnight at 37° C. and the resulting solutions were pipetted into a clear 96 well plate and quantified using a Tecan instrument with $\lambda_{ex}$ 640 nm $\lambda_{em}$ 675 nm. The biodegradation of the HA-oxime hydrogel was modeled using a non-linear fit one phase decay with least squares fit ($R^2$=0.982) with GraphPad Prism 7 and was described by the equation where:

$$\text{Fluorescence}=100.3e^{-0.01585 * \text{Days}}$$

Results: The vitreous substitute hydrogel stability and compatibility results are described below.

Figure 7A:
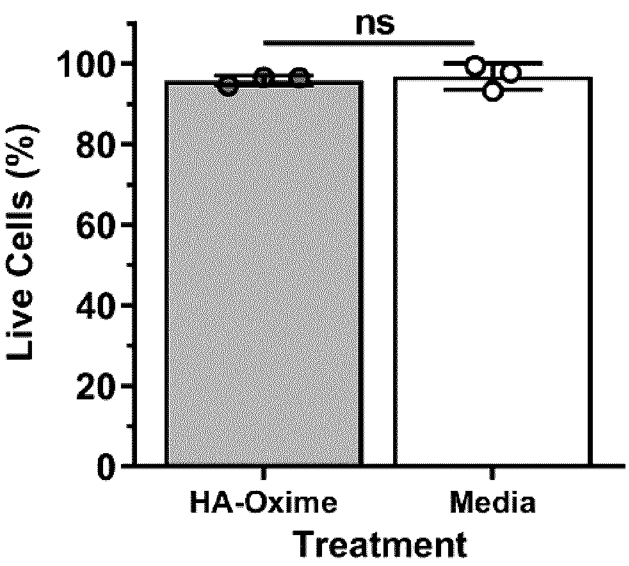
FIG. 7A, FIG. 7B, FIG. 7C, FIG. 7D illustrate in vitro cytocompatibility of HA-oxime hydrogel.
Figure 7B:
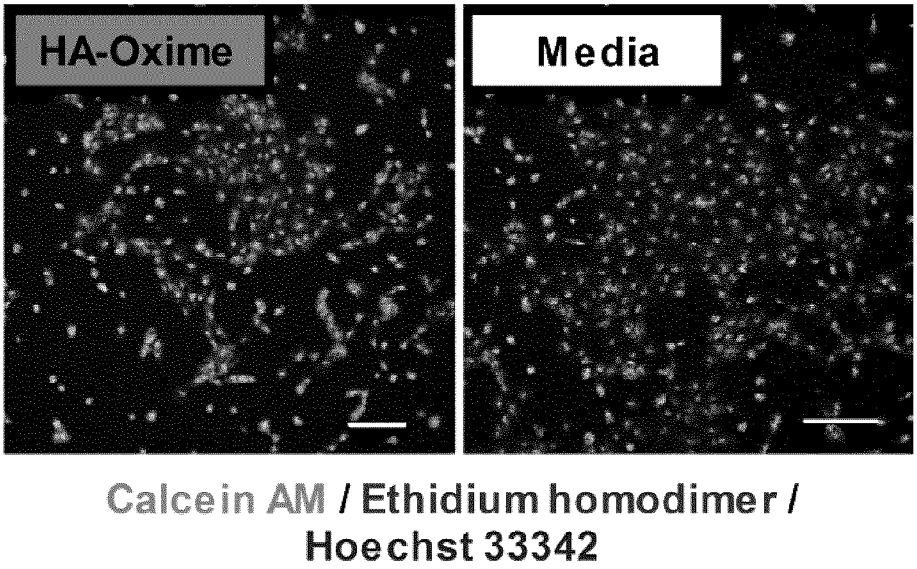
Figure 7C:
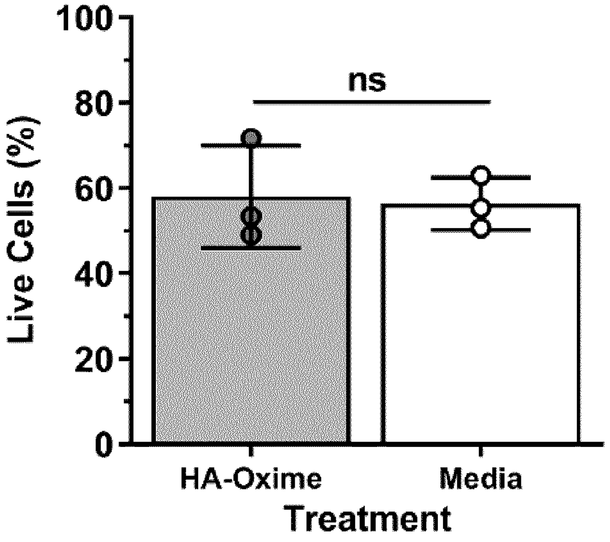
Figure 7D:
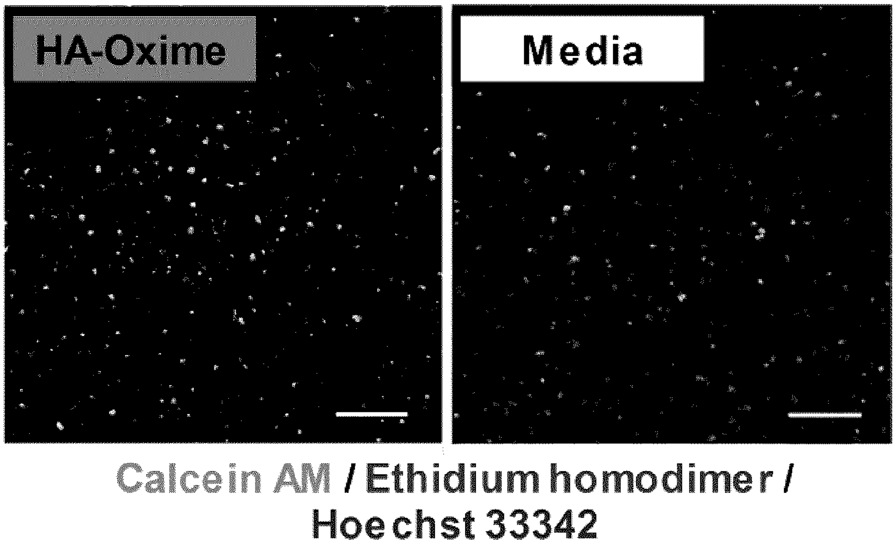
Figure 8A:
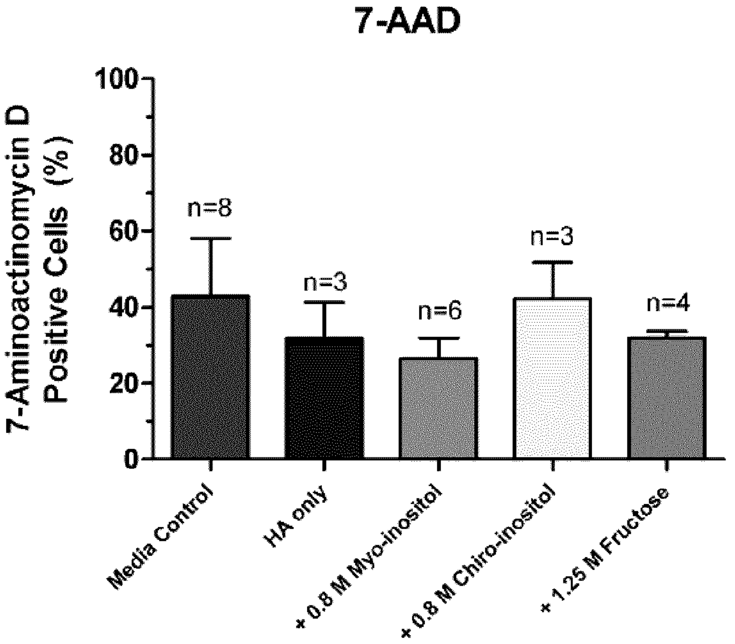
FIG. 8A and FIG. 8B show a graph illustrating the percent of dead rod photoreceptor cells from mouse retinal explants (7-AAD) (FIG. 8A) and a graph illustrating cells committed to apoptosis (Annexin V) (FIG. 8B) quantified by flow cytometry at day 7 (n>3, mean+standard deviation, one-way ANOVA Tukey's post hoc test).
Figure 8B:
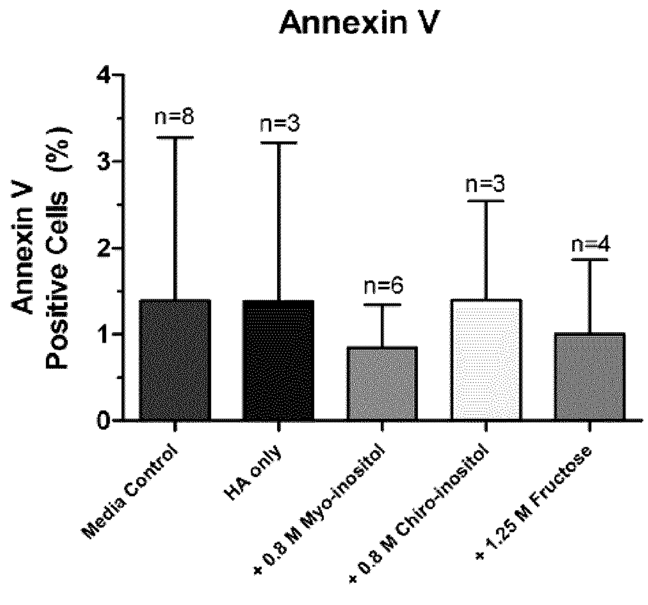
Figure 9:
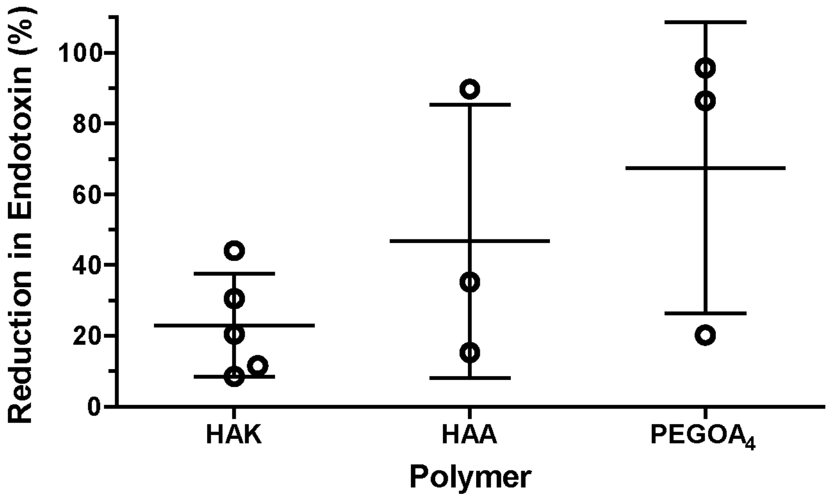
FIG. 9 is a graph illustrating quantification of endotoxins from HAK, HAA and $PEGOA_4$ polymers. Endotoxin concentrations for separate batches of polymers treated with aluminium oxide, γ-phase calculated relative to untreated polymers (n=3-5, mean±standard deviation).

Vitreous substitute hydrogel in vitro cytocompatibility: To test the cytocompatibility of the HA-oxime hydrogel, in vitro viability assays were conducted using a diversity of retinal cells: retinal pigmented epithelial cells (RPE) differentiated from the CA-1 human embryonic stem cell line (Adewumi et al., "Characterization of human embryonic stem cell lines by the International Stem Cell Initiative, Nat Biotechnol., 25:803 (2007)), mouse GFP, cone-like rod photoreceptors (cods) (Daniele et al., "Cone-like morphological, molecular, and electrophysiological features of the photoreceptors of the Nrl knockout mouse," Investigative ophthalmology & visual science, 46:2156 (2005); Akimoto et al., "Targeting of GFP to newborn rods by Nrl promoter and temporal expression profiling of flow-sorted photoreceptors," Proc. Natl. Acad. Sci. USA, 103:3890 (2006)), and mouse retinal explants. While we do not expect the hydrogel vitreous substitute to be in direct contact with either the RPE or photoreceptors, the RPE provide insight into how human cells will respond and the mouse photoreceptors are sensitive. The RPE maintained 96% viability after 24 hours when cultured on tissue culture polystyrene (TCPS) and under a thin coating of HA-oxime, based on calcein AM and ethidium homodimer staining (FIG. 7A and FIG. 7B). Similarly, cone-like photoreceptors labelled with GFP maintained similar viability when cultured beneath a thin coating of HA-oxime hydrogel as in media after 4 days (FIG. 7C and FIG. 7D). To better understand how our HA-oxime hydrogel will interact with the retina, several excipient-HA hydrogel formulations were cultured on mouse retinal explants for 24 hours, after which the photoreceptors were dissociated and quantified by flow cytometry. There was no significant difference in the number of dead photoreceptors stained with either 7-aminoactinomycin (7-AAD) or annexin V (cells committed to apoptosis) with or without hydrogel treatment (FIG. 8A and FIG. 8B). There was no adverse effects observed in vitro in terms of cytocompatibility. The hydrogels were tested in vivo with endotoxin reduced polymers (FIG. 9).

Figure 10A:
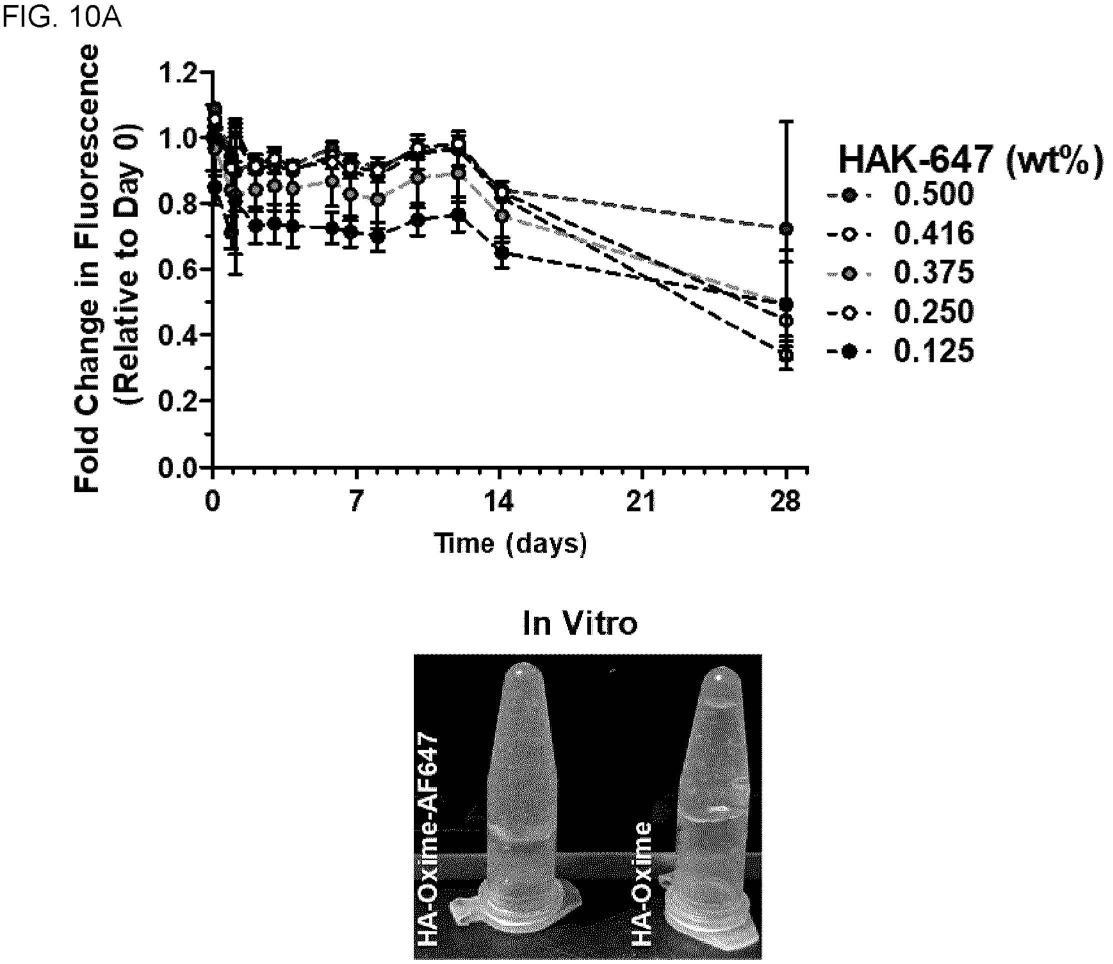
FIG. 10A and FIG. 10B illustrate the characterization and presence of the fluorescently tagged HA-oxime gel in the vitreous cavity.
Figure 10B:
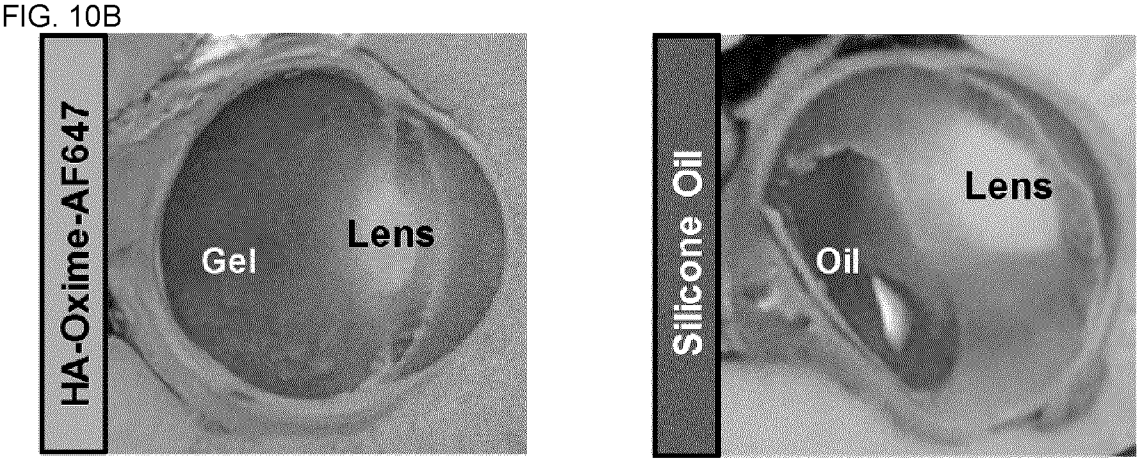
Figure 11A:
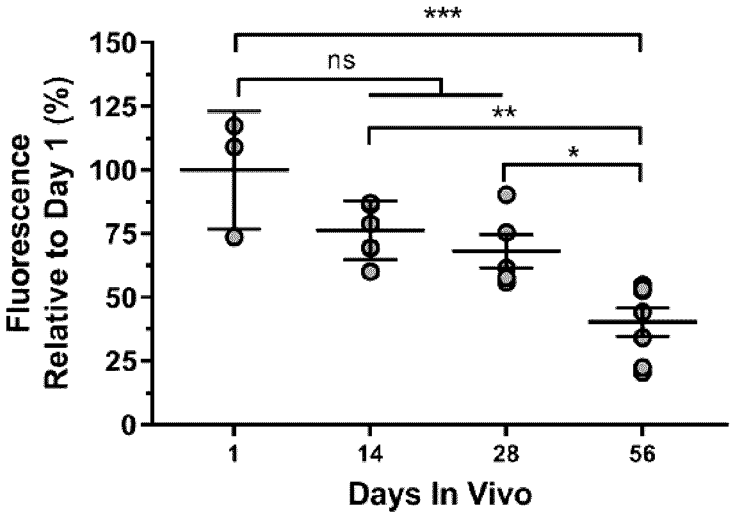
FIG. 11A, FIG. 11B and FIG. 11C illustrate the stability of the HA-oxime hydrogels dissected in rabbit eyes.
Figure 11B:
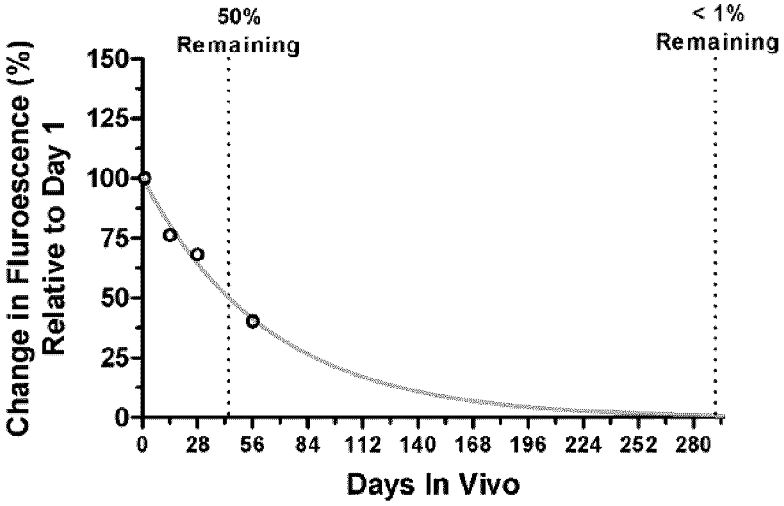
Figure 11C:
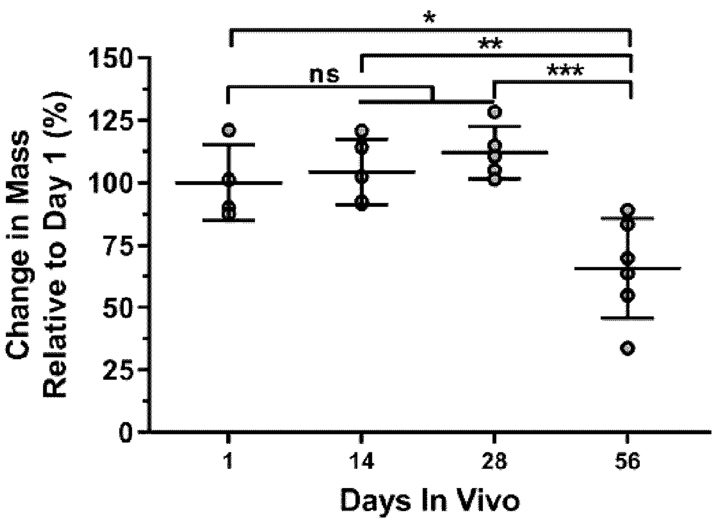

Vitreous substitute in vivo stability: Fluorescently labelled hydrogel was used to monitor the stability and degradation of a vitreous substitute in vivo. To monitor hydrogel stability, a fluorescent AlexaFluor-647-hydrazide was conjugated to carboxylate groups on HA that was also modified with the ketone functionality (FIG. 10A). This HA-oxime-AF647 hydrogel was then injected into rabbit eyes that had been victrectomized. The HA-oxime-AF647 was compared to silicone oil as a filler. The eyes were cryosectioned 1 day after injection, and it was observed that the vitreous cavity was filled with the HA-oxime hydrogel similar to that observed with silicone oil (FIG. 10B). To quantify the stability of the hydrogel, both the fluorescence and mass of HA-oxime-AF647 gels were measured overtime by removing the gels from dissected eyes. The gel was cohesive and easily removed from the vitreous. By day 28, the gel remained unchanged compared to day 1 in terms of fluorescence (FIG. 11A). By day 56, the hydrogel degraded significantly relative to day 1 to 40±15% of the initial fluorescence. Alternatively, there may have been some photobleaching to account for the greater reduction in fluorescence. Notwithstanding, the HA-oxime in vivo stability was modeled based on the fluorescence data: a half-life of 43 days and complete degradation/resorption by 300 days or 10 months (FIG. 11B) were calculated. Similarly, it was observed that the hydrogel mass was unchanged over the first 28 days of implantation in vivo but decreased significantly at day 56 (FIG. 11C). The HA-oxime hydrogel lasts sufficiently long as a vitreous substitute as clinical data has shown that patients receiving pars planar vitrectomy (PPV) achieve best-corrected visual acuity after 1 month (Minami et al., "Effect of axial length and age on the visual outcome of patients with idiopathic epiretinal membrane after pars plana vitrectomy," Scientific Reports, 9:19056 (2019).

Figure 12A:
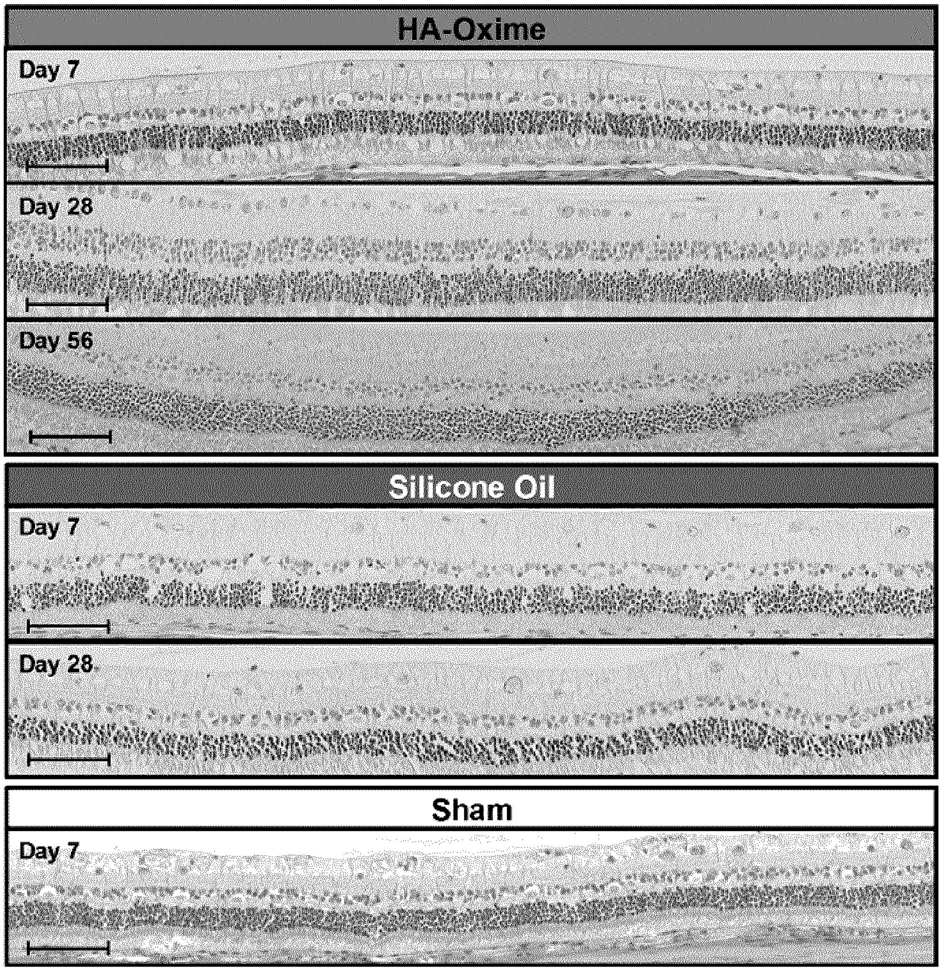
FIG. 12A, FIG. 12B, and FIG. 12C illustrate the histological analysis of the inner and outer nuclear layers of the rabbit stained with H+E.
Figure 12B:
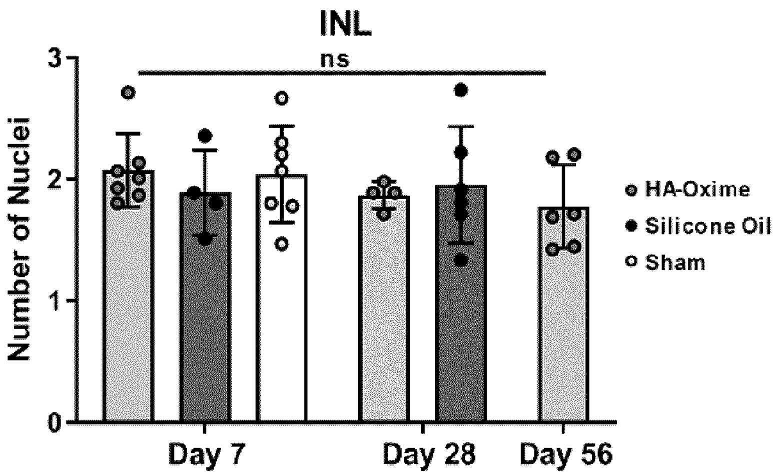
Figure 12C:
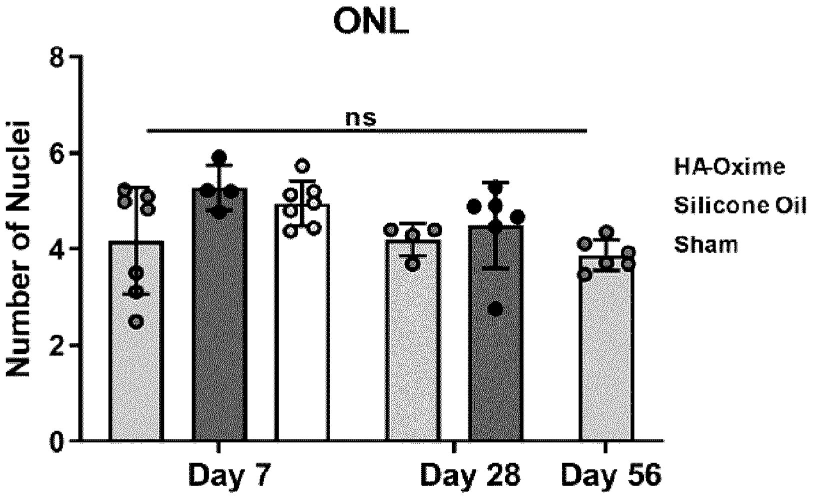
Figure 13:
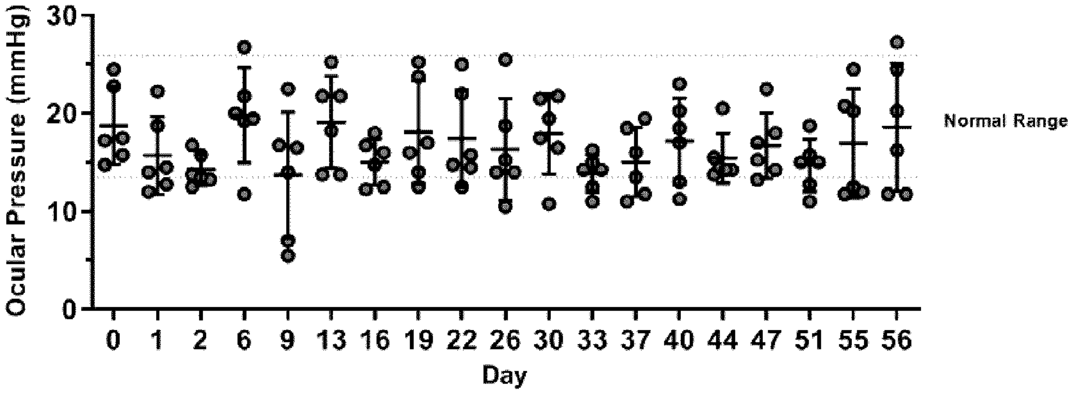
FIG. 13 is a graph illustrating the ocular pressure for rabbits injected with HA-oxime over 56 days remains within the normal range reported for New Zealand White rabbits (n=6, mean±standard deviation, p=0.780 for linear regression analysis for non-zero slope).
Figure 14A:
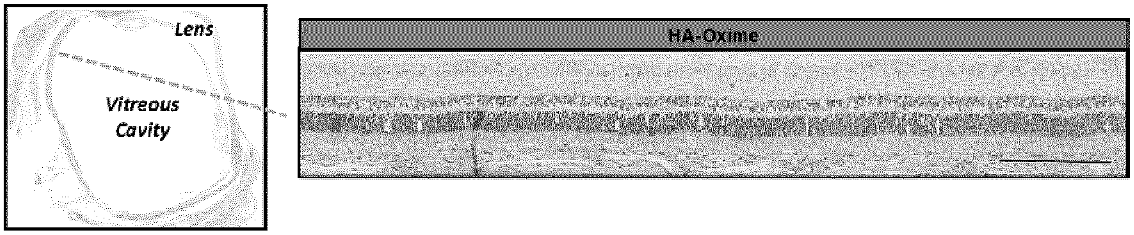
FIG. 14A and FIG. 14B show retinal detachment repair with HA-oxime in the rabbit eye.
Figure 14B:
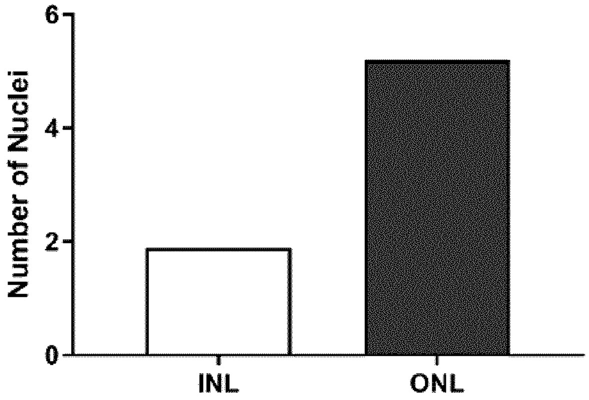
Figure 15A:
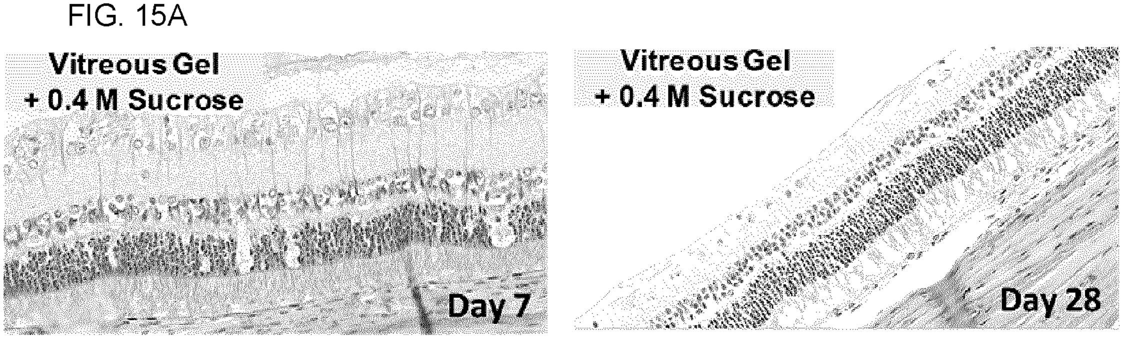
FIG. 15A, FIG. 15B, FIG. 15C illustrate the histological analysis of the inner and outer nuclear layers of the rabbit stained with H+E.
Figure 15B:
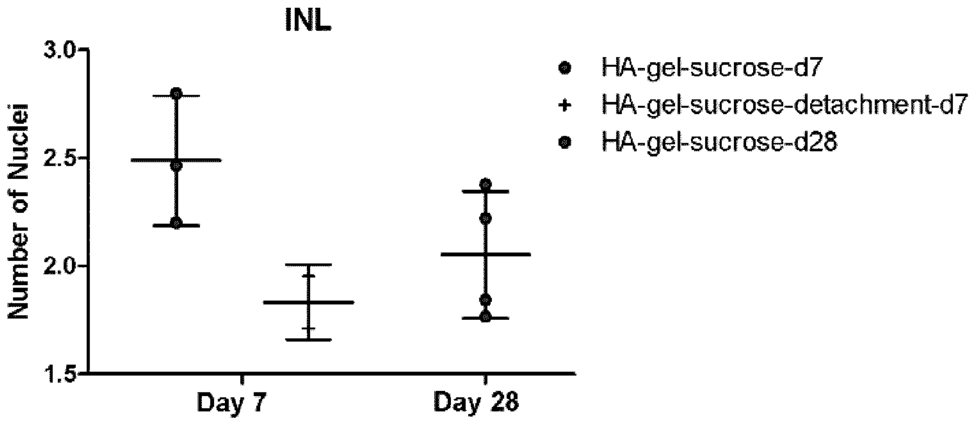
Figure 15C:
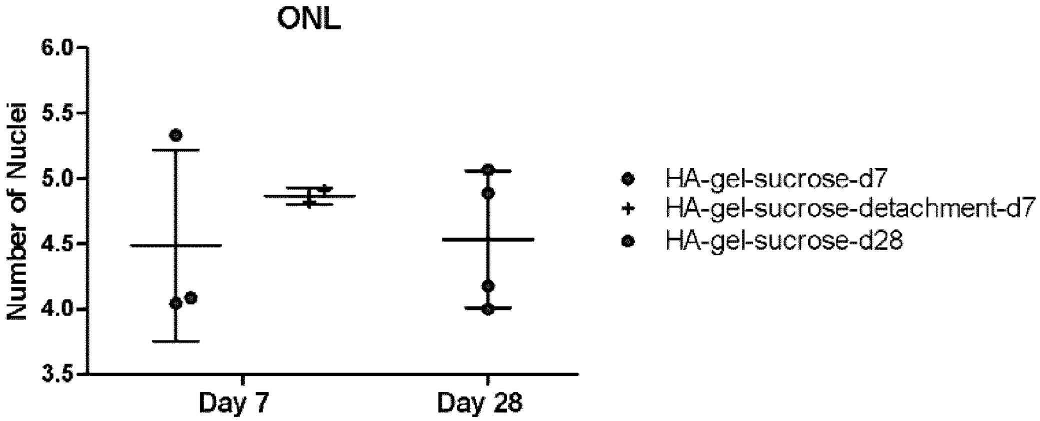
Figure 16:
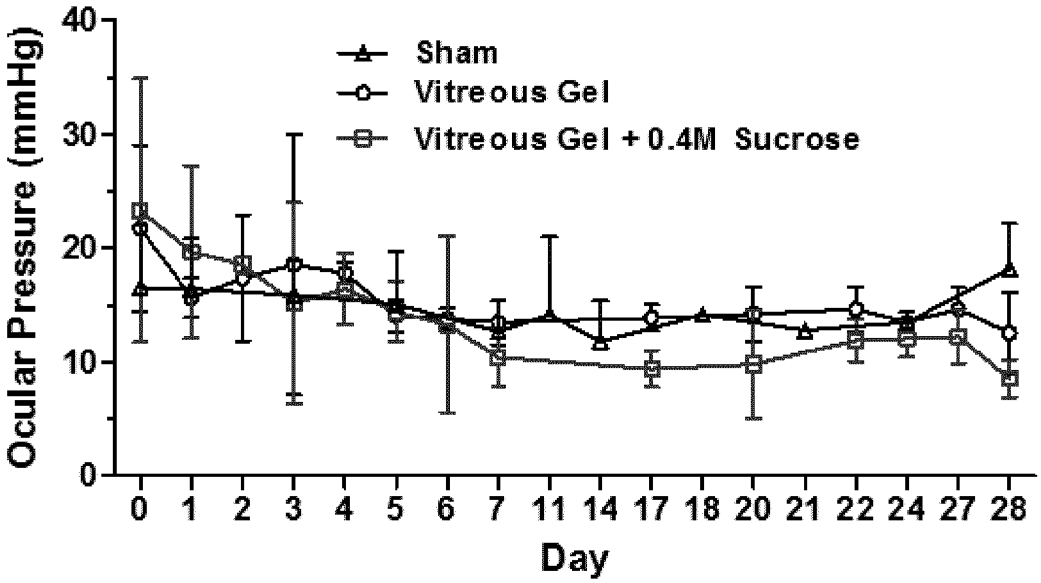
FIG. 16 is a graph illustrating the ocular pressure for rabbits injected with sham surgery, HA-oxime or HA-oxime containing 0.4M sucrose over 28 days (n=3, mean±standard deviation).

Vitreous substitute hydrogel in vivo biocompatibility: To test the biocompatibility of the HA-oxime hydrogel, the retina was examined histologically over time and compared to silicone oil and sham surgeries. Over the course of 56 days, the rabbit retina remained intact and healthy based on histology (FIG. 12A). The thickness of the inner nuclear layers (INL), which contains the bipolar, horizontal and amacrine cells, and outer nuclear layer (ONL) containing the rod and cone photoreceptors, was quantified at day 7, day 28, and day 56. The number of nuclei in both INL and ONL remained similar across all timepoints (FIG. 12B and FIG. 12C), demonstrating that the new HA-oxime hydrogel is biocompatible. The mean ocular pressure remained within the reported normal IOP range for rabbits of 13.50-25.92 mmHg (Zouache et al., "Intraocular Pressure and Aqueous Humour Flow Rate in Vertebrate Eyes," PLOS ONE 11:e0151490 (2016)) as measured by a tonometer over 56 days (FIG. 13), thereby demonstrating safety of this hydrogel in vivo (i.e., the hydrogel does not result an increased ocular pressure as it degrades). To evaluate the ability of the vitreous substitute hydrogel to flatten the retina, retinal detachment was induced in the New Zealand White rabbit eye and the retina was evaluated after 7 days by histology (FIG. 14A). The INL and ONL were intact based on the quantification of the retina (FIG. 14B). In contrast to the Vitargus hydrogel formed by hydrazone ligation that resulted in some patients with elevated IOP, there were no significant changes in ocular pressure with HA-oxime hydrogel observed in rabbits which is likely due to the slow hydrolysis rate for oxime linkages versus hydrazine (Kalia et al., "Hydrolytic stability of hydrazones and oximes," Angew. Chem. Int. Ed. Engl., 47:7523 (2008)). To demonstrate that the use of excipients would not be toxic to the retina, several excipient-HA hydrogel formulations were examined by injecting rabbit eyes following vitrectomy with the vitreous gel containing 0.4 M sucrose and compared the thickness of the inner and outer nuclear layers (INL and ONL) at days 7 and 28 (FIG. 15A, FIG. 15B, and FIG. 15C). At this point there were no obvious differences between the HA hydrogel groups and silicone oil or shams that were tested. Moreover, the intraocular pressure (IOP) remained stable and similar to normal rabbit IOP values in eyes that received either the vitreous gel containing 0.4 M sucrose or Sham surgeries (FIG. 16) (Ma et al. Scientific reports. 6:35187 (2016)).

Conclusion: The HA-oxime hydrogel matched the properties of the native vitreous in terms of refractive index, density and transparency. It was easily injected in rabbit eyes, filling the vitreous cavity and fulfilling the needs of a vitreous substitute in terms of tamponading the retina, maintaining normal ocular pressure, resorbing over time and being biocompatible. The key to the success of this hyaluronan hydrogel, when others have failed, is due to the stable click chemistry, which unlocks the potential for it to be used as a vitreous substitute to treat retinal detachment. Gases and oils have significant disadvantages for patients, requiring their replacement with an improved vitreous substitute. The hydrogel meets the design requirements to act as a substitute for gas or silicone oil tamponades currently used based on results presented in the examples provided herein.

Example 7—Synthesis, Formulation, and Characterization of HA-Oxime Hydrogels for Use in 3D Cell Culture System This example describes the synthesis of HA-oxime hydrogels including HAK, HAA, and $PEGOA_4$ for use in 3D cell culture system Background: Despite improvements in initial target identification using computational approaches (Leelananda et al., Methods 131:10 (2017)), and several proposed hydrogels to culture cells for the in vitro stage of drug discovery (Li et al., Sci. Adv. 4 (2018)), two-dimensional (2D) culture on tissue culture poly(styrene) (TCPS) continues to be used to screen cancer therapeutics. 2D culture does not represent the in vivo microenvironment either mechanically or biochemically, thereby leading to false positive (and likely false negative) drug hits (Jacobi et al., Oncotarget 8:107423 (2017)). In vivo xenograft tumour models recapitulate human disease more faithfully, but are costly, time-consuming and complicated by the use of immunocompromised mice (Hasan et al., J. Clin. Pathol. 68:746 (2015)). The inaccurate but rapid and simple method of testing drugs in 2D coupled with the complexity of xenograft models, has motivated the development of more representative three-dimensional (3D) culture platforms. A suitable 3D culture system must be sufficiently stable for drug screening and benchmarked against gold standard in vivo xenograft tumour models (Day et al., Cell 163:39 (2015)). The limited availability of such 3D models results in the continued reliance on 2D culture, even with the recognition that 2D culture does not accurately predict in vivo outcomes.

Unlike 2D culture, where breast epithelial cancer cells form a monolayer, 3D models of cancer recapitulate many disease characteristics such as formation of cancer spheroids with tight junctions, and inclusion of key biochemical and mechanical cues of the native extracellular matrix (ECM) (Ivascu et al., International Journal of Oncology, 31:1403 (2007); Todd et al., Oncotarget 7:62939 (2016); Imamura et al., Oncology reports, 33:1837 (2015)). Typically, cancer spheroids are formed by growing epithelial cancer cells in 3D using non-adherent conditions. This method is rapid and provides remarkable control of the spheroid size (Madoux et al., SLAS Discov. 22:516 (2017)). Yet, unsurprisingly, the gene expression profiles of these cancer spheroids (CS) formed by aggregation resemble cells cultured in 2D more closely than those of xenograft tumours (Boghaert et al., Neoplasia 19:695 (2017)). Therefore, spheroid formation alone does not recapitulate the in vivo microenvironment (Sero et al., Mol. Syst. Biol. 11:0790 (2015); Gencoglu et al., ACS Biomater. Sci. Eng. 4:410 (2018)). Non-adherent conditions lack critical ECM components, which both affect cell function through integrin-mediated signaling pathways, such as β1, and influence drug effectiveness (Xu et al., Integr. Biol. 3:368 (2011); Lovitt et al., BMC Cancer 18:41 (2018)).

Laminin-rich extracellular matrices, such as Matrigel®, which is derived from the Engelbreth-Holm-Swarm murine sarcoma, are favored for 3D cell culture as they contain some physiologically relevant ECM proteins that mimic the breast tumour microenvironment (Weigelt et al., Adv. Drug Deliv. Rev. 42:69-70 (2014)). However, Matrigel is ill-defined (Hughes et al., Proteomics, 10:1886 (2010)), and its composition, physicochemical, and biomechanical properties have limited tenability (Lambricht et al., Dent. Mater. 30:e349 (2014)). Moreover, Matrigel does not include key matrix components found in the breast cancer microenvironment such as hyaluronan (HA), which is produced by tumour and stromal cells and is linked to disease progression (Auvinen et al., Am. J. Pathol. 156:529 (2000)). The diversity of cell-surface integrin expression and tumour microenvironment properties across breast cancer subtypes require a model that is tunable to meet these complexities (Rizwan et al., Oncotarget 7:62939 (2016)).

Figure 17A:
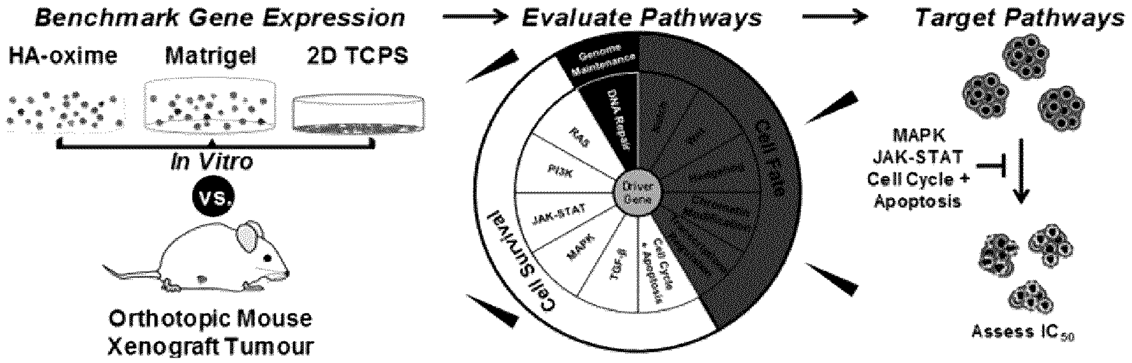
FIG. 17A, FIG. 17B, FIG. 17C, FIG. 17D, FIG. 17E, and FIG. 17F illustrate the synthesis of the HA-oxime hydrogel to model breast cancer in vitro, and the characterization of the HA-oxime hydrogel to model breast cancer in vitro.
Figure 17B:
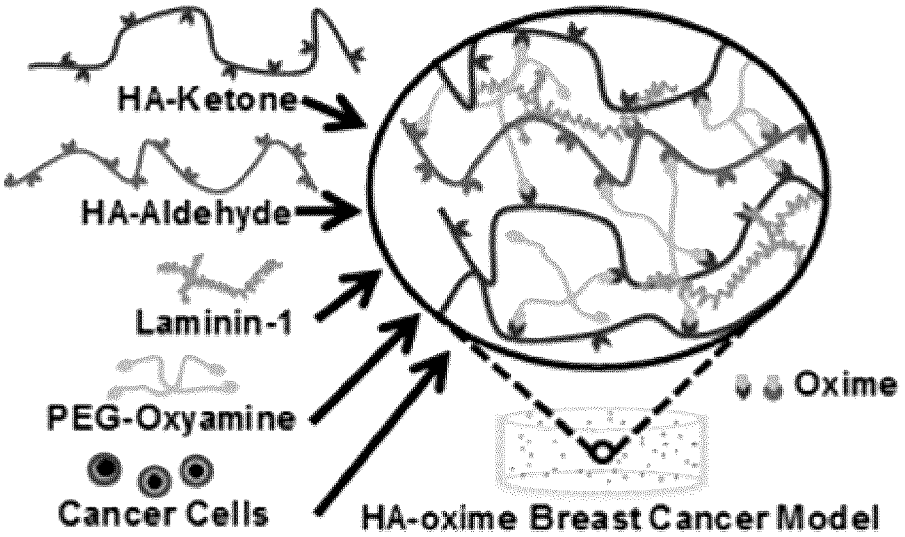

The majority of chemically crosslinked hydrogels utilize chemistries that have rapid reaction kinetics (Wang et al., Advanced Functional Materials, 27:1605609 (2017)), such as the thiol-Michael addition ligation (Saito et al., ACS Chemical Biology, 10:1026 (2015)), and limit uniform cell encapsulation, making reproducible in vitro cell culture challenging. Moreover, many scaffold components need to be stored under inert gas due to air-sensitive functional groups, such as thiols, and/or require external stimuli to promote crosslinking, which complicates scale up (Fisher et al., J. Am. Chem. Soc. 139:7416 (2017); Jha et al., Biomaterials, 89:136 (2016)). To achieve a more controlled system for cell encapsulation, fast-reacting HA-aldehyde and slow-reacting HA-ketone were combined with poly(ethylene glycol) (PEG)-oxyamine to create defined 3D hydrogels via oxime click chemistry. Oxime ligation is hydrolytically stable, thereby allowing long-term encapsulation of breast cancer cells—a key advance over current strategies that are inherently limited by reversible reactions of hydrazone or Diels-Alder chemistries for crosslinking (Kalia et al., Angew. Chem. Int. Ed. 47:7523 (2008); Kascholke et al., Biomacromolecules 18:683 (2017); Baker et al., Biomacromolecules, 18:4373 (2017)). In addition, the oxime chemistry is insensitive to oxidation, facile to use and enables controlled gelation rates, which is typically not possible with other click chemistry reactions. These newly synthesized oxime-crosslinked HA hydrogels were used to benchmark the gene expression of breast cancer cells against tumour xenografts grown in mice and evaluate drug response in comparison with conventional culture in Matrigel and 2D TCPS (FIG. 17A).

Methods: The methods for the synthesis, formulation, and characterization of HA-oxime hydrogel for use in 3D cell culture are described below.

Synthesis of HA-oxime hydrogel components: HA-oxime gels were synthesized with HA-ketone (HAK), HA-aldehyde (HAA) and PEG-oxyamine. Each component of which first needed to be synthesized.

Figure 17C:
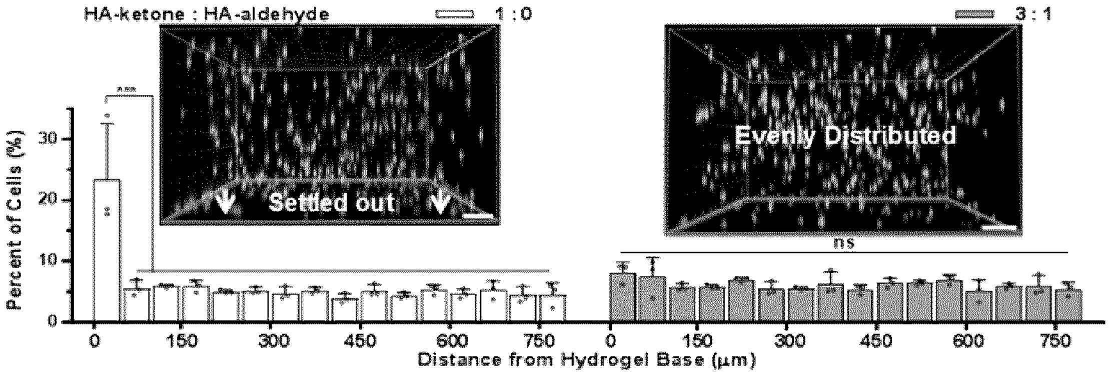
Figure 17D:
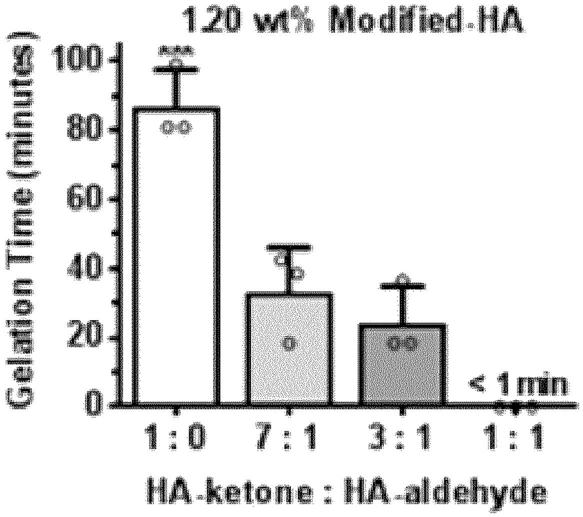
Figure 17E:
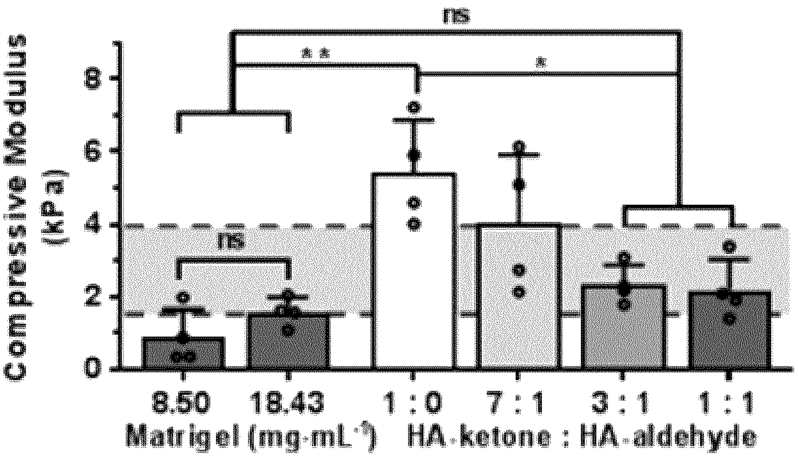
Figure 17F:
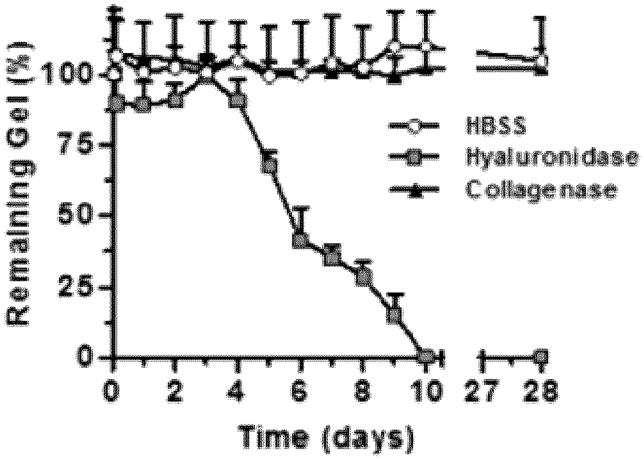
Figure 18:
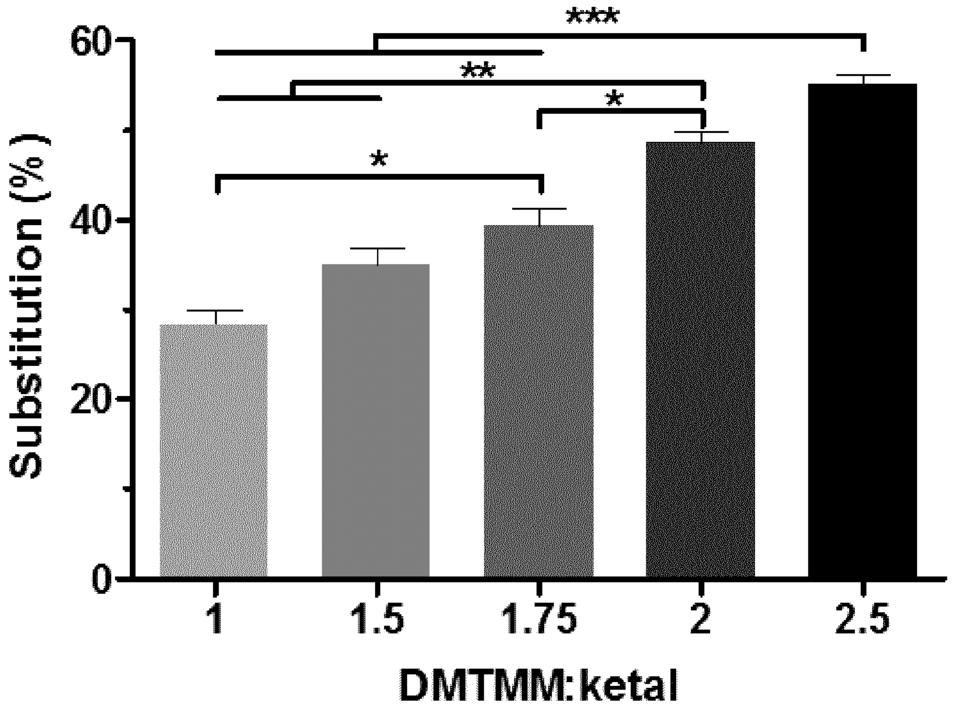
FIG. 18 illustrates the effect of increasing the equivalents of DMTMM on the degree of ketal substitution for hyaluronan (n=3 independent samples, mean+standard deviation plotted, * p<0.05, one-way ANOVA, Tukey's post-hoc test).

HAK was synthesized, for the first time, in a two-step reaction: (1) amide coupling of 3-(2-methyl-1,3-dioxolan-2-yl)propan-1-amine with 4-(4,6-dimethoxy-1,3,5-triazin-2-yl)-4-methylmorpholinium chloride (DMTMM) as an activator and (2) acid-catalyzed ketone deprotection (FIG. 17A, FIG. 17B, FIG. 17C, FIG. 17D, FIG. 17E, and FIG. 17F). HAK and HAA was combined with $PEGOA_4$ and laminin (a common extracellular matrix protein) to produce crosslinked hydrogels with tunable biochemical properties to grow breast cancer spheroids (FIG. 17A). The substitution of ketone was found to be tunable between 28±3% and 55±2% by increasing the equivalents of DMTMM from 1.0 to 2.5, respectively (FIG. 18). HAK with approximately 40% ketone substitution was used to produce hydrogels because it was water soluble and easy to handle.

Figure 19:
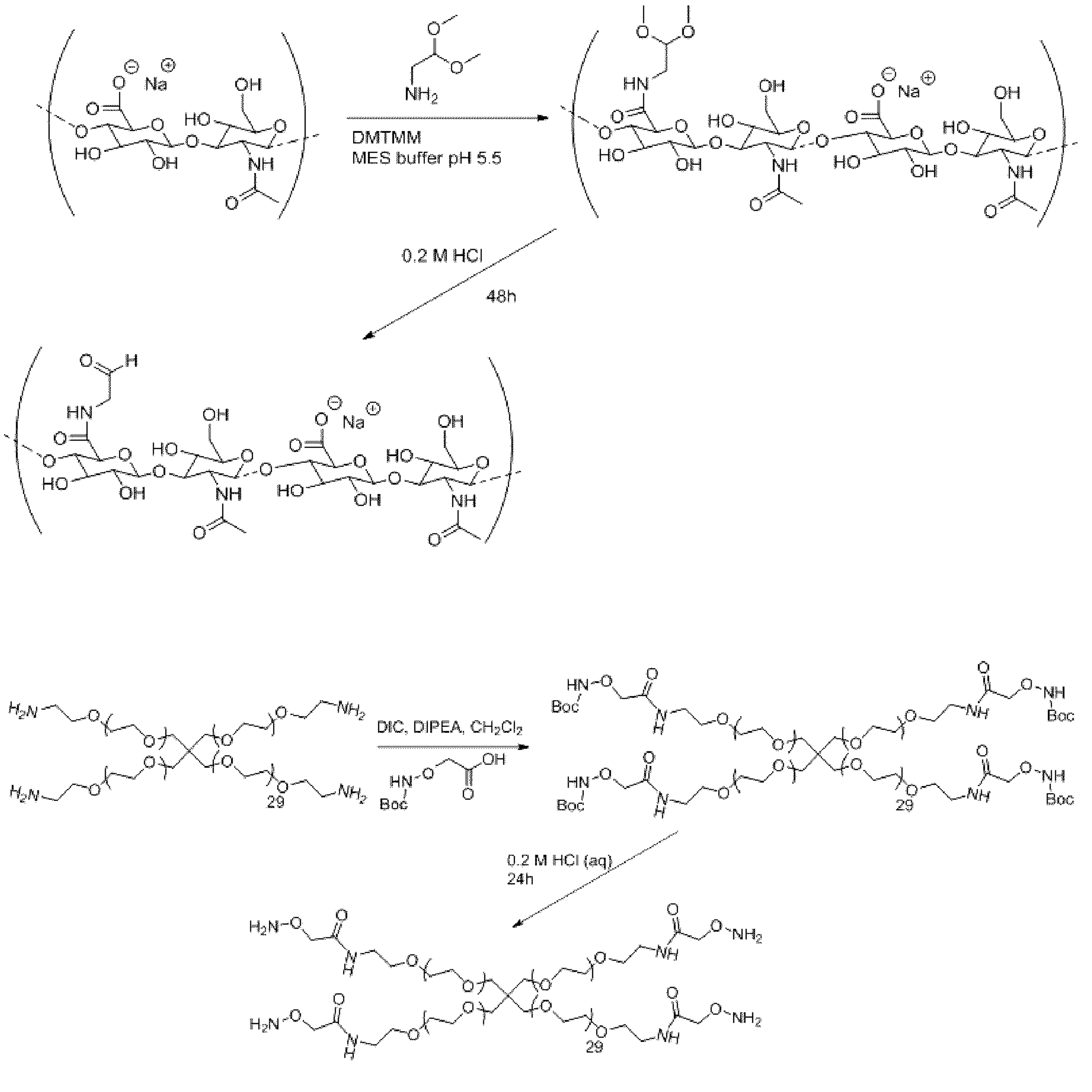
FIG. 19 illustrates the synthesis of aldehyde-substituted hyaluronan (HAA) and 4-arm poly(ethylene glycol) tetra (oxyamine) ($PEGOA_4$). HAA is synthesized over two steps: amidation of HA with aminoacetaldehyde dimethyl acetal followed by treatment of the HA-acetal with aqueous acid over 48 hours to generate HAA. $PEGOA_4$ is synthesized over two steps: first amidation of PEG tetra(amine) with N-Boc-oxyamineacetic acid followed by the deprotection in aqueous acid over 24 hours to generate $PEGOA_4$.

Similarly, aldehyde-modified HA (HAA) was synthesized in two steps: (1) amidation of carboxylic acid groups on HA with DMTMM/aminoacetaldehyde dimethyl acetal, and (2) deprotection of the resulting HA-acetal with aqueous acid (FIG. 19). The PEG-substituted oxyamine crosslinker was prepared from either 4-arm PEG-tetramine or 2-arm PEG-bisamine and (boc-aminooxy)acetic acid with carbodiimide coupling followed by acid-catalyzed deprotection to yield $PEGOA_4$ and $PEGOA_2$, respectively (FIG. 19).

Figure 20A:
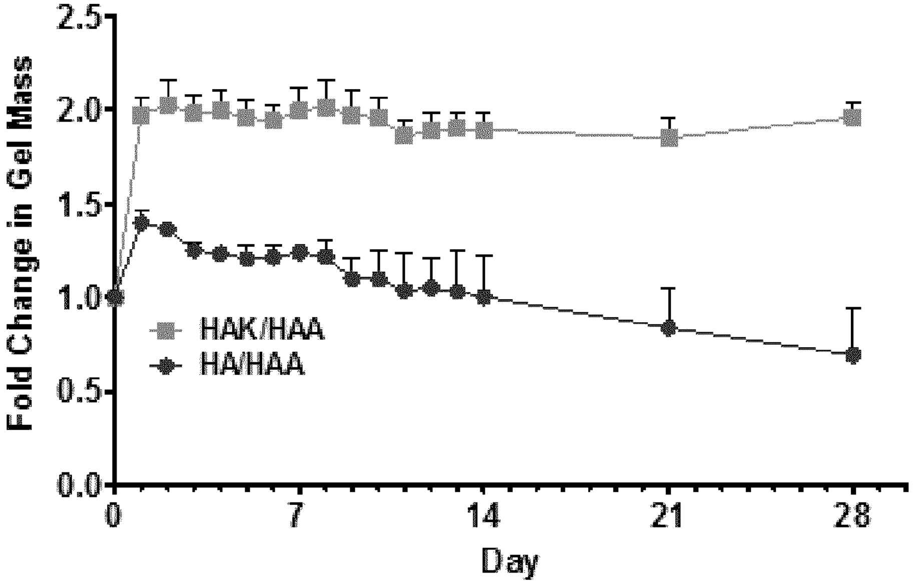
FIG. 20A, FIG. 20B, and FIG. 20C illustrate the swelling stability of HA-oxime hydrogels.
Figure 20B:
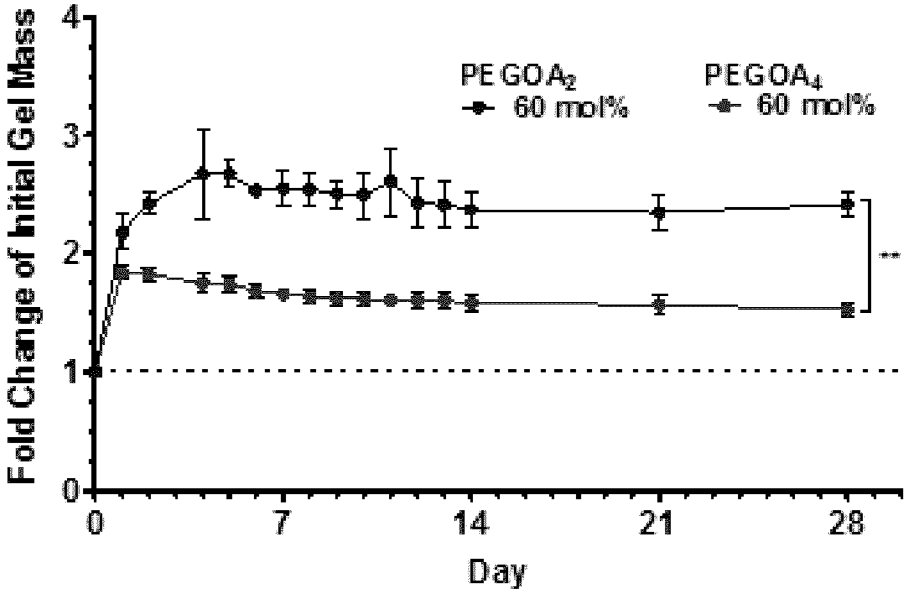
Figure 20C:
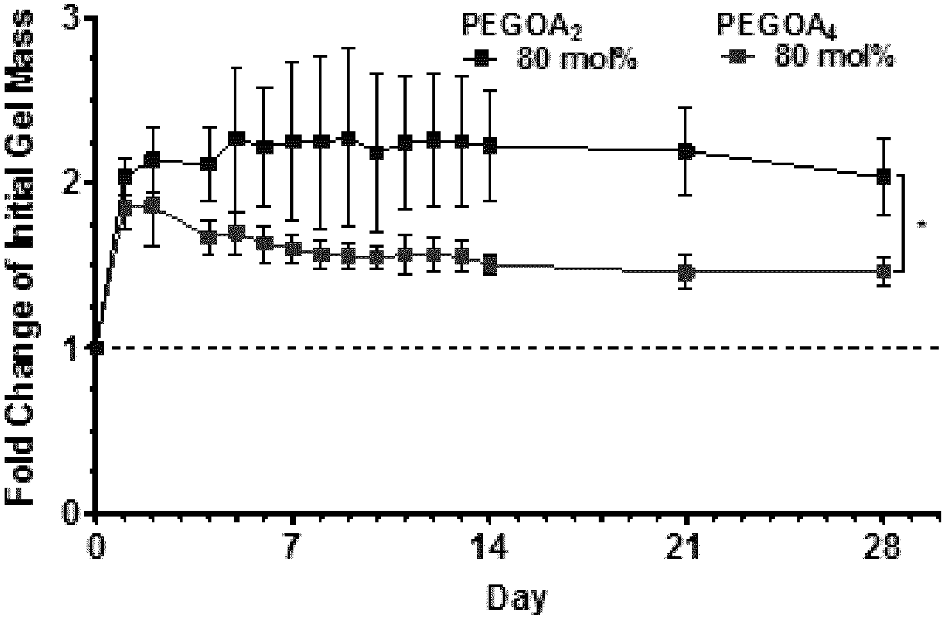
Figure 21A:
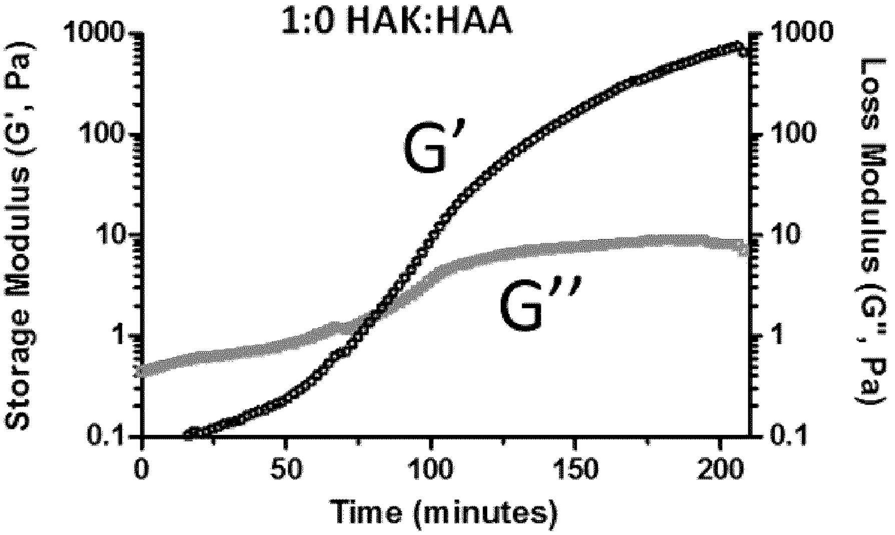
FIG. 21A, FIG. 21B, FIG. 21C, FIG. 21D, FIG. 21E, and FIG. 21F illustrate rheology of hydrogels.
Figure 21B:
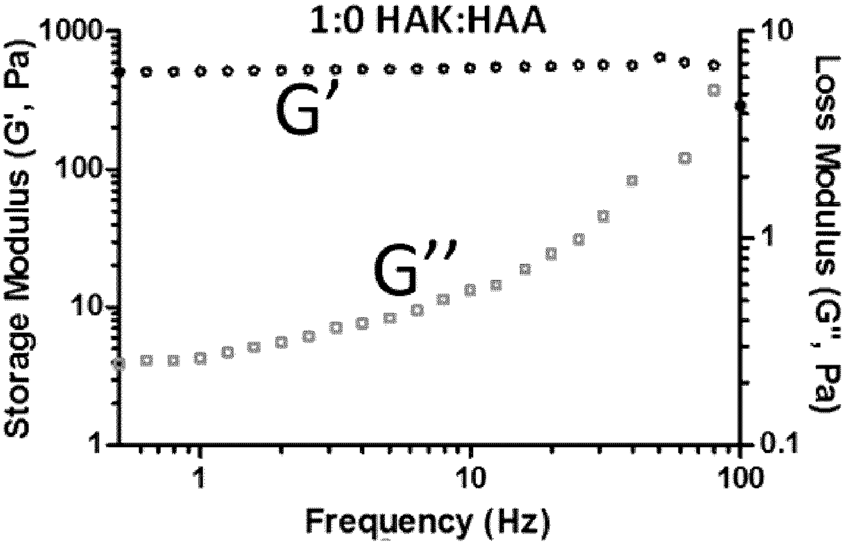
Figure 21C:
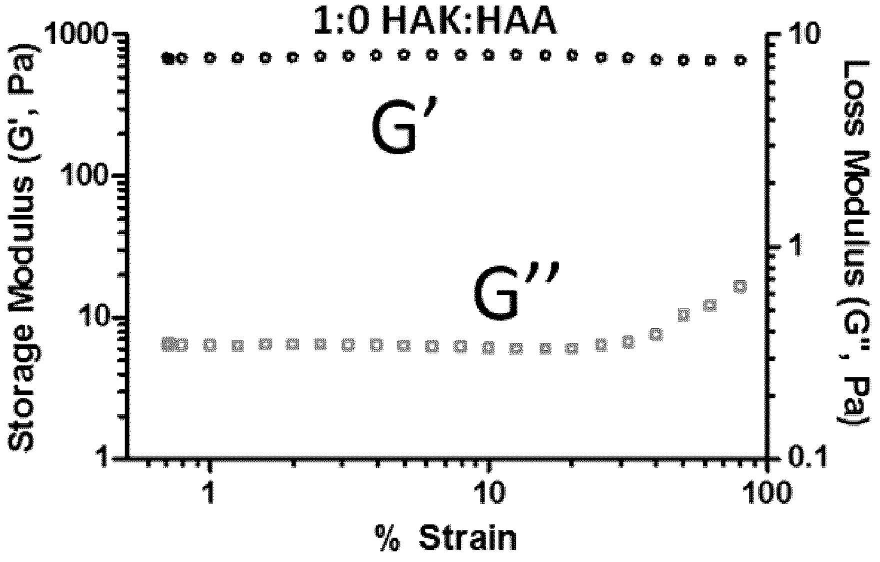
Figure 21D:
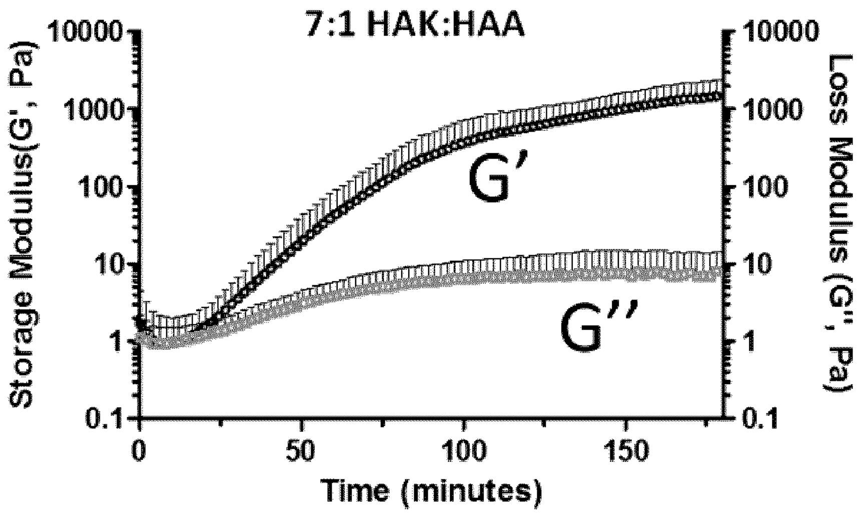
Figure 21E:
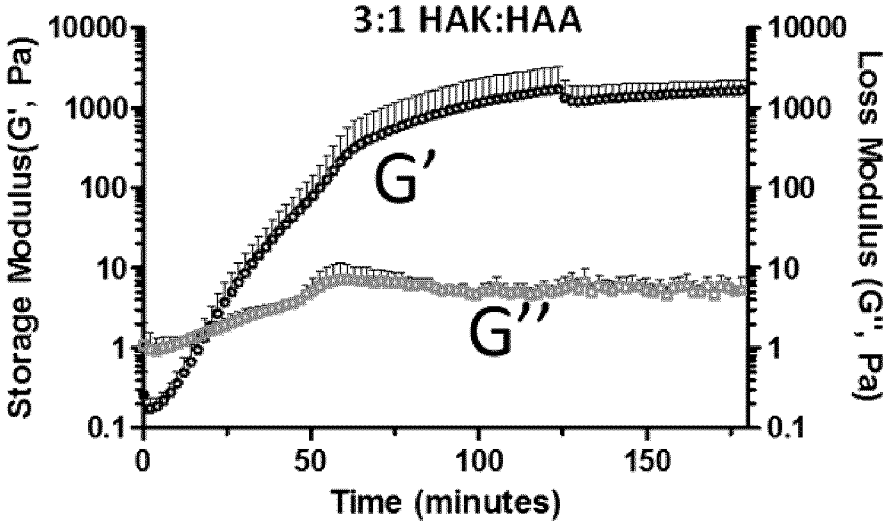
Figure 21F:
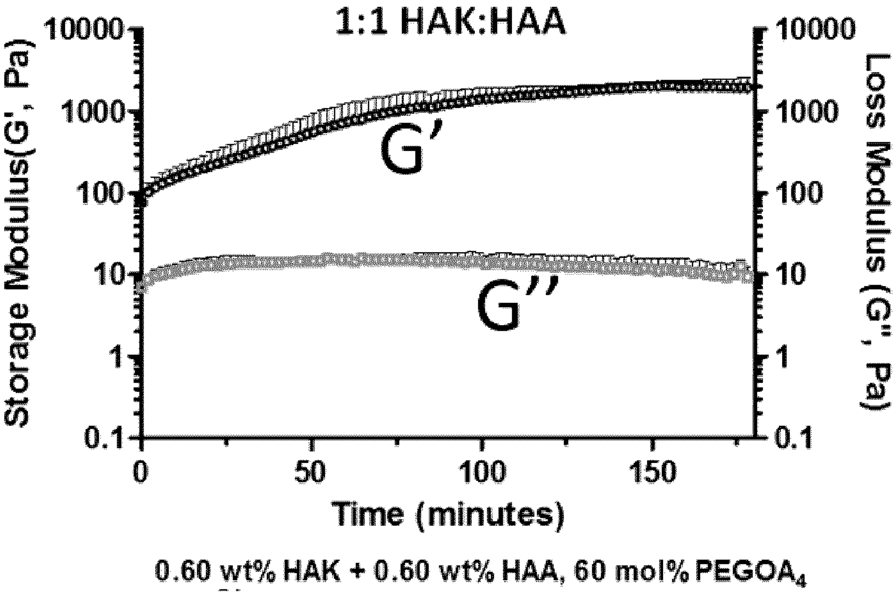

To show that both HAK and HAA biopolymers were crosslinked with PEG-oxyamine, the stability of hydrogels comprised of equal weight percent of either HAK/HAA or unmodified-HA/HAA crosslinked with PEG-oxyamine was compared: HAK/HAA hydrogels remained stable over at least 28 days (with less than 5% decrease in mass) whereas gels formed from HA/HAA slowly dissociated, losing 50±2% of their mass between day 1 and 28, reflecting the dissolution of uncrosslinked HA (FIG. 20A, FIG. 20B, and FIG. 20C). Gels crosslinked with four-armed $PEGOA_4$ swelled significantly less than those crosslinked with bifunctional $PEGOA_2$ (FIG. 20B and FIG. 20C). Although both remained intact over four weeks, $PEGOA_4$ was used in all subsequent experiments because the increased swelling of $PEGOA_2$ crosslinked gels would alter hydrogel mechanical properties and hence cell phenotype (Lin et al., Oncotarget, 6:20946 (2015)). Rheology was used to characterize the gelation rate of HA-oxime hydrogels with varying HAK: HAA mass ratios (FIG. 21A, FIG. 21B, FIG. 21C, FIG. 21D, FIG. 21E, FIG. 21F).

Cell Distribution and Viability: MDA-MB-468 cells (4,000 cells per well) were encapsulated in 1.20 wt % HA-oxime hydrogels (25 μL in 384-well format) prepared from HAK (0.60-1.20 wt %) and HAA (0-0.60 wt %) crosslinked with $PEGOA_4$ at a 0.60 oxyamine to ketone plus aldehyde ratio. After gelation (1.5-3.0 h), 75 μL of RPMI-1640 media containing 10% FBS were added. After 24 h cells were stained with calcein AM (1/250) and ethidium homodimer-1 (1/250) in media then incubated for 45 minutes. Cells were imaged using an Olympus confocal microscope at 10× magnification with z-stacks of 7 μm step size. For day 14 spheroid distribution cells were encapsulated in HA-oxime, Matrigel or HyStem-C according to manufacturer guidelines and cultured for 14 days before visualization by staining detailed above. Live and dead cells were located using spot identification in Imaris 8 software by Bitplane. Cell viability was calculated from the equation: percent viability=100×number of live cells/(number of live+dead cells). Cell or spheroid distribution analysis was performed using the z-position coordinates identified with spots and analyzed using GraphPad Prism 5 software by GraphPad Software Inc. Frequency distribution graphs were prepared with bin size set to 50 μm (day 1) or 100 μm (day 14). A minimum of 3 independent replicates consisting of different cell passages were performed for each condition.

Breast Cancer Cell Adhesion to Protein Containing HA-oxime Hydrogels: In order to determine cell adhesion to protein-containing gels, HA-oxime hydrogels containing 0.90 wt % HA-ketone, 0.30 wt % HA-aldehyde, and 60 mol % crosslinking $PEGOA_4$ (1.04 wt %) containing Ln (25, 75, 125, and 250 μg $mL^{-1}$), were prepared at 25 μL per well in a 384-well format. T47D cells were seeded at 3,000 cells $well^{-1}$ in 25 μL of RPMI-1640 media containing 10% FBS, 10 μg $mL^{-1}$ insulin, and 1% P/S and incubated for 30 minutes. Media was gently removed by pipette and replaced with PBS cooled to 4° C. to prevent further adhesion. Plates were agitated at 300 rpm for 5 minutes at room temperature with a basic variable-speed digital orbital shaker (IKA) before PBS containing detached cells were removed and gels with adherent cells were fixed with 4% PFA. T47D cells were stained with the nuclear stain, Hoechst 33342, 1/250 in PBS, 25 μL $well^{-1}$ for 4 hours. Images were obtained using an Olympus confocal microscope at 10× magnification with z-stacks of 12 μm step size to capture the meniscus. Cell number was quantified using spot identification in Imaris 8 software by Bitplane. To determine the effect of protein on cell adhesion, the fold change in adherent cell number was calculated relative to control hydrogels containing no protein. A minimum of 3 independent replicates consisting of different cell passages were performed for each condition.

Maintenance of Breast Cancer Cell Lines: Cells were passaged and grown on tissue culture flasks inside an incubator maintained at 37° C. with 5% $CO_2$ and at 95% humidity. MCF7 cells were cultured using Dulbecco's modified Eagle's medium with Ham's F-12 nutrient mixture. T47D, BT474, MDA-MB-468 and MDA-MB-231-H2N cells were cultured in RPMI-1640 medium. MCF7 and T47D media were supplemented with 10 μg $mL^{-1}$ insulin from bovine pancreas. All cell culture media were supplemented with 10% fetal bovine serum, 10 U $mL^{-1}$ penicillin, 10 μg $mL^{-1}$ streptomycin (PS). MDA-MB-231-H2N cells were a generous gift from Dr. Robert Kerbel (Sunnybrook Health Science Centre). All other cell lines were purchased from ATCC and each cell line was passaged according to supplier guidelines of 70-80% confluence for up to 20 passages.

Analysis of Spheroids: Breast cancer cells (4,000 cells per well) were encapsulated in 35 μL per well in Matrigel (8.5 mg·$mL^{-1}$ final concentration) or HA-oxime+/−Ln hydrogels crosslinked with 60 mol % $PEGOA_4$. Spheroids were imaged at 1,200 DPI and analyzed using a GelCount instrument from Oxford Optronix in 96-well format clear TCPS plates. For the quantification of spheroid diameters, proprietary algorithms developed by Oxford Optronix, which avoid counting clumped spheroids, were applied. The same masks were used for all conditions and the spheroids were detected using the CHARM optimizer with advanced preprocessing, number of spokes set to 10 and 0.30-0.60 as colony optical density. A minimum of 3 independent replicates consisting of different cell passages were performed for each condition to calculate the mean and standard deviation for the number and diameter of spheroids per well.

Proliferation of Breast Cancer Cells: MCF7, T47D, BT474, MDA-MB-231-H2N and MDA-MB-468 Breast cancer cells were plated at 4,000 cells per well on TCPS, Matrigel (8.5 mg·$mL^{-1}$, or HA-oxime hydrogels containing 0.90 wt % HA-ketone, 0.30 wt % HA-aldehyde, and 60 mol % crosslinking $PEGOA_4$ (1.04 wt %)+/−Ln at 75 μg·$mL^{-1}$. After 90 min to allow complete gelation at 37° C., 150 μL of required media was added. After 24 h, media was removed and replaced with 150 μL of PrestoBlue, which was first sterile filtered and then diluted 10× in media warmed to 37° C. After 4.5 h, fluorescence was detected using a Tecan microplate reader (Life Sciences) by exciting at 570 nm and detected at 590 nm. Every 48 h, media was removed from unmeasured wells and replaced with fresh medium. At day 7, media was removed and the PrestoBlue assay was performed as above in new wells. Cell growth was calculated by subtracting the background fluorescence of media-only controls from days 1 and 7, then dividing the day 7 fluorescence data by that at day 1. A minimum of 3 independent replicates, consisting of different cell passages, were performed for each condition to calculate the mean and standard deviation of cell growth at day 7 relative to day 1.

Breast Cancer Xenografts: All animal studies were performed in accordance with an approved protocol by the University Health Network Animal Care Committee under the guidelines of the Canadian Council on Animal Care. NOD scid gamma (NSG) mice were bred in-house and were injected with cancer cells at week 10. Mice receiving MCF7, T47D or BT474 cells were implanted with estrogen release pellets (0.72 mg, 60 day release, Innovative Research of America) one day prior to cell transplantation. For orthotopic cell transplantations, mice were anaesthetized under isoflurane-oxygen and the surgical area was depilate and cleaned with betadine. The mammary fat pad was revealed with a skin incision in the lower abdomen to the right of the midline. MCF7 ($3.37\times10^6$ cells), T47D ($7.10\times10^6$ cells per animal), BT474 ($7.80\times10^6$ cells per animal), MDA-MB-231-H2N ($1.70\times10^6$ cells per animal), or MDA-MB-468 ($9.30\times10^6$ cells per animal) cells were injected (50-80 μL) into the right inguinal region of the mammary fat pad. The number of cells injected was calculated by performing a 100× dilution of the cell suspension used for injection into PBS. Tumour volume was calculated from the length and width of the tumours measured with calipers using the formula: $V=(\pi\times(\text{short diameter})^2\times(\text{long diameter}))/6$ as previously reported (Kumacheva et al., Sci. Adv. 4 (2018)).

qPCR: RNA was isolated and purified using a Nuclespin RNA purification kit (Macherey-Nagel) and DNAse (Thermo Scientific). RNA purity was measured using a NanoDrop 1000 UV-Vis spectrometer (Themo Fisher Scientific), only samples with 260/280 ratios between 1.8-2.2 were stored at −80° C. for reverse transcription or NanoString discussed below. Reverse transcription of RNA to prepare cDNA was performed using SuperScript III reverse transcriptase (Invitrogen) and a SimpliAmp (Life Technologies) thermal cycler. Primers detailed in Table 4 were ordered from ACGT Corporation and 5 ng cDNA per reaction and three technical replicates per sample were loaded onto 384-well plates by pipette or using an epMotion 5070 liquid handling workstation (Eppendorf). Quantification of gene expression was performed using LightCycler 480 SYBR Green I Master (Roche) and a QuantStudio 6 Flex (Life Technologies) detection system. Expression levels were normalized to β-actin and calculated from delta-delta threshold cycle (ΔΔCT). All qPCR reactions were performed in triplicate. Data represents the mean $\log_2$ gene expression relative to the xenograft.

TABLE 4

| Primer Name | Description | | Bases | Sequence (5′→3′) | SEQ ID NO |
|---|---|---|---|---|---|
| Prα | Transcriptional | FP | 20 | AAATCATTGCCAGGTTTTCG | SEQ ID NO: 3 |
| | regulator | RP | 20 | TGCCACATGGTAAGGCATAA | SEQ ID NO: 4 |
| ESR1 | Proliferation | FP | 17 | GCCAACGCGCAGGTCTA | SEQ ID NO: 5 |
| | | RP | 14 | GCCGCAGCCTCAGA | SEQ ID NO: 6 |
| ESR2 | Proliferation | FP | 23 | GTCAGGCACATCAGTAACAAGGG | SEQ ID NO: 7 |
| | | RP | 24 | ATTCAGCATCTCCAGCAGCAGGTC | SEQ ID NO: 8 |
| ERBB2 | Proliferation and anti- | FP | 22 | CCTCTGACGTCCATCGTCTC | SEQ ID NO: 9 |
| | apoptosis | RP | 22 | CGGATCTTCTGCTGCCGTCG | SEQ ID NO: 10 |
| EGFR | MAPK and Akt pathway, | FP | 25 | CGCAAGTGTAAGAAGTGCGAA | SEQ ID NO: 11 |
| | proliferation | RP | 21 | CGTAGCATTTATGGAGAGTGAGTCT | SEQ ID NO: 12 |
| MCL1 | Mitochondial apoptotic | FP | 22 | ATCTCTCGGTACCTTCGGGAGC | SEQ ID NO: 13 |
| | signalling | RP | 22 | CCTGATGCCACCTTCTAGGTCC | SEQ ID NO: 14 |
| BCL6 | Transcriptional modulator | FP | 20 | CTGCAGATGGAGCATGTTGT | SEQ ID NO: 15 |
| | | RP | 20 | TCTTCACGAGGAGGCTTGAT | SEQ ID NO: 16 |
| PIK3CA | Cell proliferation, | FP | 20 | ATGATGCTTGGCTCTGGAAT | SEQ ID NO: 17 |
| | DNA repair, apoptosis | RP | 20 | GGTCTTTGCCTGCTGAGAGT | SEQ ID NO: 18 |
| AIB1 | Transcriptional coactivator | FP | 18 | GCGGCGAGTTTCCGATTT | SEQ ID NO: 19 |
| | | RP | 19 | GCTCCCGTCTCCGTTTTTC | SEQ ID NO: 20 |
| TP53 | Apoptosis 61enabilit and | FP | 20 | TACTCCCCTGCCCTCAACAA | SEQ ID NO: 21 |
| | DNA repair | RP | 20 | CATCGCTATCTGAGCAGCGC | SEQ ID NO: 22 |
| NOTCH1 | Cell growth and division | FP | 22 | GAAGAACGGGGCTAACAAAGAT | SEQ ID NO: 23 |
| | | RP | 22 | GTCCATATGATCCGTGATGTCC | SEQ ID |

TABLE 4-continued

| Primer Name | Description | | Bases | Sequence (5'→3') | SEQ ID NO |
|---|---|---|---|---|---|
| | | | | | NO: 24 |
| ABCA1 | Cholesterol efflux | FP | 21 | TGCAAGGCTACCAGTTACATT | SEQ ID NO: 25 |
| | regulatory promoter | RP | 21 | TTAGTGTTCTCAGGATTGGCT | SEQ ID NO: 26 |
| FASN | Catalyzes the synthesis of | FP | 19 | TCGTGGGCTACAGCATGGT | SEQ ID NO: 27 |
| | fatty acids | RP | 22 | GCCCTCTGAAGTCGAAGAAGAA | SEQ ID NO: 28 |
| β-actin | Cytoskeleton, housekeeping | FP | 21 | CATGTACGTTGCTATCCAGGC | SEQ ID NO: 29 |
| | gene | RP | 21 | CTCCTTAATGTCACGCACGAT | SEQ ID NO: 30 |

Immunocytochemistry: At day 21, media was removed and replaced with PBS. After 10 min, PBS was replaced with 4% PFA and cells were fixed for 20 min at room temperature. Cells were washed 3× with PBS, 10 min each, and then permeabilized with 0.5% saponin containing 1% BSA in PBS for 2 h. Cells were washed 3× with PBS containing 100 mM glycine, 10 min each, and then primary antibodies were added in 10% goat serum with 1× immunofluorescence (IF) wash prepared from 10×IF stock solution. 10×IF was prepared as previously reported (Jacobi et al., Oncotarget, 8:107423 (2017)). The following primary antibodies were used as follows: anti-CD44 (1/10), rabbit monoclonal anti-HIF-1α (1/50), mouse monoclonal anti-E-Cadherin (1/100), rabbit polyclonal anti-integrin-$\beta_1$ (1/100). The diluted primary antibodies were added at 150 μL or 50 μL for 96-well or 384-well culture format, respectively, and maintained at 4° C. overnight. After 16 h, primary antibodies were removed and washed 3× with IF wash. Goat anti-mouse IgG (H+L), highly cross-adsorbed secondary antibody tagged with Alexa Fluor 488, and goat anti-rabbit IgG (H+L) Alexa Fluor 647 were added 1/150 in 1×IF wash containing 10% goat serum. After 4 h the secondary was removed and replaced with 1×IF, which was again replaced after 1 h and 16 h. Cells were stained for nuclei and F-actin using Hoechst 33342 (1/100) and rhodamine-labelled phalloidin (1/100 of a 300 unit solution in 1.5 mL of methanol) for 3 h in 1×IF wash. Higher concentrations of fluorescent probes are typically required to image within hydrogels. The staining solution was removed after 3 h and replaced with 1×IF wash for imaging. Hydrogels were transferred to a magnetic 4-well chamber slide (Quorum Technologies Inc.) and imaged using an Olympus confocal microscope at 40× magnification through No. 1.5 glass coverslips (VWR). Only the spheroids within the first 200 μm of hydrogel were imaged using a 40× objective (E-cadherin, CD44, integrin-β1, HIF-1α) while spheroids throughout the hydrogel were imaged with a 10× long working distance objective.

Pan-Cancer Panel Gene Expression: Purified RNA from BT474, MDA-MB-231-H2N, and MDA-MB-468 cells cultured on 2D TCPS, in growth factor reduced Matrigel, or HA-oxime+/−Ln for 21 days and as xenografts in mice described above was analyzed using an nCounter PanCancer Human Pathways Panel (NanoString Technologies). RNA (100 ng per sample) was hybridized following the manufacturer's protocol. For each analysis, 12 samples were loaded on the cassettes using the nCounter Prep Station (NanoString Technologies), followed by analysis of gene expression using an nCounter Digital Analyzer instrument (NanoString Technologies). Data was processed using nSolver Analysis Software version 3.0 by NanoString Technologies. First quality control flags were analyzed according to data analysis guidelines followed by normalization of gene expression counts using housekeeping genes shown in Supplementary Table 4. All NanoString analysis was performed with at least three independent replicates. Normalized counts of gene expression were analyzed by one-way ANOVA and Tukey's post-hoc test. A complete list of the genes represented in the Venn diagrams are listed in Tables 5A, 5B, 6A, 6B, 7A, and 7B. The association of these genes to specific pathways were analyzed using GSVA with pathway classification information obtained from NanoString available online at nCounter® PanCancer Pathways Panel as a downloadable file.

TABLE 5A

| HA-oxime vs. Xenograft (12) | |
|---|---|
| Down-regulated (5) | Up-regulated (7) |
| FGF1 | CACNA1E |
| LAMB3 | CACNB2 |
| NOTCH2 | EFNA2 |
| PRKAR2B | FLT3 |
| WNT5A | GLI1 |
| | HNF1A |
| | IFNA2 |
| HA-oxime ∩ Matrigel vs. Xenograft (6) | |
| Down-regulated (0) | Up-regulated (6) |
| | CEBPE |
| | H2AFX |
| | PAK7 |
| | PPP3CC |
| | RASGRF2 |
| | SPP1 |
| HA-oxime ∩ 2D TCPS vs. Xenograft (5) | |
| Down-regulated (0) | Up-regulated (5) |
| | CDKN1A |
| | FAS |
| | FBXW7 |
| | IL11RA |
| | SOCS2 |
| Matrigel vs. Xenograft (137) | |

TABLE 5A-continued

| Down-regulated (31) | Up-regulated (106) | | |
|---|---|---|---|
| AR | ACVR1C | GAS1 | NR4A3 |
| ARID1A | AMH | GRIN1 | NTRK1 |
| ARID1B | BID | GRIN2B | PAX3 |
| BCL2 | BNIP3 | GZMB | PAX5 |
| CACNA2D2 | CACNA2D3 | HGF | PAX8 |
| CCND1 | CARD11 | HHEX | PCK1 |
| CIC | CBLC | HMGA2 | PDGFRA |
| DTX4 | CCNA2 | HOXA10 | PDGFRB |
| DUSP10 | CCNO | HPGD | PHF6 |
| EP300 | CCR7 | IBSP | PIK3CG |
| FANCF | CD19 | IFNA17 | PIM1 |
| FANCG | COL24A1 | IFNA7 | PITX2 |
| FUT8 | COL3A1 | IFNG | PLA1A |
| GATA3 | COL4A6 | IL10 | PLA2G5 |
| GHR | COL6A6 | IL12B | PPARG |
| GNAQ | CREB3L3 | IL12RB2 | PPP3R2 |
| GPC4 | CRLF2 | IL1R2 | PRKACG |
| HSPA1A | CSF1R | IL23A | PRL |
| HSPB1 | CSF2 | IL24 | PTCRA |
| IKBKB | CSF3 | IL2RA | PTPN5 |
| KITLG | DKK2 | IL5RA | PTPRR |
| KMT2D | DTX1 | IL6 | RXRG |
| MAPK8IP1 | EYA1 | IRAK3 | TCL1B |
| MYCN | FGF14 | ITGB3 | TGFB2 |
| NF2 | FGF17 | JAK3 | THEM4 |
| NFATC1 | FGF19 | LEFTY2 | TLX1 |
| NSD1 | FGF3 | MAPK8 | TNFRSF10C |
| PDGFB | FGF5 | MMP3 | TNFRSF10D |
| PIK3R1 | FGF6 | MMP7 | TNN |
| PPP2R2C | FGF8 | MMP9 | UTY |
| SYK | FLT1 | MNAT1 | WNT10A |
| | FOSL1 | MPL | WNT5B |
| | FOXL2 | NFE2L2 | WT1 |
| | FST | NGF | XRCC4 |
| | FZD10 | NODAL | |
| | FZD2 | NPM2 | |

TABLE 6A

| HA-oxime vs. Xenograft (28) | |
|---|---|
| Down-regulated (16) | Up-regulated (12) |
| BNIP3 | B2M |
| CASP3 | CACNA2D3 |
| EGFR | CDK2 |
| FST | DLL3 |
| HMGA2 | H2AFX |
| HSP90B1 | IL1R1 |
| IGFBP3 | LAMC2 |
| IL1RAP | LEP |
| ITGA6 | LIF |
| ITGB8 | MMP3 |
| MAP2K1 | RASGRP2 |
| PPP3CA | UTY |
| PTPN11 | |
| RAD21 | |
| TBL1XR1 | |
| WNT5A | |
| **HA-oxime ∩ Matrigel vs. Xenograft (23)** | |
| Down-regulated (11) | Up-regulated (12) |
| FN1 | CD14 |
| FZD8 | DUSP10 |
| POLR2H | GATA2 |
| PPP3R1 | IKBKG |
| PRKAR2A | LAMA5 |
| PRKDC | MLLT4 |
| RB1 | RAC2 |
| RFC3 | RASGRF1 |
| SOCS2 | SPRY4 |
| TFDP1 | STAT3 |
| TGFBR2 | STK11 |
| | TNFRSF10B |
| **HA-oxime ∩ 2D TCPS vs. Xenograft (20)** | |

TABLE 5B

| Matrigel ∩ 2D TCPS vs. Xenograft (27) | | 2D TCPS vs. Xenograft (45) | | HA-oxime ∩ Matrigel ∩ 2D TCPS Xenograft (28) | |
|---|---|---|---|---|---|
| Down-regulated (13) | Up-regulated (14) | Down-regulated (28) | Up-regulated (17) | Down-regulated (19) | Up-regulated (9) |
| CDC25B | CACNG6 | AKT1 | ATRX | CACNA1G | GADD45A |
| ITGB6 | DDIT3 | BAD | CALML6 | COL1A2 | IGFBP3 |
| MAPK3 | EPHA2 | BMPR1B | CREB5 | FGF18 | LEF1 |
| MAPK8IP2 | H3F3C | C19orf40 | DKK1 | FGF2 | MPO |
| MCM2 | ID1 | CACNA2D1 | DLL4 | GRIA3 | PLA2G4C |
| MTOR | LEPR | CCND3 | FGF20 | HSPA2 | RRAS2 |
| PIK3R2 | LIG4 | DNMT1 | FOS | IL20RA | TNFRSF10B |
| PLA2G4F | MAML2 | ERBB2 | ID4 | INHBA | WNT6 |
| SIX1 | MET | FGFR1 | IL12A | PLA2G10 | XPA |
| SMC1A | PLCE1 | GNA11 | JUN | PRKCB | |
| SOX9 | PLD1 | GNAS | MDM2 | RUNX1T1 | |
| WNT11 | SMAD9 | GRB2 | MLLT4 | SFRP2 | |
| WNT7B | SPRY1 | HDAC1 | MYC | SFRP4 | |
| | TSLP | ITGB4 | NFKBIZ | THBS1 | |
| | | LAMA3 | RASA4 | THBS4 | |
| | | MCM4 | SPOP | TRAF7 | |
| | | NBN | STAT4 | TSPAN7 | |
| | | NTRK2 | | WNT16 | |
| | | PDGFD | | ZBTB16 | |
| | | PKMYT1 | | | |
| | | POLR2D | | | |
| | | PRKACA | | | |
| | | PRKAR1B | | | |
| | | PRKDC | | | |
| | | SFN | | | |
| | | SMARCB1 | | | |
| | | TGFBR2 | | | |
| | | TIAM1 | | | |

TABLE 6A-continued

| Down-regulated (12) | Up-regulated (8) |
|---|---|
| BMP2 | BAMBI |
| DUSP6 | CASP8 |
| ETS2 | FANCL |
| INHBA | ID2 |
| LAMB3 | KAT2B |
| NF2 | PLA2G4C |
| NOG | STAT1 |
| PDGFC | TIAM1 |
| PRDM1 | |
| PRKACB | |
| RUNX1 | |
| WNT5B | |
| **Matrigel vs. Xenograft (49)** | |
| Down-regulated (28) | Up-regulated (21) |
| ALKBH3 | ARID1A |
| ARID1B | BAIAP3 |
| BAD | BCL2A1 |
| CCNA2 | DDIT3 |
| CCNE1 | DUSP8 |
| CDC6 | EFNA5 |
| CHEK1 | EGFR |
| CTNNB1 | FGFR1 |
| GADD45G | FLNC |
| GPC4 | FOXO4 |
| GRIA3 | GNAQ |
| HIST1H3B | ITGB3 |
| HIST1H3H | LIFR |
| HSPB1 | MED12 |
| JAG1 | NFKB1 |
| JUN | POLD4 |
| KRAS | PRKAA2 |
| MCM7 | SGK2 |
| MDM2 | SPRY2 |
| NBN | TGFB2 |
| NTRK2 | ZAK |

TABLE 6A-continued

| | |
|---|---|
| PIK3R3 | |
| POLE2 | |
| RBX1 | |
| SFRP4 | |
| TSPAN7 | |
| UBB | |
| XRCC4 | |
| **Matrigel ∩ 2D TCPS vs. Xenograft (41)** | |
| Down-regulated (22) | Up-regulated (19) |
| CCNB1 | BDNF |
| CCND1 | BRAF |
| CDC25A | CCND2 |
| COL1A1 | EPOR |
| DNMT1 | HDAC11 |
| E2F1 | HDAC5 |
| ETV4 | IGF1R |
| EZH2 | INHBB |
| FEN1 | ITGA3 |
| FGF18 | LEPR |
| HDAC1 | MET |
| HRAS | NOTCH2 |
| MAP2K6 | PIK3CB |
| MCM2 | PLD1 |
| PCNA | RPS6KA6 |
| PKMYT1 | SOS2 |
| PML | SPRY1 |
| RAC3 | TCF3 |
| SFN | VEGFA |
| SMC1A | |
| SRSF2 | |
| STMN1 | |

TABLE 6B

| 2D TCPS vs. Xenograft (62) | | HA-oxime ∩ Matrigel ∩ 2D TCPS Xenograft (73) | |
|---|---|---|---|
| Down-regulated (33) | Up-regulated (29) | Down-regulated (31) | Up-regulated (42) |
| AKT1 | BRCA1 | BCL2L1 | ARNT2 |
| CDC25B | CASP7 | CAPN2 | BCOR |
| CDKN2C | CDKN2D | CCNA1 | BIRC3 |
| COL27A1 | CUL1 | CCNE2 | CDKN1A |
| COL4A6 | FUBP1 | CDC7 | COL4A5 |
| EIF4EBP1 | GNG12 | CDK4 | CSF2 |
| ERCC2 | GSK3B | CDK6 | CSF3 |
| FANCA | HDAC2 | COL1A2 | CYLD |
| FANCG | HDAC6 | FUT8 | DUSP4 |
| FLNA | HHEX | GNAS | EFNA1 |
| FOSL1 | IRS1 | GTF2H3 | ERBB2 |
| FZD2 | ITGB6 | H3F3A | ERCC6 |
| GNA11 | JAK1 | HHIP | ETV1 |
| GNAQ | KIT | HMGA1 | FBXW7 |
| GRB2 | KLF4 | HSPA6 | FGFR3 |
| HDAC10 | MAP2K4 | LTBP1 | FZD7 |
| HSPA1A | MNAT1 | MAP2K2 | GADD45A |
| IFNA17 | NCOR1 | MCM4 | ID1 |
| LEFTY2 | PHF6 | MCM5 | IL1A |
| MLLT3 | PPP2CB | NRAS | IL1B |
| MYB | PTEN | PLAU | IL24 |
| MYC | RELA | PRKCB | IL6 |
| NOTCH1 | SF3B1 | RHOA | IL7R |
| PIK3R1 | SMAD2 | SFRP2 | IL8 |
| PIK3R2 | SMARCA4 | SMARCB1 | IRAK2 |
| POLD1 | SOS1 | SOX9 | JAG2 |
| POLR2D | STAG2 | SYK | LAMA3 |
| PPP3CB | TBL1XR1 | THBS4 | MAP3K5 |
| SMO | TET2 | TNC | MAP3K8 |
| SP1 | | TRAF7 | MAPK12 |

TABLE 6B-continued

| 2D TCPS vs. Xenograft (62) | | HA-oxime ∩ Matrigel ∩ 2D TCPS Xenograft (73) | |
|---|---|---|---|
| Down-regulated (33) | Up-regulated (29) | Down-regulated (31) | Up-regulated (42) |
| TGFB1 | | U2AF1 | NFE2L2 |
| TGFB3 | | | NFKBIA |
| WHSC1 | | | NFKBIZ |
| | | | NGF |
| | | | PPARG |
| | | | RASA4 |
| | | | SHC1 |
| | | | SMAD3 |
| | | | TLR4 |
| | | | VHL |
| | | | WNT2B |
| | | | ZIC2 |

TABLE 7A

| HA-oxime vs. Xenograft (21) | | Matrigel vs. Xenograft (17) | | Matrigel ∩ 2D TCPS vs. Xenograft (18) | |
|---|---|---|---|---|---|
| Down-regulated (17) | Up-regulated (4) | Down-regulated (16) | Up-regulated (1) | Down-regulated (12) | Up-regulated (6) |
| CCR7 | DUSP10 | ACVR2A | HSPA6 | AXIN1 | EIF4EBP1 |
| CD19 | EGF | BAX | | BMP6 | ERCC6 |
| CSF3 | PLAT | CAPN2 | | BRIP1 | FANCB |
| EGFR | SMAD3 | DDB2 | | CCND3 | IGFBP3 |
| FANCC | | KRAS | | CDC6 | INHBB |
| FGF5 | | LAMB3 | | E2F1 | MNAT1 |
| FGF8 | | MAPK3 | | FEN1 | |
| HPGD | | MDM2 | | FZD9 | |
| IFNG | | MECOM | | GRB2 | |
| IRS1 | | MSH2 | | MAP3K1 | |
| ITGA7 | | MSH6 | | MDC1 | |
| PIK3CD | | PGF | | PRKAR1B | |
| RASGRF2 | | PIK3R2 | | | |
| SPRY1 | | PPP3R1 | | | |
| TLR4 | | RHOA | | | |
| VEGFC | | SFRP1 | | | |
| WNT5A | | | | | |

| HA-oxime ∩ Matrigel vs. Xenograft (34) | | HA-oxime ∩ 2D TCPS vs. Xenograft (11) | |
|---|---|---|---|
| Down-regulated (29) | Up-regulated (5) | Down-regulated (2) | Up-regulated (9) |
| CACNA1C | BAIAP3 | CDK6 | ALKBH3 |
| CACNA1G | IL1R1 | HSPA1A | ETS2 |
| CACNA2D4 | KDM5C | | HDAC11 |
| CARD11 | POLD4 | | LIFR |
| CDH1 | TNFRSF10C | | MEN1 |
| CREB5 | | | MYB |
| CRLF2 | | | PRKCA |
| CTNNB1 | | | TET2 |
| FGF18 | | | TGFB1 |
| FLNA | | | |
| GATA2 | | | |
| GRIA3 | | | |
| IL24 | | | |
| MAML2 | | | |
| MAP2K6 | | | |
| MCM7 | | | |
| MMP7 | | | |
| NBN | | | |
| NOTCH2 | | | |
| NTF3 | | | |
| PIK3CA | | | |
| PRKDC | | | |
| RFC3 | | | |
| SF3B1 | | | |
| SMC3 | | | |
| TFDP1 | | | |
| WIF1 | | | |
| WNT6 | | | |
| ZBTB32 | | | |

TABLE 7B

| 2D TCPS vs. Xenograft (68) | | HA-oxime ∩ Matrigel ∩ 2D TCPS Xenograft (119) | | |
|---|---|---|---|---|
| Down-regulated (31) | Up-regulated (37) | Down-regulated (77) | | Up-regulated (42) |
| ABL1 | ARID1B | AKT1 | PKMYT1 | ACVR1C |
| AKT2 | BRAF | ANGPT1 | PLCB1 | AXIN2 |
| AMER1 | CACNA2D4 | B2M | PML | BMP7 |
| APC | CDC14A | BAP1 | PRKCB | CEBPA |
| CCND1 | COL5A1 | BCL2L1 | PROM1 | CSF3R |
| CDK4 | COL5A2 | BMP2 | RAD21 | DUSP4 |
| CDKN1B | CRLF2 | BMP5 | RASAL1 | EFNA3 |
| CDKN2A | FGF13 | BRCA2 | SFRP2 | ERBB2 |

TABLE 7B-continued

| 2D TCPS vs. Xenograft (68) | | HA-oxime ∩ Matrigel ∩ 2D TCPS Xenograft (119) | | |
|---|---|---|---|---|
| Down-regulated (31) | Up-regulated (37) | Down-regulated (77) | | Up-regulated (42) |
| CDKN2B | FGF22 | CACNA2D1 | SFRP4 | GADD45A |
| CHUK | FN1 | CACNB3 | SHC4 | GLI3 |
| CIC | GNG12 | CALML5 | SKP2 | HDAC6 |
| CREB3L1 | GSK3B | CDC25A | SMAD4 | ID1 |
| DUSP2 | HDAC2 | COL1A2 | SMARCB1 | IL1RAP |
| EZH2 | HOXA10 | COL4A4 | SMO | IL20RA |
| GNAQ | HSPB1 | DAXX | SPRY2 | ITGA3 |
| H2AFX | IL24 | DNMT1 | SRSF2 | JAG1 |
| HDAC1 | LEPR | DNMT3A | STAT1 | JAG2 |
| ID2 | LTBP1 | E2F5 | STAT3 | WHSC1 |
| IFNA17 | MAPK9 | ETV1 | STK11 | KITLG |
| IKBKG | MLF1 | ETV4 | STMN1 | MAP3K5 |
| LEFTY2 | NF1 | FANCE | SYK | NFE2L2 |
| MLLT3 | NTF3 | FANCG | TCF7L1 | NKD1 |
| NOTCH1 | PBX3 | FGF2 | TGFBR2 | NOTCH3 |
| NRAS | PIK3CB | FGFR1 | THBS1 | NUMBL |
| POLR2D | PPP2CB | FST | THBS4 | NUPR1 |
| PRKX | PPP3CA | FZD7 | TNC | PLA2G2A |
| PRLR | PTEN | GNA11 | TP53 | PPARG |
| SETD2 | PTPN11 | HMGA1 | TRAF7 | PRKAA2 |
| SMC1A | RAC1 | HRAS | TSPAN7 | PRKACB |
| TGFB3 | RASGRF2 | INHBA | U2AF1 | PRKAR2B |
| WNT11 | RPS27A | ITGA6 | WHSC1 | RAC2 |
| | SETBP1 | ITGA9 | | RASA4 |
| | SKP1 | ITGB4 | | RRAS2 |
| | SOCS3 | ITGB8 | | SHC3 |
| | TBL1XR1 | MAPK8IP2 | | SOS1 |
| | VEGFC | MCM2 | | TIAM1 |
| | ZBTB32 | MCM4 | | TNFSF10 |
| | | MCM5 | | WNT2B |
| | | MET | | WNT4 |
| | | MYCN | | WNT7B |
| | | MYD88 | | WT1 |
| | | NF2 | | ZIC2 |
| | | NGFR | | |
| | | NSD1 | | |
| | | PDGFC | | |
| | | PDGFD | | |

Results: The cell distribution and mechanical properties of the HA-oxime hydrogel used in 3D cell culture.

Figure 22A:
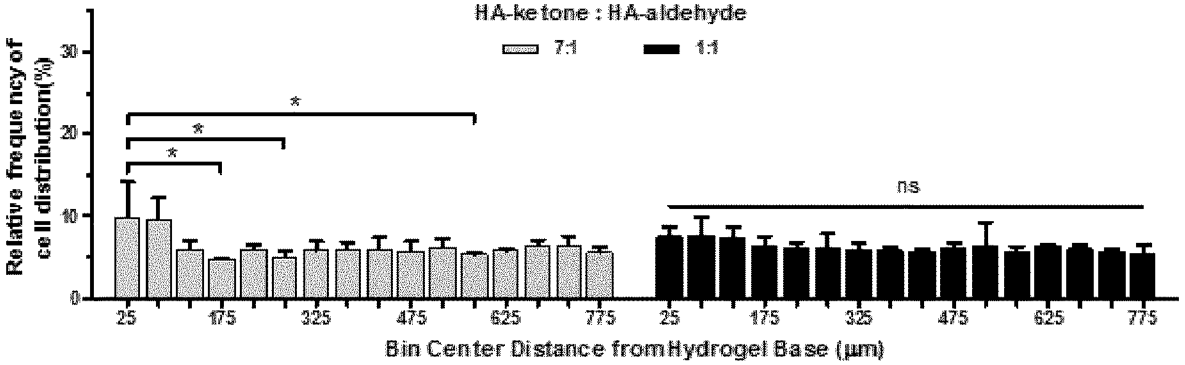
FIG. 22A, FIG. 22B, and FIG. 22C illustrate distribution and viability of MDA-MB-468 cells in HA-oxime hydrogels with increasing weight percent of HAA after 24 h of culture.
Figure 22B:
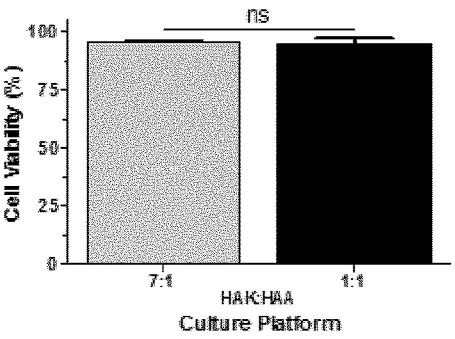
Figure 22C:
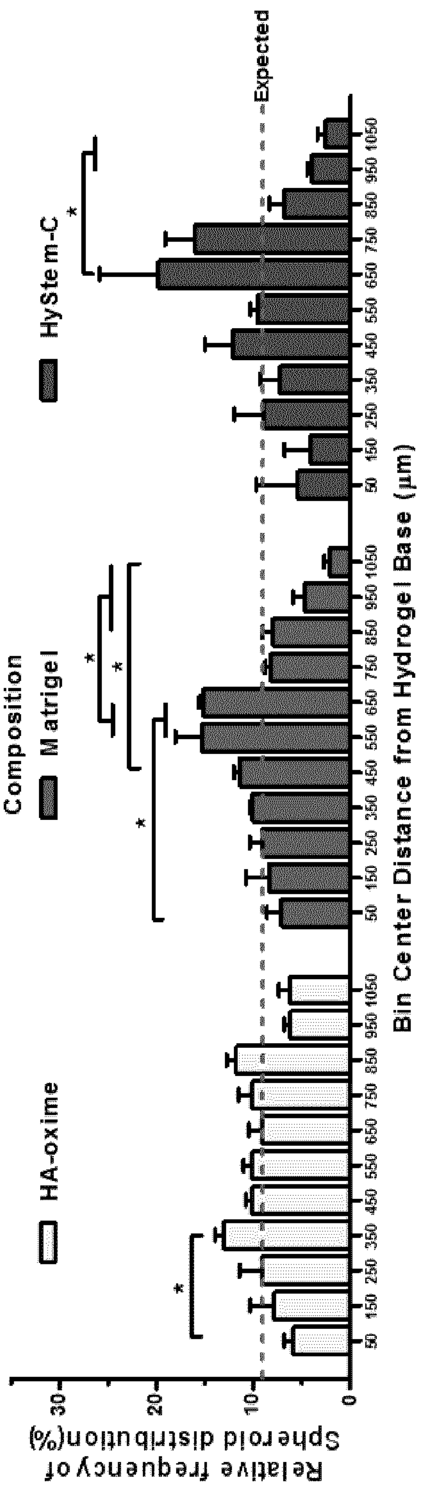

Tunable Gelation of HA-oxime Hydrogels Influences 3D Cell Distribution: To achieve uniform 3D cell distribution, hydrogels must form rapidly enough to avoid cell aggregation due to gravity during gelation, but slow enough for practical use. HAA only crosslinked hydrogels (0:1 HAK:HAA) formed too quickly for cell encapsulation, requiring cells to be cultured on top of those gels versus within (Baker et al., Biomacromolecules, 18:4373 (2017)). In contrast, hydrogels synthesized with only HAK (1:0, HAK:HAA) and $PEGOA_4$ formed too slowly, with gelation at 87±11 min. Consequently, when single breast cancer cells were encapsulated in HAK-only HA-oxime gels, cells accumulated in the bottom of the well, due to the slow crosslinking reaction between ketones and oxyamines (FIG. 17C). The gelation rate increased significantly with an increasing amount of HAA (FIG. 21A, FIG. 21B, FIG. 21C, FIG. 21D, FIG. 21E, and FIG. 21F). HA-oxime hydrogels produced with HAK:HAA mass ratios of either 7:1 or 3:1, at a constant oxyamine to ketone/aldehyde mole ratio of 0.60, resulted in mean gelation times of 35 and 25 min, respectively. At higher weight percentages of the faster gelling HAA (HAK:HAA of 1:1), the resulting crosslinked gel formed too rapidly for quantification by rheology. HAK:HAA of 3:1 was used in subsequent assays and found a uniform distribution of viable cells (FIG. 13C, FIG. 22A, and FIG. 22B). This uniform distribution was maintained for a longer time when cells were grown in HA-oxime hydrogels versus those in Matrigel or a commercially available HA-based hydrogel, HyStem-C(HA-thiol/gelatin-thiol crosslinked with PEG diacrylate) (FIG. 22C).

Figure 23:
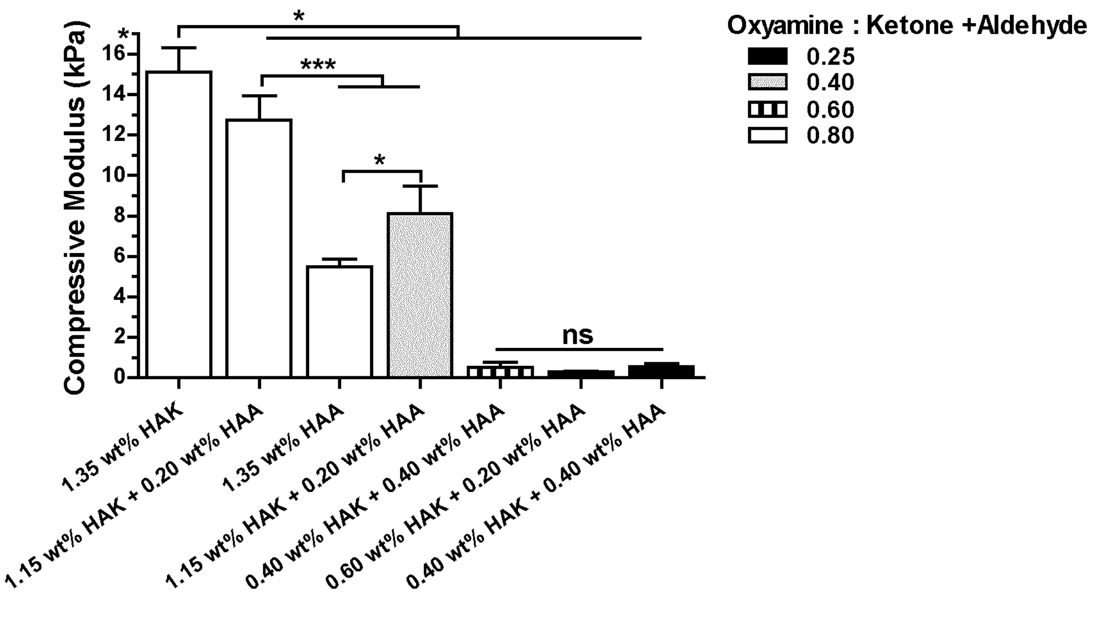
FIG. 23 illustrates compressive modulus of HA-oxime hydrogels prepared with HAK, HAA and $PEGOA_4$ (n=3-4 independent samples, data represents mean+standard deviation, *$p<0.05$; ***$p<0.001$, one-way ANOVA, Tukey's post-hoc test).

Composition-controlled Mechanical Properties and Enzyme-specific Degradation of HA-oxime Hydrogels: The following study was conducted to investigate the mechanical tunability of HA-oxime hydrogels in relation to Matrigel, the current standard for 3D cell and organoid culture. Matrigel compositions, purchased with protein concentrations of 8.50 and 18.43 $mg \cdot mL^{-1}$, had compressive moduli of 0.9±0.7 kPa and 1.6±0.4 kPa, respectively, which were not significantly different from each other (FIG. 17E). These formulations are typically used for in vitro culture and underscore the limited mechanical tunability offered by Matrigel (Smolina et al., Analyst, 141:620 (2016)). In contrast, the stiffness of HA-oxime hydrogels varied with the ratio of HAK to HAA. HA-oxime hydrogels are highly tunable over 2 orders of magnitude, between 0.3 and 15 kPa, by either varying the crosslinking density or the weight percent of HA (FIG. 23). This range covers the stiffness reported for mouse mammary tumours (~1.5-4.0 kPa), and human breast cancer tissue (~5-16 kPa), as measured by compression and atomic force microscopy, respectively (Paszek et al., Cancer cell 8:241 (2005); Levental et al., Cell 139:891 (2009); Ansardamavandi et al., J. Mech. Behav. Biomed. Mater. 60:234 (2016)).

Figure 24:
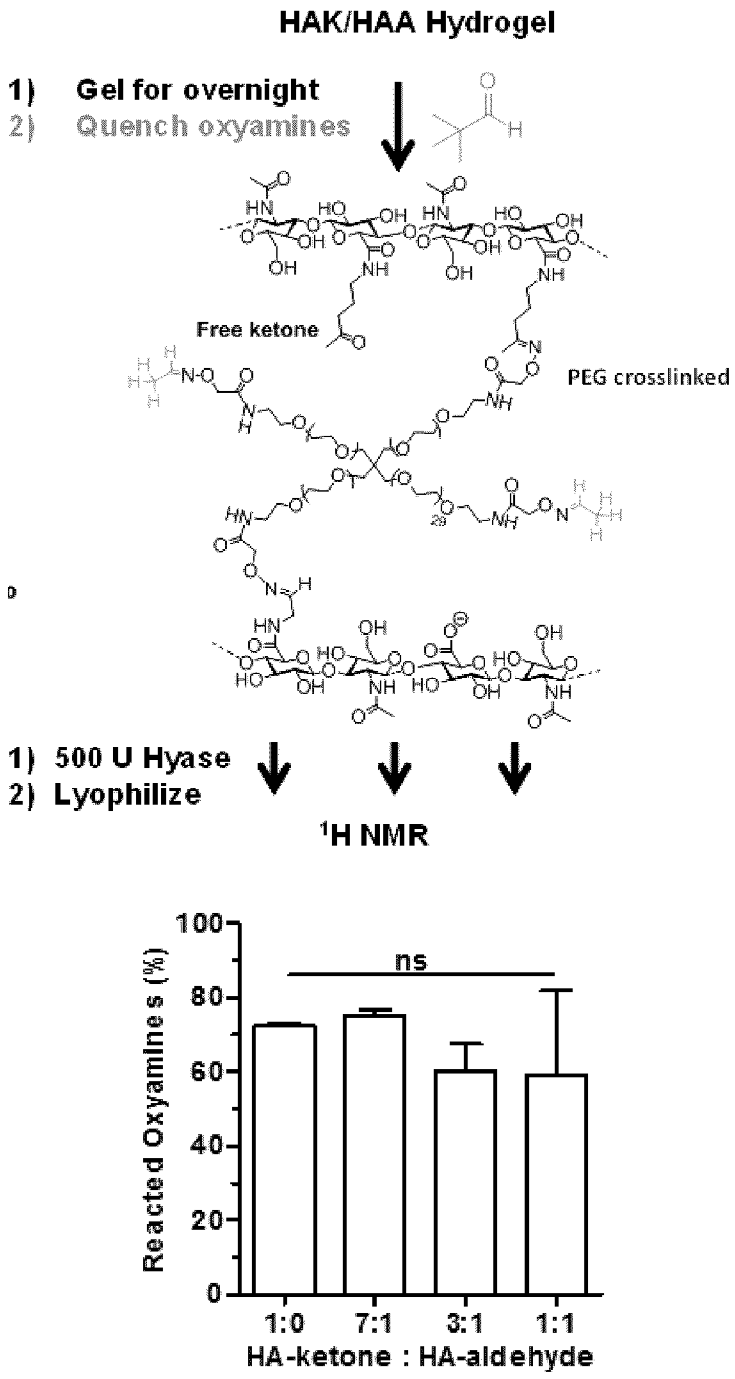
FIG. 24 is a scheme illustrating oxyamine quantification of HAK/HAA hydrogels crosslinked with $PEGOA_4$ with a ratio of oxyamine to aldehyde and ketone of 0.60. After gelation, hydrogels were quenched with pivalaldehyde and degraded for $^1H$ NMR analyses. The crosslinking efficiency of HA-oxime hydrogels calculated by $^1H$ NMR using pivalaldehyde (n=3 independent samples, mean+standard deviation plotted, no significance (ns) by one-way ANOVA, Tukey's post-hoc test).

HAK-only (1.35 wt %) hydrogels were significantly stiffer (15±1 kPa) than HAA-only (1.35 wt %) hydrogels (5.5±0.4 kPa) at a constant mole ratio (0.80) of oxyamine to ketone/aldehyde (FIG. 23). The difference in modulus of HAK-oxime and HAA-oxime hydrogels was attributed to the difference in molar mass. While the same molar mass of HA was used, synthesis of HAK resulted in a molar mass of 311 $kg \cdot mol^{-1}$ whereas that of HAA resulted in a molar mass of 122 $kg \cdot mol^{-1}$ as measured by gel permeation chromatography. Importantly, there was no change in oxyamine to oxime conversion with all HAK and HAA formulations, as quantified by $^{1}H$ NMR spectroscopy (FIG. 24), further indicating that the molar mass difference accounted for the difference in compressive modulus. The stiffness of gel formulations with 3:1 and 1:1 HAK:HAA weight ratios were not statistically different from Matrigel, so a 3:1 ratio was used for future experiments as it was easier to handle. HA-oxime gels were stable for 28 days when swollen in PBS or when treated with collagenase and degraded only in the presence of hyaluronidase, highlighting the enzyme-specific degradability (FIG. 17F). Importantly, breast cancer cells are known to produce hyaluronidase, which allows dynamic, cell-based spatiotemporal remodeling of the HA-oxime hydrogels during cell growth (Edjekouane et al., Journal of tissue engineering and regenerative medicine, 5:790 (2011)).

Hydrogel Stability and Degradation: HA-oxime hydrogels containing 0.90 wt % HA-ketone, 0.30 wt % HA-aldehyde, and 60 mol % crosslinking $PEGOA_4$ (1.04 wt %) were prepared in pre-weighed 2 mL maximum recovery tubes (Axygen) overnight at 37° C. Hydrogel mass was taken after swelling the hydrogels with 200 μL of Hank's balanced salt solution (HBSS) overnight which was then replaced with HBSS containing either 20 μg $mL^{-1}$ collagenase type IV, 50 U $mL^{-1}$ or 400 U $mL^{-1}$ hyaluronidase type IV-S were added to the hydrogels which were incubated at 37° C. Every 24 hours, buffer was removed and hydrogel mass was recorded and replaced with fresh solutions until hydrogels degraded at day 10 and again on day 28. Degradation data was recorded as a ratio of initial HBSS swollen gel mass at day 0 to HBSS, hyaluronidase or collagenase treated hydrogel mass. Experiments were performed with 3 independent samples to calculate the mean and standard deviation.

Quantification of Ln in Hydrogels by ELISA: To determine the amount of laminin-1 (Ln) released after encapsulation and how much is retained in HA-oxime hydrogels, an ELISA kit (Abcam ab119572) was used. Mouse Ln (Corning) 75 and 250 $\mu g \cdot mL^{1}$ was encapsulated in HA-oxime hydrogels prepared from HAK and HAA with $PEGOA_4$. After gelling overnight at 37° C., PBS was added and samples were incubated at 37° C. After 24 h, PBS was removed and stored at −80° C. Hydrogel samples were incubated in PBS for a further 6 days before 100 μL of hyaluronidase (2500 $U \cdot mL^{-1}$) was added to the gels. After 48 h, the degraded gels were compared to Ln standards diluted in Tris-balanced saline with 24 h release samples. A minimum of 3 independent replicates were performed for each condition.

Figure 25A:
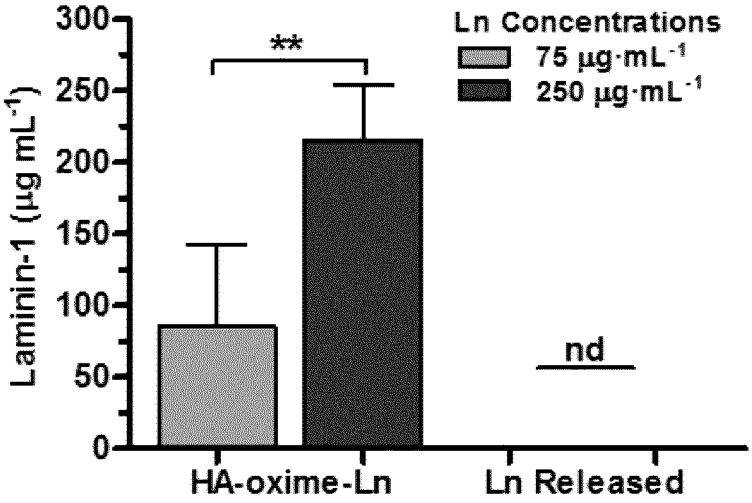
FIG. 25A and FIG. 25B illustrate impact of laminin in HA-oxime hydrogels.

Biochemically-tuned Laminin-containing HA-oxime Hydrogels Interact with Cells: To mimic the heterogeneity of the extracellular matrix in breast cancer and enhance cell interaction with the HA-oxime hydrogels (Caldwell et al., Adv. Healthc Mater. 6:1700254 (2017)), laminin-1 (Ln) was mixed with the polymers prior to gelation and found that it was retained in the gels obviating the need for covalent immobilization: Ln incorporated at either 75 or 250 $\mu g \cdot mL^{-1}$ was completely retained in hydrogels after 7 days, with no soluble Ln detected in the PBS supernatant (FIG. 25A). Given the large size of Ln (850 kDa), it was likely physically entrapped or entangled within the HA-oxime polymer chains, but may have also be retained by either (or both) electrostatic interactions between positively charged Ln and negatively charged hyaluronan-carboxylate groups (Rinaudo et al., Int. J. Biol. Macromol., 43:444 (2008)) or reversible Schiff-base formation between basic lysine groups on laminin and HA-ketone/aldehyde groups (Stabenfeldt et al., J. Biomed. Mater. Res., Part A, 77:718 (2006)).

Figure 25B:
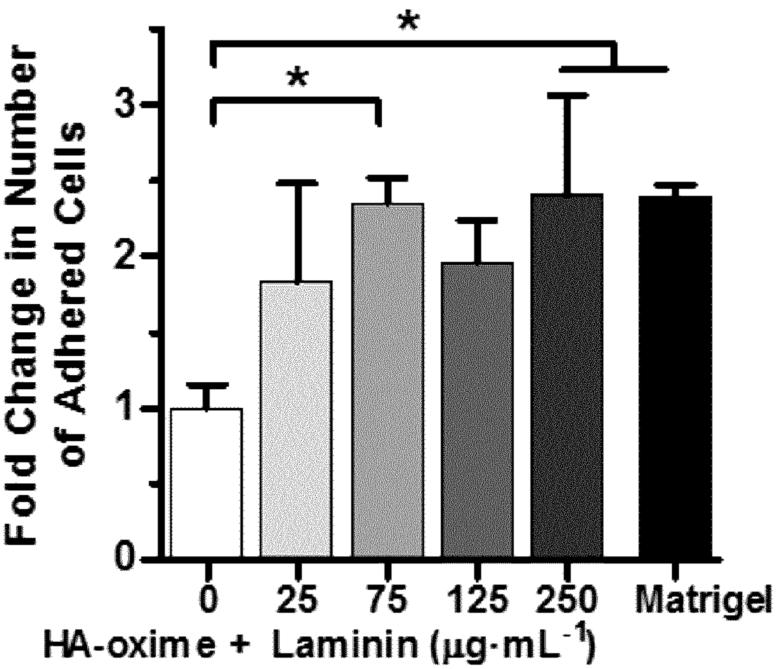
Figure 26A:
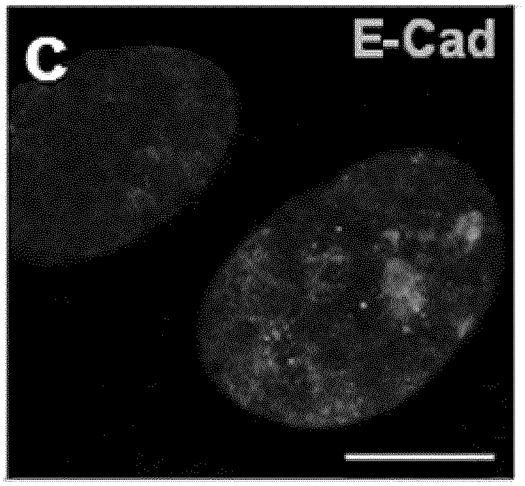
FIG. 26A, FIG. 26B, FIG. 26C, FIG. 26D, FIG. 26E, FIG. 26F, FIG. 26G, and FIG. 26H show representative immunocytochemistry images (50 μm scale) of MDA-MB-468 cells encapsulated in HA-oxime hydrogels after 21 days stained for nuclei (with Hoechst) and actin (with phalloidin which binds to F-actin) (FIG. 26A and FIG. 26B); E-cadherin (FIG. 26C and FIG. 26D); CD44 (FIG. 26E and FIG. 26F); and $\beta_1$ integrin and HIF-1α (FIG. 26G and FIG. 26H).
Figure 26B:
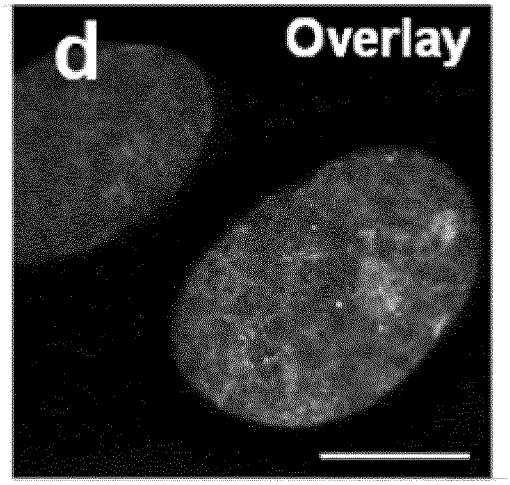
Figure 26C:
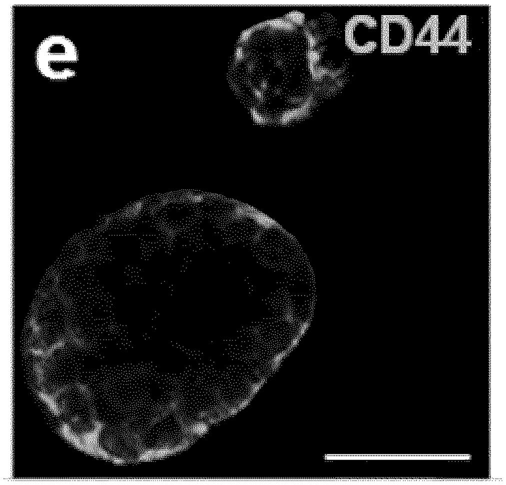
Figure 26D:
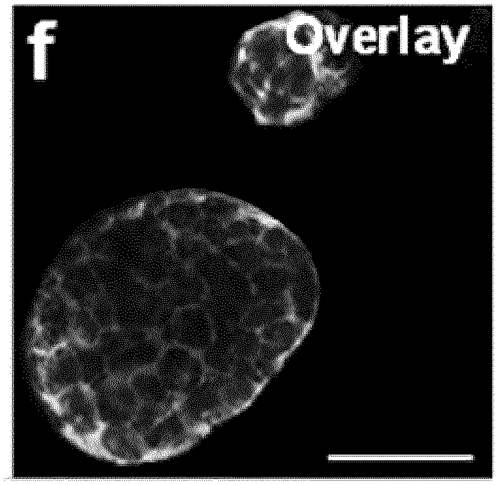
Figure 26E:
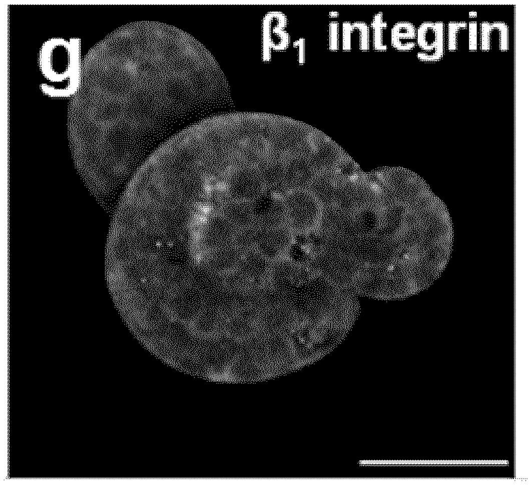
Figure 26F:
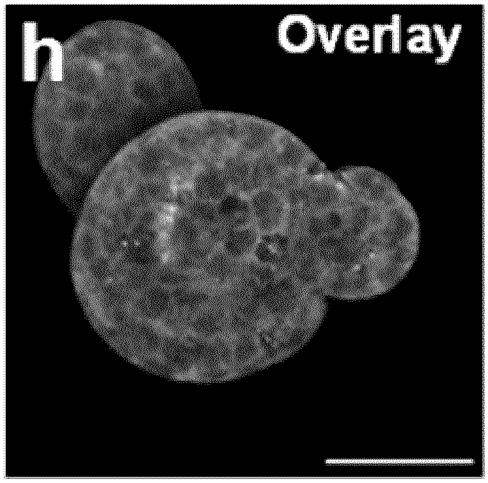
Figure 26G:
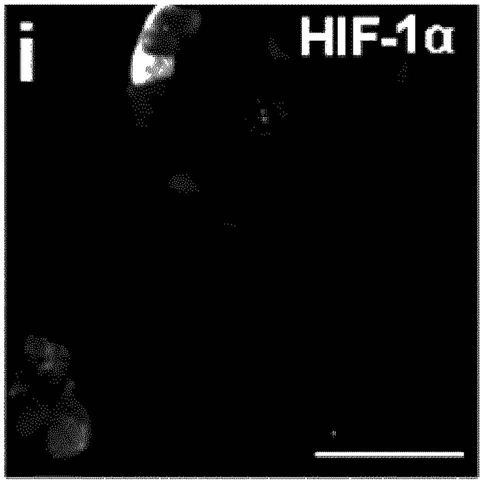
Figure 26H:
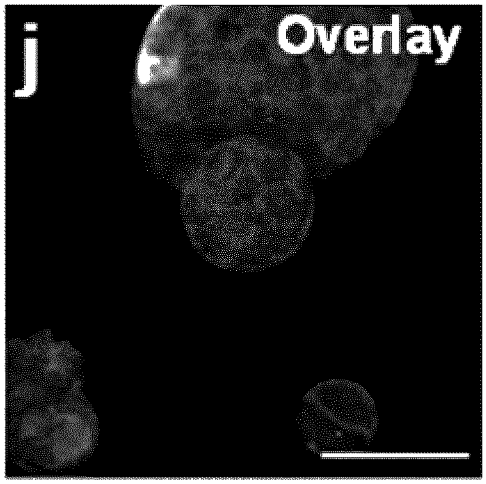
Figure 27A:
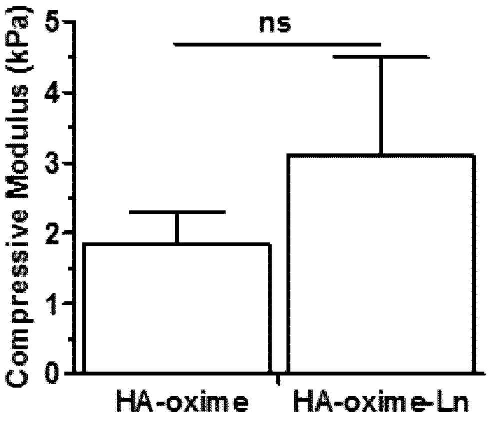
FIG. 27A, FIG. 27B, FIG. 27C, FIG. 27D, FIG. 27E, FIG. 27F, and FIG. 27G illustrate characterization of laminin-1 (Ln) incorporation in HA-oxime hydrogels and effect on cell distribution and spheroid growth.
Figure 27B:
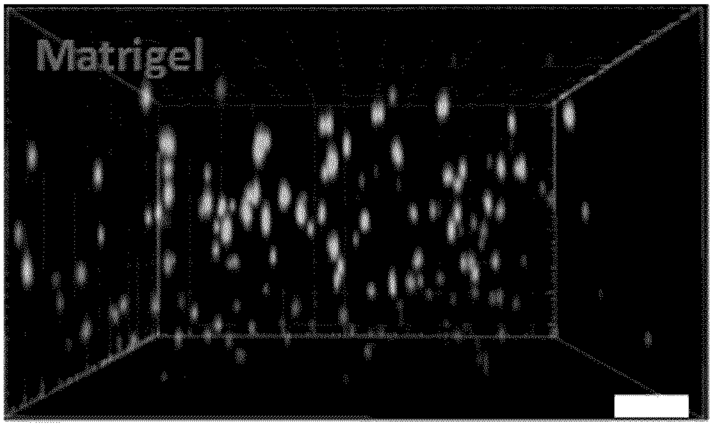
Figure 27C:
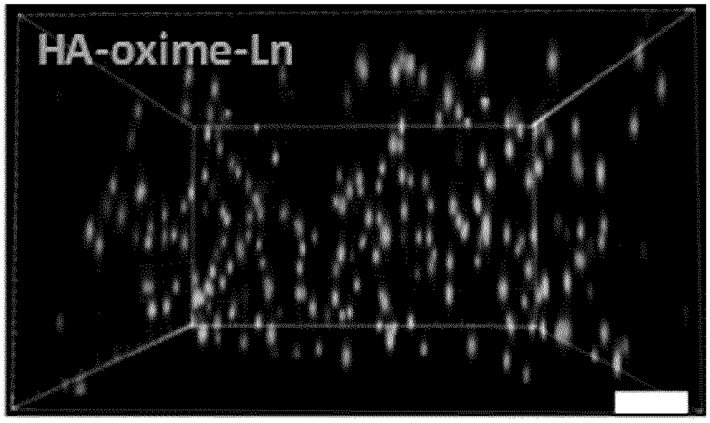
Figure 27D:
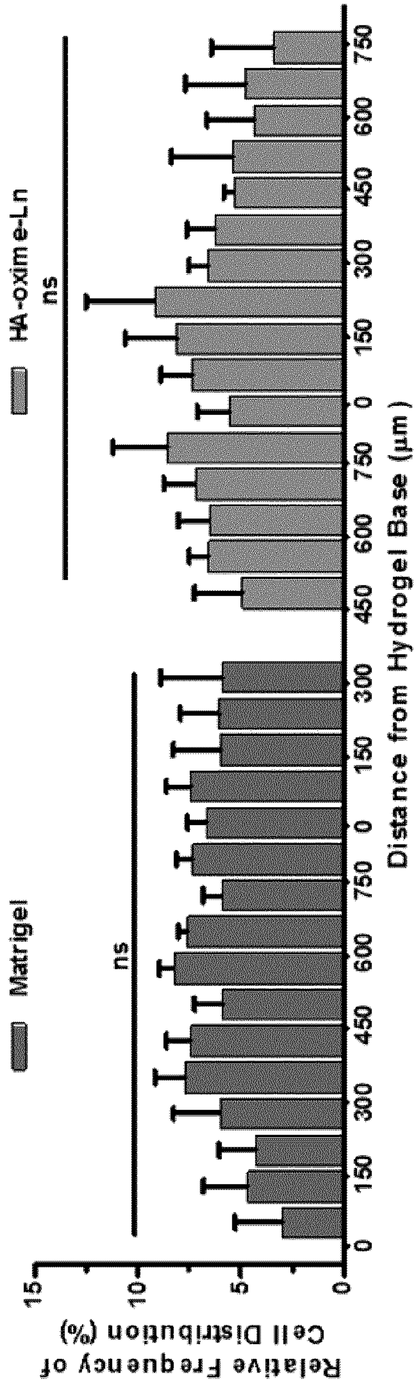
Figure 27E:
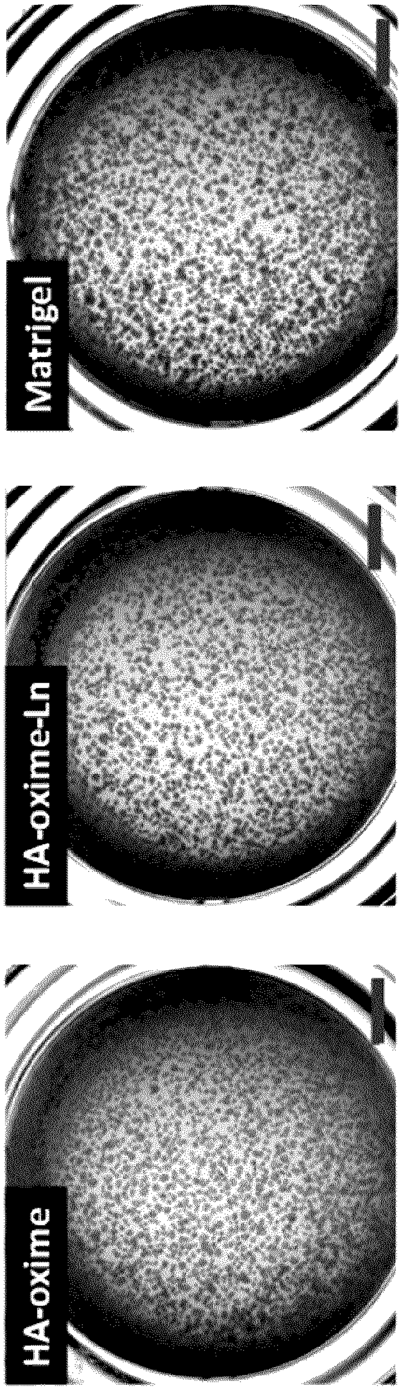
Figure 27F:
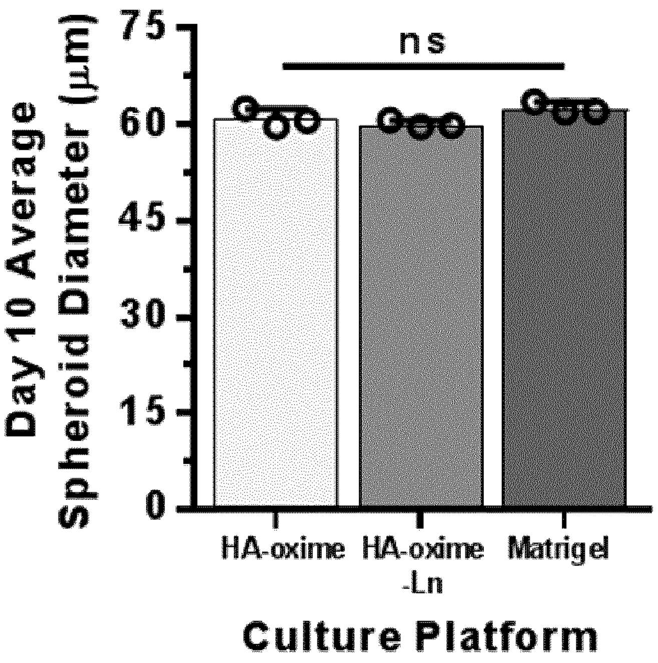
Figure 27G:
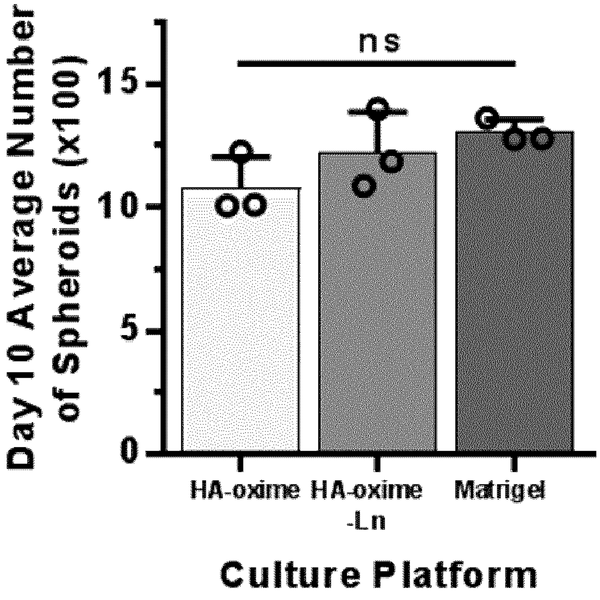
Figure 28A:
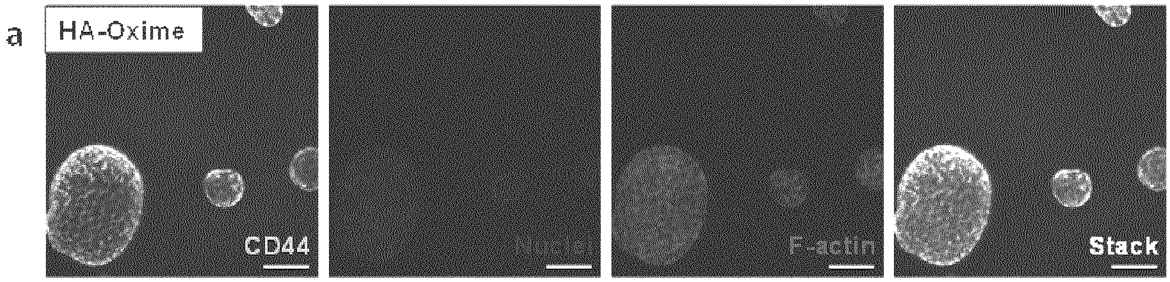
FIG. 28A, FIG. 28B, FIG. 28C, and FIG. 28D are representative immunocytochemistry confocal images of MDA-MB-468 cells cultured for 21 days in HA-oxime hydrogels (50 μm scale).
Figure 28B:
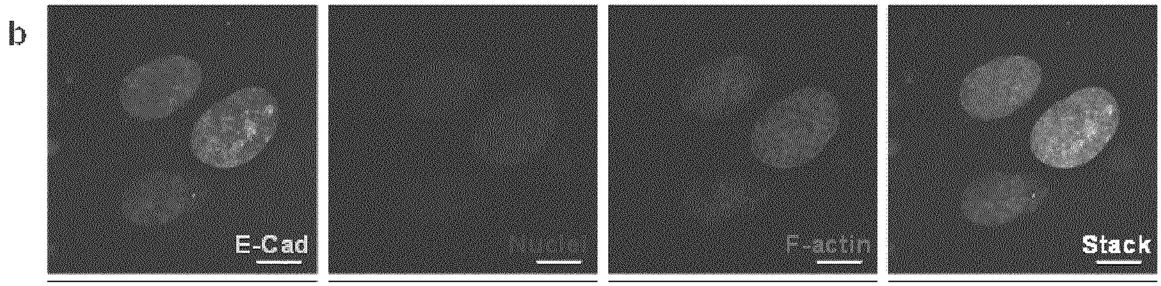
Figure 28C:
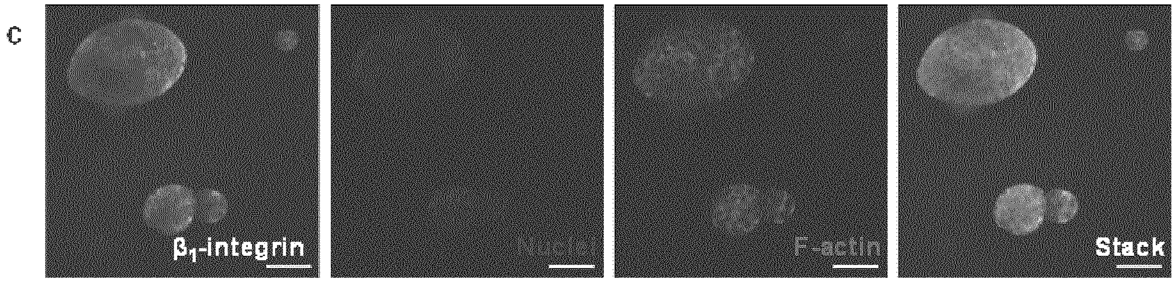
Figure 28D:
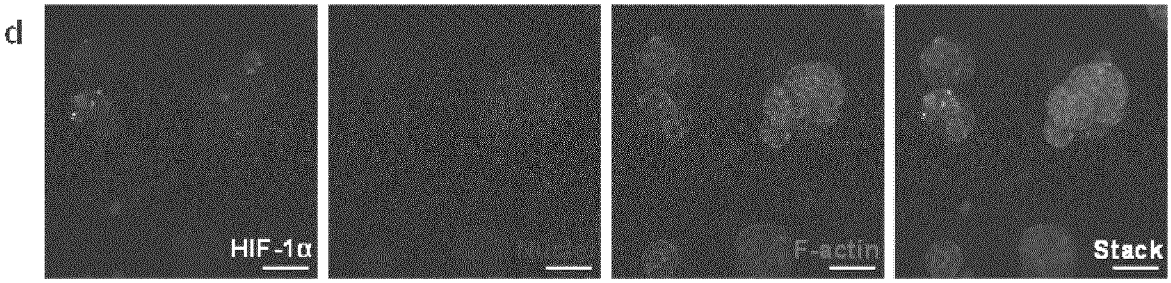

To investigate cell-Ln interactions, cell adhesion to HA-oxime gels with or without Ln was compared. More than double the amount of T47D luminal A breast cancer cells adhered to the surface of hydrogels containing 75 $\mu g \cdot mL^{-1}$ Ln, similar to Matrigel versus controls without Ln (FIG. 25B Cells within the spheroids interacted with each other, as demonstrated by E-cadherin expression, a marker of tight junctions (FIG. 26A and FIG. 26B). Cells also interacted with the HA-oxime hydrogel through CD44, a hyaluronan receptor, and expressed β1-integrin, a Ln receptor (FIG. 26C, FIG. 26D, FIG. 26E, and FIG. 26F). CD44 is essential to the growth of breast cancer cells and β1-integrin is involved in the PI3K pathway, which is upregulated in breast cancer and constitutes a drug target (Godar et al., Cell, 134:62 (2008); Fotovati et al., Cancer Res., 70:2840 (2010); Castello-Crós et al., BMC Cancer, 9:94 (2009)). Evidence of HIF-1α expression, a marker for either reactive oxygen species or hypoxia typically observed in breast cancer tumours (FIG. 26G and FIG. 26H), was observed. With or without Ln, the mechanical properties of the hydrogel were unchanged and breast cancer cells encapsulated in HA-oxime hydrogels were equally viable and evenly distributed, and the size and number of spheroids were similar (FIG. 27A, FIG. 27B, FIG. 27C, FIG. 27D, FIG. 27E, FIG. 27F, and FIG. 27G). E-cadherin, CD44, β1-integrin, and HIF-1α expression were observed either throughout the spheroids or at the periphery, which has been observed in other cancer spheroids and likely represents reactive oxygen species versus hypoxia at the core because oxygen can diffuse though the ~70 μm diameter spheroids (FIG. 28A, FIG. 28B, FIG. 28C, and FIG. 28D) (Wang et al., Polymer Chemistry, 6:283 (2015)). Given the relevance of hyaluronan in breast cancer (Heldin et al., Int. J. Cancer 132:531 (2013)) and the interaction of cells with the HA-oxime hydrogels, the impact of culturing in HA-oxime with or without laminin on gene expression levels compared to those in Matrigel and conventional 2D TCPS was investigated.

Figure 29:
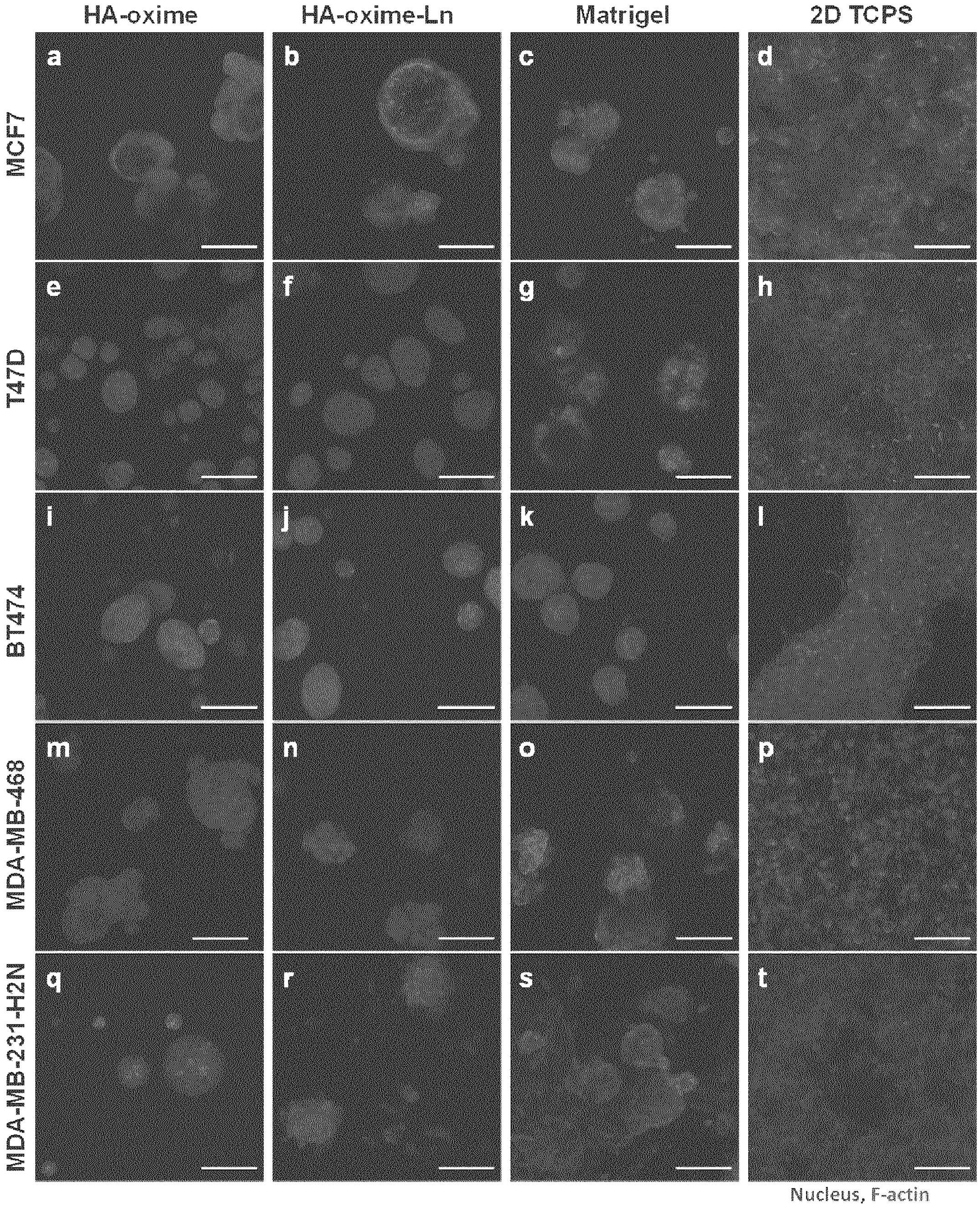
FIG. 29 details representative images of breast cancer cell phenotype after 21 days of culture in HA-oxime+/−Ln, in Matrigel, and on TCPS. Images (a)-(d) are MCF7 cells. Images (e)-(h) are T47D cells. Images (i)-(l) are BT474 cells. Images (m)-(p) are MDA-MB-468 cells. Images (q)-(t) are MDA-MB-231-H2N cells stained with DAPI and phalloidin (F-actin). Compressed z-stack of images were taken using Fluoview from Olympus. Scale bar represents 100 μm.

HA-oxime Hydrogels Enable Spheroid Formation of 5 Different Breast Cancer Cell Lines and Patient-derived Primary Breast Cancer Cells: When cells from 5 different breast cancer cell lines were cultured for 21 days in HA-oxime hydrogels+/−Ln they formed spheroids, which was not observed in 2D culture (FIG. 29). These cells represent 4 breast cancer subtypes with different expression profiles of estrogen receptor (ER), progesterone receptor (PR), and human epidermal growth factor receptor 2 (HER2): luminal A MCF7 and T47D ($ER^+$, $PR^+$, $HER2^-$), luminal B BT474 ($ER^+$, $PR^+$, $HER2^+$), $HER2^+$ overexpressing MDA-MB-231-H2N ($ER^-$, $PR^-$, $HER2^+$), and triple negative MDA-MB-468 ($ER^-$, $PR^-$, $HER2^-$) cells. Proliferation was examined in 2D and 3D, and between different hydrogel cultures.

Figure 30A:
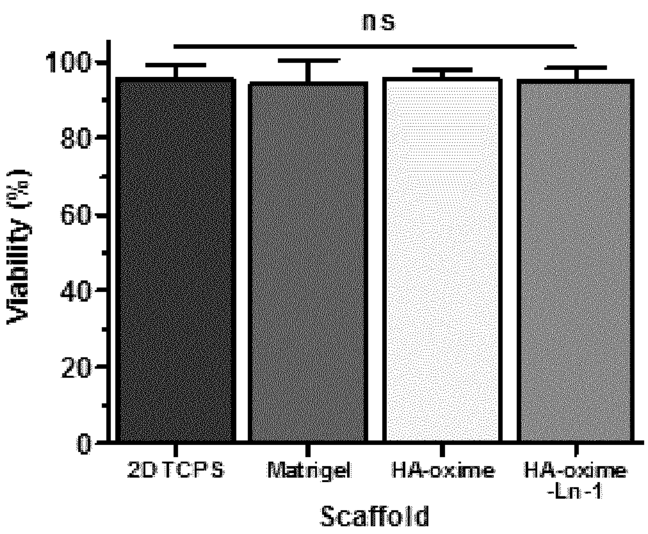
FIG. 30A and FIG. 30B illustrate the viability of primary luminal breast cancer cells grown on 2D TCPS, or embedded in Matrigel, HA-oxime or HA-oxime-Ln hydrogels after 24 hours of culture visualized with MitoTracker and Sytox (FIG. 30A). Viability was quantified using Imaris from Bitplane (n=3 independent experiments; mean+standard deviation plotted, no significant differences (ns) by one-way ANOVA, Tukey's post-hoc test).
Figure 30B:
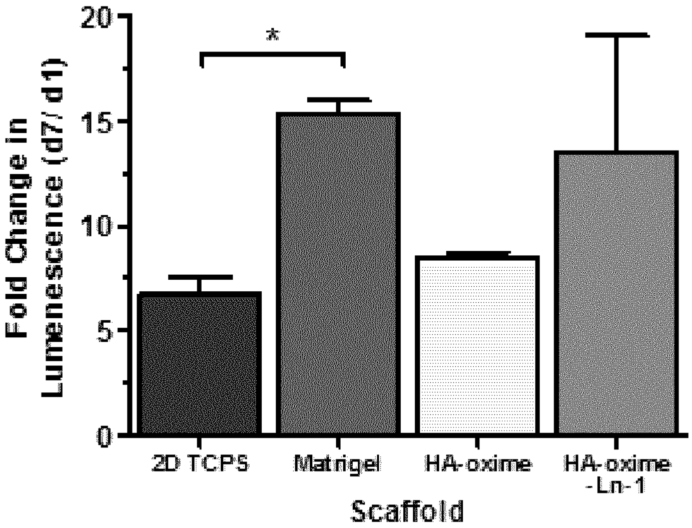
Figure 31A:
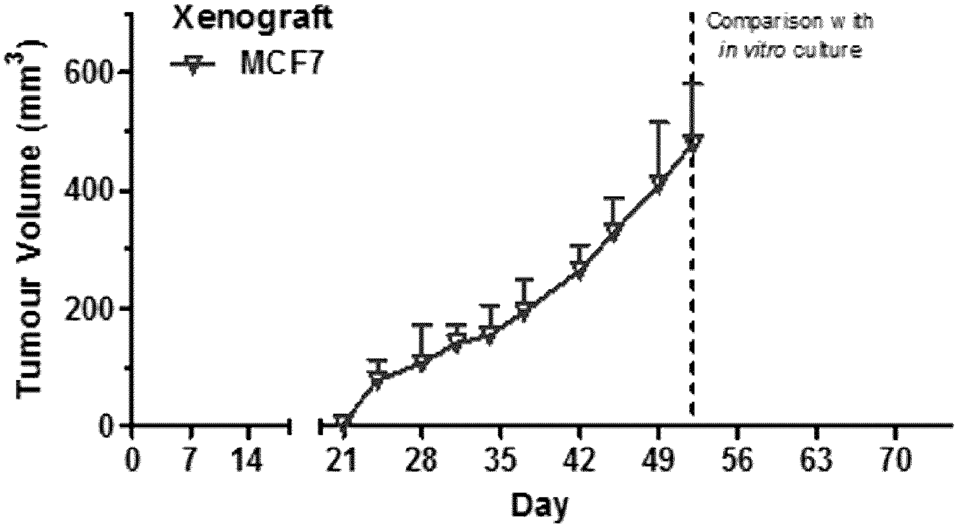
FIG. 31A, FIG. 31B, FIG. 31C, FIG. 31D, and FIG. 31E illustrate tumor growth curves for breast cancer cell lines injected into the mammary fat pad of NOD scid gamma mice (n=6 animals, mean+standard deviation plotted).
Figure 31B:
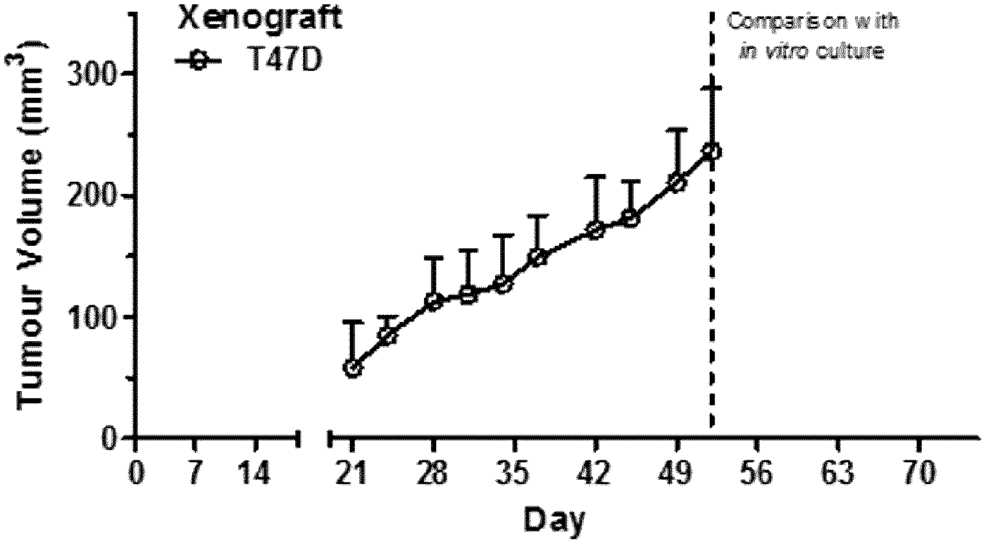
Figure 31C:
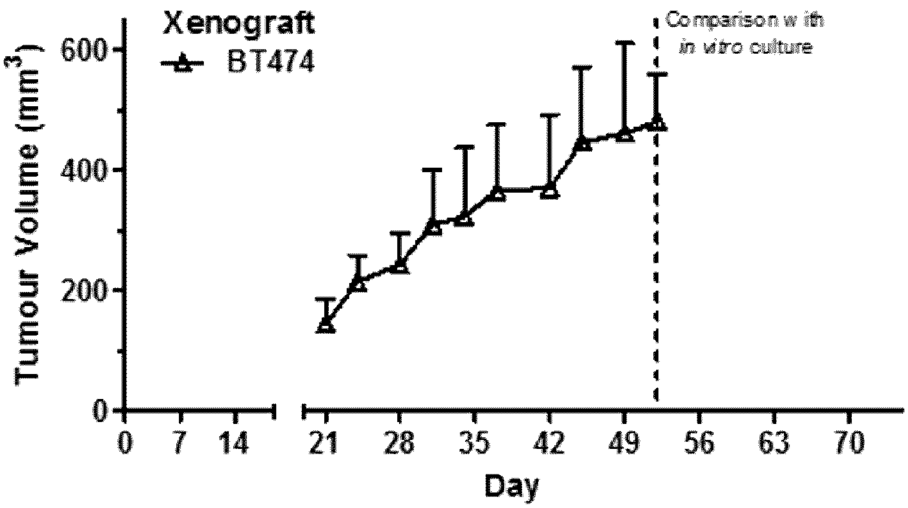
Figure 31D:
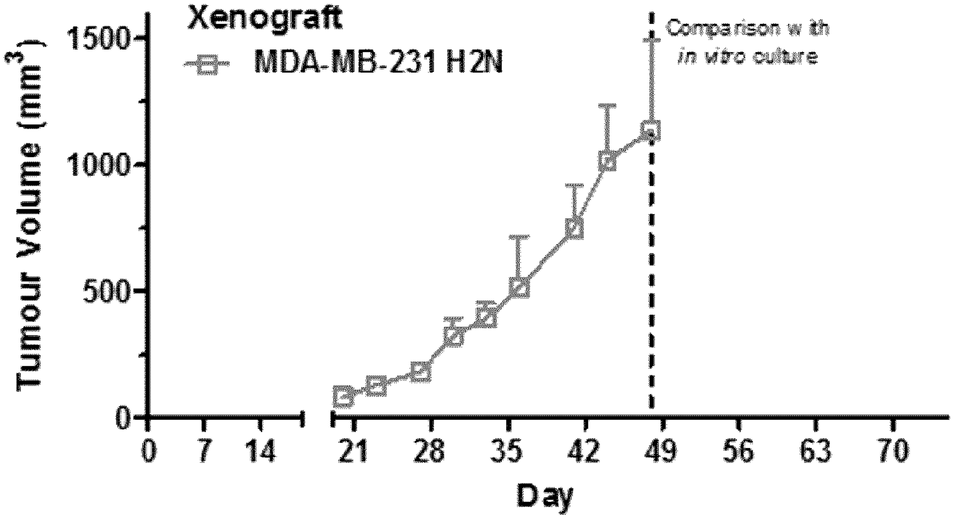
Figure 31E:
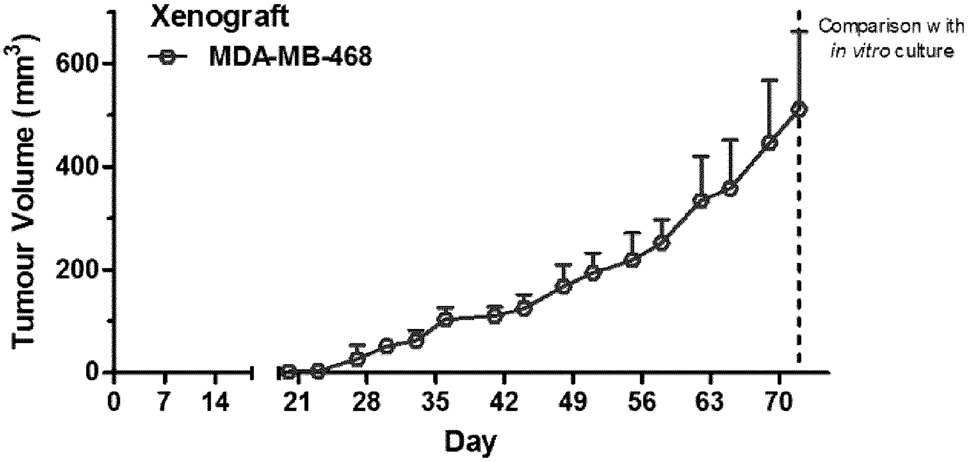

Recent efforts to develop in vitro cancer models that recapitulate the features of human breast cancer for preclinical testing or personalized medicine have used poorly-defined Matrigel to grow 3D tumour organoids. To test the HA-oxime hydrogel for these applications, patient-derived primary luminal B breast cancer cells were encapsulated in 3D therein and observed their survival and proliferation: the patient-derived cells grew as spheroids in the hydrogel but proliferated as monolayers on 2D TCPS (FIG. 30A and FIG. 30B). Impressively, encapsulated primary breast cancer cells from a dissociated patient biopsy formed spheroids in both HA-oxime+/−Ln and Matrigel after 21 days of culture. It is possible that over the 21 days of culture within the 3D hydrogel, glucose and/or oxygen gradients will form and result in heterogeneity that more closely mimics the tumour microenvironment within the xenograft versus that of 2D TCPS. These results led us to perform a more extensive comparison of gene expression between the mouse xenografts and in vitro models in order to better understand the biological differences between these in vitro models.

Figure 32A:
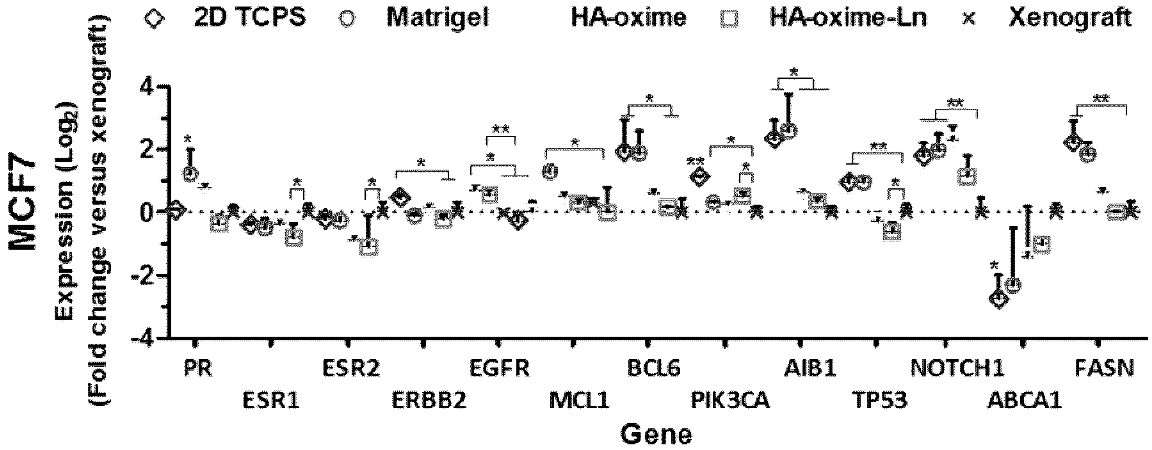
FIG. 32A, FIG. 32B, FIG. 32C, FIG. 32D, and FIG. 32E illustrate gene expression for breast cancer cells cultured on 2D TCPS, in Matrigel, HA-oxime+/−Ln after 21 days relative to mouse xenograft. The graphs illustrate qPCR for MCF7, T47D, BT474, MDA-MB-231-H2N, and MDA-MB-468. n=biological replicates; mean+standard deviation plotted, *$p<0.05$, $p<0.01$ one-way ANOVA, Tukey's post-hoc test).
Figure 32B:
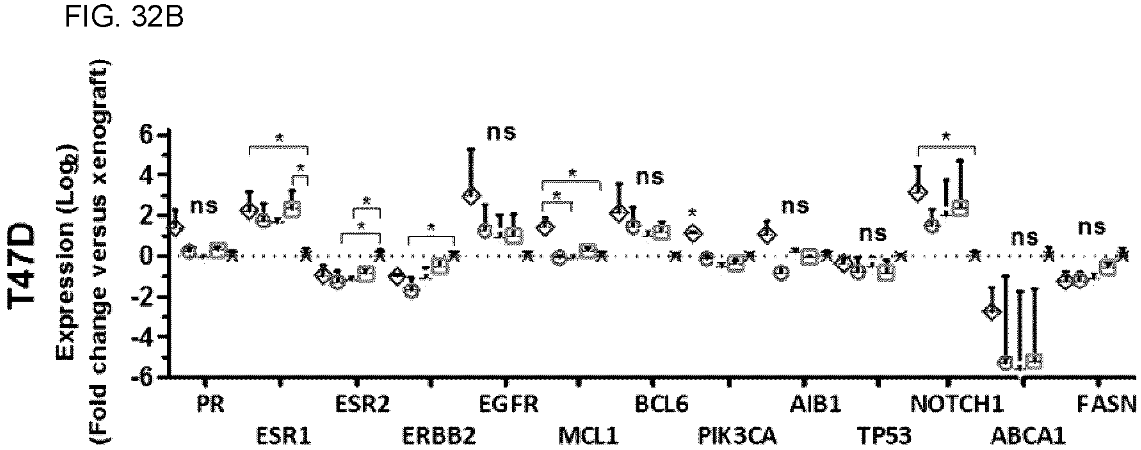
Figure 32C:
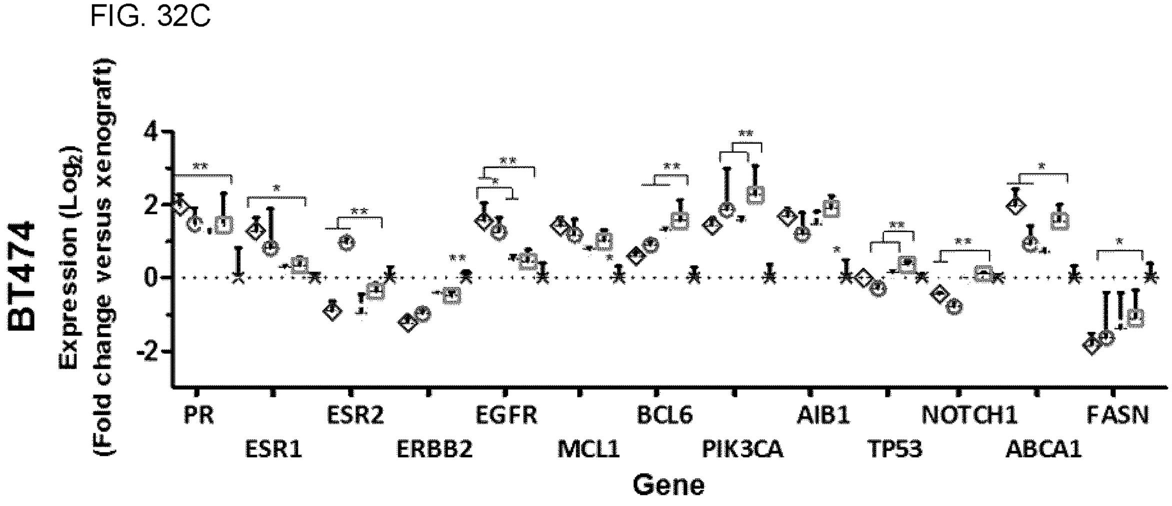
Figure 32D:
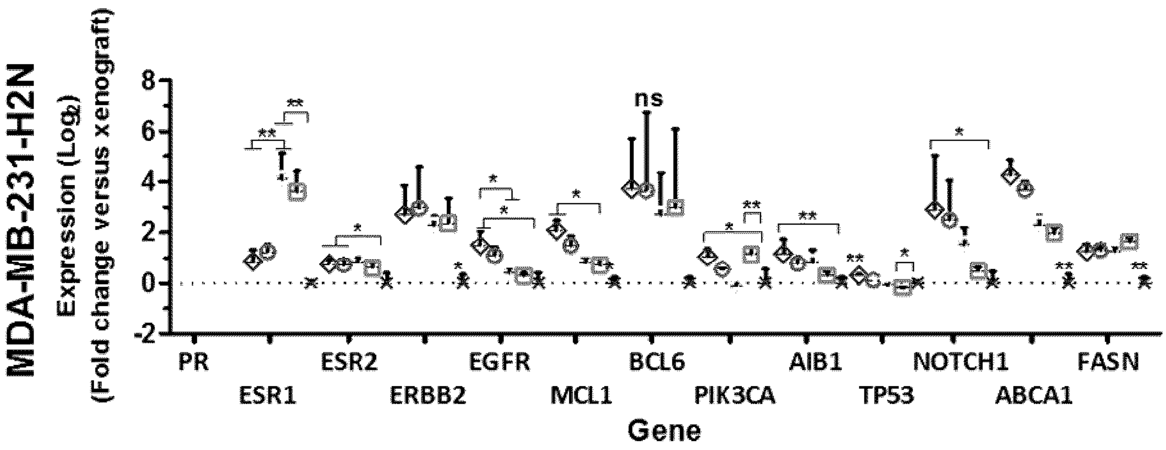
Figure 32E:
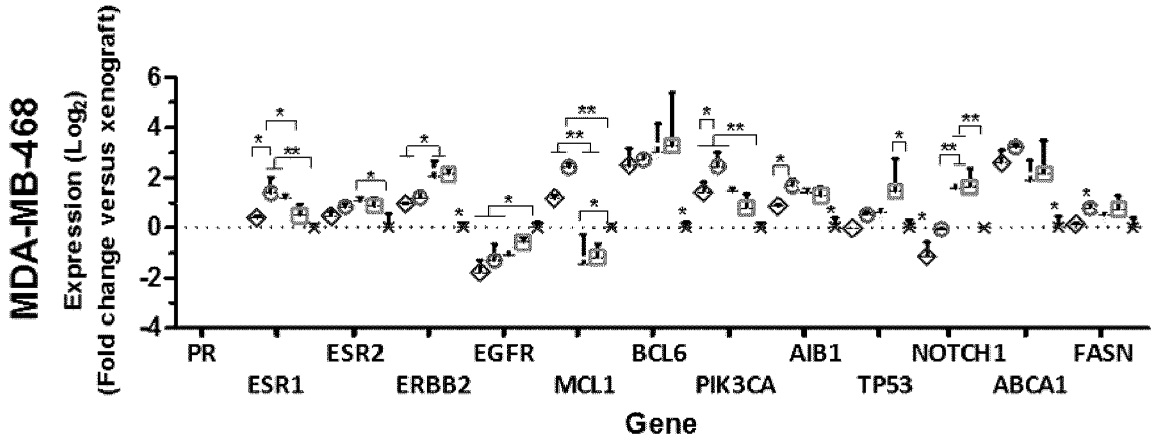
Figure 33:
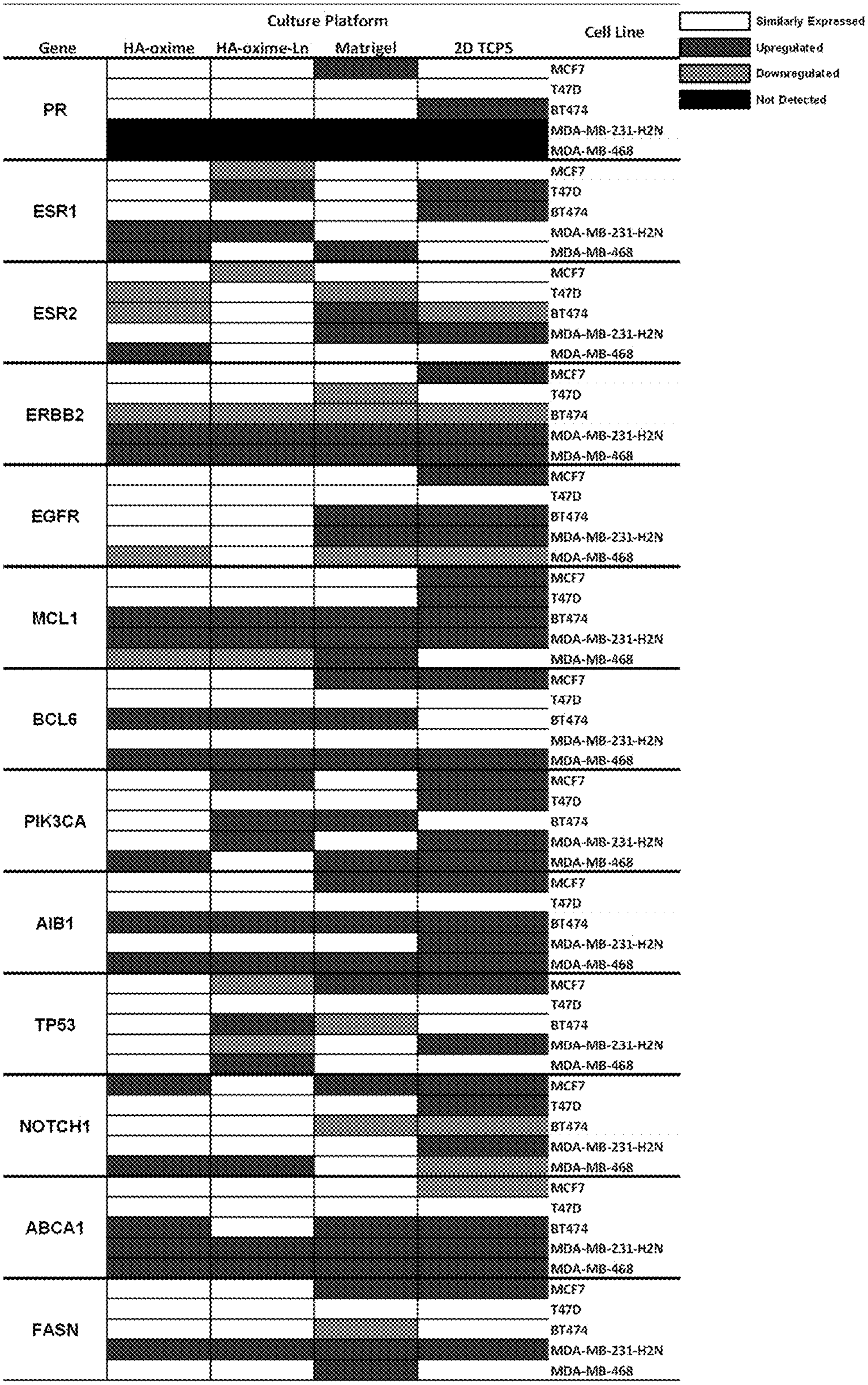
FIG. 33 illustrates the differential gene expression profile of MCF7, T47D, BT474, MDA-MB-231-H2N, and MDA-MB-468 cell lines using different culture platforms.
Figure 34A:
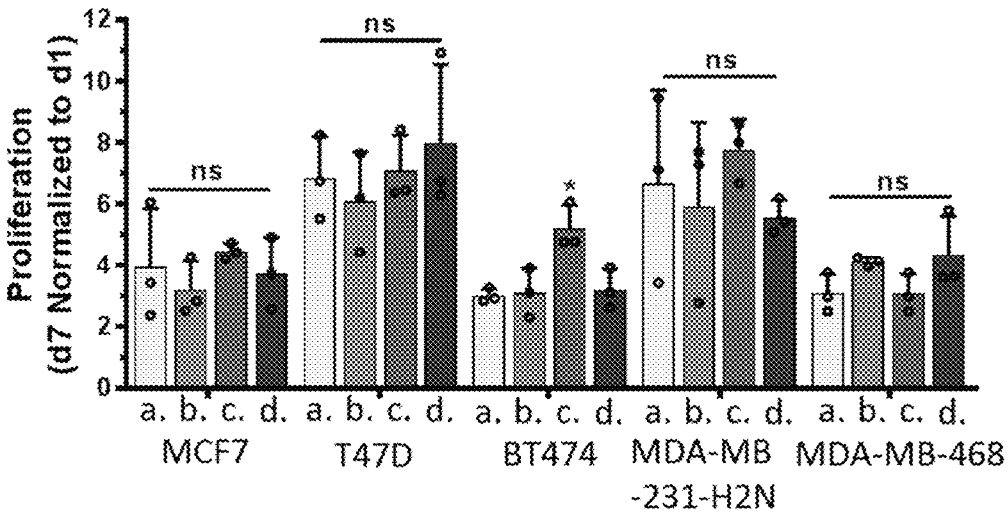
FIG. 34A and FIG. 34B illustrate the evaluation of patient-derived and 5 different breast cancer cell lines in HA-oxime+/−Ln versus Matrigel and 2D TCPS.
Figure 34B:
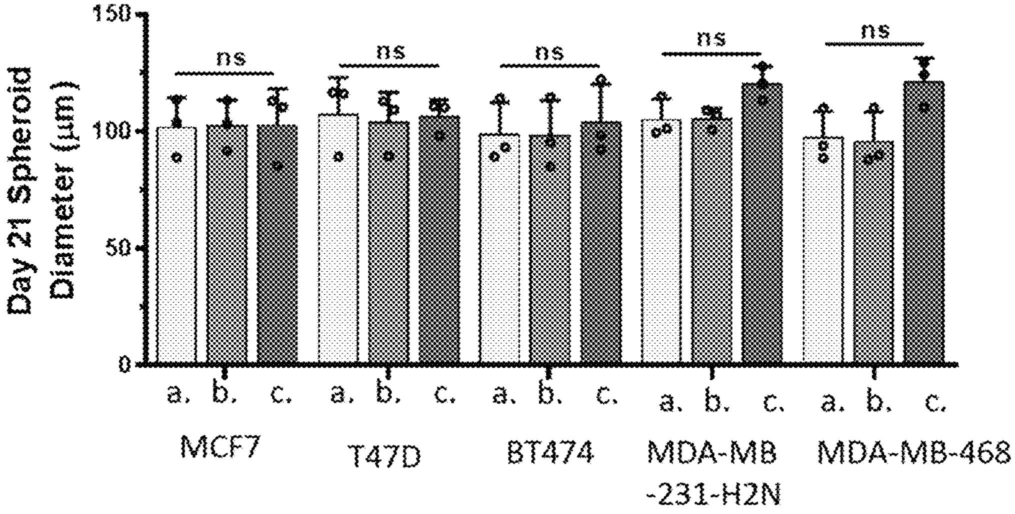

Gene Expression of 5 Distinct Breast Cancer Cell Lines Cultured In Vitro vs. In Vivo Growth as Tumour Xenografts: In order to understand how breast cancer markers and drug-targetable pathways are impacted by culture platform, the gene expression of 5 cell lines cultured in HA-oxime+/−Ln against orthotopic mouse xenografts in NOD SCID gamma mice were benchmarked and compared to those in Matrigel or 2D TCPS (FIG. 31A, FIG. 31B, FIG. 31C, FIG. 31D, and FIG. 31E). In general, the gene expression of breast cancer cells cultured in either HA-oxime hydrogels+/−Ln or Matrigel were more similar to that of mouse xenograft models than cells cultured on 2D TCPS (FIG. 32A, FIG. 32B, FIG. 32C, FIG. 32D, and FIG. 32E). Several genes were differentially expressed compared to tumour xenografts when cultured on 2D TCPS, but not when cultured in HA-oxime hydrogels, including epidermal growth factor receptor (EGFR), human epidermal growth factor receptor 2 (ERBB2) and phosphatidylinositol-4,5-bisphosphate 3-kinase catalytic subunit alpha (PIK3CA) which are implicated in drug targetable pathways (FIG. 33). All breast cancer cell lines grown in vitro exhibited similar proliferation rates in HA-oxime+/−Ln hydrogels compared to Matrigel except BT474 cells, where proliferation was increased in Matrigel (FIG. 34A). In addition, all cells formed spheroids of similar diameter ~100 μm, suitable for oxygen and nutrient penetration (Curcio et al., Biomaterials, 28:5487 (2007)) at 21 days in HA-oxime hydrogels and Matrigel (FIG. 34B), indicating phenotypic equivalence at minimum.

The expression of both ERBB2 and EGFR can result in changes to cell phenotype and tumourigenicity, and may also influence response to therapy, including agents targeting these receptors directly (Ingthorsson et al., Oncogene, 35:4244 (2015)). In addition, patients with PIK3CA-positive breast tumours have shorter disease-free survival across all molecular subtypes indicating its potential as a therapeutic target (Aleskandarany et al., Breast Cancer Res. Treat. 122:45 (2010)). Thus, these results further underscore the need to use representative 3D models to study breast cancer over traditional 2D culture.

A potential strategy for treating breast cancer beyond traditional kinase inhibitors includes emerging metabolic targets such as FASN, which is responsible for lipid synthesis. Currently, the FASN inhibitor TVB-2640 is being evaluated for the treatment of advanced breast cancer in a clinical trial (Menendez et al., Expert opinion on therapeutic targets, 21:1001 (2017); Monaco et al., Oncotarget, 8:29487 (2017)). Due to observed differences in cellular fatty acid and cholesterol content between 2D culture and xenograft models (Mori et al, Front. Oncol., 6:262 (2016)), we hypothesized that the expression of lipid metabolic genes would be more similar in 3D cell culture than 2D culture relative to the xenograft tumours. The expression of FASN, which is responsible for lipid synthesis, and ATP-binding cassette transporter (ABCA1), which regulates intracellular phospholipid and cholesterol homeostasis, depended upon both cell line and culture system. For example, luminal A MCF7 cells had similar ABCA1 and FASN expression between tumour xenograft and HA-oxime hydrogel culture, but an upregulated FASN expression when cultured on 2D TCPS or Matrigel (FIG. 32A and FIG. 32B). This shows that FASN expression is influenced by the ECM and that gene expression levels of xenograft tumours for luminal A breast cancer were recapitulated using the HA-oxime hydrogel. However, $HER2^-$ overexpressing MDA-MB-231-H2N cells upregulated FASN and ABCA1 across all in vitro models, which suggests altered lipid metabolism and secretion compared to xenograft tumours. These differences in FASN expression were not observed for other breast cancer subtypes, which supports breast cancer subtype-dependent lipid metabolism in 2D (Lane et al., Metab. Eng., 43:125 (2017)). Considering the similar gene expression of breast cancer cells cultured in HA-oxime hydrogels and grown as xenograft tumours, more rigorous benchmarking with a pan-cancer gene expression panel was conducted.

Pan-Cancer Gene Expression Benchmarks In Vitro Breast Cancer Models: In order to better understand the predictive powers of 3D in vitro culture of breast cancer cells, 3 distinct cell lines, representing 3 different breast cancer subtypes, were benchmarked to tumour xenografts: luminal B (BT474); $HER2^-$ overexpressing (MDA-MB-231-H2N); and triple negative (MDA-MB-468). Cells were cultured in 3D in HA-oxime, Matrigel or in 2D on TCPS and compared the gene expression panel of 730 cancer-related genes. Relative to tumour xenografts, luminal B, BT474 cells had the fewest number of differentially expressed genes when cultured in HA-oxime gels (24 downregulated and 27 upregulated of 730 genes) compared to those cultured in Matrigel (63 downregulated and 135 upregulated) and on 2D TCPS (60 downregulated, 45 upregulated) (Tables 9A and 9B). Surprisingly, there were more differences when cells were cultured in Matrigel than on 2D TCPS relative to xenografts, which both reflects the unsuitability of Matrigel and demonstrates that 3D culture alone is insufficient for predictive drug screening.

TABLE 9A

| HA-oxime vs. Xenograft (12) | |
|---|---|
| Down-regulated (5) | Up-regulated (7) |
| FGF1 | CACNA1E |
| LAMB3 | CACNB2 |
| NOTCH2 | EFNA2 |
| PRKAR2B | FLT3 |
| WNT5A | GLI1 |
| | HNF1A |
| | IFNA2 |
| **HA-oxime ∩ Matrigel vs. Xenograft (6)** | |
| Down-regulated (0) | Up-regulated (6) |
| | CEBPE |
| | H2AFX |
| | PAK7 |
| | PPP3CC |
| | RASGRF2 |
| | SPP1 |
| **HA-oxime ∩ 2D TCPS vs. Xenograft (5)** | |
| Down-regulated (0) | Up-regulated (5) |
| | CDKN1A |
| | FAS |

TABLE 9A-continued

| | | | |
|---|---|---|---|
| | | FBXW7 | |
| | | IL11RA | |
| | | SOCS2 | |
| Matrigel vs. Xenograft (137) | | | |

TABLE 9A-continued

| | | | |
|---|---|---|---|
| PPP2R2C | FGF8 | MMP9 | UTY |
| SYK | FLT1 | MNAT1 | WNT10A |
| | FOSL1 | MPL | WNT5B |
| | FOXL2 | NFE2L2 | WT1 |
| | FST | NGF | XRCC4 |
| | FZD10 | NODAL | |
| | FZD2 | NPM2 | |

TABLE 9B

| Matrigel ∩ 2D TCPS vs. Xenograft (27) | | 2D TCPS vs. Xenograft (45) | | HA-oxime ∩ Matrigel ∩ 2D TCPS Xenograft (28) | |
|---|---|---|---|---|---|
| Down-regulated (13) | Up-regulated (14) | Down-regulated (28) | Up-regulated (17) | Down-regulated (19) | Up-regulated (9) |
| CDC25B | CACNG6 | AKT1 | ATRX | CACNA1G | GADD45A |
| ITGB6 | DDIT3 | BAD | CALML6 | COL1A2 | IGFBP3 |
| MAPK3 | EPHA2 | BMPR1B | CREB5 | FGF18 | LEF1 |
| MAPK8IP2 | H3F3C | C19orf40 | DKK1 | FGF2 | MPO |
| MCM2 | ID1 | CACNA2D1 | DLL4 | GRIA3 | PLA2G4C |
| MTOR | LEPR | CCND3 | FGF20 | HSPA2 | RRAS2 |
| PIK3R2 | LIG4 | DNMT1 | FOS | IL20RA | TNFRSF10B |
| PLA2G4F | MAML2 | ERBB2 | ID4 | INHBA | WNT6 |
| SIX1 | MET | FGFR1 | IL12A | PLA2G10 | XPA |
| SMC1A | PLCE1 | GNA11 | JUN | PRKCB | |
| SOX9 | PLD1 | GNAS | MDM2 | RUNX1T1 | |
| WNT11 | SMAD9 | GRB2 | MLLT4 | SFRP2 | |
| WNT7B | SPRY1 | HDAC1 | MYC | SFRP4 | |
| | TSLP | ITGB4 | NFKBIZ | THBS1 | |
| | | LAMA3 | RASA4 | THBS4 | |
| | | MCM4 | SPOP | TRAF7 | |
| | | NBN | STAT4 | TSPAN7 | |
| | | NTRK2 | | WNT16 | |
| | | PDGFD | | ZBTB16 | |
| | | PKMYT1 | | | |
| | | POLR2D | | | |
| | | PRKACA | | | |
| | | PRKAR1B | | | |
| | | PRKDC | | | |
| | | SFN | | | |
| | | SMARCB1 | | | |
| | | TGFBR2 | | | |
| | | TIAM1 | | | |

TABLE 9A-continued

| Down-regulated (31) | Up-regulated (106) | | |
|---|---|---|---|
| AR | ACVR1C | GAS1 | NR4A3 |
| ARID1A | AMH | GRIN1 | NTRK1 |
| ARID1B | BID | GRIN2B | PAX3 |
| BCL2 | BNIP3 | GZMB | PAX5 |
| CACNA2D2 | CACNA2D3 | HGF | PAX8 |
| CCND1 | CARD11 | HHEX | PCK1 |
| CIC | CBLC | HMGA2 | PDGFRA |
| DTX4 | CCNA2 | HOXA10 | PDGFRB |
| DUSP10 | CCNO | HPGD | PHF6 |
| EP300 | CCR7 | IBSP | PIK3CG |
| FANCF | CD19 | IFNA17 | PIM1 |
| FANCG | COL24A1 | IFNA7 | PITX2 |
| FUT8 | COL3A1 | IFNG | PLA1A |
| GATA3 | COL4A6 | IL10 | PLA2G5 |
| GHR | COL6A6 | IL12B | PPARG |
| GNAQ | CREB3L3 | IL12RB2 | PPP3R2 |
| GPC4 | CRLF2 | IL1R2 | PRKACG |
| HSPA1A | CSF1R | IL23A | PRL |
| HSPB1 | CSF2 | IL24 | PTCRA |
| IKBKB | CSF3 | IL2RA | PTPN5 |
| KITLG | DKK2 | IL5RA | PTPRR |
| KMT2D | DTX1 | IL6 | RXRG |
| MAPK8IP1 | EYA1 | IRAK3 | TCL1B |
| MYCN | FGF14 | ITGB3 | TGFB2 |
| NF2 | FGF17 | JAK3 | THEM4 |
| NFATC1 | FGF19 | LEFTY2 | TLX1 |
| NSD1 | FGF3 | MAPK8 | TNFRSF10C |
| PDGFB | FGF5 | MMP3 | TNFRSF10D |
| PIK3R1 | FGF6 | MMP7 | TNN |

Twelve pathways and driver genes were analyzed by gene set variation analysis and found that BT474 cells cultured in Matrigel altered the expression of several pathways including JAK-STAT and MAPK versus tumour xenografts whereas cells cultured in HA-oxime gels did not. This further motivates the use of representative, benchmarked 3D in vitro models, such as the HA-oxime hydrogel, to recapitulate gene expression and to evaluate new drug candidates against JAK-STAT and MAPK (Garcia-Aranda t al., International journal of molecular sciences, 18:2543 (2017)).

Comparing the gene expression of MDA-MB-231-1H2N tumours to 3D hydrogels and 20 culture, we found that fewer genes were differentially expressed when cells were grown in HA-oxime gels (16 downregulated, 12 upregulated) versus both Matrigel (28 downregulated, 21 upregulated) and 2D TCPS (33 downregulated, 29 upregulated) (Tables 10A and 1 OB). Altered gene expression of a therapeutic target in cells used in an in vitro drug screen would generate misleading data. Differences in the JAK-STAT pathway were identified between cells cultured in HA-oxime, Matrigel or 20 TCPS relative to the tumour xenografts after analyzing the pathways regulating cell survival and cell fate between the in vitro models and tumour xenografts of MDA-MB-231-H2N cells.

TABLE 10A

| HA-oxime vs. Xenograft (28) | |
|---|---|
| Down-regulated (16) | Up-regulated (12) |
| BNIP3 | B2M |
| CASP3 | CACNA2D3 |
| EGFR | CDK2 |
| FST | DLL3 |
| HMGA2 | H2AFX |
| HSP90B1 | IL1R1 |
| IGFBP3 | LAMC2 |
| IL1RAP | LEP |
| ITGA6 | LIF |
| ITGB8 | MMP3 |
| MAP2K1 | RASGRP2 |
| PPP3CA | UTY |
| PTPN11 | |
| RAD21 | |
| TBL1XR1 | |
| WNT5A | |

| HA-oxime ∩ Matrigel vs. Xenograft (23) | |
|---|---|
| Down-regulated (11) | Up-regulated (12) |
| FN1 | CD14 |
| FZD8 | DUSP10 |
| POLR2H | GATA2 |
| PPP3R1 | IKBKG |
| PRKAR2A | LAMA5 |
| PRKDC | MLLT4 |
| RB1 | RAC2 |
| RFC3 | RASGRF1 |
| SOCS2 | SPRY4 |
| TFDP1 | STAT3 |
| TGFBR2 | STK11 |
| | TNFRSF10B |

| HA-oxime ∩ 2D TCPS vs. Xenograft (20) | |
|---|---|
| Down-regulated (12) | Up-regulated (8) |
| BMP2 | BAMBI |
| DUSP6 | CASP8 |
| ETS2 | FANCL |
| INHBA | ID2 |
| LAMB3 | KAT2B |
| NF2 | PLA2G4C |
| NOG | STAT1 |
| PDGFC | TIAM1 |
| PRDM1 | |
| PRKACB | |
| RUNX1 | |
| WNT5B | |

| Matrigel vs. Xenograft (49) | | Matrigel ∩ 2D TCPS vs. Xenograft (41) | |
|---|---|---|---|
| Down-regulated (28) | Up-regulated (21) | Down-regulated (22) | Up-regulated (19) |
| ALKBH3 | ARID1A | CCNB1 | BDNF |
| ARID1B | BAIAP3 | CCND1 | BRAF |
| BAD | BCL2A1 | CDC25A | CCND2 |
| CCNA2 | DDIT3 | COL1A1 | EPOR |
| CCNE1 | DUSP8 | DNMT1 | HDAC11 |
| CDC6 | EFNA5 | E2F1 | HDAC5 |
| CHEK1 | EGFR | ETV4 | IGF1R |
| CTNNB1 | FGFR1 | EZH2 | INHBB |
| GADD45G | FLNC | FEN1 | ITGA3 |
| GPC4 | FOXO4 | FGF18 | LEPR |
| GRIA3 | GNAQ | HDAC1 | MET |
| HIST1H3B | ITGB3 | HRAS | NOTCH2 |
| HIST1H3H | LIFR | MAP2K6 | PIK3CB |
| HSPB1 | MED12 | MCM2 | PLD1 |
| JAG1 | NFKB1 | PCNA | RPS6KA6 |
| JUN | POLD4 | PKMYT1 | SOS2 |
| KRAS | PRKAA2 | PML | SPRY1 |
| MCM7 | SGK2 | RAC3 | TCF3 |
| MDM2 | SPRY2 | SFN | VEGFA |
| NBN | TGFB2 | SMC1A | |
| NTRK2 | ZAK | SRSF2 | |

TABLE 10A-continued

| | |
|---|---|
| PIK3R3 | STMN1 |
| POLE2 | |
| RBX1 | |
| SFRP4 | |
| TSPAN7 | |
| UBB | |
| XRCC4 | |

TABLE 10B

| 2D TCPS vs. Xenograft (62) | | HA-oxime ∩ Matrigel ∩ 2D TCPS Xenograft (73) | |
|---|---|---|---|
| Down-regulated (33) | Up-regulated (29) | Down-regulated (31) | Up-regulated (42) |
| AKT1 | BRCA1 | BCL2L1 | ARNT2 |
| CDC25B | CASP7 | CAPN2 | BCOR |
| CDKN2C | CDKN2D | CCNA1 | BIRC3 |
| COL27A1 | CUL1 | CCNE2 | CDKN1A |
| COL4A6 | FUBP1 | CDC7 | COL4A5 |
| EIF4EBP1 | GNG12 | CDK4 | CSF2 |
| ERCC2 | GSK3B | CDK6 | CSF3 |
| FANCA | HDAC2 | COL1A2 | CYLD |
| FANCG | HDAC6 | FUT8 | DUSP4 |
| FLNA | HHEX | GNAS | EFNA1 |
| FOSL1 | IRS1 | GTF2H3 | ERBB2 |
| FZD2 | ITGB6 | H3F3A | ERCC6 |
| GNA11 | JAK1 | HHIP | ETV1 |
| GNAQ | KIT | HMGA1 | FBXW7 |
| GRB2 | KLF4 | HSPA6 | FGFR3 |
| HDAC10 | MAP2K4 | LTBP1 | FZD7 |
| HSPA1A | MNAT1 | MAP2K2 | GADD45A |
| IFNA17 | NCOR1 | MCM4 | ID1 |
| LEFTY2 | PHF6 | MCM5 | IL1A |
| MLLT3 | PPP2CB | NRAS | IL1B |
| MYB | PTEN | PLAU | IL24 |
| MYC | RELA | PRKCB | IL6 |
| NOTCH1 | SF3B1 | RHOA | IL7R |
| PIK3R1 | SMAD2 | SFRP2 | IL8 |
| PIK3R2 | SMARCA4 | SMARCB1 | IRAK2 |
| POLD1 | SOS1 | SOX9 | JAG2 |
| POLR2D | STAG2 | SYK | LAMA3 |
| PPP3CB | TBL1XR1 | THBS4 | MAP3K5 |
| SMO | TET2 | TNC | MAP3K8 |
| SP1 | | TRAF7 | MAPK12 |
| TGFB1 | | U2AF1 | NFE2L2 |
| TGFB3 | | | NFKBIA |
| WHSC1 | | | NFKBIZ |
| | | | NGF |
| | | | PPARG |
| | | | RASA4 |
| | | | SHC1 |
| | | | SMAD3 |
| | | | TLR4 |
| | | | VHL |
| | | | WNT2B |
| | | | ZIC2 |

When triple-negative breast cancer (TNBC) MDA-MB-468 cells were cultured in HA-oxime gels, Matrigel or 20 TCPS, a similar number of genes were downregulated compared to the xenograft tumours (125, 134 and 122, respectively) while the number of upregulated genes was higher in 2D TCPS (94) versus HA-oxime and Matrigel (60 and 54 genes, respectively) (Tables 11A and 11B).

TABLE 11A

| HA-oxime vs. Xenograft (21) | | Matrigel vs. Xenograft (17) | |
|---|---|---|---|
| Down-regulated (17) | Up-regulated (4) | Down-regulated (16) | Up-regulated (1) |
| CCR7 | DUSP10 | ACVR2A | HSPA6 |
| CD19 | EGF | BAX | |
| CSF3 | PLAT | CAPN2 | |
| EGFR | SMAD3 | DDB2 | |

TABLE 11A-continued

| | |
|---|---|
| FANCC | KRAS |
| FGF5 | LAMB3 |
| FGF8 | MAPK3 |
| HPGD | MDM2 |
| IFNG | MECOM |
| IRS1 | MSH2 |
| ITGA7 | MSH6 |
| PIK3CD | PGF |
| RASGRF2 | PIK3R2 |
| SPRY1 | PPP3R1 |
| TLR4 | RHOA |
| VEGFC | SFRP1 |
| WNT5A | |

| HA-oxime ∩ Matrigel vs. Xenograft (34) | | HA-oxime ∩ 2D TCPS vs. Xenograft (11) | |
|---|---|---|---|
| Down-regulated (29) | Up-regulated (5) | Down-regulated (2) | Up-regulated (9) |
| CACNA1C | BAIAP3 | CDK6 | ALKBH3 |
| CACNA1G | IL1R1 | HSPA1A | ETS2 |
| CACNA2D4 | KDM5C | | HDAC11 |
| CARD11 | POLD4 | | LIFR |
| CDH1 | TNFRSF10C | | MEN1 |
| CREB5 | | | MYB |
| CRLF2 | | | PRKCA |
| CTNNB1 | | | TET2 |
| FGF18 | | | TGFB1 |
| FLNA | | | |
| GATA2 | | | |
| GRIA3 | | | |
| IL24 | | | |
| MAML2 | | | |
| MAP2K6 | | | |
| MCM7 | | | |
| MMP7 | | | |
| NBN | | | |
| NOTCH2 | | | |
| NTF3 | | | |
| PIK3CA | | | |
| PRKDC | | | |
| RFC3 | | | |
| SF3B1 | | | |
| SMC3 | | | |
| TFDP1 | | | |
| WIF1 | | | |
| WNT6 | | | |
| ZBTB32 | | | |

TABLE 11B

| Matrigel ∩ 2D TCPS vs. Xenograft (18) | | 2D TCPS vs. Xenograft (68) | | HA-oxime ∩ Matrigel ∩ 2D TCPS Xenograft (119) | | |
|---|---|---|---|---|---|---|
| Down-regulated (12) | Up-regulated (6) | Down-regulated (31) | Up-regulated (37) | Down-regulated (77) | | Up-regulated (42) |
| AXIN1 | EIF4EBP1 | ABL1 | ARID1B | AKT1 | RASAL1 | ACVR1C |
| BMP6 | ERCC6 | AKT2 | BRAF | ANGPT1 | SFRP2 | AXIN2 |
| BRIP1 | FANCB | AMER1 | CACNA2D4 | B2M | SFRP4 | BMP7 |
| CCND3 | IGFBP3 | APC | CDC14A | BAP1 | SHC4 | CEBPA |
| CDC6 | INHBB | CCND1 | COL5A1 | BCL2L1 | SKP2 | CSF3R |
| E2F1 | MNAT1 | CDK4 | COL5A2 | BMP2 | SMAD4 | DUSP4 |
| FEN1 | | CDKN1B | CRLF2 | BMP5 | SMARCB1 | EFNA3 |
| FZD9 | | CDKN2A | FGF13 | BRCA2 | SMO | ERBB2 |
| GRB2 | | CDKN2B | FGF22 | CACNA2D1 | SPRY2 | GADD45A |
| MAP3K1 | | CHUK | FN1 | CACNB3 | SRSF2 | GLI3 |
| MDC1 | | CIC | GNG12 | CALML5 | STAT1 | HDAC6 |
| PRKAR1B | | CREB3L1 | GSK3B | CDC25A | STAT3 | ID1 |
| | | DUSP2 | HDAC2 | COL1A2 | STK11 | IL1RAP |
| | | EZH2 | HOXA10 | COL4A4 | STMN1 | IL20RA |
| | | GNAQ | HSPB1 | DAXX | SYK | ITGA3 |
| | | H2AFX | IL24 | DNMT1 | TCF7L1 | JAG1 |
| | | HDAC1 | LEPR | DNMT3A | TGFBR2 | JAG2 |
| | | ID2 | LTBP1 | E2F5 | THBS1 | WHSC1 |
| | | IFNA17 | MAPK9 | ETV1 | THBS4 | KITLG |
| | | IKBKG | MLF1 | ETV4 | TNC | MAP3K5 |
| | | LEFTY2 | NF1 | FANCE | TP53 | NFE2L2 |
| | | MLLT3 | NTF3 | FANCG | TRAF7 | NKD1 |
| | | NOTCH1 | PBX3 | FGF2 | TSPAN7 | NOTCH3 |
| | | NRAS | PIK3CB | FGFR1 | U2AF1 | NUMBL |
| | | POLR2D | PPP2CB | FST | WHSC1 | NUPR1 |
| | | PRKX | PPP3CA | FZD7 | | PLA2G2A |
| | | PRLR | PTEN | GNA11 | | PPARG |
| | | SETD2 | PTPN11 | HMGA1 | | PRKAA2 |
| | | SMC1A | RAC1 | HRAS | | PRKACB |
| | | TGFB3 | RASGRF2 | INHBA | | PRKAR2B |
| | | WNT11 | RPS27A | ITGA6 | | RAC2 |
| | | | SETBP1 | ITGA9 | | RASA4 |
| | | | SKP1 | ITGB4 | | RRAS2 |
| | | | SOCS3 | ITGB8 | | SHC3 |
| | | | TBL1XR1 | MAPK8IP2 | | SOS1 |
| | | | VEGFC | MCM2 | | TIAM1 |
| | | | ZBTB32 | MCM4 | | TNFSF10 |
| | | | | MCM5 | | WNT2B |
| | | | | MET | | WNT4 |
| | | | | MYCN | | WNT7B |
| | | | | MYD88 | | WT1 |
| | | | | NF2 | | ZIC2 |
| | | | | NGFR | | |
| | | | | NSD1 | | |
| | | | | PDGFC | | |
| | | | | PDGFD | | |
| | | | | PKMYT1 | | |
| | | | | PLCB1 | | |
| | | | | PML | | |
| | | | | PRKCB | | |
| | | | | PROM1 | | |
| | | | | RAD21 | | |

Subsequent analysis of affected pathways revealed that the hedgehog pathway was altered when cultured in HA-oxime, Matrigel or 2D TCPS relative to the tumour xenografts. Since only 30% of triple-negative breast cancers involve paracrine hedgehog (Hh) signalling, which has been studied in the context of cancer-associated fibroblasts, co-culture models may be required to target this pathway (Hui et al., Journal of Clinical Oncology, 36:e24216 (2018)).

Our gene expression pathway analyses show that the JAK-STAT pathway was altered in both HER2$^+$ BT474 and MDA-MB-231-H2N cell lines when cultured in Matrigel or on 2D TCPS relative to xenograft and HA-oxime. This underlines the need to evaluate drugs targeting specific pathways on validated models. Remarkably, while Matrigel is thought to be the gold standard for in vitro culture, it has not been benchmarked previously and our data clearly demonstrate that it is sub-optimal. Overall, HA-oxime gels were the most similar to xenografts, with only 294 differentially expressed genes vs. 434 for Matrigel and 371 for 2D TCPS. The number of differentially expressed genes for the same cell lines was similar between HA-oxime and HA-oxime-Ln hydrogels (294 versus 308 genes, respectively) compared to the xenograft tumours. Thus, 3D culture reduces, but does not eliminate, differences in gene expression between 2D culture and xenografts. 3D culture in HA-oxime better emulates the gene expression profile of xenografts than culture in Matrigel.

Evaluating Differences in Drug Response Between 2D and 3D Models: To understand if these differences in gene expression could influence cell response in drug screening, we specifically chose drugs that target pathways differentially expressed between xenograft and in vitro culture in Matrigel and 2D TCPS and that were not differentially expressed in HA-oxime (Tables 12A, 12B, 12C, and 12D).

We tested a series of drugs that target the MAPK (such as Rac signaling) and JAK-STAT pathways of BT474 cells grown in HA-oxime vs. Matrigel and 2D TCPS.

TABLE 12A

| HA-oxime vs. Xenograft (21) | | Matrigel vs. Xenograft (17) | |
|---|---|---|---|
| Down-regulated (17) | Up-regulated (4) | Down-regulated (16) | Up-regulated (1) |
| CCR7 | DUSP10 | ACVR2A | HSPA6 |
| CD19 | EGF | BAX | |
| CSF3 | PLAT | CAPN2 | |
| EGFR | SMAD3 | DDB2 | |
| FANCC | | KRAS | |
| FGF5 | | LAMB3 | |
| FGF8 | | MAPK3 | |
| HPGD | | MDM2 | |
| IFNG | | MECOM | |
| IRS1 | | MSH2 | |
| ITGA7 | | MSH6 | |
| PIK3CD | | PGF | |
| RASGRF2 | | PIK3R2 | |
| SPRY1 | | PPP3R1 | |
| TLR4 | | RHOA | |
| VEGFC | | SFRP1 | |
| WNT5A | | | |

TABLE 12B

| Matrigel ∩ 2D TCPS vs. Xenograft (18) | | HA-oxime ∩ 2D TCPS vs. Xenograft (11) | |
|---|---|---|---|
| Down-regulated (12) | Up-regulated (6) | Down-regulated (2) | Up-regulated (9) |
| AXIN1 | EIF4EBP1 | CDK6 | ALKBH3 |
| BMP6 | ERCC6 | HSPA1A | ETS2 |
| BRIP1 | FANCB | | HDAC11 |
| CCND3 | IGFBP3 | | LIFR |
| CDC6 | INHBB | | MEN1 |
| E2F1 | MNAT1 | | MYB |
| FEN1 | | | PRKCA |
| FZD9 | | | TET2 |
| GRB2 | | | TGFB1 |
| MAP3K1 | | | |
| MDC1 | | | |
| PRKAR1B | | | |

TABLE 12 C

| HA-oxime ∩ Matrigel vs. Xenograft (34) | | 2D TCPS vs. Xenograft (68) | | HA-oxime ∩ Matrigel ∩ 2D TCPS Xenograft (119) | | |
|---|---|---|---|---|---|---|
| Down-regulated (29) | Up-regulated (5) | Down-regulated (31) | Up-regulated (37) | Down-regulated (77 | | Up-regulated (42) |
| CACNA1C | BAIAP3 | ABL1 | ARID1B | AKT1 | SMO | ACVR1C |
| CACNA1G | IL1R1 | AKT2 | BRAF | ANGPT1 | SPRY2 | AXIN2 |
| CACNA2D4 | KDM5C | AMER1 | CACNA2D4 | B2M | SRSF2 | BMP7 |
| CARD11 | POLD4 | APC | CDC14A | BAP1 | STAT1 | CEBPA |
| CDH1 | TNFRSF10C | CCND1 | COL5A1 | BCL2L1 | STAT3 | CSF3R |
| CREB5 | | CDK4 | COL5A2 | BMP2 | STK11 | DUSP4 |
| CRLF2 | | CDKN1B | CRLF2 | BMP5 | STMN1 | EFNA3 |
| CTNNB1 | | CDKN2A | FGF13 | BRCA2 | SYK | ERBB2 |
| FGF18 | | CDKN2B | FGF22 | CACNA2D1 | TCF7L1 | GADD45A |
| FLNA | | CHUK | FN1 | CACNB3 | TGFBR2 | GLI3 |
| GATA2 | | CIC | GNG12 | CALML5 | THBS1 | HDAC6 |
| GRIA3 | | CREB3L1 | GSK3B | CDC25A | THBS4 | ID1 |
| IL24 | | DUSP2 | HDAC2 | COL1A2 | TNC | IL1RAP |
| MAML2 | | EZH2 | HOXA10 | COL4A4 | TP53 | IL20RA |
| MAP2K6 | | GNAQ | HSPB1 | DAXX | TRAF7 | ITGA3 |
| MCM7 | | H2AFX | IL24 | DNMT1 | TSPAN7 | JAG1 |
| NBN | | HDAC1 | LEPR | DNMT3A | U2AF1 | JAG2 |
| NOTCH2 | | ID2 | LTBP1 | E2F5 | WHSC1 | WHSC1 |
| NTF3 | | IFNA17 | MAPK9 | ETV1 | | KITLG |
| PIK3CA | | IKBKG | MLF1 | ETV4 | | MAP3K5 |
| PRKDC | | LEFTY2 | NF1 | FANCE | | NFE2L2 |
| RFC3 | | MLLT3 | NTF3 | FANCG | | NKD1 |
| SF3B1 | | NOTCH1 | PBX3 | FGF2 | | NOTCH3 |
| SMC3 | | NRAS | PIK3CB | FGFR1 | | NUMBL |
| TFDP1 | | POLR2D | PPP2CB | FST | | NUPR1 |
| WIF1 | | PRKX | PPP3CA | FZD7 | | PLA2G2A |
| WNT6 | | PRLR | PTEN | GNA11 | | PPARG |
| ZBTB32 | | SETD2 | PTPN11 | HMGA1 | | PRKAA2 |
| | | SMC1A | RAC1 | HRAS | | PRKACB |
| | | TGFB3 | RASGRF2 | INHBA | | PRKAR2B |
| | | WNT11 | RPS27A | ITGA6 | | RAC2 |
| | | | SETBP1 | ITGA9 | | RASA4 |
| | | | SKP1 | ITGB4 | | RRAS2 |
| | | | SOCS3 | ITGB8 | | SHC3 |
| | | | TBL1XR1 | MAPK8IP2 | | SOS1 |
| | | | VEGFC | MCM2 | | TIAM1 |
| | | | ZBTB32 | MCM4 | | TNFSF10 |
| | | | | MCM5 | | WNT2B |
| | | | | MET | | WNT4 |
| | | | | MYCN | | WNT7B |
| | | | | MYD88 | | WT1 |
| | | | | NF2 | | ZIC2 |
| | | | | NGFR | | |
| | | | | NSD1 | | |
| | | | | PDGFC | | |
| | | | | PDGFD | | |
| | | | | PKMYT1 | | |
| | | | | PLCB1 | | |
| | | | | PML | | |
| | | | | PRKCB | | |
| | | | | PROM1 | | |
| | | | | RAD21 | | |
| | | | | RASAL1 | | |
| | | | | SFRP2 | | |
| | | | | SFRP4 | | |
| | | | | SHC4 | | |
| | | | | SKP2 | | |
| | | | | SMAD4 | | |
| | | | | SMARCB1 | | |

TABLE 12D

| BT474 | | MDA-MB-231-H2N | |
|---|---|---|---|
| ∩ MDA-MB-231-H2N | ∩ MDA-MB-468 | ∩ MDA-MB-468 | |
| | FGF2 | BCL2L1 | ∩ BT474 |
| | IL20RA | DUSP4 | COL1A2 |
| | INHBA | ERBB2 | GADD45A |
| | RRAS2 | ETV1 | PRKCB |
| | SFRP4 | FZD7 | SFRP2 |
| | THBS1 | HMGA1 | THBS4 |

TABLE 12D-continued

| BT474 | | MDA-MB-231-H2N | |
|---|---|---|---|
| ∩ MDA-MB-231-H2N | ∩ MDA-MB-468 | ∩ MDA-MB-468 | |
| | TSPAN7 | ID1 | TRAF7 |
| | | IL24 | |
| | | JAG2 | |
| | | MAP3K5 | |
| | | MCM4 | |
| | | MCM5 | |

TABLE 12D-continued

| BT474 | | MDA-MB-231-H2N |
| --- | --- | --- |
| ∩ MDA-MB-231-H2N | ∩ MDA-MB-468 | ∩ MDA-MB-468 |
| | | NFE2L2<br>PPARG<br>RASA4<br>SMARCB1<br>SYK<br>TNC<br>U2AF1<br>WNT2B<br>ZIC2 |

BT474 cells treated with EHT-1864 (Rac inhibitor, targeting the MAPK/ERK pathway) were more responsive when cultured in HA-oxime than in Matrigel. In addition, BT474 cells cultured in HA-oxime were more responsive to AZD6482 (PI3Kβ inhibitor involved in the JAK-STAT pathway) than those cultured in Matrigel or on 2D TCPS. To gain biological insight into the mechanism underlying the observed differences in drug responsiveness, we quantified the number of genes involved in MAPK and JAK-STAT signaling pathways with differential expression levels relative to tumour xenografts: cells cultured in HA-oxime had fewer differentially expressed genes (14 for MAPK and 4 for JAK-STAT) compared to cells cultured in both Matrigel (43 for MAPK and 29 for JAK-STAT) and on 2D TCPS (23 for MAPK and 10 for JAK-STAT). Together these results demonstrate the superiority of HA-oxime over Matrigel and 2D TCPS in drug screening where specific pathways are targeted.

Figure 35:
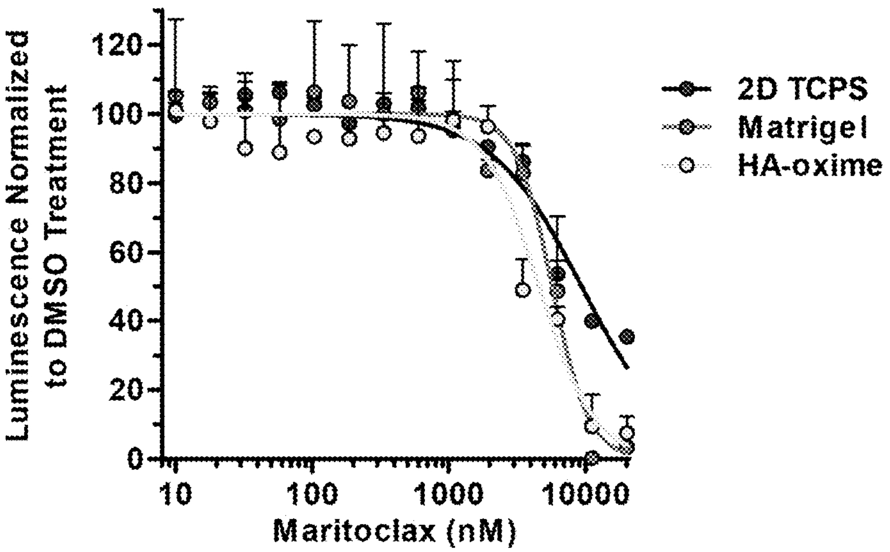
FIG. 35 illustrates dose response curves for tumor derived mammary luminal epithelial cells cultured over 72 h of treatment on 2D TCPS or in 3D with Matrigel or HA-oxime after 7 days of treatment with Maritoclax (Mci-1). All screens were quantified by RealTime-Glo MT Cell Viability Assay (n=3 independent studies; mean+standard deviation, plotted with best fit curve).

Interestingly, cells cultured in HA-oxime were over tenfold more sensitive to maritoclax, an Mci-1 inhibitor which prevents the normal anti-apoptotic signaling by Mci-1 on the mitochondria resulting in apoptosis, with an $IC_{50}$ of 0.59 μM than those cultured in 2D TCPS with $IC_{50}$ of 5.5 μM. Moreover, primary, human patient tumour luminal B breast cancer cells were significantly more sensitive to maritoclax when cultured in 3D HA-oxime than those cultured on 2D TCPS as well, demonstrating both the potential of the HA-oxime hydrogels in personalized medicine and the importance of culture conditions in drug screening (FIG. 35). Maritoclax targets the apoptosis pathway as an inhibitor of anti-apoptotic protein Mcl-1 on the mitochondria. Regulators of this apoptosis pathway, BAD (pro-apoptotic) and BCL2 (anti-apoptotic), had decreased levels in BT474 cells cultured on 2D TCPS relative to 3D culture, which explains the observed differences in drug response.

We highlight the results of the in vitro drug screening performed with BT474 cells where $IC_{50}$ values differed between HA-oxime, Matrigel and 2D TCPS. Since the decision to test drugs in animal models of disease is often based on in vitro screening, maritoclax, EHT-1864 and AZD6482 would have been excluded based on culture in Matrigel and/or 2D TCPS, thereby reflecting the importance of culture in a representative matrix, such as HA-oxime. The differences between 2D and 3D culture of breast cancer cells are significant in terms of gene expression and drug response. While cell response did not always differ between the 3 culture conditions (as shown with ZSTK474 and afatinib), to ensure comprehensive screening, a validated, representative system, like HA-oxime, is required.

Figure 36A:
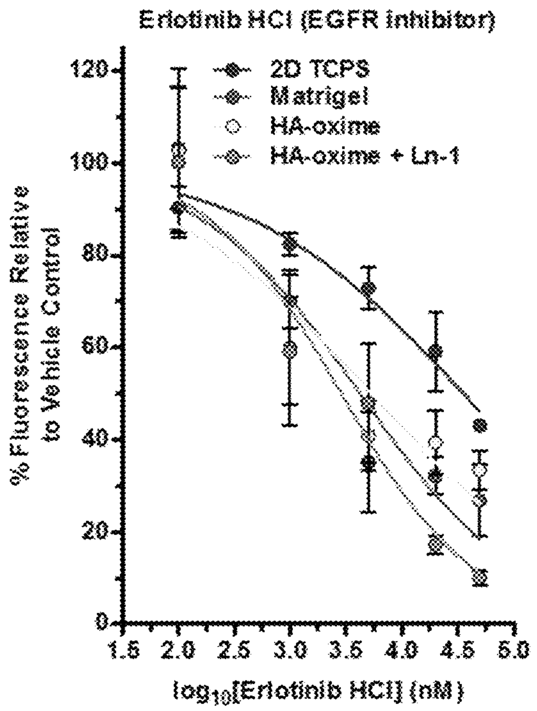
FIG. 36A and FIG. 36B illustrate comparison of MDA-MB-468 cell sensitivity to erlotinib (EGFR inhibitor).
Figure 36B:
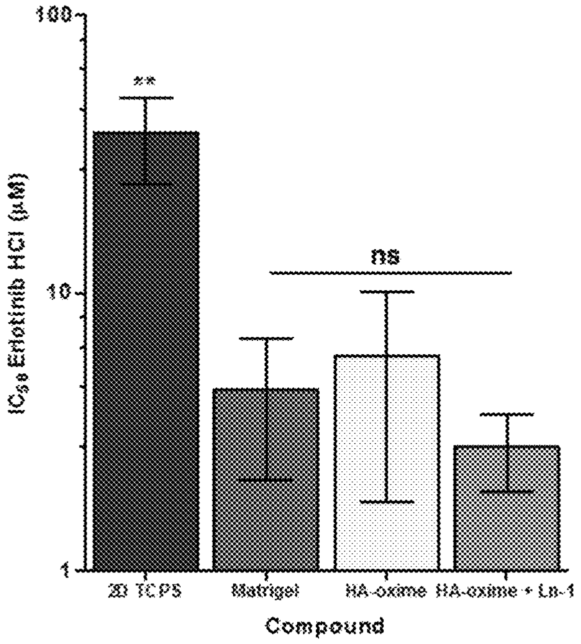

To gain insight into the broader utility of the HA-oxime hydrogels with other cell types, we investigated the efficacy of erlotinib, an EGFR inhibitor, against TNBC MDA-MB-468 cells. Cells that were grown on 2D TCPS, in Matrigel or HA-oxime for 21 days and treated with erlotinib for 7 days had a significantly higher $IC_{50}$ of 37.6 μM ($p<0.01$) compared to those cultured in 3D of ~4.5 μM (FIG. 36A and FIG. 36B). MDA-MB-468 cells cultured on 2D were less sensitive to erlotinib than other cancer cell lines, despite its established effectiveness in breast cancer xenografts in mice (Yamasaki et al., Mol. Cancer Ther., 6:2168 (2007); Lau et al., Oncotarget, 5:10503 (2014)), further highlighting the importance of relevant screening assays.

Conclusion: 3D cell culture has several features which make it attractive for drug screening, yet is limited by the use of Matrigel, which does not faithfully recapitulate the gene expression profile of the tumour xenograft and is chemically ill-defined. The newly synthesized HA-oxime hydrogels have controlled and tunable gelation, mechanical properties, and chemical properties that mimic the breast ECM, which are not possible with 2D TCPS and limited with Matrigel. By benchmarking to the in vivo gold standard for the first time, we demonstrate that breast cancer cells grown in HA-oxime hydrogels most closely resemble orthotopic xenografts in terms of gene expression profiles of 3 distinct breast cancer subtypes. This impacts the value of in vitro drug screening. Formulating the HA-oxime hydrogels with laminin did not reduce the number of differentially expressed genes expressed by the breast cancer spheroids compared to the tumour xenografts. Our analysis of canonical signaling pathways using the gene expression data suggest breast cancer subtype-dependent changes to gene expression with culture platform. We demonstrated the ability to grow patient-derived breast cancer cells in HA-oxime hydrogels and thereby identify relevant drug candidates. Thus, hyaluronan-oxime hydrogels bridge the gap between 2D drug screening in vitro and in vivo mouse xenograft models, opening the door to personalized medicine and more predictive drug screening. To take full advantage of this opportunity, scale up and simultaneous screening of multiple drugs is required. This well-defined hydrogel platform opens up the possibility for more complex 3D models with co-culture of multiple cell types, thereby better emulating the complexity of tumours.

Example 8—Drug Screening

The following example describes experiments conducted to calculate $IC_{50}$ values using a non-linear fit in Graphpad Prism by GraphPad Software Inc.

BT474: BT474 cells were grown on 2D, in Matrigel, and in HA-oxime+/−Ln hydrogels at a seeding density of 4,000 cells per well in 96-well format. Cells grown in 2D were dosed starting after 24 h with either EHT-1864, AZD6482, Maritoclax, ZSTK474, Afatinib, TW-37, ABT-199, ABT-263 and Temsirolimus between 50 nM and up to 20 μM using an Hewlett-Packard (HP) D300 digital dispenser containing up to 0.2% DMSO then treated again 48 h following the first dose and ended after 72 h of treatment. Cells grown in 3D were dosed after 14 days with up to 0.2% DMSO every 48 h for 7 days. Cell viability was assessed by removing media and replacing it with 100 μL of sterile RealTime-Glo MT (Promega) which was diluted 1000× in media warmed to 37° C. After 1 h luminescence was detected using a Tecan microplate reader (Life Sciences) with 1 second integration time. Cell viability was calculated by subtracting background luminescence from all groups; treatment was compared to control wells, which received up to 0.2% DMSO. Data represents 3 independent replicates consisting of different cell passages for each condition to calculate the mean and standard deviation of cell viability.

MDA-MB-468: MDA-MB-468 cells were grown on 2D, in Matrigel or in HA-oxime+/−Ln hydrogels for 21 days at a seeding density of 4,000 cells per well in 96-well format. Cells were dosed with 0.1, 1, 5, 20 and 50 μM Erlotinib-HCl containing 0.27% DMSO every 48 h for 7 days. Cell viability was assessed by removing media and replacing it with 150 μL of sterile, PrestoBlue which was diluted 10× in media warmed to 37° C. After 2.5 hours fluorescence was detected using a Tecan microplate reader (Life Sciences) by exciting at 570 nm and detected at 590 nm. Cell viability was calculated by subtracting background fluorescence from all groups; treatment was compared to control wells, which received 0.27% DMSO. Data represents 3 independent replicates consisting of different cell passages for each condition to calculate the mean and standard deviation of cell viability.

Primary Cell Survival: A patient biopsy characterized as luminal A ($ER^+$, $PR^+$, $HER2^-$) was dissociated and cells were suspended in serum-free breast cancer organoid medium as reported (Hasan et al., J. Clin. Pathol., 68:746 (2015)). Cells were seeded at 80,000 cells per 600 μL on 2D TCPS or encapsulated (80,000 cells per 50 μL) in Matrigel (8.5 mg·mL) or 3:1 HAK/HAA ($PEGOA_4$ crosslinked) hydrogels+/−Ln, which were plated in 24-well plates. After 1 hour, warmed medium (600 μL) was added to the hydrogels. Media was changed every 48 hours until 14 days when cells were visualized using Hoechst (1:100 of 1 mg·mL), Mito Tracker Deep Red FM (1:3,000 of 1 mM) and Sytox green (1:200,000 of 5 mM). After 2 h cells were imaged using an Olympus confocal microscope at 10× magnification.

Tumor derived mammary luminal epithelial cells (Lot #: LUMM062314, Female Age 41) were acquired from Zen-Bio at passage 2 and cultured until after passage 4 using mammary luminal growth medium (Zen-Bio, LCM-1). Cells were grown on 2D, in Matrigel or HA-oxime+/−Ln hydrogels at a seeding density of 3,000 cells per well. After 24 h cells were visualized using 1:200,000 Sytox green (Thermo Fisher Scientific) and 1:3,000 MitoTracker Deep Red FM (Thermo Fisher Scientific) in media. After 1 h cells were imaged using an Olympus confocal microscope at 10× magnification. Cell number was quantified using spot identification in Imaris 8 software by Bitplane. Data represents 3 independent replicates consisting of separate cell passages.

Drug Screening with Primary Cells: Tumor derived mammary luminal epithelial cells were grown on 2D, in Matrigel or HA-oxime hydrogels at a seeding density of 4,000 cells per well. Cells grown in 2D were dosed after 24 h with Maritoclax between 10 nM and up to 20 μM using an Hewlett-Packard (HP) D300 digital dispenser containing up to 0.2% DMSO then treated again 48 h following the first dose and ended after 72 h of treatment. Cells grown in 3D were dosed after 14 days with up to 0.2% DMSO every 48 h for 7 days. Cell viability was assessed by removing media and replacing it with 100 μL of sterile RealTime-Glo MT (Promega) which was diluted 1000× in media warmed to 37° C. After 1 h luminescence was detected using a Tecan microplate reader (Life Sciences) with 1 second integration time. Cell viability was calculated by subtracting background luminescence from all groups; treatment was compared to control wells, which received up to 0.2% DMSO. $IC_{50}$ values were calculated using a non-linear fit in Graphpad Prism by GraphPad Software Inc. Data represents 3 independent replicates consisting of different cell passages for each condition to calculate the mean and standard deviation of cell viability.

Statistical Analysis: All statistical analyses were performed using GraphPad Prism software versions 5 and 7 by GraphPad Software Inc. Differences between more than two groups were analyzed using one-way analysis of variance (ANOVA) and Tukey's post-hoc test. NanoString data was first normalized to a panel of housekeeping genes (Table 13) using nSolver Analysis Software 3.0 (NanoString Technologies). The normalized gene expression values were used to calculate fold change, GSVA pathway using gene set variation analysis, one-way ANOVA p-value, and Tukey's post-hoc test by R version 3.3.3. A list of 36 housekeeping genes used to normalize gene expression for NanoString experiments is described in Table 13.

TABLE 13

| Housekeeping Genes | |
|---|---|
| ACAD9 | PIAS1 |
| AGK | PIK3R4 |
| C10orf76 | PRPF38A |
| CNOT10 | RBM45 |
| CNOT4 | SAP130 |
| COG7 | SF3A3 |
| DDX50 | SLC4A1AP |
| DHX16 | TLK2 |
| DNAJC14 | TMUB2 |
| EDC3 | TRIM39 |
| EIF2B4 | TTC31 |
| ERCC3 | USP39 |
| FCF1 | VPS33B |
| HDAC3 | ZC3H14 |
| MRPS5 | ZKSCAN5 |
| MTMR14 | ZNF143 |
| NOL7 | ZNF346 |
| NUBP1 | ZNF384 |

Example 9—Synthesis of HA-Oxime Hydrogels with Peptide Cross-Linker for Use in 3D Cell Culture System This example describes the synthesis of a hydrogel with peptide cross-linker.

Methods: A hydrogel containing covalently immobilized peptide was synthesized. Specifically, a hydrogel with covalently attached fibronectin mimicking peptide, GRGDS-PASSKKG (RGD), was synthesized.

The peptide was synthesized by solid-phase peptide synthesis (SPPS), and subsequently modified with an oxyamine group to allow coupling with ketone and aldehyde groups on HA. Oxyamine peptide synthesis is challenging due to reports of N-overacylation during coupling with 2-(((tert-butoxycarbonyl)amino)oxy)acetic acid and reactions of oxyamine-peptides with plasticizers (Decostaire et al., Tetrahedron Lett. 47:7057-7060 (2006); Mezb et al., J. Pept. Sci, 17:39-46 (2011); Bure et al., Rapid Commun. Mass Spectrom. 14:2158-2164 (2000); Wahl et al., Tetrahedron Left. 37:6861-6864 (1996)). To overcome these challenges, 6-(((tert-butoxycarbonyl)amino)oxy)hexanoic acid (compound 9-c) was first prepared in three steps as detailed below.

Synthesis of 6-(((tert-butoxycarbonyl)amino)oxy)hexanoic acid

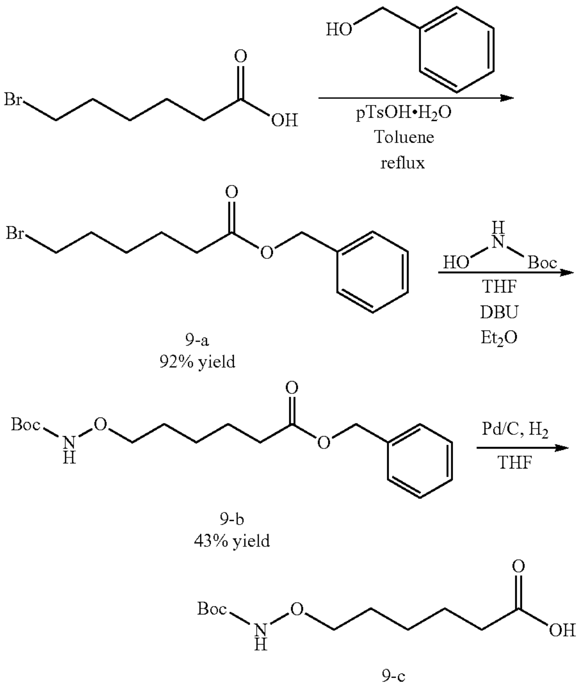

9-a
92% yield 9-b
43% yield 9-c
quantitative yield
1.8 g

Synthesis of benzyl 6-bromohexanoate (9-a): 6-Bromohexanoic acid (1.0 g, 5.1 mmol) was dissolved in toluene (50 mL) and benzyl alcohol (0.8 mL, 7.7 mmol) and p-toluenesulfonic acid monohydrate (48.6 mg, 0.26 mmol) was added. The reaction was refluxed at 140° C. with a Dean-Stark apparatus overnight before left cool to room temperature. The crude was washed with 25 mL of saturated sodium bicarbonate and extracted three times with toluene (25 mL). The combined organic fractions were washed with 25 mL of saturated sodium chloride and dried over magnesium sulfate. Solvent was removed and purified by flash chromatography with silica using 10% ethyl acetate and hexanes. A colorless oil was obtained (1.35 g, 92% yield). $^1$H NMR ($CDCl_3$, 400 MHz) 1.47-1.51 (m, 2H), 1.61-1.72 (m, 2H), 1.83-1.90 (m, 2H), 2.38 (t, J=8 Hz, 2H), 3.39 (t, J=8 Hz, 2H), 5.12 (s, 2H), 7.32-7.39 (m, 5H). $^{13}$C NMR ($CDCl_3$, 100 MHz) 24.2, 27.8, 32.5, 33.6, 34.2, 66.3, 128.4, 128.7, 136.1. (DART ESI): $[M+H]^+$ calcd. For $C_{13}H_{18}Br_1O_2$: 285.0490; found 285.0498.

Synthesis of benzyl 6-(((tert-butoxycarbonyl)amino)oxy)hexanoate (9-b): To a solution of benzyl hexanoate (10) (4.76 g, 16.7 mmol) dissolved in acetonitrile (50 mL), N-Boc-hydroxylamine (3.11 g, 23.4 mmol) was added followed by 1,8-diazabicyclo(5.4.0)undec-7-ene (3.8 g, 25 mmol). The reaction was stirred for 15 hours at 50° C. before being concentrated in vacuo. The crude was resuspended in 100 mL ethyl acetate and extracted against 50 mL of 0.1 M, pH 8.0 potassium bisulfate three times. The combined aqueous fractions were extracted with an additional 100 mL of ethyl acetate and organic fractions were washed with 100 mL of distilled water followed by 50 mL of saturated sodium chloride. The organic fractions were dried over sodium sulfate, and purified by flash chromatography with silica using 20-40% ethyl acetate and petroleum ether. A colorless oil was obtained (2.44 g, 43% yield). $^1$H NMR ($CD_2Cl_2$, 400 MHz) 1.40 (m, 2H), 1.46 (s, 9H), 1.57-1.70 (m, 4H), 2.36 (t, J=8 Hz, 2H), 3.80 (t, J=8 Hz, 2H), 5.10 (s, 2H), 7.23 (bs, 1H), 7.35 (m, 5H). $^{13}$C NMR ($CD_2Cl_2$, 100 MHz) 24.7, 25.4, 27.6, 27.9, 28.0, 34.0, 65.9, 76.3, 81.1, 128.0, 128.4, 136.4, 156.6, 173.2.

Synthesis of 6-(((tert-butoxycarbonyl)amino)oxy)hexanoic acid (9-c): To a degassed solution of 11 (2.44 g, 7.3 mmol) in THF (60 mL), Pd/C (0.1 g, 10% loading) was added. The suspension was degassed with nitrogen and stirred under hydrogen for 2 h before degassing with nitrogen and filtering off the catalyst. The solvent was removed in vacuo to yield a colorless oil (1.79 g, quantitative).

$^1$H NMR ($CDCl_3$, 400 MHz) 1.40-1.43 (m, 2H), 1.48 (s, 9H), 1.61-1.70 (m, 4H), 2.36 (t, J=8 Hz, 2H), 3.84 (t, J=8 Hz, 2H), 7.33 (bs, 1H). $^{13}$C NMR ($CDCl_3$, 100 MHz) 24.9, 25.9, 28.1, 28.7, 34.3, 82.2, 100.4, 157.6, 179.6. (DART ESI): $[M+NH_4]^+$ calcd. For $C_{11}H_{25}N_2O_5$: 265.1763; found 265.1762.

Synthesis of Oxyamine-modified Peptides: Compound 9-c was then conjugated to RGD in order to prepare oxyamine-modified RGD (RGDOA) as detailed below. RGDOA is prepared over five steps using compound 9-c to modify the peptide prepared by standard Fmoc chemistry with solid phase peptide synthesis. RGDOA peptide was prepared in 17% yield.

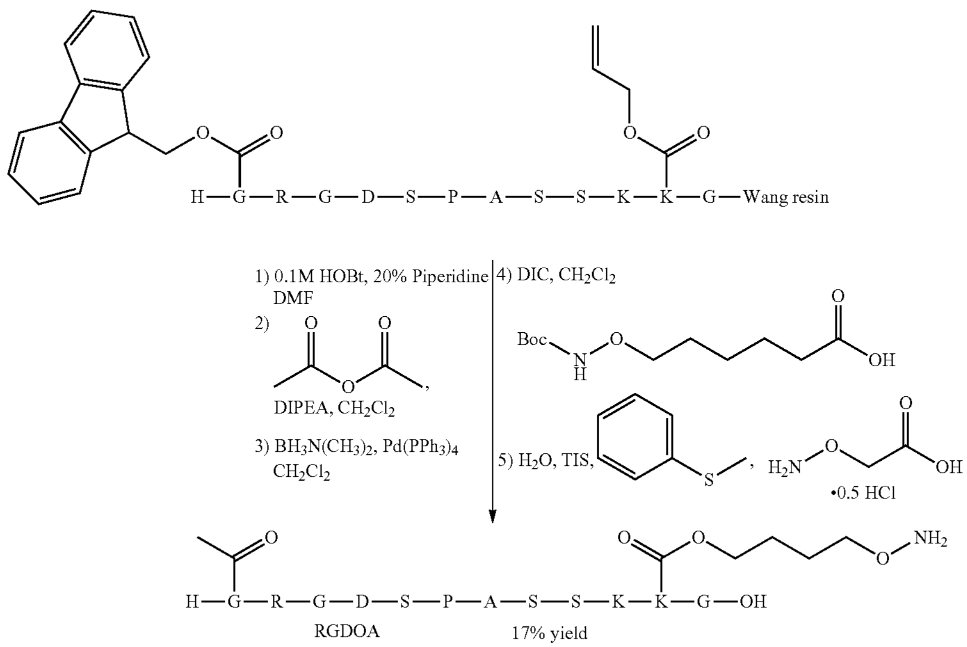

In addition to incorporation of adhesive peptides, many hydrogels are designed to have an enzymatically degradable peptide cross-linker, which are often degradable by matrix metalloproteinases (MMP) secreted by cells (Jha et al., Biomaterials, 89:136-147 (2016)). Oxyamine-modified MMP ($MMPOA_2$)-degradable peptide was prepared by SPPS in four steps as shown below. $MMPOA_2$ peptide is prepared over four steps using 6-(((tert-butoxycarbonyl) amino)oxy)hexanoic acid to modify the peptide prepared by standard Fmoc chemistry with solid phase peptide synthesis. $MMPOA_2$ peptide was prepared in 30% yield and is cleavable at the highlighted sequence.

a

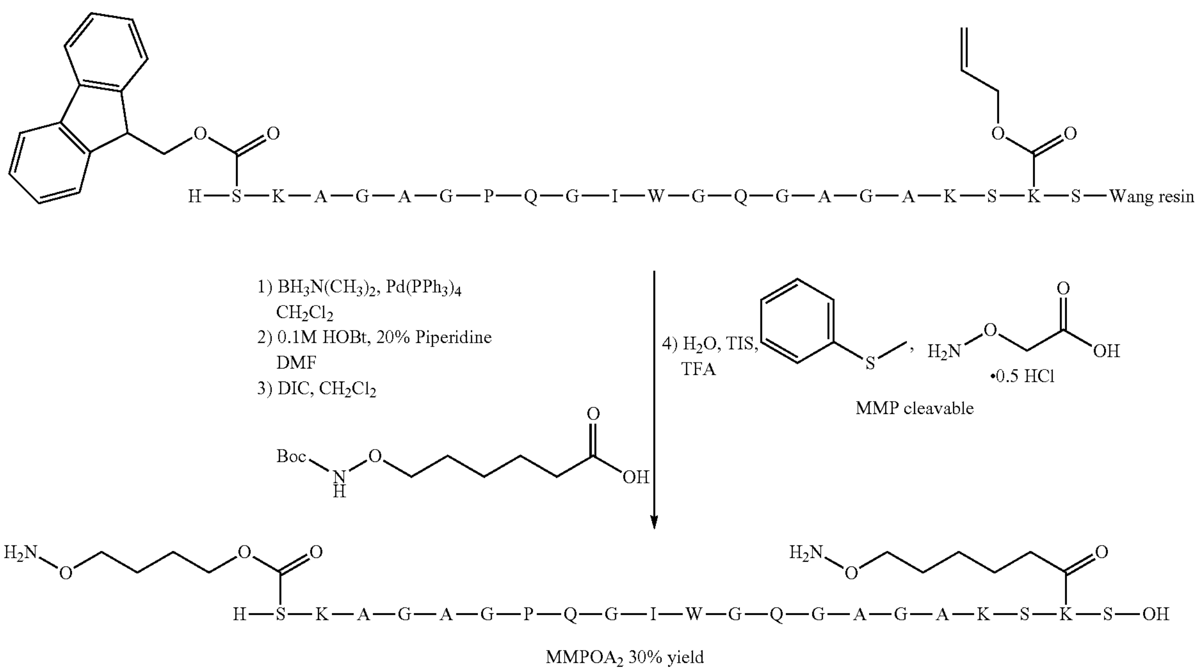

-continued b

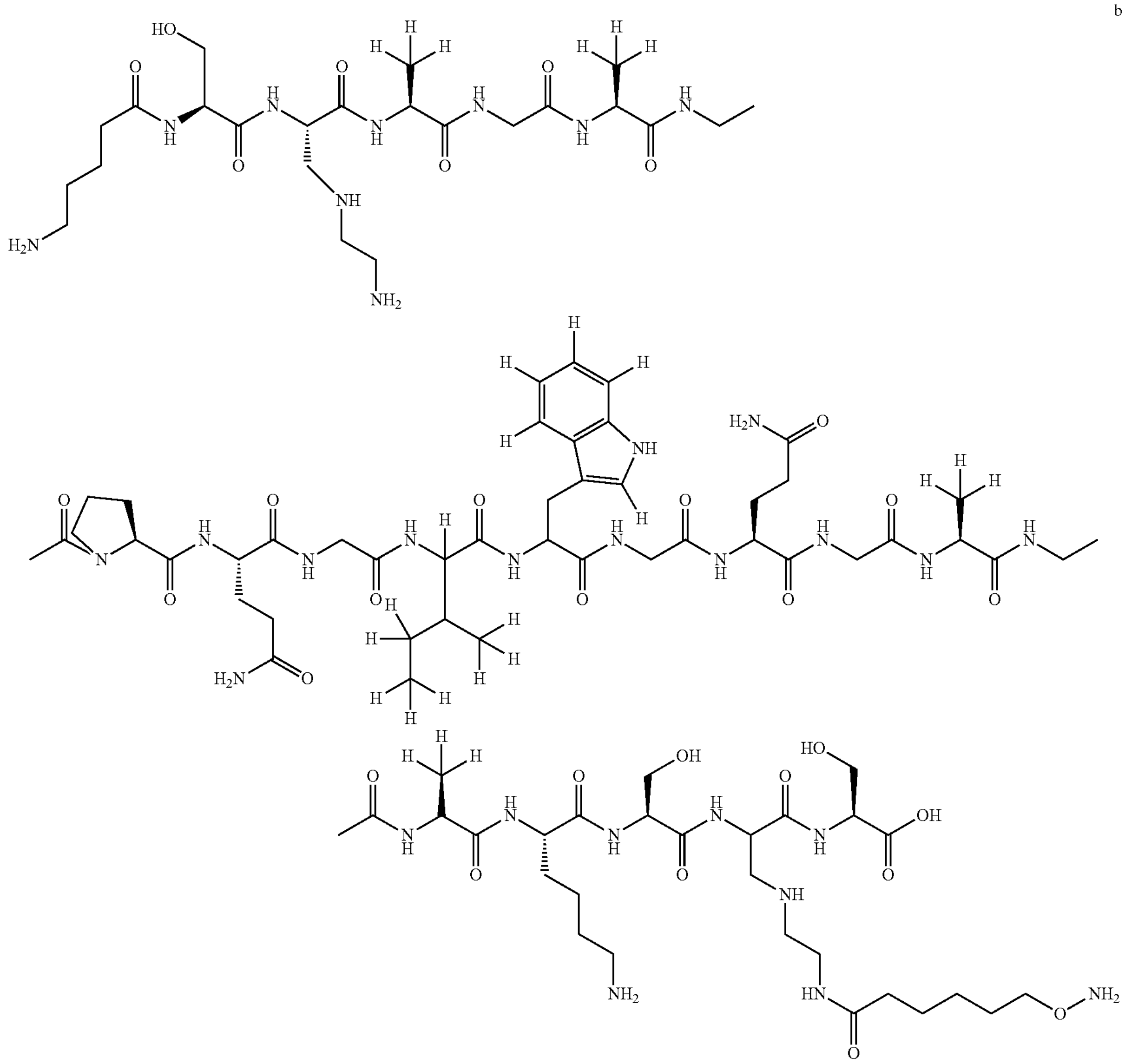

II

Synthesis of RGD: Peptides were prepared using standard Fmoc chemistry using a Liberty Blue peptide synthesizer connected to a Discover microwave (CEM). Peptides were purified by HPLC using water and acetonitrile containing 0.1% trifluoroacetic acid. Flow rate and gradients were regulated by a 1525 binary HPLC pump (Waters) connected to a xBridge BEH C8 OBD prep column, 5 μm, 19 mm×150 mm. Fractions containing peptide were identified using a 2489 UV/Vis detector (Waters) and samples were collected using a fraction collector III (Waters). After removing acetonitrile under airflow, fractions were concentrated by lyophilisation analyzed by mass spectroscopy. Purified peptides were stored at −20° C. in glass vials.

Synthesis of Acetyl-GRGDSPASSKK(OA)G: Fmoc-Gly-Wang resin (0.5 mmol) was swollen in DMF for 10 min then F-moc deprotected and washed using the Liberty Blue peptide synthesizer. A solution containing Fmoc-Lys(Alloc)-OH (0.57 g, 1.25 mmol), HBTU (0.95 g, 2.5 mmol), DIPEA (0.52 mL, 3 mmol) in 5 mL of DMF was added to the resin and allowed to stand for 10 min. An additional 5 mL of DMF was added and a microwave coupling was performed. The coupling of the Fmoc-Lys(Alloc)-OH on the Gly-Wang resin was confirmed by colorimetric TNBS test (10-15 resin beads in DMF with 5 drops of TNBS reagent and 10 drops of DIPEA), and the remaining sequence was synthesized. The resin was removed from the reaction vessel and treated with 8 mL of Fmoc deprotection solution containing 1.6 mL piperidine and 1 M 1-hydroxybenzotriazole hydrate (HOBt) for 2 h. The resin was washed with DMF and $CH_2Cl_2$ before adding N,N-diisopropylethylamine (0.9 mL, 5 mmol) and acetic anhydride (0.9 mL, 9.5 mmol). After stirring for 2 h the solution was drained and washed extensively with $CH_2Cl_2$, DMF and $CH_2Cl_2$ again. The protection was confirmed using the TNBS test, and the resin was stirred in $CH_2Cl_2$ (8 mL) and degassed under nitrogen. Borane dimethylamine complex (20 mg, 0.34 mmol) and tetrakis(triphenylphosphine)palladium(0) (45 mg, 0.04 mmol) were added to the resin suspension and the reaction was stirred overnight protected from light. The solution was drained and the resin was washed with $CH_2Cl_2$. 6-(((tert-butoxycarbonyl)amino)oxy)hexanoic acid (0.22 g, 0.9 mmol) and DIC (142 mg, 1.12 mmol) were combined in 5 mL of $CH_2Cl_2$ for 1 h before adding the solution to the resin. After 24 h the solution was removed and the resin was washed with $CH_2Cl_2$ and dried. The resin was treated with trifluoroacetic acid (4 mL), triisopropylsilane (0.15 mL), thioanisole (0.15 mL), water (0.15 mL) and aminooxy)acetic acid hemihydrochloride (0.24 mg) for 2.5 h. The peptide was precipitated in cold diethyl ether (50 mL) and washed two additional times. After purification, RGDOA was obtained as a white crystalline solid (114.9 mg, 17% yield). ESI calculated for $C_{53}H_{92}N_{18}O_{21}$ $[M]^+$: 1316.67; found 1316.67.

Synthesis of OA-SKAGAGPQGIQGQGAGKAK(OA)S: Fmoc-Ser(tBu)-Wang resin (0.5 mmol) was swollen in DMF for 10 min then F-moc deprotected and washed using the Liberty Blue peptide synthesizer. A solution containing Fmoc-Lys(Alloc)-OH (0.57 g, 1.25 mmol), HBTU (0.95 g, 2.5 mmol), DIPEA (0.52 mL, 3 mmol) in 5 mL of DMF was added to the resin and let stand for 10 min. An additional 5 mL of DMF was added and a microwave coupling was performed. The coupling of the Fmoc-Lys(Alloc)-OH on the Ser(tBu)-Wang resin was confirmed by colorimetric TNBS test and the remaining sequence was synthesized. Resin was transferred from the reaction vessel and was washed and then stirred in $CH_2Cl_2$ (8 mL) under nitrogen. Borane dimethylamine complex (20 mg, 0.34 mmol) and tetrakis (triphenylphosphine)palladium(0) (45 mg, 0.04 mmol) were added to the resin suspension and the reaction was stirred overnight protected from light. The solution was drained and the resin was washed with $CH_2Cl_2$ followed by DMF. Resin was treated with 5 mL of Fmoc deprotection solution containing 1 mL piperidine and 1 M 1-hydroxybenzotriazole hydrate (HOBt) for 2 h before being washed with $CH_2Cl_2$. 6-(((tert-butoxycarbonyl)amino)oxy)hexanoic acid (0.30 g, 1.2 mmol) and DIC (193 mg, 1.5 mmol) were combined in 4 mL of $CH_2Cl_2$ for 1 h before adding the solution to the resin. After 24 h the solution was removed and the resin was washed with $CH_2Cl_2$ and dried. The resin was treated with trifluoroacetic acid (7.2 mL), triisopropylsilane (0.26 mL), thioanisole (0.26 mL), water (0.26 mL) and aminooxy)acetic acid hemihydrochloride (0.50 mg) for 3.5 h. The peptide was precipitated in cold diethyl ether (50 mL) and washed two additional times. After purification, $MMPOA_2$ was obtained as an off-white crystalline solid (326 mg, 30% yield). ESI calculated for $C95H157N_{29}O_{31}$ $[M]^+$: 2201.16; found 2200.16.

Quantification of Peptide Immobilization: HA-oxime hydrogels containing 0.90 wt % HA-ketone, 0.30 wt % HA-aldehyde, and 60 mol % crosslinking $PEGOA_4$ (1.04 wt %) crosslinker were prepared with PBS in pre-weighed 2 mL maximum recovery tubes (Axygen) overnight at 37° C. Three independent samples for each condition of 100 μL hydrogel was briefly washed with 200 μL PBS for 10 min, and then 100 μL of RGDOA solution was added to give a final concentration of 250 μM or 1 mM in PBS. Adsorption controls were prepared by treating PBS washed hydrogels with 100 μL of 13.75 mg $mL^{-1}$ carboxymethoxylamine hemihydrochloride in a 0.5 M MES buffer pH 6.6 over 24 h to quench unreacted aldehyde and ketones before adding RGDOA solutions. Unreacted RGDOA solutions were removed after either 1 h or 24 h and gels were washed with PBS over 48 h. Hydrogels were mechanically destroyed using a DAC 150 FVZ Speedmixer (Flack Tec) for 30 s at 3500 rpm. A 100 μL solution of hyaluronidase type IV-S was added at 250 U $mL^{-1}$ in Hank's balanced salt solution and samples were completely digested after 48 h at 37° C. Samples were lyophilized, then reconstituted in PBS at 5 mg $mL^{-1}$ and were hydrolyzed with 6M HCl for 24 h at 110° C. HCl was removed and amino acids were modified using phenylisothiocyanate (PITC). Amino acids were separated and quantified using an Acquity UPLC BEH C18 column (2.1 mm×10 cm) and Acquity TUV detector measuring 254 nm. Calibration was performed using Pierce amino acid standard H, results were processed using Empower 2 (Waters) and arginine and alanine values were used for analysis. To calculate the concentration of immobilized RGDOA peptide on HA-oxime hydrogels, the amount of immobilized peptide was subtracted from adsorption controls, and then compared to standard solutions of known concentrations of RGDOA with HA-oxime gel components. The concentration of immobilized RGDOA after 1 h and 24 h from a 250 μM solution are 34±12 μM and 65±14 μM, respectively. The concentration of immobilized RGDOA after 24 h from a 1 mM solution is 242±76 μM. The concentration of RGDOA immobilized after 1 h from a 250 μM solution is 65±14 μM immobilized peptide.

RGDOA Cell Adhesion assay: HA-oxime hydrogels containing 0.90 wt % HA-ketone, 0.30 wt % HA-aldehyde, and 60 mol % crosslinking $PEGOA_4$ (1.04 wt %) were prepared at 25 μL per well in a 384-well format with RPMI-1640 media containing 10% FBS and 1% PS. After gelling for 2 h at 37° C., 25 μL of 125, 250, 500, and 1000 μM RGDOA solutions in media described above were added to hydrogels. After treatment with RGDOA solutions for 1 h at 37° C., the media was removed and gels were washed three times with media at 25 μL per well. MDA-MB-468 cells were seeded on the surface of the hydrogels at a density of 3000 cells $well^{-1}$ in 25 μL of media and incubated for 30 min. Media was gently removed by pipette and replaced with PBS cooled to 4° C. Plates were agitated at 300 rpm for 5 min at room temperature with a basic variable-speed digital orbital shaker (IKA) before PBS containing detached cells were removed and gels with adherent cells were fixed with 4% PFA. Cells nuclei were stained with Hoechst 33342, 1/250 in PBS, 25 μL $well^{-1}$ for 4 h. Images were obtained using an Olympus confocal microscope at 10× magnification with z-stacks of 12 μm step size. Cell number was quantified using spot identification in Imaris 8 software by Bitplane. The fold change in cell number was calculated from control hydrogels containing no RGDOA peptide. A minimum of 3 independent replicates consisting of different cell passages were performed for each condition.

Hydrogel Stability and Degradation: HA-oxime hydrogels containing 0.90 wt % HA-ketone, 0.30 wt % HA-aldehyde, and 60 mol % crosslinking $PEGOA_4$ (1.04 wt %) or 60 mol % crosslinking $MMPOA_2$ (0.83 wt %) were prepared in pre-weighed 2 mL maximum recovery tubes (Axygen) overnight at 37° C. Hydrogel mass was taken after swelling the hydrogels with 200 μL of Hank's balanced salt solution (HBSS) overnight which was then replaced with PBS or HBSS containing either 20 μg $mL^{-1}$ collagenase type IV, 50 U $mL^{-1}$ or 400 U $mL^{-1}$ hyaluronidase type IV-S were added to the hydrogels which were incubated at 37° C. Every 24 h buffer was removed, and hydrogel mass was recorded and replaced with fresh solutions until hydrogels degraded at day 10 and again on day 28. Degradation data was recorded as a ratio of initial HBSS swollen gel mass at day 0 to PBS, hyaluronidase or collagenase treated hydrogel mass. Experiments were performed with 3 independent samples to calculate the mean and standard deviation.

Figure 37A:
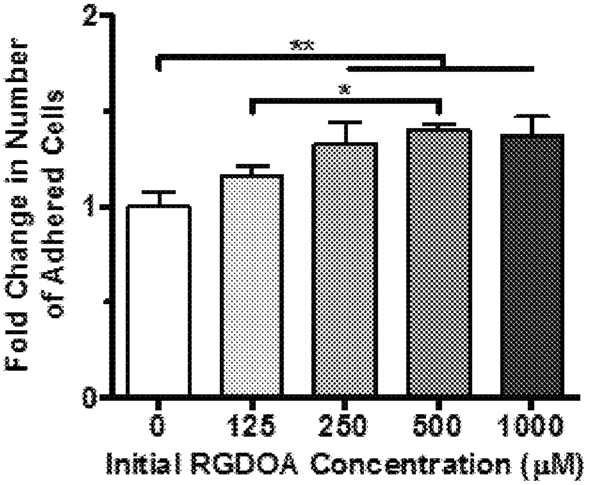
FIG. 37A and FIG. 37B illustrate adhesion of MDA-MB-468 cells to RGDOA peptide and quantification of immobilized RGDOA peptide.
Figure 37B:
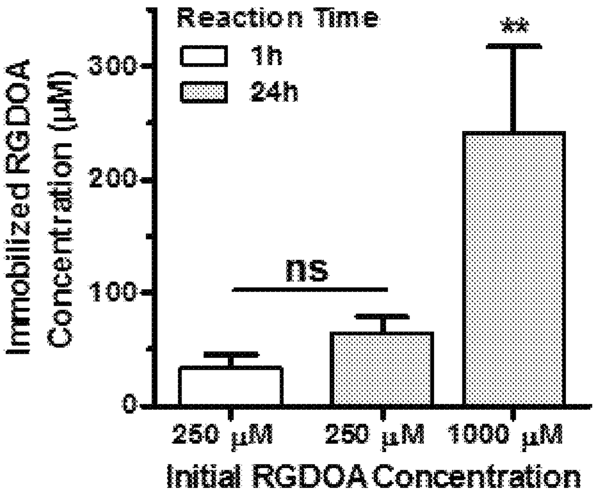

Results: When various concentrations of RGDOA were conjugated to HA-oxime hydrogels for only 1 hour in the presence of full media containing serum, MDA-MB-468 cells showed an increase in the number of adherent cells with increased RGDOA concentration 250-1000 μM (FIG. 37A and FIG. 37B).

Figure 38:
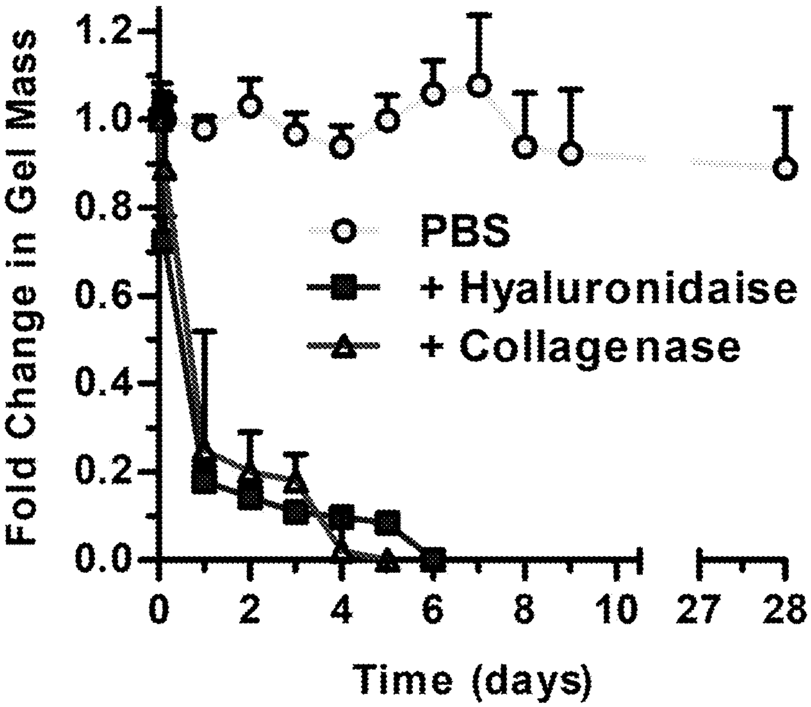
FIG. 38 illustrates swelling and degradation of HA-oxime hydrogel prepared from 0.90 wt % HA-ketone and 0.30 wt % HA-aldehyde crosslinked with 60 mol % $MMPOA_2$ over 28 days at 37° C. in Hank's balanced salt solution containing hyaluronidase or collagenase.

HA-oxime $MMPOA_2$ crosslinked hydrogels were stable for 28 days, and degradable with both collagenase and hyaluronidase (FIG. 38). Breast cancer MDA-MB-468 cells encapsulated in HA-oxime hydrogels crosslinked with $MMPOA_2$ formed spheroids over the course of 21 days which indicate it is suitable for 3D cell culture.

Example 10—Synthesis of HA-Oxyamine

The scheme below describes the synthesis of HA-oxyamine. First, HA is reduced on the end groups to form end-capped HA. Then sodium hyaluronate is stirred with DMTMM and tert-butyl-(2-aminoethoxy)carbamate to generate a Boc-protected HA-oxyamine. The HA-Boc-oxyamine is then deprotected under acidic conditions to give HA-oxyamine.

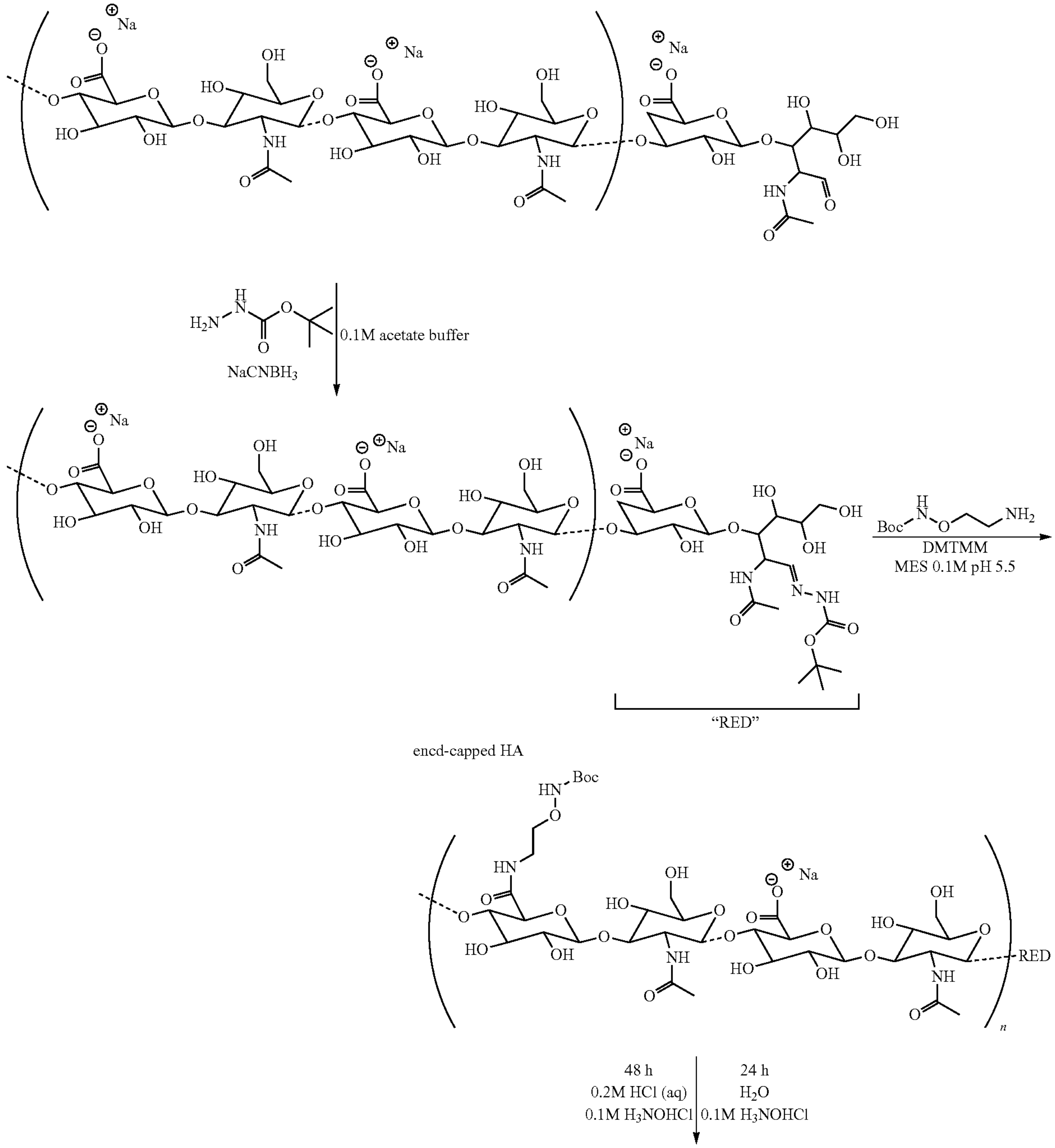

-continued

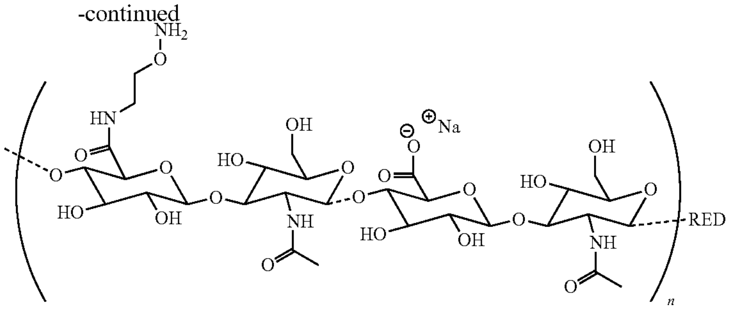

HA-oxyamine

Example 11—Synthesis of Hyaluronan Modified with Ketone and Aldehyde (HAKA)

This example describes the synthesis of HA modified with ketone and aldehyde functional groups. The synthetic steps are outlined in the scheme below.

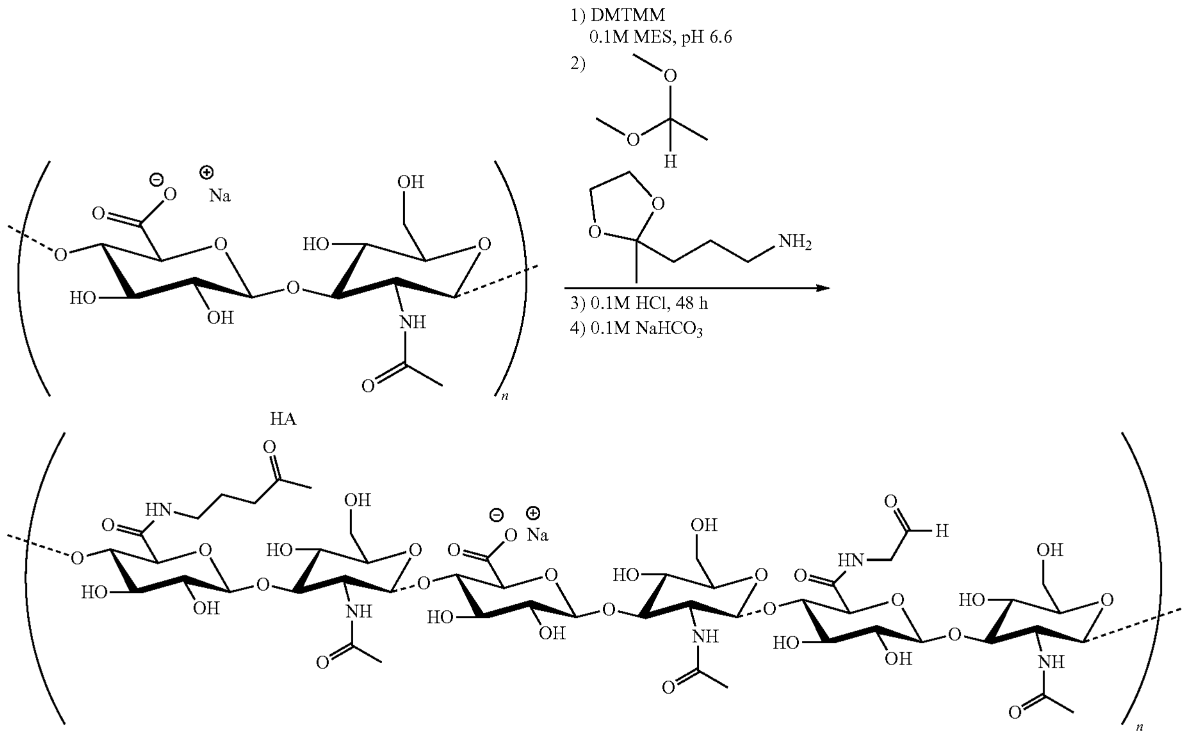

HA

HA-ketone-aldehyde

Figure 39:
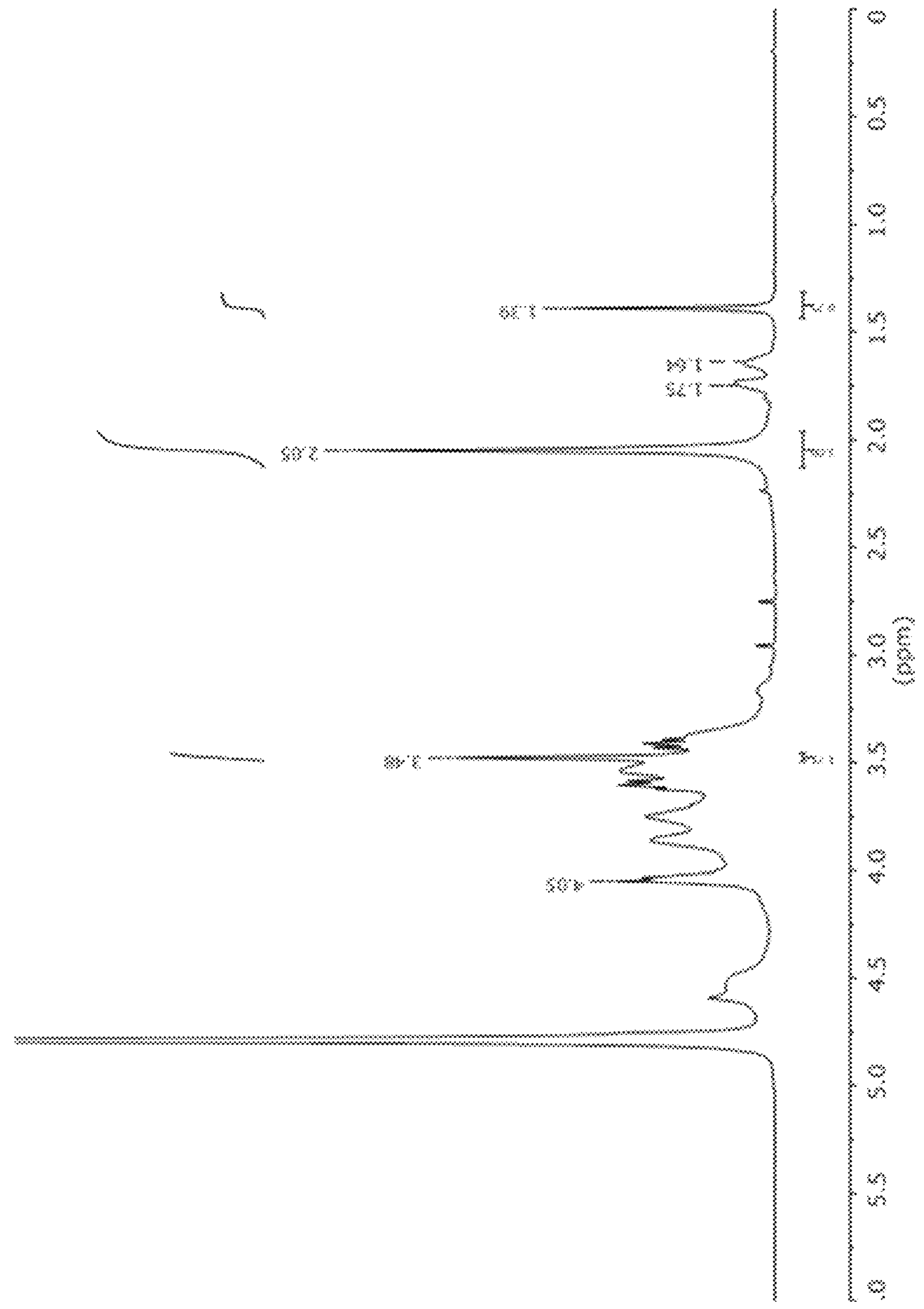
FIG. 39 illustrates characterization of HAKA by $^1H$ NMR performed in $D_2O$.

The procedures for the DMTMM steps and deprotection step are similar to those described in Example 1. The $^{1}H$ NMR used to characterize HAKA is shown in FIG. 39.

Example 12—Synthesis of Hyaluronan Modified with Ketone and Norbornene (HANK)

This example describes the synthesis of HA modified with ketone and norbornene functional groups. The synthetic steps are outlined in the scheme below.

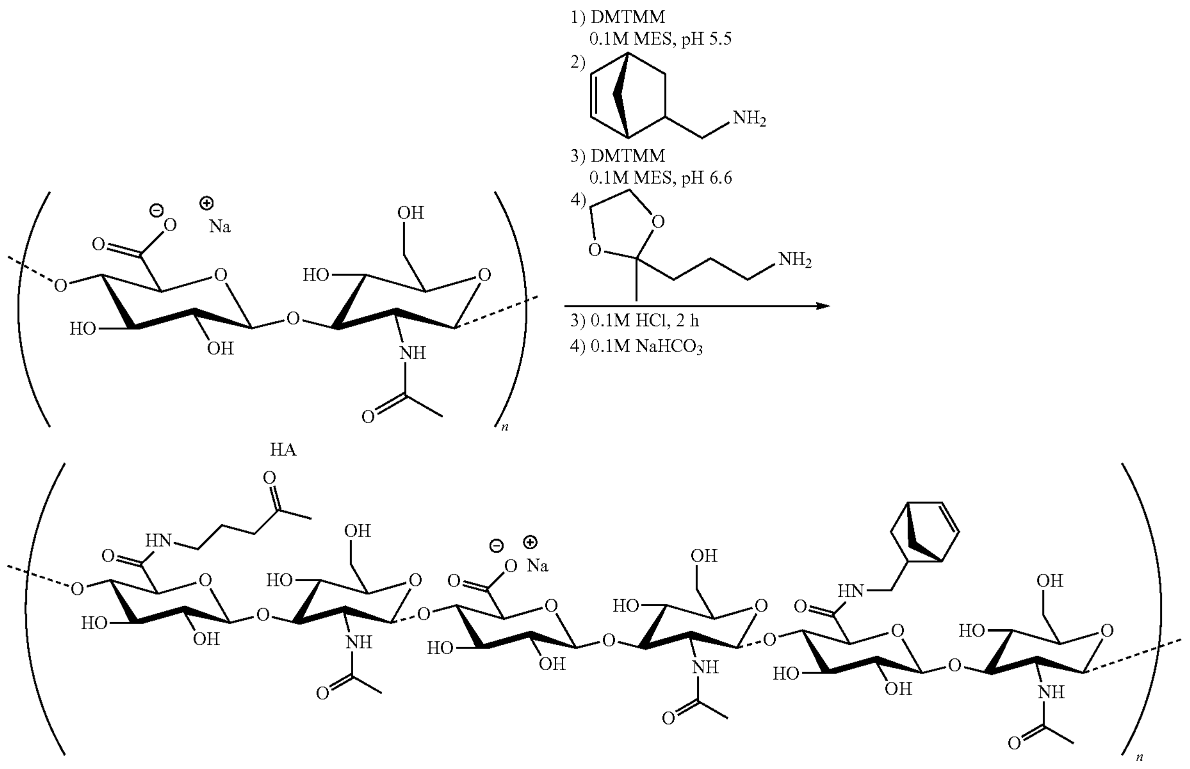

HA

HA-ketone-norbornene

The procedures for the DMTMM steps and deprotection step are similar to those described in Example 1.

Figure 40:
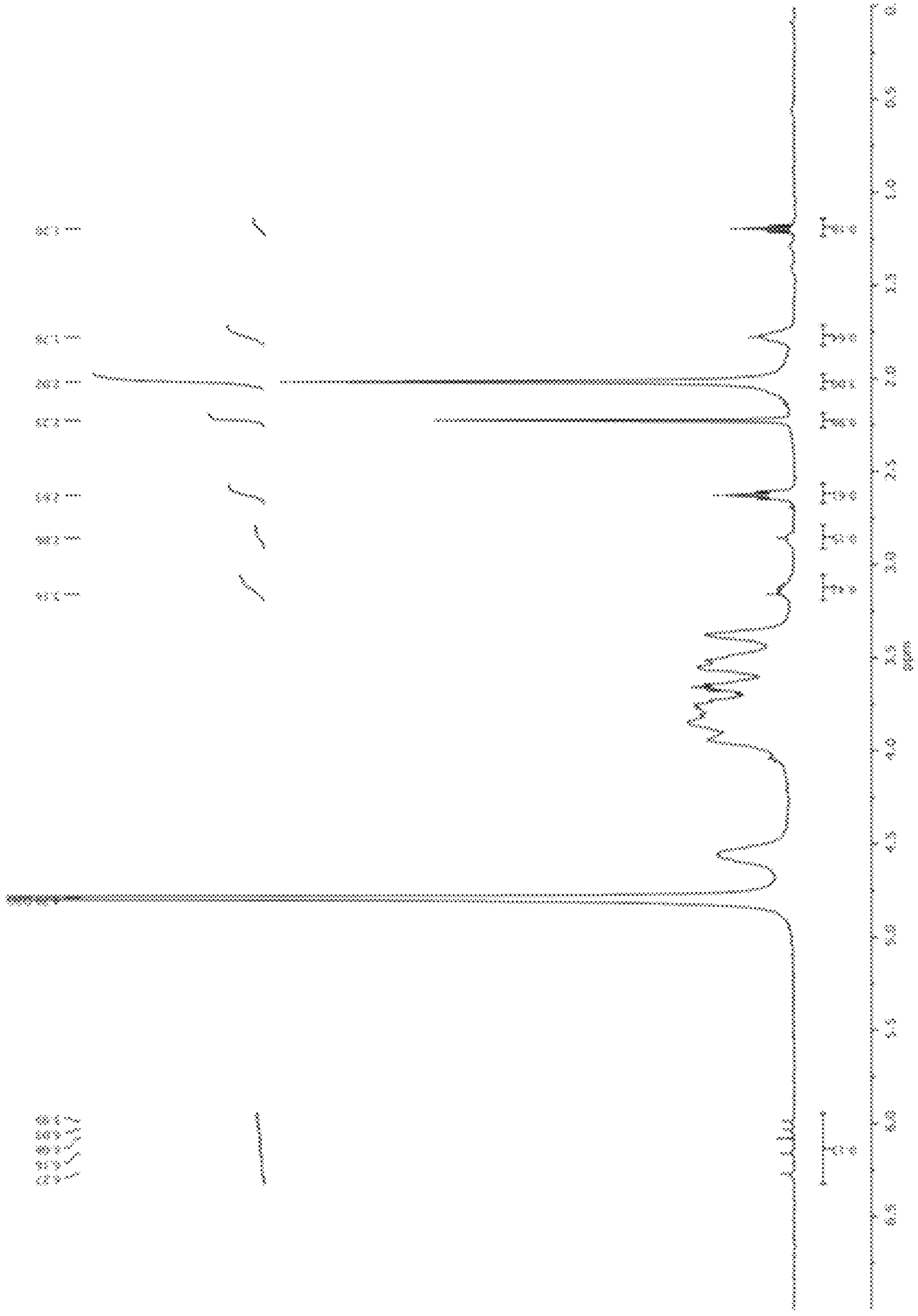
FIG. 40 illustrates characterization of HANK by $^1H$ NMR performed in $D_2O$.

The $^1$H NMR used to characterize HANK is shown in FIG. 40.

Example 13—Injectable Hydrogel for the Treatment of Osteoarthritis

This example describes the application of HA-oxime gels using HA modified with ketone for the application as an injectable hydrogel for the treatment of osteoarthritis (OA).

Background: Managing the pain symptoms of OA is commonly achieved using oral medication but these treatments do not delay disease progression (Callhoff et al., "Disease Burden of Patients With Osteoarthritis: Results of a Cross-Sectional Survey Linked to Claims Data," Arthritis Care & Research, 72:193-200 (2019)). Standard treatments include acetaminophen, nonsteroidal anti-inflammatory agents (NSAIDs), cyclooxygenase-2 (COX-2) inhibitors, opioids and intra articular therapies of glucocorticoids or HA. There are several possible mechanisms that mediate HA efficacy in managing OA including lubrication, analgesia, anti-inflammatory and chondroprotection (Avenoso, et al., "Hyaluronan in the experimental injury of the cartilage: biochemical action and protective effects," Inflamm. Res., 67:5-20 (2018); Brandt et al., "Intraarticular injection of hyaluronan as treatment for knee osteoarthritis: what is the evidence?" Arthritis Rheum., 43:1192-1203 (2000); and Kawasaki et al., "Hyaluronic acid enhances proliferation and chondroitin sulfate synthesis in cultured chondrocytes embedded in collagen gels," J. Cell Physiol., 179:142-148 (1999)). One concern with the use of HA is the mixed clinical results which can likely be attributed to the differences in injection volume, frequency of injections, polymer molecular weight and formulation. All these variables can impact the therapeutic window and ultimately determine how rapidly it is cleared from the joint. Crosslinked (Synvisc®), chemical derivatives (Hylan G-F 20®) and unmodified (Hyalgan®) products have all been injected into the synovial cavity. Uncrosslinked hyaluronan is often cleared rapidly and the half-life is short (<7 days) with other derivatives lasting more than a month in rabbit knees. In some clinical studies, injections are given between weekly and every 3 weeks to replace the cleared materials. Most studies focus on characterizing the viscosity of the synovial fluid; however, the synovial fluid viscosity following injection is less than the viscosity of HA-solutions that are injected because the synovial fluid is rapidly cleared (Goto, et al., "Intra-articular injection of hyaluronate (SI-6601D) improves joint pain and synovial fluid prostaglandin E2 levels in rheumatoid arthritis: a multicenter clinical trial," Clin. Exp. Rheumatol., 19:377-383 (2001).

Methods: The procedures to prepare the HA-oxime gel for osteoarthritis are similar to those described in Example 1 and Example 5.

Figure 41A:
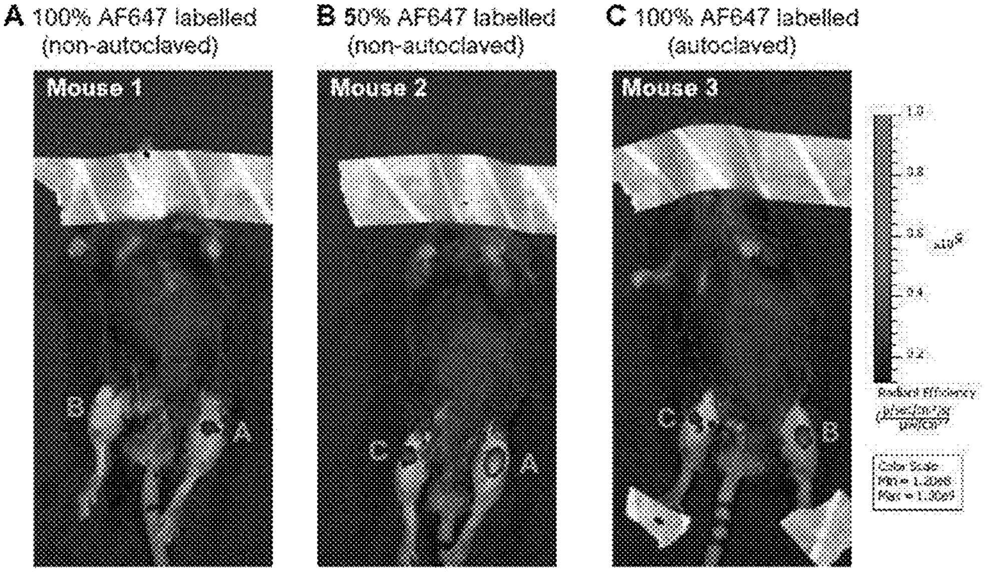
FIG. 41A, FIG. 41B illustrates the injection of HA-oxime gels with Alexa Fluor-647 into the synovial cavity of 12-week male C57BL6/J mice with 3 μL of hydrogel into the knee joints through a 33 gauge needle.
Figure 41B:
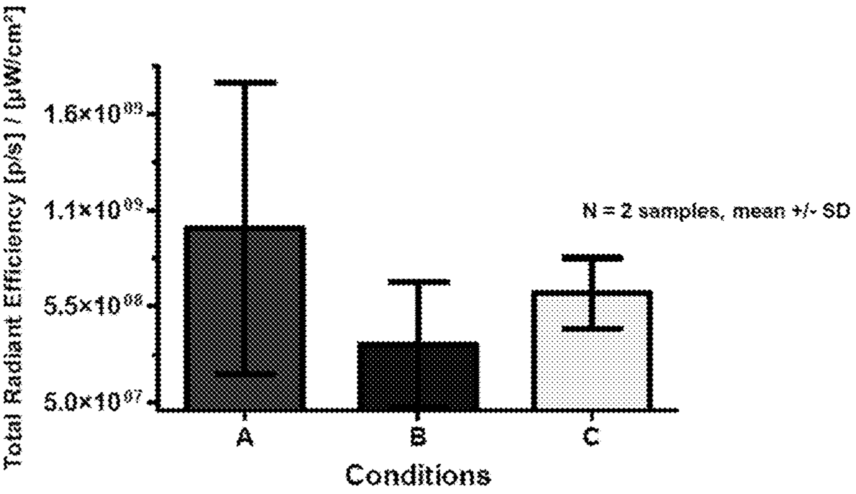

Results: HA-oxime gels labelled with Alexa Fluor-647 are injectable in the synovial cavity of mice with a 33 gauge needle (FIG. 41A). The procedures to prepare the HA-oxime gel for osteoarthritis are similar to those described in Example 1 and Example 5.

Example 14—Injectable Hydrogel for Cell Transplantation

This example describes the application of HA-oxime gels using HA modified with ketone for the application as an injectable hydrogel for cell delivery in vivo.

Methods: The procedures to prepare the HA-oxime gel for cell transplantation are similar to those described in Example 1 and the preparation of the matrix metalloproteinase peptide crosslinker ($MMPOA_2$) Example 9.

Patient derived xenografts: Cells taken from a breast cancer patient with metastasis to the liver were established in organoids taken from a PDX tumour (DCXTO.58). The cells were expanded in 50 μL Matrigel at 400,000 cells-$mL^{-1}$ until passage 11. To prepare the cells for injection the medium was removed from the wells and the organoids were dissociated with 500 μL TrypLE express enzyme and incubated for 30 minutes. The Matrigel was disrupted by pipetting with the tips coated with 1% FBS in PBS to prevent adsorption of the matrix or organoids. After a further 10 minutes of incubation the contents of the wells were combined and centrifuged at 1,000 RPM for 5 minutes. The supernatant was removed, and the pellet was re-suspended in 5 mL of cold complete medium and pelleted again. After removing the supernatant, the cells were washed twice with PBS, pelleted by centrifugation and the cell density was quantified by performing a 1 in 10 dilution. Cells were mixed with HA solutions and stored on ice before injection by combining laminin (2 $mg \cdot mL^{1}$) or collagen (0.5 $mg \cdot mL^{1}$) with the respective the HA-oxime soft hydrogels with 1.6 mM of $MMPOA_2$ peptide crosslinker matching the in vitro studies. For DCXTO.58 PDX, 20 female SCID mice at least 5 weeks of age were anesthetized, and an incision was made in the lower abdomen, a 27-gauge needle was used to deliver 100 μL of matrix containing $1 \times 10^6$ cells into the mammary fat pad. The wound was closed using clips and mice were given analgesics post-surgery to reduce post-surgical pain. Tumour growth was followed two weeks after cell implantation and was calculated using the equation volume=0.5×length×width×height.

Figure 42:
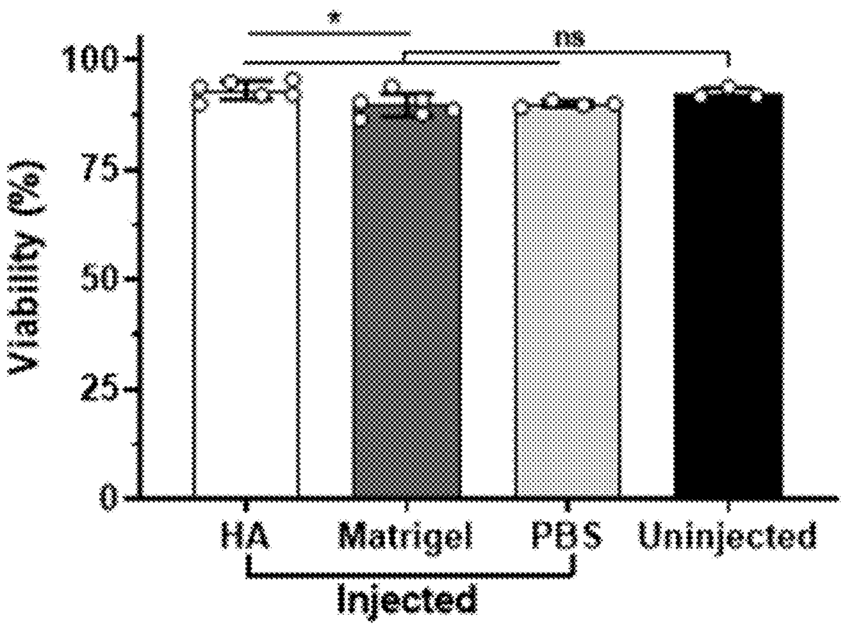
FIG. 42 is a graph which illustrates viability of A549 lung carcinoma cells following injection through a 27-gauge needle was higher when encapsulated in HA Soft versus Matrigel both were similar to uninjected cells quantified from live and dead images (n=3-6 replicates, mean±standard deviation, not significant (ns), *p<0.05 one-way ANOVA, Tukey's post hoc test).
Figure 43:
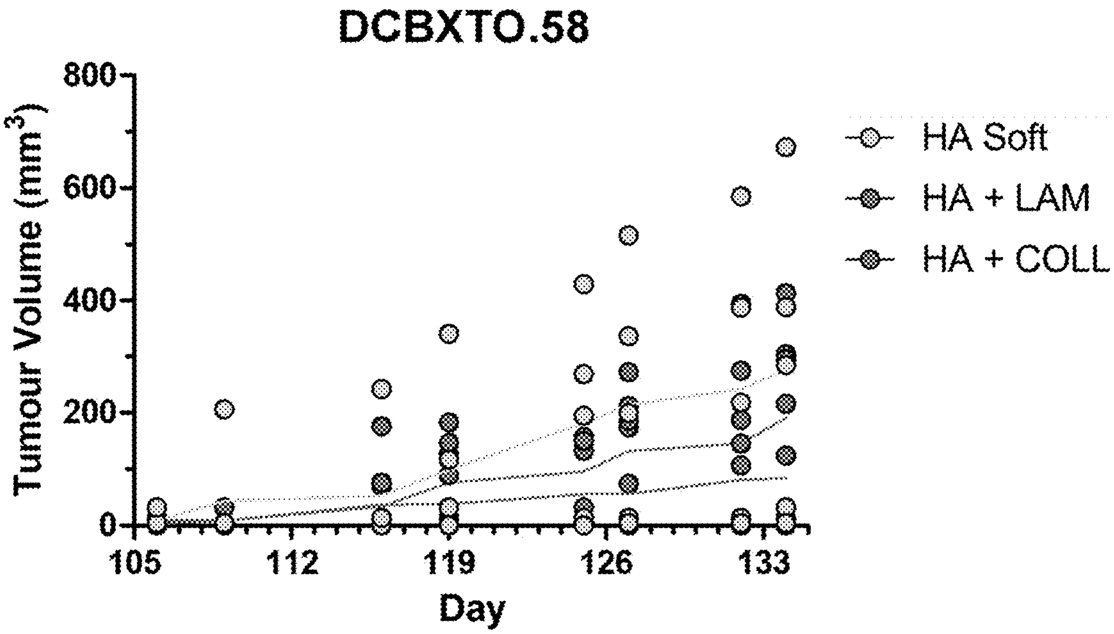
FIG. 43 illustrates the use of HA-oxime as an injectable hydrogel for cell transplantation. Tumour growth curves of DCBXTO.58 cells implanted in NOD scid mice with hydrogels (n=5, mean+standard deviation).

Results: Cells survive injection through a 27-gauge when formulated with the HA-oxime hydrogel similar to Matrigel (FIG. 42). To investigate the utility of the HA-oxime hydrogel for cell transplantation we use clinically relevant triple negative (DCBXTO.58) cells originated from a patient tumour characterized as triple negative breast cancer ($ER^-$, $PR^-$, $HER2^-$) with metastasis to the liver where the biopsy was taken. Three hydrogel formulations were compared: 3 HA-oxime formulations containing 0.8 wt % HA with 1.6 mM $MMPOA_2$ and either no additives (HA Soft), laminin (LAM) (2,000 $\mu g \cdot mL^{-1}$), collagen (COLL) (500 $\mu g \cdot mL^{-1}$). Cells were then encapsulated within HA Soft, HA+LAM, and HA+COLL then injected into mammary fat pads within scid mice which demonstrates they support in vivo growth (FIG. 43).

Example 15—Synthesis of Hyaluronan Modified with Cyclobutanone (HAC)

This example describes the synthesis of HA modified with cyclobutanone functional groups. The synthetic steps are outlined in the scheme below.

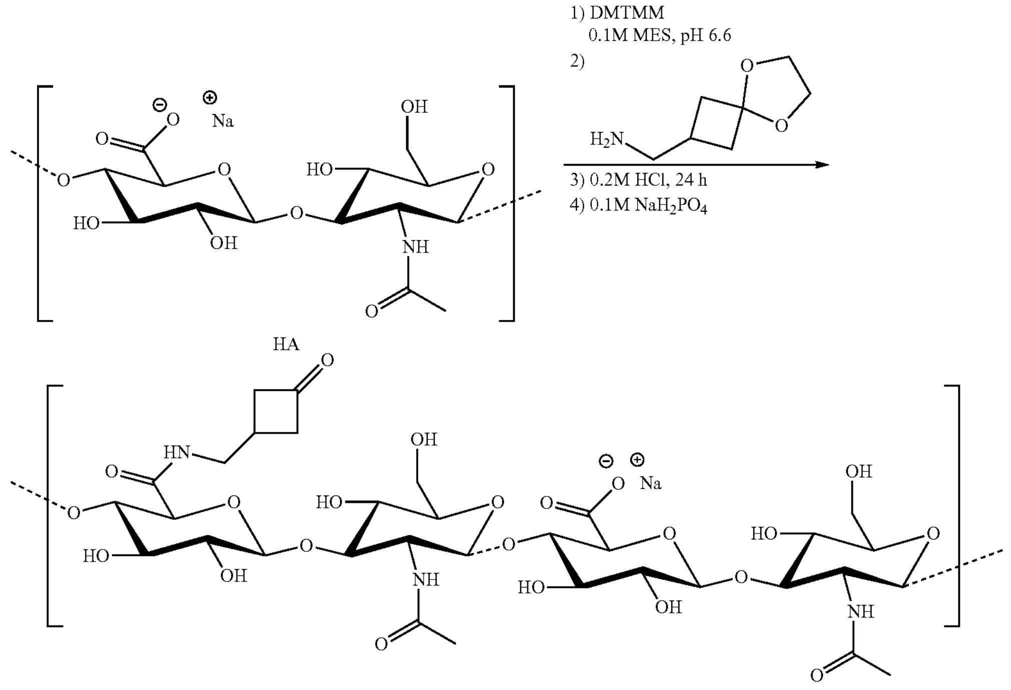

HA

HA-cyclobutanone

Figure 44:
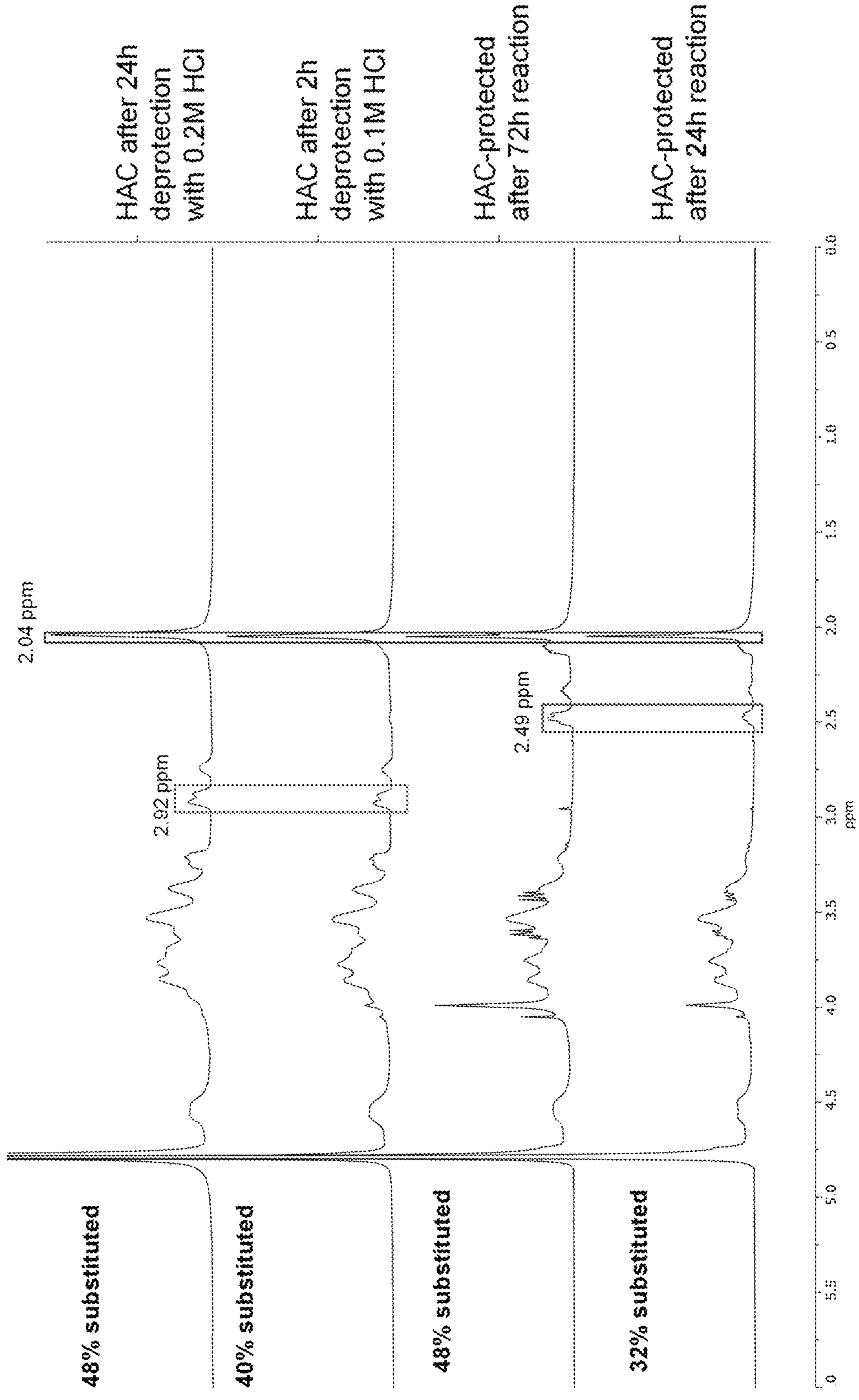
FIG. 44 illustrates characterization of HAC by $^1H$ NMR performed in $D_2O$.

The procedures for the DMTMM steps and deprotection step are similar to those described in Example 1. The $^1H$ NMR used to characterize HAC is shown in FIG. 44.

OTHER EMBODIMENTS

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

This application claims the benefit of U.S. Provisional Ser. No. 62/870,497, filed Jul. 3, 2019, which is herein incorporated by reference in its entirety.

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

What is claimed is:

1. A compound of formula (I):

HAP-K (I), wherein

HAP is a hyaluronan polymer; and

K is a moiety covalently linked to the hyaluronan polymer having the structure of formula (Ia) or formula (Ib):

(Ia)

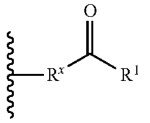

or (Ib)

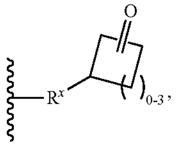

wherein $R^X$ is $C_{1-20}$ alkylene, $C_{2-20}$ alkenylene, $C_{2-20}$ alkynylene, $C_{1-20}$ heteroalkylene, $C_{2-20}$ heteroalkenylene, or $C_{2-20}$ heteroalkynylene, any of which is optionally substituted with one or more of oxo, halogen, hydroxyl, alkoxy, azido, cyano, nitro, amino, and thiol; and $R^1$ is $C_{1-6}$ alkyl, $C_{2-6}$ alkenyl, $C_{2-6}$ alkynyl, $C_{1-6}$ heteroalkyl, $C_{2-6}$ heteroalkenyl, $C_{2-6}$ heteroalkynyl, $C_{3-10}$ carbocyclyl, $C_{6-10}$ aryl, $C_{2-9}$ heterocyclyl, or $C_{2-9}$ heteroaryl, any of which is optionally substituted with one or more of oxo, halogen, hydroxyl, alkoxy, azido, cyano, nitro, amino, and thiol, or a salt thereof.

2. The compound of claim 1, further described by formula (III):

$$[A]_n[B]_m[C]_{1-(n+m)} \quad \text{(III)},$$

wherein [A] has the structure of formula (IIIa):

(IIIa)

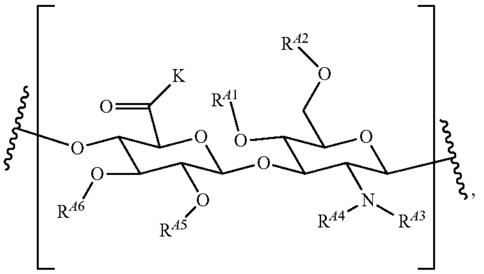

wherein each of $R^{A1}$, $R^{A2}$, $R^{A3}$, $R^{A4}$, $R^{A5}$, and $R^{A6}$ is, independently, H, $C_{1-12}$ alkyl optionally substituted with one or more of oxo, halogen, hydroxyl, alkoxy, azido, cyano, nitro, amino, and thiol, or $C_{1-12}$ heteroalkyl optionally substituted with one or more of oxo, halogen, hydroxyl, alkoxy, azido, cyano, nitro, amino, and thiol; and K is a moiety covalently linked to the hyaluronan polymer having the structure of formula (Ia) or formula (Ib):

(Ia)

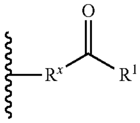

or (Ib)

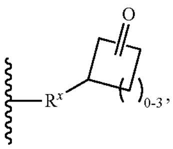

wherein $R^X$ is $C_{1-20}$ alkylene, $C_{2-20}$ alkenylene, $C_{2-20}$ alkynylene, $C_{1-20}$ heteroalkylene, $C_{2-20}$ heteroalkenylene, or $C_{2-20}$ heteroalkynylene, any of which is optionally substituted with one or more of oxo, halogen, hydroxyl, alkoxy, azido, cyano, nitro, amino, and thiol; and $R^1$ is $C_{1-6}$ alkyl, $C_{2-6}$ alkenyl, $C_{2-6}$ alkynyl, $C_{1-6}$ heteroalkyl, $C_{2-6}$ heteroalkenyl, $C_{2-6}$ heteroalkynyl, $C_{3-10}$ carbocyclyl, $C_{6-10}$ aryl, $C_{2-9}$ heterocyclyl, or $C_{2-9}$ heteroaryl, any of which is optionally substituted with one or more of oxo, halogen, hydroxyl, alkoxy, azido, cyano, nitro, amino, and thiol;

[B] has the structure of formula (IIIb):

(IIIb)

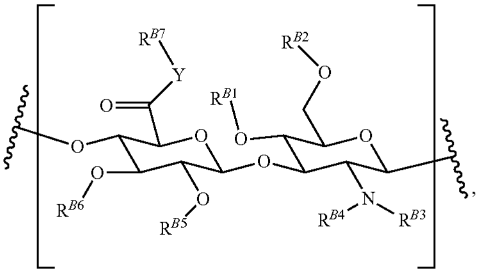

wherein each of $R^{B1}$, $R^{B3}$, $R^{B4}$, $R^{B5}$, and $R^{B6}$ is, independently, H, $C_{1-12}$ alkyl optionally substituted with one or more of oxo, halogen, hydroxyl, alkoxy, azido, cyano, nitro, amino, and thiol, or $C_{1-12}$ heteroalkyl optionally substituted with one or more of oxo, halogen, hydroxyl, alkoxy, azido, cyano, nitro, amino, and thiol;

$R^{B2}$ is H, $C_{1-12}$ acyl, $C_{1-12}$ alkyl, or $C_{1-12}$ heteroalkyl, each of which is optionally substituted with one or more of oxo, halogen, hydroxyl, alkoxy, azido, cyano, nitro, amino, and thiol;

$R^{B7}$ is H or $C_{1-6}$ alkyl;

Y is $NR^{B8}$, O, or S;

Z is $NR^{B9}$, O, or S; and each of $R^{B8}$ and $R^{B9}$ is, independently, H or $C_{1-6}$ alkyl;

[C] has the structure of formula (IIIc):

(IIIc)

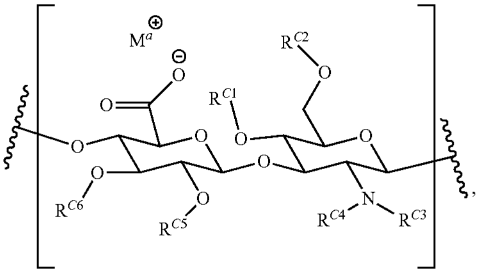

wherein each of $R^{C1}$, $R^{C2}$, $R^{C3}$, $R^{C4}$, $R^{C5}$, and $R^{C6}$ is, independently, H, $C_{1-12}$ alkyl optionally substituted with one or more of oxo, halogen, hydroxyl, alkoxy, azido, cyano, nitro, amino, and thiol, or $C_{1-12}$ heteroalkyl optionally substituted with one or more of oxo, halogen, hydroxyl, alkoxy, azido, cyano, nitro, amino, and thiol; and $M^a$ is a cation;

and each of n and m is, independently, a fraction greater than zero and less than 1, wherein $(n+m)<1$.

3. The compound of claim 1 wherein K has the structure of formula (Ia):

(Ia)

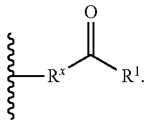

4. The compound of claim 1, wherein $R^1$ is $C_{1-6}$ alkyl, $C_{2-6}$ alkene, $C_{2-6}$ alkyne, or $C_{1-6}$ heteroalkyl.

5. The compound of claim 1 wherein K has the structure of formula (Ib):

(Ib)

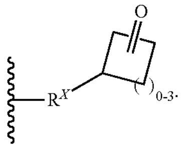

6. The compound of claim 5, wherein K has the structure of

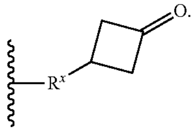

7. The compound of claim 2, wherein $R^{A1}$ is H; $R^{A2}$ is H; $R^{A3}$ is H; $R^{A4}$ is

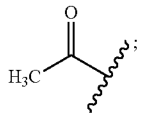

$R^{A5}$ is H; $R^{A6}$ is H; $R^{B1}$ is H; $R^{B2}$ is H; $R^{B3}$ is H; $R^{B4}$ is

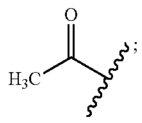

$R^{B5}$ is H; $R^{B6}$ is H; $R^{B7}$ is H; $Y^1$ is O; $Z^1$ is O; $R^{C1}$ is H; $R^{C2}$ is H; $R^{C4}$ is

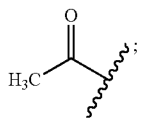

$R^{C5}$ is H; and $R^{C6}$ is H.

8. The compound of claim 2, wherein m and n are between 0.35 and 0.65.

9. The compound of claim 1, wherein $R^X$ is $C_{1-20}$ alkylene or $C_{2-20}$ heteroalkenylene, any of which is optionally substituted with one or more of oxo, halogen, hydroxyl, alkoxy, azido, cyano, nitro, amino, and thiol.

10. The compound of claim 1, wherein $R^X$ is $C_{2-20}$ heteroalkenylene, which is optionally substituted with one or more of oxo, halogen, hydroxyl, alkoxy, azido, cyano, nitro, amino, and thiol.

11. The compound of claim 2, wherein [A] has the structure of formula (A1):

(A1)

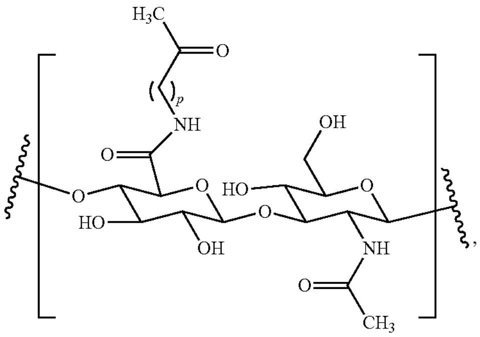

wherein p is 1, 2, 3, 4, 5, or 6.

12. The compound of claim 11, wherein p is 3.

13. The compound of claim 2, wherein [B] has the structure of formula (B1):

(B1)

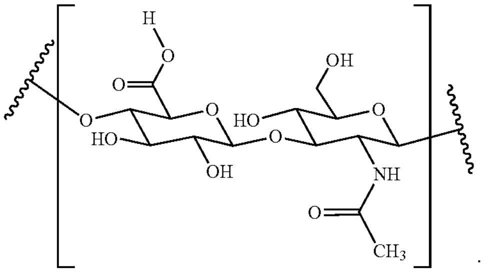

14. The compound of claim 2, wherein [C] has the structure of formula (C1):

(C1)

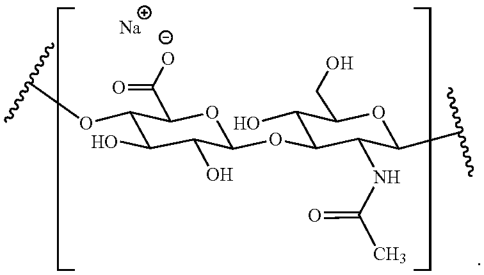

* * * * *